US008273740B2

(12) United States Patent
Fretz et al.

(10) Patent No.: US 8,273,740 B2
(45) Date of Patent: Sep. 25, 2012

(54) 2-SULFANYL-BENZOIMIDAZOL-1-YI-ACETIC ACID DERIVATIVES AS CRTH2 ANTAGONISTS

(75) Inventors: Heinz Fretz, Riehen (CH); Markus Gude, Sissach (CH); Kurt Hilpert, Hofstetten (CH); Julien Pothier, Saint-Louis (FR); Markus Riederer, Liestal (CH); Matthias Steger, Zürich (CH)

(73) Assignee: Actelion Pharmaceuticals, Ltd., Allschwil (CH)

( * ) Notice: Subject to any disclaimer, the term of this patent is extended or adjusted under 35 U.S.C. 154(b) by 1191 days.

(21) Appl. No.: 11/660,907

(22) PCT Filed: Aug. 23, 2005

(86) PCT No.: PCT/EP2005/009083
§ 371 (c)(1),
(2), (4) Date: Feb. 23, 2007

(87) PCT Pub. No.: WO2006/021418
PCT Pub. Date: Mar. 2, 2006

(65) Prior Publication Data
US 2008/0108638 A1 May 8, 2008

(30) Foreign Application Priority Data

Aug. 26, 2004 (WO) .................. PCT/EP2004/009521

(51) Int. Cl.
*A61K 31/4184* (2006.01)
*A61K 31/425* (2006.01)
*A61K 31/4439* (2006.01)
*A61K 31/445* (2006.01)
*A61K 31/4709* (2006.01)
*A61P 1/00* (2006.01)
*A61P 1/04* (2006.01)
*A61P 5/00* (2006.01)
*A61P 9/00* (2006.01)
*A61P 9/10* (2006.01)
*A61P 11/00* (2006.01)
*A61P 11/06* (2006.01)
*A61P 17/00* (2006.01)
*A61P 19/02* (2006.01)
*A61P 27/02* (2006.01)

(52) U.S. Cl. ................ 514/239.5; 514/266.23; 514/322; 514/338; 514/373; 514/395; 544/284; 546/199; 546/273.7; 548/307.1

(58) Field of Classification Search ............... 514/239.5, 514/266.23, 322, 338, 373, 395; 544/284; 546/199, 273.7; 548/307.1, 209
See application file for complete search history.

(56) References Cited

U.S. PATENT DOCUMENTS

| 5,504,082 | A | 4/1996 | Kawakita et al. |
| 5,817,756 | A | 10/1998 | Kyle et al. |
| 2002/0052403 | A1* | 5/2002 | Holton ........................ 514/449 |
| 2004/0162311 | A1* | 8/2004 | Tsuchiya et al. .............. 514/303 |

FOREIGN PATENT DOCUMENTS

| EP | 0 167 943 A2 | 1/1986 |
| EP | 1097926 | * 5/2001 |
| GB | 1152814 | 5/1969 |
| GB | 2 388 540 A | 11/2003 |
| WO | WO-95/07294 A1 | 3/1995 |
| WO | WO-2005/060956 A1 | 7/2005 |
| WO | WO-2005/094816 A1 | 10/2005 |

OTHER PUBLICATIONS

Morissette et al. "High-throughput crystallization: polymorphs, salts, co-crystals and solvates of pharmaceutical solids" Advanced Drug Delivery Reviews, 2004, 56, 275-300.*
Seddon et al. "Pseudopolymorph: A Polemic" Crystal Growth and Design, 2004, 4, 1087.*
Vippagunta et al. "Crystalline solids" Advanced Drug Delivery Reviews, 2001, 48, 3-26.*
Braga et al. "Making crystals from crystals: a green route to crystal engineering and polymorphism" Chem. Commun. 2005, 3635-3645.*
Stella, Valentino J., "Prodrugs as therapeutics" Expert Opinion of Therapeutic Patents, 2004 14(3), 277-280.*
Wolff et al. Burger's Medicinal Chemistry, 5th Ed., vol. 1, pp. 975-977, 1994.*
Testa, Bernard, "Prodrug Research: futile or fertile?" Biochemical Pharmacology, 2004, 68 2097-2106.*
Ettmayer, Peter, "Lessons Learned from Marketed and Investigational Prodrugs", Medicinal Chemistry, 2004, 47(10), 2394-2404.*
Gardiner et al. ("Synthesis of Novel 1-, 1,4- and 1,7-substituted 2-Mercapto- and 2-Methylmercapto—Benzimidazoles: Acyclic Analogues of the HIV-I RT Inhibitor, TIBO" Tetrahedron, 1995, 51(42), 11515-11530).*
Database HCAPLUS 'Online! Chemical Abstracts Service, Columbus, Ohio, US.; Labaanauskas, L K et al.; "Synthesis and antiphlogistic activity of novel 5, 6-dialkoxy-2-mercaptobenzimidazolylaceti c acid derivatives" XP-002357548, 1998.
Khimiko-Farmatsevticheskii Zhurnal, vol. 32, No. 2, 1998, pp. 15-16,—& Database Registry STN; CAS Registry No. 209327-35-5, Aug. 2, 1998, "1H-Benzimidazole-1-acetic acid, 5, 6-diethoxy-2-(ethylthio)-"; XP-002362212 abstract. Database Registry STN; CAS Registry No. 209327-33-3, Aug. 2, 1998, "1H-Benzimidazole-1-acetic acid, 2-(ethylithio)-5, 6-dimethoxy-"; XP-002362213 abstract.
Huang, N. et al.; "Identification of Non-Phosphate-Containing Small Molecular Weight Inhibitors of the Tyrosine Kinase p56 Lck SH2 Domain via in Silico Screening against the pY + 3 Binding Site"; J. Med. Chem, vol. 47, Apr. 6, 2004, pp. 3502-3511.
Database WPI Week 199213; Derwent Publications Ltd., London, GB; AN 1992-101154; XP-00235705 "New silver halide photograph material contains specific diazole compound".
Sugimoto, H. et al.; "An Orally Bioavailable Small Molecule Antagonists of CRTH2, Ramatroban (Bay u3405), Inhibits Prostaglandin $D_2$-Induced Eosinophil Migration in Vitro"; The Journal of Pharmacology and Experimental Therapeutics, vol. 305, No. 1, pp. 347-352, 2003.
Berge, S. et al.; "Pharmaceutical Salts"; Journal of Pharmaceutical Sciences, Jan. 1977, vol. 66, No. 1, pp. 1-19.
Bundard, H.; "Design of Prodrugs"; pp. 7-9, 21-24, Elsevier, Amsterdam (1985).

(Continued)

*Primary Examiner* — Kortney L Klinkel
(74) *Attorney, Agent, or Firm* — Hunton & Williams LLP

(57) ABSTRACT

The invention relates to 2-sulfanyl-benzoimidazol-1-yl-acetic acid derivatives and their use as potent "chemoattractant receptor-homologous molecule expressed on Th2 cells" antagonists in the treatment of prostaglandin mediated diseases, to pharmaceutical compositions containing these derivatives and to processes for their preparation.

14 Claims, No Drawings

OTHER PUBLICATIONS

Silverman R. B., "The Organic Chemistry of Drug Design and Drug Action"; pp. 352-401, Academic Press, San Diego, CA (1992).

Sawyer N. et al.; "Molecular pharmacology of the human prostaglandin $D_2$ receptor, CRTH2"; British Journal of Pharmacology (2002), 137, pp. 1163-1172.

Migawa, M.T. et al.; "Design, Synthesis, and Antiviral Activity of α-Nucleosides: D- and L-Isomers of Lyxofuranosyl- and (5-Deoxylyxofuranosyl) benzimidazoles"; J. Med. Chem, 1998, vol. 41, pp. 1242-1251.

McFarlane, M.D. et al.; "o—Nitroaniline Derivatives. Part 10. $^1$5- and 6-Amino-1$H$-benzimidazole 3-Oxides"; J. Chem. Soc. Perkin Trans. I, 1988, pp. 691-696.

Wright, J. L. et al.; "Subtype-Selective $N$-Methyl-D-Aspartate Receptor Antagonists: Synthesis and Biological Evaluation of 1-(Heteroarylalkynyl)-4-benzylpiperidines"; J. Med. Chem., 2000, vol. 43, pp. 3408-3419.

Breslin, H.J. et al; "Synthesis and Anti-HIV-1 Activity of 4,5,6,7-Tetrahydro-5-methylimidazo-[4,5,1-$jk$][1,4] benzodiazepin-2(1$H$)-one (TIBO) Derivatives. 3"; J. Med. Chem, 1995, vol. 38, pp. 771-793.

Slyn'ko, N.M. et al.; "A Simple Modification of the Known Preparation Procedure of 2-Phenoxyethyl Bromides Providing High Yields"; Russian Journal of Organic Chemistry, vol. 36, No. 2, 2000, pp. 254-257.

Brinner, K. M. et al.; "Novel and Potent Anti-malarial Agents"; Bioorganic & Medicinal Chemistry 10, 2002, pp. 3649-3661.

Puls, C. et al.; "Preparation and Properties of New Methano-Bridged Dibezo[$c,g$] phenanthrenes"; Chem. Ber., 1993, vol. 126, pp. 1635-1641.

McKillop, A. et al.; "A simple and Inexpensive Procedure for Chloromethylation of Certain Aromatic Compounds"; Tetrahedron Letters, vol. 24, No. 18, pp. 1933-1936, 1983.

Mandoli, A., et al.; "An insoluble polymer-bound phosphoramidite for the copper-catalysed enantioselective 1,4-addition of $ZnEt_2$ to 2-cyclohexenone"; Tetrahedron: Asymmetry, 2003, vol. 14, pp. 3647-3650.

Yeh, C. et al.; "Liquid-phase synthesis of 2-(alkylthio) benzimidazoles"; Tetrahedron Letters, 1999, vol. 40, pp. 7247-7250.

Kuehler, T. C., et al.; "Novel Structures Derived from 2-[[(2-Pyridyl)methyl]thio]-1$H$-benzimidazole as Anti-*Helicobacter pylori* Agents, Part 1"; J. Med. Chem., 2002, vol. 45, pp. 4282-4299.

Matthews, C. J. et al.; "Synthesis and crystal structures of some bis-benzimidazoles, -benzothiazoles and -benzoxazoles by an alternative route: their complexation with copper (II) salts"; J. Chem. Soc., Dalton Trans., 1996, pp. 1531-1538.

Terashima, K. et al.; "Studies on Antiulcer Agents. III. 1) Plausible Mechanism of Antisecretory Action of Ethyl 2-[(1$H$-Benzimidazol-2-yl)sulfinylmethyl]-4-dimethylamino-5-pyrimidinecarboxylate, an H+/K+-ATPase Inhibitor, Based on Its Reaction with Thiols"; Chem. Pharm. Bull, 1995, vol. 43, pp. 1985-1991.

Ram, S., et al.; "Synthesis of 2-Thiobenzimidazole Derivatives as Potential Antifilarial Agents"; Heterocyclic Chem., 1985, vol. 22, pp. 1269-1274.

Naef, R., et al.; "280. Synthesis, Structure and Photochemical Properties of 4,4',7,7'-Tetra-substituted 1,1',3,3'-Tetraethylbenzimidazolotriazatrimethine Cyanines"; Helvetica Chimica Acta, 1978, vol. 61, pp. 2958-2973.

Jung, F. et al; "Synthesis and Structure-Activity Relationship of new Cephalosporins with Amino Heterocycles at c-7. Dependence of the Antibacterial Spectrum and β-Lactamase Stability on the $pK_a$ of the C-7 Heterocycle"; J. Med. Chem, 1991, vol. 34, pp. 1110-1116.

Ikeda, K., et al.; "Preparation of Imidazo[2,1-b]Thiazoles and Thiazolo[3,2-a]-Benzimidazoles Using S-Ethenylsulfilimines"; OPPI Briefs, 2000, vol. 32, No. 4, pp. 401-405.

Kuehler, T.C., et al.; "Structure-Activity Relationship of Omeprazole and Analogues as *Helicobacter pylori* Urease Inhibitors"; J. Med. Chem, 1995, vol. 38, pp. 4906-4916.

Lew, A., et al.; "Blockers of Human T Cell KV1.3 Potassium Channels Using De Novo Ligand Design and Solid-Phase Parallel Combinatorial Chemistry"; Bioorganic & Medicinal Chemistry Letters 9, 1999, pp. 3267-3272.

Hermitage, S.A. et al.; "An Efficient, Practical Approach to the Synthesis of 2,4-Disubstituted Thiazoles and Oxazoles: Application to the Synthesis of GW475151"; Organic Process Research & Development, 2001, vol. 5, pp. 37-44.

Greene, T.W., "Protection for the Amino Group", Protecting Groups in Organic Synthesis, $3^{rd}$ Ed (1999) pp. 23-147, 369-441 and 494-653.

Higuchi, T. et al. Pro Drugs as Novel Drug Delivery Systems, A.S.S. Symposium Series, vol. 14, pp. 196-223 (1975).

Larock, Comprehensive Organic Transformations—A guide to Functional Group Preparations, Index and pp. 381; 1941-1949, © 1999.

* cited by examiner

2-SULFANYL-BENZOIMIDAZOL-1-YI-ACETIC ACID DERIVATIVES AS CRTH2 ANTAGONISTS

The present invention relates to 2-sulfanyl-benzoimidazol-1-yl-acetic acid derivatives and their use as potent "chemoattractant receptor-homologous molecule expressed on Th2 cells" (hereinafter called CRTH2) antagonists in the treatment of prostaglandin mediated diseases, to pharmaceutical compositions containing these derivatives and to processes for their preparation. In particular, such derivatives may be used in pharmaceutical compositions for the treatment of both chronic and acute allergic/immune disorders comprising allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, basophil-related diseases, such as basophilic leukemia and basophilic leukocytosis in humans and other mammals.

Prostaglandin D2 is a known agonist of the thromboxane A2 (TxA2) receptor, the PGD2 (DP) receptor and the recently identified G-protein-coupled "chemoattractant receptor-homologous molecule expressed on Th2 cells" (CRTH2).

The response to allergen exposure in a previously sensitized host results in a cascade effect involving numerous cell types and release of a number of cytokines, chemokines, and multiple mediators. Among these critical initiators are the cytokines interleukin (IL)-4, IL-13, and IL-5, which play critical roles in Th2 cell differentiation, immunoglobulin (Ig)E synthesis, mast cell growth and differentiation, upregulation of CD23 expression, and the differentiation, recruitment, and activation of eosinophils. The stimulated release of the array of mediators, causes end-organ damage, including constriction and hyperresponsiveness, vascular permeability, edema, mucous secretion, and further inflammation.

Because of the number of responses targeted, corticosteroids have proven to be the most effective therapy. Rather than antagonizing these specific responses in a directed way, another approach is to alter the immune response, that is, to change the nature of the immunological response to allergen. CRTH2 is preferentially expressed on Th2 cells and is a chemoattractant receptor for PGD2 that mediates PGD2-dependent migration of blood Th2 cells. Chemoattractants are responsible for the recruitment of both Th2 cells and other effector cells of allergic inflammation and may provide the conceptual basis for the development of new therapeutic strategies, especially in allergic conditions.

So far, few compounds having CRTH2 antagonistic activity have been reported in the patent literature. In GB Patent Specification No. 2388540 Bayer AG claims the use of Ramatroban ((3R)-3-(4-fluorobenzene-sulfonamido)-1,2,3,4-tetrahydrocarbazole-9-propionic acid) for the prophylaxis and treatment of allergic diseases, such as asthma, allergic rhinitis or allergic conjuvatitis. Further, (2-tert.-butoxycarbonyl-1,2,3,4-tetrahydro-pyrido[4,3-b]indol-5-yl)-acetic acid and (2-ethoxycarbonyl-1,2,3,4-tetrahydro-pyrido[4,3-b]indol-5-yl)-acetic acid are disclosed by Kyle F. et al. in two patent specifications i.e. in U.S. Pat. No. 5,817,756 and WO 95/07294, respectively.

Furthermore, a certain oral bioavailability of Ramatroban and its ability to inhibit prostaglandin D2-induced eosinophil migration in vitro has been reported in Journal of Pharmacology and Experimental Therapeutics., 305(1), p. 347-352 (2003).

The present invention relates to the use of 2-sulfanyl-benzoimidazol-1-yl-acetic acids of the general Formula I

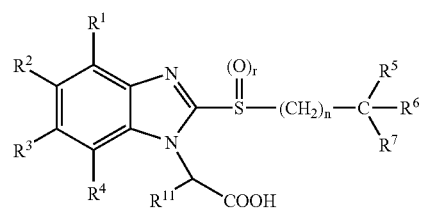

wherein
$R^1$, $R^2$, $R^3$ and $R^4$ each independently represent hydrogen; alkyl; haloalkyl; halogen; nitro; cyano; formyl; methylsulfonyl; or methylcarbonyl;
n is 0 or an integer from 1 to 10;
r is 0 or the integer 1, preferably 0;
$R^5$, $R^6$ and $R^7$ each independently represent hydrogen; alkyl; alkenyl; cycloalkyl; aryl; aryloxy; alkylcarbonyl; cycloalkylcarbonyl; alkoxycarbonyl, arylcarbonyl; arylalkylcarbonyl; N-alkyl-N-aryl-carbamoyl; N-alkyl-N-arylalkyl-carbamoyl; N-arylalkyl-N-aryl-carbamoyl; heterocyclyl (especially furanyl, oxazolyl or pyridinyl, all substituted by alkoxycarbonyl and optionally an additional halogen); heterocyclyloxy (especially 1-ethyloxycarbonyl-indazol-3-yl-oxy); heterocyclylcarbonyl (especially 3,4-dihydro-2H-quinolin-1-yl-carbonyl); or an amino of Formula $NR^8R^9$; or two of $R^5$-$R^7$ together with the carbon atom to which they are attached form cycloalkyl or saturated heterocyclyl;
$R^8$ represents hydrogen or $R^9$;
$R^9$ independently from $R^8$ represents cycloalkyl; cycloalkylalkyl; aryl; cycloalkylarylalkyl; arylalkyl; (diaryl)-alkyl; alkylcarbonyl; alkenylcarbonyl; cycloalkylcarbonyl; cycloalkylalkylcarbonyl; alkoxycarbonyl; alkoxydicarbonyl; arylcarbonyl; arylalkylcarbonyl; arylalkenylcarbonyl; (diaryl)-alkylcarbonyl; cycloalkylarylalkylcarbonyl; heterocyclylcarbonyl, especially furanylcarbonyl or pyridinylcarbonyl; alkylcarbamoyl; arylcarbamoyl; arylalkylcarbamoyl; alkylsulfonyl; arylsulfonyl; arylalkylsulfonyl; or
$R^8$ and $R^9$, together with the nitrogen atom to which they are attached, form a heterocyclyl group;
$R^{11}$ is hydrogen or methyl, preferably hydrogen; and optically pure enantiomers, mixtures of enantiomers, racemates, optically pure diastereoisomers, mixtures of diastereoisomers, diastereoisomeric racemates, mixtures of diastereoisomeric racemates, meso forms, geometric isomers, and prodrugs of compounds in which a prodrug forming group is present, as well as solvates and pharmaceutically acceptable salts of such compounds, and morphological forms; for the manufacture of medicaments for the control of disorders responding to CRTH2 receptor antagonist treatment.

The present invention also relates to the use of a compound of Formula I as defined above, wherein $R^1$, $R^2$, $R^3$ and $R^4$ each independently represent hydrogen, alkyl, haloalkyl, halogen, nitro, cyano or formyl; r is 0; and $R^{11}$ is hydrogen.

The present invention relates to compounds of Formula I as defined above, with the exception of:
(2-octylsulfanyl-benzoimidazol-1-yl)-acetic acid;
(2-butylsulfanyl-benzoimidazol-1-yl)-acetic acid;
(2-propylsulfanyl-benzoimidazol-1-yl)-acetic acid;
15 (2-ethylsulfanyl-benzoimidazol-1-yl)-acetic acid;

(2-methylsulfanyl-benzoimidazol-1-yl)-acetic acid;
(2-isopropylsulfanyl-benzoimidazol-1-yl)-acetic acid;
(2-sec-butylsulfanyl-benzoimidazol-1-yl)-acetic acid;
2-[(2-methylpropyl)thio]-1H-benzimidazole-1-acetic acid;
(2-allylsulfanyl-benzoimidazol-1-yl)-acetic acid;
(2-cyclohexylsulfanyl-benzoimidazol-1-yl)-acetic acid;
(2-benzylsulfanyl-benzoimidazol-1-yl)-acetic acid;
(2-phenethylsulfanyl-benzoimidazol-1-yl)-acetic acid;
[2-(naphthalen-1-ylmethylsulfanyl)-benzoimidazol-1-yl]-acetic acid;
{2-[2-(4-tert-butyl-phenoxy)-ethylsulfanyl]-benzoimidazol-1-yl}-acetic acid;
{2-[2-(4-propoxy-phenoxy)-ethylsulfanyl]-benzoimidazol-1-yl}-acetic acid;
{2-[2-(4-ethoxy-phenoxy)-ethylsulfanyl]-benzoimidazol-1-yl}-acetic acid;
{2-[2-(3,4-dimethyl-phenoxy)-ethylsulfanyl]-benzoimidazol-1-yl}-acetic acid;
{2-[2-(3-methylphenoxy)-ethylsulfanyl]-benzoimidazol-1-yl}-acetic acid;
{2-[2-(naphthalen-2-yloxy)-ethylsulfanyl]-benzoimidazol-1-yl}-acetic acid;
{2-[2-(4-methoxy-phenoxy)-ethylsulfanyl]-benzoimidazol-1-yl}-acetic acid;
{2-[2-(4-butoxy-phenoxy)-ethylsulfanyl]-benzoimidazol-1-yl}-acetic acid;
{2-[2-(4-methylphenoxy)-ethylsulfanyl]-benzoimidazol-1-yl}-acetic acid;
[2-(2-phenoxy-ethylsulfanyl)-benzoimidazol-1-yl]-acetic acid;
{2-[2-(4-ethyl-phenoxy)-ethylsulfanyl]-benzoimidazol-1-yl}-acetic acid;
{2-[2-(2-methylphenoxy)-ethylsulfanyl]-benzoimidazol-1-yl}-acetic acid;
{2-[2-(4-chloro-phenoxy)-ethylsulfanyl]-benzoimidazol-1-yl}-acetic acid;
{2-[2-(2-isopropyl-4-methyl-phenoxy)-ethylsulfanyl]-benzoimidazol-1-yl}-acetic acid;
{2-[2-(naphthalen-1-yloxy)-ethylsulfanyl]-benzoimidazol-1-yl}-acetic acid;
{2-[2-(2,6-dimethyl-phenoxy)-ethylsulfanyl]-benzoimidazol-1-yl}-acetic acid;
{2-[2-(4-isopropoxy-phenoxy)-ethylsulfanyl]-benzoimidazol-1-yl}-acetic acid;
{2-[2-(2-fluoro-phenoxy)-ethylsulfanyl]-benzoimidazol-1-yl}-acetic acid;
{2-[2-(2-methoxy-phenoxy)-ethylsulfanyl]-benzoimidazol-1-yl}-acetic acid; and
{2-[3-methyl-4-(2-morpholin-4-yl-ethylsulfanyl)-pyridin-2-ylmethylsulfanyl]-benzoimidazol-1-yl}-acetic acid (U.S. Pat. No. 5,504,082).

A subgroup of novel compounds falling under Formula I are those wherein
$R^5$ represents hydrogen;
$R^6$ represents hydrogen; alkyl; or alkoxycarbonyl; and
$R^7$ represents alkoxycarbonyl; N-alkyl-N-arylalkyl-carbamoyl; N-alkyl-N-aryl-carbamoyl; alkylcarbonyl; N-arylalkyl-N-aryl-carbamoyl; arylalkylcarbonyl; arylcarbonyl; cycloalkylcarbonyl; heterocyclylcarbonyl; heterocyclyloxy; an amino of Formula $NR^8R^9$; aryl substituted with one or two of alkoxy, alkylcarbonyl, and alkoxycarbonyl and optionally an additional halogen; or heterocyclyl substituted with alkylcarbonyl, cycloalkylcarbonyl, alkoxycarbonyl, arylcarbonyl, arylalkylcarbonyl, (diaryl)alkyl carbonyl or heterocyclylcarbonyl and optionally an additional halogen; or
$R^6$ represents alkyl or alkoxycarbonyl and $R^7$ represents aryl; or
$R^6$ and $R^7$ together with the carbon atom to which they are attached form cycloalkyl or saturated heterocyclyl.

The present invention especially relates to compounds of Formula I, wherein
$R^1$, $R^2$, $R^3$ and $R^4$ each independently represent hydrogen; alkyl; haloalkyl; halogen; nitro; cyano; formyl; methylsulfonyl; or methylcarbonyl;
n is 0 or an integer from 1 to 5;
r is 0 or the integer 1;
$R^5$, $R^6$ and $R^7$ each independently represent hydrogen; alkyl; alkenyl; cycloalkyl, especially cyclohexyl; aryl, wherein aryl is especially phenyl, optionally mono- or di-substituted wherein the substitutents are independently selected from the group consisting of hydroxy-alkyl, alkoxy, alkoxyalkyl, alkoxycarbonyl, halo, alkylcarbonyl, phenyl, 2,3-dihydro-indole-1-carbonyl, alkylcarbamoyl, morpholine-4-carbonyl, benzylcarbamoyl, N,N-dialkylcarbamoyl, N-alkyl-N-benzyl-carbamoyl, hydroxyalkoxy and benzoyl, or wherein aryl is especially 3-oxo-indan-5-yl or 8-oxo-5,6,7,8-tetrahydro-naphthalen-2-yl, both substituted by alkoxy; aryloxy, wherein aryl is especially naphthyl or phenyl, wherein phenyl is optionally substituted by halo; alkoxycarbonyl; arylcarbonyl, wherein aryl is especially phenyl; N-alkyl-N-aryl-carbarnoyl, wherein aryl is especially phenyl; N-alkyl-N-arylalkyl-carbamoyl, wherein aryl is especially phenyl; N-arylalkyl-N-aryl-carbamoyl, wherein aryl is especially phenyl; heterocyclyl, especially furanyl, oxazolyl or pyridinyl, all substituted by alkoxycarbonyl and optionally an additional halogen; heterocyclyloxy, especially 1-alkoxycarbonyl-indazol-3-yl-oxy; heterocyclylcarbonyl, especially 3,4-dihydro-2H-quinolin-1-yl-carbonyl; or an amino of Formula $NR^8R^9$; or two of $R^5$-$R^7$ together with the carbon atom to which they are attached form cycloalkyl, especially cyclopentyl, cyclohexyl or bicyclo[4.2.0]octa-1,3,5-trien-7-yl; or or two of $R^5$-$R^7$ together with the carbon atom to which they are attached form saturated heterocyclyl, especially a 5- or 6-membered nitrogen containing saturated heterocyclyl containing one nitrogen ring atom (preferably piperidin-3-yl or pyrrolidin-3-yl), wherein this nitrogen ring atom contains a substituent $R^{10}$, wherein $R^{10}$ is as defined hereinbelow;
$R^8$ represents hydrogen or $R^9$;
$R^9$ independently from $R^8$ represents cycloalkyl, especially cyclopropyl or cyclohexyl; cycloalkylalkyl, wherein cycloalkyl is especially cyclohexyl; aryl, especially phenyl which is optionally substituted by alkoxycarbonyl or piperidinyl; arylalkyl, wherein aryl is especially phenyl; (diaryl)-alkyl, wherein aryl is especially phenyl; alkylcarbonyl; cycloalkylcarbonyl, wherein cycloalkyl is especially cyclopropyl or cyclohexyl; cycloalkylalkylcarbonyl, wherein cycloalkyl is especially cyclopentyl; alkoxycarbonyl; alkoxydicarbonyl; arylcarbonyl, wherein aryl is especially naphthyl or phenyl, wherein phenyl is optionally substituted by alkoxy, halogen or phenyl; arylalkylcarbonyl, wherein aryl is especially phenyl, and wherein the alkyl moiety may optionally be substituted by cyclohexyl; arylalkenylcarbonyl, wherein aryl is especially phenyl; (diaryl)-alkylcarbonyl, wherein aryl is especially phenyl; heterocyclylcarbonyl, wherein heterocyclyl is especially furanyl or pyridinyl; alkylcarbamoyl; arylcarbamoyl, wherein aryl is especially phenyl; arylalkylcarbamoyl, wherein aryl is especially phenyl; alkylsulfonyl; arylsulfonyl, wherein aryl is especially phenyl; arylalkylsulfonyl, wherein aryl is especially phenyl; or
$R^8$ and $R^9$, together with the nitrogen atom to which they are attached, form a heterocyclyl group, especially 1,3-dioxo-1, 3-dihydro-isoindol-2-yl, 2,3-dihydro-1-ethyloxycarbonyl-3-oxo-indazol-2-yl, 1-oxo-1,3-dihydro-isoindol-2-yl, 2-oxo-2, 3-dihydro-benzoimidazol-1-yl, 1-oxo-1H-phthalazin-2-yl, 2,4-dioxo-1,4-dihydro-2H-quinazolin-3-yl, or 1,1,3-trioxo-1,3-dihydro-1$\lambda^6$-benzo[d]isothiazol-2-yl; and
$R^{11}$ is hydrogen or methyl; with the exception of the following compounds:
(2-octylsulfanyl-benzoimidazol-1-yl)-acetic acid;
(2-butylsulfanyl-benzoimidazol-1-yl)-acetic acid;
(2-propylsulfanyl-benzoimidazol-1-yl)-acetic acid;
(2-ethylsulfanyl-benzoimidazol-1-yl)-acetic acid;
(2-methylsulfanyl-benzoimidazol-1-yl)-acetic acid;
(2-isopropylsulfanyl-benzoimidazol-1-yl)-acetic acid;
(2-sec-butylsulfanyl-benzoimidazol-1-yl)-acetic acid;
(2-isobutylsulfanyl-benzoimidazol-1-yl)-acetic acid;
(2-allylsulfanyl-benzoimidazol-1-yl)-acetic acid;
(2-cyclohexylsulfanyl-benzoimidazol-1-yl)-acetic acid;
(2-benzylsulfanyl-benzoimidazol-1-yl)-acetic acid;
(2-phenethylsulfanyl-benzoimidazol-1-yl)-acetic acid;
[2-(naphthalen-1-ylmethylsulfanyl)-benzoimidazol-1-yl]-acetic acid;
{2-[2-(4-tert-butyl-phenoxy)-ethylsulfanyl]-benzoimidazol-1-yl}-acetic acid;
{2-[2-(4-propoxy-phenoxy)-ethylsulfanyl]-benzoimidazol-1-yl}-acetic acid;
{2-[2-(4-ethoxy-phenoxy)-ethylsulfanyl]-benzoimidazol-1-yl}-acetic acid;
{2-[2-(3,4-dimethyl-phenoxy)-ethylsulfanyl]-benzoimidazol-1-yl}-acetic acid;
{2-[2-(3-methylphenoxy)-ethylsulfanyl]-benzoimidazol-1-yl}-acetic acid;
{2-[2-(naphthalen-2-yloxy)-ethylsulfanyl]-benzoimidazol-1-yl}-acetic acid;
{2-[2-(4-methoxy-phenoxy)-ethylsulfanyl]-benzoimidazol-1-yl}-acetic acid;
{2-[2-(4-butoxy-phenoxy)-ethylsulfanyl]-benzoimidazol-1-yl}-acetic acid;
{2-[2-(4-methylphenoxy)-ethylsulfanyl]-benzoimidazol-1-yl}-acetic acid;
[2-(2-phenoxy-ethylsulfanyl)-benzoimidazol-1-yl]-acetic acid;
{2-[2-(4-ethyl-phenoxy)-ethylsulfanyl]-benzoimidazol-1-yl}-acetic acid;
{2-[2-(2-methylphenoxy)-ethylsulfanyl]-benzoimidazol-1-yl}-acetic acid;
{2-[2-(4-chloro-phenoxy)-ethylsulfanyl]-benzoimidazol-1-yl}-acetic acid;
{2-[2-(2-isopropyl-4-methyl-phenoxy)-ethylsulfanyl]-benzoimidazol-1-yl}-acetic acid;
{2-[2-(naphthalen-1-yloxy)-ethylsulfanyl]-benzoimidazol-1-yl}-acetic acid;
{2-[2-(2,6-Dimethyl-phenoxy)-ethylsulfanyl]-benzoimidazol-1-yl}-acetic acid;
{2-[2-(4-isopropoxy-phenoxy)-ethylsulfanyl]-benzoimidazol-1-yl}-acetic acid;
{2-[2-(2-fluoro-phenoxy)-ethylsulfanyl]-benzoimidazol-1-yl}-acetic acid;
{2-[2-(2-methoxy-phenoxy)-ethylsulfanyl]-benzoimidazol-1-yl}-acetic acid; and
{2-[3-methyl-4-(2-morpholin-4-yl-ethylsulfanyl)-pyridin-2-ylmethylsulfanyl]-benzoimidazol-1-yl}-acetic acid.

In the above compounds of Formula I, aryl groups (preferably phenyl or naphthyl, especially phenyl) present as $R^5$-$R^8$, especially $R^5$-$R^9$, alone or in combination, are preferably unsubstituted or mono- or di-substituted with substituents independently selected from lower alkyl; lower alkoxy; halogen; cyano; lower alkoxycarbonyl; lower alkylcarbonyl; aryl, especially phenyl; aryl-lower alkyl; cycloalkyl; and heterocyclyl, such as especially piperidinyl.

In another embodiment, aryl groups (preferably phenyl, naphthyl, 3-oxo-indan-5-yl, or 8-oxo-5,6,7,8-tetrahydro-naphthalen-2-yl, especially phenyl) present as $R^5$-$R^9$, alone or in combination, are preferably unsubstituted or mono- or di-substituted with substituents independently selected from lower alkyl; hydroxy-lower alkyl; lower alkoxy; lower alkoxy-lower alkyl; halogen; cyano; lower alkoxycarbonyl; lower alkylcarbonyl; aryl, especially phenyl; aryl-lower alkyl; cycloalkyl; 2,3-dihydro-indole-1-carbonyl; lower alkylcarbamoyl; morpholine-4-carbonyl; aryl-lower alkyl-carbamoyl, especially benzylcarbamoyl; N,N-di-lowei alkylcarbamoyl; N-lower alkyl-N-aryl-lower alkyl-carbamoyl, especially N-lower alkyl-N-benzyl-carbamoyl; hydroxy-lower alkoxy; arylcarbonyl, especially benzoyl; and heterocyclyl, such as especially piperidinyl. Preferably the substitutents are independently selected from hydroxy-lower alkyl; lower alkoxy; lower alkoxy-lower alkyl; halogen; lower alkoxycarbonyl; lower alkylcarbonyl; phenyl; 2,3-dihydro-indole-1-carbonyl; lower alkylcarbamoyl; morpholine-4-carbonyl; benzylcarbamoyl; N,N-di-lower alkylcarbamoyl; N-lower alkyl-N-benzyl-carbamoyl; hydroxy-lower alkoxy; benzoyl; and piperidinyl.

Where two of $R^5$-$R^7$ together with the carbon atom, to which they are attached, form saturated heterocyclyl (preferably piperidinyl or pyrrolidinyl), this group may contain one nitrogen atom which is substituted with $R^{10}$, wherein $R^{10}$ represents alkylcarbamoyl; alkylcarbonyl; alkoxycarbonyl; alkylsulfonyl; arylalkylcarbamoyl; arylalkylcarbonyl; arylalkoxycarbonyl; arylalkylsulfonyl; arylcarbamoyl; arylcarbonyl; aryloxycarbonyl; arylsulfonyl; cycloalkylcarbamoyl; cycloalkylcarbonyl; cycloalkyloxycarbonyl; cycloalkylsulfonyl; heterocyclylcarbamoyl; heterocyclylcarbonyl; heterocyclyloxycarbonyl; or heterocyclylsulfonyl.

In another preferred embodiment of the invention $R^5$-$R^7$ together with the carbon atom, to which they are attached, form saturated heterocyclyl (preferably piperidinyl or pyrrolidinyl), this group may contain one nitrogen atom which is substituted with $R^{10}$, wherein $R^{10}$ represents alkylcarbamoyl; alkylcarbonyl; alkoxycarbonyl; alkylsulfonyl; arylalkylcarbamoyl; arylalkylcarbonyl; arylalkoxycarbonyl; arylalkylsulfonyl; arylcarbamoyl; arylcarbonyl; (diaryl)-alkylcarbonyl; aryloxycarbonyl; arylsulfonyl; arylalkenylsulfonyl; cycloalkylcarbamoyl; cycloalkylalkylcarbonyl; cycloalkylcarbonyl; cycloalkyloxycarbonyl; cycloalkylsulfonyl; heterocyclylcarbamoyl; heterocyclylcarbonyl; heterocyclyloxycarbonyl; or heterocyclylsulfonyl. Preferably $R^{10}$ represents alkylcarbonyl; alkylsulfonyl; arylalkylcarbonyl, wherein aryl is especially phenyl; arylalkoxycarbonyl, wherein aryl is especially phenyl; arylalkylsulfonyl, wherein aryl is especially phenyl; arylcarbonyl, wherein aryl is especially phenyl substituted by alkoxy or halo or wherein aryl is naphthyl; (diaryl)-alkylcarbonyl, wherein aryl is especially phenyl; arylsulfonyl, wherein aryl is especially phenyl substituted by alkyl or alkoxy or wherein aryl is naphthyl; arylalkenylsulfonyl, wherein aryl is especially phenyl; cycloalkylalkylcarbonyl, wherein cycloalkyl is especially cyclopentyl; cycloalkylcarbonyl, wherein cycloalkyl is especially cyclohexyl; heterocyclylcarbonyl, wherein heterocyclyl is especially furyl; or heterocyclylsulfonyl, wherein heterocyclyl is especially thienyl.

Preferably, in a compound of Formula I substituents $R^1$, $R^2$, $R^3$ and $R^4$ each independently represent hydrogen; methyl; trifluoromethyl; fluoro, chloro, bromo; nitro; cyano; formyl; methylsulfonyl; or methylcarbonyl.

Also preferably, in a compound of Formula I substituents $R^1$, $R^2$, $R^3$ and $R^4$ each independently represent hydrogen; methyl; trifluoromethyl; fluoro, chloro, bromo; nitro; cyano; or formyl.

In the subgroups (aspects) enumerated below $R^1$-$R^4$ are as above or as in Formula I.

In a preferred aspect, n in Formula I is 1 or 2; $R^5$ and $R^6$ each represent hydrogen; $R^7$ represents an amino of Formula $NR^8R^9$;
$R^8$ represents hydrogen or $R^9$; and
$R^9$ independently from $R^8$ represents cycloalkyl; cycloalkylalkyl; aryl; arylalkyl; (diaryl)-alkyl; alkylcarbonyl; cycloalkylcarbonyl; cycloalkylalkylcarbonyl; alkoxycarbonyl; alkoxydicarbonyl; arylcarbonyl; arylalkylcarbonyl; arylalkenylcarbonyl; (diaryl)-alkylcarbonyl; heterocyclylcarbonyl; alkylcarbamoyl; arylcarbamoyl; arylalkylcarbamoyl; alkylsulfonyl; arylsulfonyl; arylalkylsulfonyl, wherein aryl groups present as $R^8$ and/or $R^9$, alone or in combination with other groups, preferably represent phenyl or naphthyl, especially phenyl, wherein the phenyl is optionally substituted by alkoxy, alkoxycarbonyl, halogen, phenyl or piperidinyl; or $R^8$ and $R^9$, together with the nitrogen atom to which they are attached, form a heterocyclyl group, wherein said heterocyclyl group preferably represents 1,3-dioxo-1,3-dihydro-isoindol-2-yl, 2,3-dihydro-1-ethyloxycarbonyl-3-oxo-indazol-2-yl, 1-oxo-1,3-dihydro-isoindol-2-yl, 2-oxo-2,3-dihydro-benzoimidazol-1-yl, 1-oxo-1H-phthalazin-2-yl, 2,4-dioxo-1,4-dihydro-2H-quinazolin-3-yl, or 1,1,3-trioxo-1,3-dihydro-1$\lambda^6$-benzo[d]isothiazol-2-yl.

In another preferred embodiment, n in Formula I is 2 or 3, especially 1 or 2; $R^5$ and $R^6$ each represent hydrogen; $R^7$ represents an amino of Formula $NR^8R^9$;
$R^8$ represents hydrogen; and
$R^9$ represents cycloalkyl; aryl; arylalkyl; (diaryl)-alkyl; alkylcarbonyl; cycloalkyl-alkylcarbonyl; cycloalkylcarbonyl; alkenylcarbonyl; alkoxycarbonyl; alkoxydicarbonyl; arylcarbonyl; arylalkylcarbonyl; (diaryl)-alkylcarbonyl; heterocyclylcarbonyl; alkylcarbamoyl; arylcarbamoyl; arylalkylcarbamoyl; alkylsulfonyl; arylsulfonyl; arylalkylsulfonyl; or
$R^8$ represents cycloalkyl; arylalkyl; aryl; alkoxycarbonyl; and
$R^9$ represents cycloalkyl; cyclylalkyl-alkyl; aryl; arylalkyl; (diaryl)-alkyl; cycloalkyl-alkylcarbonyl; alkylcarbonyl; arylalkylcarbonyl; (diaryl)-alkylcarbonyl; alkylcarbamoyl; arylcarbamoyl; arylalkylcarbamoyl; alkylsulfonyl; arylsulfonyl; arylalkylsulfonyl; or
$R^8$ and $R^9$, together with the nitrogen atom to which they are attached, form a phthalazinyl; isoindolyl; benzoimidazolyl; indazolyl; quinazolinyl; or benzoisothiazolyl ring system, such as especially 1,3-dioxo-1,3-dihydro-isoindol-2-yl, 2,3-dihydro-1-ethyloxycarbonyl-3-oxo-indazol-2-yl, 1-oxo-1,3-dihydro-isoindol-2-yl, 2-oxo-2,3-dihydro-benzoimidazol-1-yl, 1-oxo-1H-phthalazin-2-yl, 2,4-dioxo-1,4-dihydro-2H-quinazolin-3-yl, or 1,1,3-trioxo-1,3-dihydro-1$\lambda^6$-benzo[d]isothiazol-2-yl.

In a preferred aspect of the invention, $R^8$ represents hydrogen; and
$R^9$ represents particularly 3-phenyl-acryloyl; butoxycarbonyl, tert-butoxycarbonyl; ethoxydicarbonyl; propylcarbamoyl; 2,2-dimethyl-propionyl; 3,3-dimethyl-butyryl, 3-octanoyl, pentanoyl; butane-1-sulfonyl; 4-piperidin-1-yl-phenyl, phenyl, 2,2-diphenyl-ethyl, 3-benzyl; 2-cyclohexyl-2-phenyl-acetyl, 3,3-diphenyl-propionyl, 3-phenyl-propionyl, diphenylacetyl, phenylacetyl; phenylmethanesulfonyl; phenylcarbamoyl; 4-bromo-benzoyl, 4-methoxy-benzoyl, biphenyl-4-carbonyl, naphthalene-1-carbonyl, benzenesulfonyl; cyclohexanecarbonyl, cyclopropanecarbonyl, 3-cyclopentyl-propionyl; furan-2-carbonyl, or pyridine-3-carbonyl; or
$R^8$ represents particularly butoxycarbonyl, tert-butoxycarbonyl; 4-carboethoxyphenyl, 4-piperidin-1-yl-phenyl, phenyl; benzyl, 2,2-diphenyl-ethyl, phenethyl; cyclopropyl; and
$R^9$ represents particularly propylcarbamoyl; pentanoyl; butane-1-sulfonyl; 4-piperidin-1-yl-phenyl, phenyl, benzyl, phenethyl, 2,2-diphenyl-ethyl; benzylcarbamoyl; 2-cyclohexyl-2-phenyl-acetyl, 2-phenylacetyl, 3,3-diphenyl-propionyl, diphenylacetyl, phenylmethanesulfonyl; phenylcarbamoyl; benzenesulfonyl; cyclohexyl, cyclopropyl; or cyclohexylmethyl; or
$R^8$ and $R^9$, together with the nitrogen atom to which they are attached, represent particularly 1-oxo-1H-phthalazin-2-yl; 1-oxo-1,3-dihydro-isoindol-2-yl; 2-oxo-2,3-dihydro-benzoimidazol-1-yl; 1-ethoxycarbonyl-3-oxo-2,3-dihydro-indazole-2-yl; 2,4-dioxo-1,4-dihydro-2H-quinazolin-3-yl; or 1,3-dioxo-1,3-dihydro-isoindol-2-yl; 1,1,3-trioxo-1,3-dihydro-1%$^6$-benzo[d]isothiazol-2-yl.

In another preferred aspect, n in Formula I is 0;
$R^5$ and $R^6$ each represent hydrogen;
$R^7$ represents phenyl; furanyl, oxazolyl, pyridinyl or thiazolyl, all substituted with one or two of alkoxy, alkylcarbonyl, and alkoxycarbonyl and optionally an additional halogen.

In this aspect, $R^7$ represents particularly halogen or alkoxy substituted (alkoxycarbonyl)phenyl; (alkylcarbonyl)phenyl; (alkoxycarbonyl)furanyl, or (alkoxycarbonyl)pyridinyl;
more particularly halogen or alkoxy substituted 3-(alkoxycarbonyl)phenyl; 3-(alkylcarbonyl)phenyl; 5-(alkoxycarbonyl)furan-2-yl, 5-(alkoxycarbonyl)pyridin-3-yl; or 4-(alkoxycarbonyl)pyridin-2-yl; most particularly, $R^7$ represents 3-(methoxycarbonyl)phenyl; 2-bromo-3-(methoxycarbonyl)phenyl, 4-bromo-3-(methoxycarbonyl)phenyl, 5-bromo-3-(methoxycarbonyl)phenyl, 2-bromo-5-(methoxycarbonyl)phenyl, 2-methoxy-5-(methoxycarbonyl)phenyl; 3-acetyl-phenyl, 5-acetyl-2-methoxy-phenyl; 5-(methoxycarbonyl)pyridine-3-yl, 6-chloro-4-(methoxycarbonyl)pyridine-2-yl; or 5-(ethoxycarbonyl)furan-2-yl; most preferred 5-acetyl-2-methoxy-phenyl.

A preferred embodiment of the invention n in Formula I is 0; $R^5$ and $R^6$ each represent hydrogen; and $R^7$ represents phenyl, optionally mono- or di-substituted wherein the substitutents are independently selected from the group consisting of hydroxy-alkyl, alkoxy, alkoxyalkyl, alkoxycarbonyl, halo, alkylcarbonyl, phenyl, 2,3-dihydro-indole-1-carbonyl, alkylcarbamoyl, morpholine-4-carbonyl, benzylcarbamoyl, N,N-dialkylcarbamoyl, N-alkyl-N-benzyl-carbamoyl, hydroxyalkoxy and benzoyl; or $R^7$ represents 3-oxo-indan-5-yl or 8-oxo-5,6,7,8-tetrahydro-naphthalen-2-yl, both substituted by alkoxy.

In a more preferred aspect, n in Formula I is 1;
$R^5$ represents hydrogen;
$R^6$ and $R^7$ together with the carbon atom to which they are attached form a 5- or 6-membered nitrogen containing saturated heterocyclyl containing one nitrogen ring atom, wherein this nitrogen ring atom contains a substituent $R^{10}$, wherein $R^{10}$ is as defined hereinabove;
most preferred in this aspect, $R^6$ and $R^7$ form a piperidinyl, particularly a piperidin-3-yl ring; and
$R^{10}$ represents particularly acetyl, butyryl, heptanoyl; 1-phenylacetyl, 3-phenyl-propionyl, diphenylacetyl; naphthalene-1-carbonyl, 2-methoxy-benzoyl, 3-chloro-benzoyl, 4-bromo-benzoyl; 1-cyclohexanecarbonyl, 3-cyclopentyl-propionyl; or furan-2-carbonyl, most preferred butyryl.

Most preferred novel compounds of the present invention include:
{2-[3-(butoxycarbonyl-phenethyl-amino)-propylsulfanyl]-5-nitro-benzoimidazol-1-yl}-acetic acid;
rac[2-(3-{(2-cyclohexyl-2-phenyl-acetyl)-[(4-ethyloxycarbonyl)-phenyl]-amino}-propylsulfanyl)-benzoimidazol-1-yl]-acetic acid; and
[2-(5-acetyl-2-methoxy-benzylsulfanyl)-benzoimidazol-1-yl]-acetic acid.

The present invention also especially relates to a compound selected from:
[2-(5-acetyl-2-methoxy-benzylsulfanyl)-benzoimidazol-1-yl]-acetic acid;
rac[2-(1-butyryl-piperidin-3-ylmethylsulfanyl)-benzoimidazol-1-yl]-acetic acid;
{2-[3-(butoxycarbonyl-phenethyl-amino)-propylsulfanyl]-benzoimidazol-1-yl}-acetic acid;
{2-[3-(pentanoyl-phenethyl-amino)-propylsulfanyl]-benzoimidazol-1-yl}-acetic acid;
and pharmaceutically acceptable salts, especially the sodium salt, of these compounds.

Particularly preferred novel compounds of the present invention include:
{2-[3-(butoxycarbonyl-phenethyl-amino)-propylsulfanyl]-benzoimidazol-1-yl}-acetic acid and its sodium salt;
{2-[3-(pentanoyl-phenethyl-amino)-propylsulfanyl]-benzoimidazol-1-yl}-acetic acid;
(2-{3-[(2,2-diphenyl-ethyl)-pentanoyl-amino]-propylsulfanyl}-benzoimidazol-1-yl)-acetic acid;
[2-(3-methoxycarbonyl-benzylsulfanyl)-5-nitro-benzoimidazol-1-yl]-acetic acid;
rac{2-[1-(4-bromo-benzoyl)-piperidin-3-ylmethylsulfanyl]-benzoimidazol-1-yl}-acetic acid;
rac[2-(1-butyryl-piperidin-3-ylmethylsulfanyl)-benzoimidazol-1-yl]-acetic acid;
{2-[(6-methoxy-3-methoxycarbonyl)-benzylsulfanyl]-benzoimidazol-1-yl}-acetic acid;
[5-fluoro-2-(3-methoxycarbonyl-benzylsulfanyl)-benzoimidazol-1-yl]-acetic acid and its 6-fluoro regioisomer;
{2-[(6-bromo-3-methoxycarbonyl)-benzylsulfanyl]-benzoimidazol-1-yl}-acetic acid;
[2-(3-{butyloxycarbonyl-[(4-ethyloxycarbonyl)-phenyl]-amino}-propylsulfanyl)-benzoimidazol-1-yl]-acetic acid;
[5-cyano-2-(3-methoxycarbonyl-benzylsulfanyl)-benzoimidazol-1-yl]-acetic acid and its 6-cyano regioisomer;
[2-(4-ethyloxycarbonyl-butylsulfanyl)-5-nitro-benzoimidazol-1-yl]-acetic acid;
[2-(3-{diphenylacetyl-[(4-ethyloxycarbonyl)-phenyl]-amino}-propylsulfanyl)-benzoimidazol-1-yl]-acetic acid;
[2-(3-{[(4-ethyloxycarbonyl)-phenyl]-pentanoyl-amino}-propylsulfanyl)-benzoimidazol-1-yl]-acetic acid;
rac{2-[1-(furan-2-carbonyl)-piperidin-3-ylmethylsulfanyl]-benzoimidazol-1-yl}-acetic acid;
{2-[3-(benzyl-butoxycarbonyl-amino)-propylsulfanyl]-benzoimidazol-1-yl}-acetic acid;
rac{2-[1-(3-phenyl-propionyl)-piperidin-3-ylmethylsulfanyl]-benzoimidazol-1-yl}-acetic acid;
(2-{3-[(4-ethyloxycarbonylphenyl)-(phenylacetyl)-amino]-propylsulfanyl}-benzoimidazol-1-yl)-acetic acid;
{2-[3-(benzyl-pentanoyl-amino)-propylsulfanyl]-benzoimidazol-1-yl}-acetic acid;
{2-[3-(cyclopropyl-diphenylacetyl-amino)-propylsulfanyl]-benzoimidazol-1-yl}-acetic acid; and
[2-(3-{diphenylpropionyl-[(4-ethyloxycarbonyl)-phenyl]-amino}-propylsulfanyl)-benzoimidazol-1-yl]-acetic acid.

Preferred novel compounds of the present invention include:
rac[2-(1-methyl-2-oxo-2-phenyl-ethylsulfanyl)-benzoimidazol-1-yl]-acetic acid;
[2-(3-methoxycarbonyl-benzylsulfanyl)-5-trifluoromethyl-benzoimidazol-1-yl]-acetic acid and its 6-trifluoromethyl regioisomer;
[2-(3,3-diphenyl-propylsulfanyl)-6-nitro-benzoimidazol-1-yl]-acetic acid;
(2-benzylsulfanyl-5-nitro-benzoimidazol-1-yl)-acetic acid and its 6-nitro isomer;
{2-[3-(1-phenethyl-3-propyl-ureido)-propylsulfanyl]-benzoimidazol-1-yl}-acetic acid;
rac{2-[1-(3-chloro-benzoyl)-piperidin-3-ylmethylsulfanyl]-benzoimidazol-1-yl}-acetic acid;
{2-[3-(1,3-dioxo-1,3-dihydro-isoindol-2-yl)-propylsulfanyl]-5-nitro-benzoimidazol-1-yl}-acetic acid;
{2-[3-(1,1,3-trioxo-1,3-dihydro-1$\lambda^{6}$-benzo[d]isothiazol-2-yl)-propylsulfanyl]-benzoimidazol-1-yl}-acetic acid;
(2-{3-[(2,2-diphenyl-ethyl)-(3,3-diphenyl-propionyl)-amino]-propylsulfanyl}-benzoimidazol-1-yl)-acetic acid;
(2-{3-[cyclopropyl-(3,3-diphenyl-propionyl)-amino]-propylsulfanyl}-benzoimidazol-1-yl)-acetic acid;
rac (2-{3-[(2-cyclohexyl-2-phenyl-acetyl)-cyclopropyl-amino]-propylsulfanyl}-benzoimidazol-1-yl)-acetic acid;
(2-{3-[diphenylacetyl-(2,2-diphenyl-ethyl)-amino]-propylsulfanyl}-benzoimidazol-1-yl)-acetic acid;
rac[2-(1-heptanoyl-piperidin-3-ylmethylsulfanyl)-benzoimidazol-1-yl]-acetic acid;
{2-[3-(3,3-diphenyl-propionylamino)-propylsulfanyl]-benzoimidazol-1-yl}-acetic acid;
(2-{3-[(butane-1-sulfonyl)-phenethyl-amino]-propylsulfanyl}-benzoimidazol-1-yl)-acetic acid;
{2-[3-(benzyl-(phenylmethanesulfonyl)-amino)-propylsulfanyl]-benzoimidazol-1-yl}-acetic acid;
(2-{3-[(2,2-diphenyl-ethyl)-(phenylacetyl)-amino]-propylsulfanyl}-benzoimidazol-1-yl)-acetic acid;
{2-[3-(benzenesulfonyl-cyclopropyl-amino)-propylsulfanyl]-benzoimidazol-1-yl}-acetic acid;
{2-[3-(phenethyl-(phenylmethanesulfonyl)-amino)-propylsulfanyl]-benzoimidazol-1-yl}-acetic acid;
[2-(3,3-diphenyl-propylsulfanyl)-benzoimidazol-1-yl]-acetic acid;
{2-[3-(phenethyl-(phenylacetyl)amino)-propylsulfanyl]-benzoimidazol-1-yl}-acetic acid;
{2-[3-(diphenylacetyl-phenethyl-amino)-propylsulfanyl]-benzoimidazol-1-yl}-acetic acid;
(2-{[(2-chloro-4-methyloxycarbonyl)-pyridin-6-yl]-methylsulfanyl}-benzoimidazol-1-yl)-acetic acid;
rac[2-(bicyclo[4.2.0]octa-1,3,5-trien-7-ylsulfanyl)-benzoimidazol-1-yl]-acetic acid;
[2-(3-acetyl-benzylsulfanyl)-benzoimidazol-1-yl]-acetic acid;
[5-fluoro-2-(2-phenoxy-ethylsulfanyl)-benzoimidazol-1-yl]-acetic acid and its 6-fluoro regioisomer;
[2-(3-phenylmethanesulfonylamino-propylsulfanyl)-benzoimidazol-1-yl]-acetic acid;
[2-(4-ethyloxycarbonyl-butylsulfanyl)-6-nitro-benzoimidazol-1-yl]-acetic acid;
{2-[3-(1,3-dioxo-1,3-dihydro-isoindol-2-yl)-propylsulfanyl]-benzoimidazol-1-yl}-acetic acid;
{2-[3-(1,3-dioxo-1,3-dihydro-isoindol-2-yl)-propylsulfanyl]-6-nitro-benzoimidazol-1-yl}-acetic acid;
(2-{3-[phenylmethanesulfonyl-(4-piperidin-1-yl-phenyl)-amino]-propylsulfanyl}-benzoimidazol-1-yl)-acetic acid;
[2-(4-ethyloxycarbonyl-butylsulfanyl)-5-fluoro-benzoimidazol-1-yl]-acetic acid and its 6-fluoro regioisomer;

[2-(3-diphenylacetylamino-propylsulfanyl)-5-nitro-benzoimidazol-1-yl]-acetic acid;
{2-[3-(cyclopropyl-(phenylmethanesulfonyl)-amino)-propylsulfanyl]-benzoimidazol-1-yl}-acetic acid;
{2-[(5-bromo-3-methoxycarbonyl)-benzylsulfanyl]-benzoimidazol-1-yl}-acetic acid;
{5-nitro-2-[2-(4-chloro-phenoxy)-ethylsulfanyl]-benzoimidazol-1-yl}-acetic acid;
[2-(3,3-diphenyl-propylsulfanyl)-5-nitro-benzoimidazol-1-yl]-acetic acid;
{2-[3-(2,4-dioxo-1,4-dihydro-2H-quinazolin-3-yl)-propylsulfanyl]-benzoimidazol-1-yl}-acetic acid;
{2-[3-(benzyl-(phenylacetyl)-amino)-propylsulfanyl]-benzoimidazol-1-yl}-acetic acid;
(2-{3-[(2,2-diphenyl-ethyl)-(phenylmethanesulfonyl)-amino]-propylsulfanyl}-benzoimidazol-1-yl)-acetic acid;
rac[2-(1-acetyl-piperidin-3-ylmethylsulfanyl)-benzoimidazol-1-yl]-acetic acid;
(2-{3-[benzyl-(3,3-diphenyl-propionyl)-amino]-propylsulfanyl}-benzoimidazol-1-yl)-acetic acid;
{2-[3-(cyclopropyl-(phenylacetyl)-amino)-propylsulfanyl]-benzoimidazol-1-yl}-acetic acid;
rac[2-(1-methyloxycarbonyl-1-phenyl-methylsulfanyl)-benzoimidazol-1-yl]-acetic acid;
{2-[3-(butoxycarbonyl-cyclohexyl-amino)-propylsulfanyl]-benzoimidazol-1-yl}-acetic acid;
[2-(3-diphenylacetylamino-propylsulfanyl)-benzoimidazol-1-yl]-acetic acid;
{2-[3-(1,3-diphenyl-ureido)-propylsulfanyl]-benzoimidazol-1-yl}-acetic acid;
(2-benzylsulfanyl-6-nitro-benzoimidazol-1-yl)-acetic acid;
rac[2-(1-diphenylacetyl-piperidin-3-ylmethylsulfanyl)-benzoimidazol-1-yl]-acetic acid;
{2-[3-(cyclopropyl-pentanoyl-amino)-propylsulfanyl]-benzoimidazol-1-yl}-acetic acid;
(2-{3-[benzenesulfonyl-(4-piperidin-1-yl-phenyl)-amino]-propylsulfanyl}-benzoimidazol-1-yl)-acetic acid;
{2-[3-(benzyl-diphenylacetyl-amino)-propylsulfanyl]-benzoimidazol-1-yl}-acetic acid;
{2-[3-(tert-butoxycarbonyl-phenyl-amino)-propylsulfanyl]-benzoimidazol-1-yl}-acetic acid;
[2-(3-phenyl-propylsulfanyl)-benzoimidazol-1-yl]-acetic acid;
[2-(3-methoxycarbonyl-benzylsulfanyl)-benzoimidazol-1-yl]-acetic acid;
[2-(3-benzenesulfonylamino-propylsulfanyl)-benzoimidazol-1-yl]-acetic acid;
{2-[3-(1-benzyl-3-propyl-ureido)-propylsulfanyl]-benzoimidazol-1-yl}-acetic acid;
(2-{3-[1-(2,2-diphenyl-ethyl)-3-propyl-ureido]-propylsulfanyl}-benzoimidazol-1-yl)-acetic acid;
[2-(4-ethyloxycarbonyl-butylsulfanyl)-5-trifluoromethyl-benzoimidazol-1-yl]-acetic acid and its 6-trifluoromethyl regioisomer;
[5-cyano-2-(4-ethyloxycarbonyl-butylsulfanyl)-benzoimidazol-1-yl]-acetic acid and its 6-cyano regioisomer;
[2-(5-ethyloxycarbonyl-pentylsulfanyl)-benzoimidazol-1-yl]-acetic acid;
(2-{3-[(3,3-diphenyl-propionyl)-phenyl-amino]-propylsulfanyl}-benzoimidazol-1-yl)-acetic acid;
{2-[3-(butoxycarbonyl-(cyclohexylmethyl)-amino)-propylsulfanyl]-benzoimidazol-1-yl}-acetic acid;
(2-{3-[tert-butoxycarbonyl-(4-piperidin-1-yl-phenyl)-amino]-propylsulfanyl}-benzoimidazol-1-yl)-acetic acid;
(2-{3-[phenylacetyl-(4-piperidin-1-yl-phenyl)-amino]-propylsulfanyl}-benzoimidazol-1-yl)-acetic acid;
{2-[3-(2,3-dihydro-1-ethyloxycarbonyl-3-oxo-indazol-2-yl)-propylsulfanyl]-benzoimidazol-1-yl}-acetic acid;
rac{2-[1-(3-cyclopentyl-propionyl)-piperidin-3-ylmethylsulfanyl]-benzoimidazol-1-yl}-acetic acid;
(2-{3-[tert-butoxycarbonyl-(2,2-diphenyl-ethyl)-amino]-propylsulfanyl}-benzoimidazol-1-yl)-acetic acid;
{2-[3-(benzenesulfonyl-phenethyl-amino)-propylsulfanyl]-benzoimidazol-1-yl}-acetic acid; and
{2-[5-(3,4-dihydro-2H-quinolin-1-yl)-5-oxo-pentylsulfanyl]-benzoimidazol-1-yl}-acetic acid.

Further preferred novel compounds of the present invention include:
{2-[3-(phenyl-phenylacetyl-amino)-propylsulfanyl]-benzoimidazol-1-yl}-acetic acid;
(2-{3-[(3,3-diphenyl-propionyl)-phenethyl-amino]-propylsulfanyl}-benzoimidazol-1-yl)-acetic acid;
rac[2-(1-cyclohexanecarbonyl-piperidin-3-ylmethylsulfanyl)-benzoimidazol-1-yl]-acetic acid;
{2-[3-(3-benzyl-1-phenyl-ureido)-propylsulfanyl]-benzoimidazol-1-yl}-acetic acid;
{2-[3-(butane-1-sulfonylamino)-propylsulfanyl]-benzoimidazol-1-yl}-acetic acid;
{2-[3-(2-oxo-2,3-dihydro-benzoimidazol-1-yl)-propylsulfanyl]-benzoimidazol-1-yl}-acetic acid;
{2-[3-(benzyl-tert-butoxycarbonyl-amino)-propylsulfanyl]-benzoimidazol-1-yl}-acetic acid;
{2-[3-(diphenylacetyl-phenyl-amino)-propylsulfanyl]-benzoimidazol-1-yl}-acetic acid;
rac[2-(1-phenylacetyl-piperidin-3-ylmethylsulfanyl)-benzoimidazol-1-yl]-acetic acid;
[2-(2-cyclohexyl-ethylsulfanyl)-benzoimidazol-1-yl]-acetic acid;
[2-(3-phenoxy-propylsulfanyl)-benzoimidazol-1-yl]-acetic acid;
{2-[3-(1-oxo-1,3-dihydro-isoindol-2-yl)-propylsulfanyl]-benzoimidazol-1-yl}-acetic acid;
[2-(2-methoxy-benzylsulfanyl)-benzoimidazol-1-yl]-acetic acid;
(2-{3-[(butane-1-sulfonyl)-cyclopropyl-amino]-propylsulfanyl}-benzoimidazol-1-yl)-acetic acid;
[5-cyano-2-(2-phenoxy-ethylsulfanyl)-benzoimidazol-1-yl]-acetic acid and its 6-cyano regioisomer;
{2-[3-(benzenesulfonyl-benzyl-amino)-propylsulfanyl]-benzoimidazol-1-yl}-acetic acid;
{2-[3-(benzenesulfonyl-phenyl-amino)-propylsulfanyl]-benzoimidazol-1-yl}-acetic acid;
(2-hexylsulfanyl-benzoimidazol-1-yl)-acetic acid;
{2-[2-(4-chloro-phenoxy)-ethylsulfanyl]-5-methyl-benzoimidazol-1-yl}-acetic acid and its 6-methyl regioisomer;
rac (2-{3-[benzyl-(2-cyclohexyl-2-phenyl-acetyl)-amino]-propylsulfanyl}-benzoimidazol-1-yl)-acetic acid;
{2-[(4-bromo-3-methoxycarbonyl)-benzylsulfanyl]-benzoimidazol-1-yl}-acetic acid;
{2-[3-(pentanoyl-phenyl-amino)-propylsulfanyl]-benzoimidazol-1-yl}-acetic acid;
rac{2-[1-(2-methoxy-benzoyl)-piperidin-3-ylmethylsulfanyl]-benzoimidazol-1-yl}-acetic acid;
rac[2-(1-phenyl-ethylsulfanyl)-benzoimidazol-1-yl]-acetic acid;
[2-(4-ethyloxycarbonyl-butylsulfanyl)-benzoimidazol-1-yl]-acetic acid;
{2-[3-(3-phenyl-propionylamino)-propylsulfanyl]-benzoimidazol-1-yl}-acetic acid;
{2-[4-(benzyl-phenyl-carbamoyl)-butylsulfanyl]-benzoimidazol-1-yl}-acetic acid;
{2-[(2-bromo-3-methoxycarbonyl)-benzylsulfanyl]-benzoimidazol-1-yl}-acetic acid;

{2-[2-(3-phenyl-ureido)-ethylsulfanyl]-benzoimidazol-1-yl}-acetic acid;
{2-[3-(3-phenyl-ureido)-propylsulfanyl]-benzoimidazol-1-yl}-acetic acid;
{2-[4-(butyl-phenyl-carbamoyl)-butylsulfanyl]-benzoimidazol-1-yl}-acetic acid;
{2-[3-(4-bromo-benzoylamino)-propylsulfanyl]-benzoimidazol-1-yl}-acetic acid;
{2-[3-(1-oxo-1H-phthalazin-2-yl)-propylsulfanyl]-benzoimidazol-1-yl}-acetic acid;
{2-[3-(tert-butoxycarbonyl-phenethyl-amino)-propylsulfanyl]-benzoimidazol-1-yl}-acetic acid;
(2-{3-[pentanoyl-(4-piperidin-1-yl-phenyl)-amino]-propylsulfanyl}-benzoimidazol-1-yl)-acetic acid;
(2-{3-[(3,3-diphenyl-propionyl)-(4-piperidin-1-yl-phenyl)-amino]-propylsulfanyl}-benzoimidazol-1-yl)-acetic acid;
rac{2-[1-(naphthalene-1-carbonyl)-piperidin-3-ylmethylsulfanyl]-benzoimidazol-1-yl}-acetic acid;
[5-nitro-2-(2-phenoxy-ethylsulfanyl)-benzoimidazol-1-yl]-acetic acid;
[2-(3-benzoylamino-propylsulfanyl)-benzoimidazol-1-yl]-acetic acid;
{2-[3-(2,2-diphenyl-ethylamino)-propylsulfanyl]-benzoimidazol-1-yl}-acetic acid;
[2-(3-phenylacetylamino-propylsulfanyl)-benzoimidazol-1-yl]-acetic acid;
[2-(4-phenoxy-butylsulfanyl)-benzoimidazol-1-yl]-acetic acid;
{2-[3-(cyclohexanecarbonyl-amino)-propylsulfanyl]-benzoimidazol-1-yl}-acetic acid;
[2-(3-phenylamino-propylsulfanyl)-benzoimidazol-1-yl]-acetic acid;
(2-{3-[(naphthalene-1-carbonyl)-amino]-propylsulfanyl}-benzoimidazol-1-yl)-acetic acid;
[2-(2-diphenylacetylamino-ethylsulfanyl)-benzoimidazol-1-yl]-acetic acid;
rac (2-{3-[(2-cyclohexyl-2-phenyl-acetyl)-phenyl-amino]-propylsulfanyl}-benzoimidazol-1-yl)-acetic acid;
{2-[3-(1,2-dioxo-2-ethyloxy-ethylamino)-propylsulfanyl]-benzoimidazol-1-yl}-acetic acid;
{2-[2-(4-chloro-phenoxy)-ethylsulfanyl]-4-methyl-benzoimidazol-1-yl}-acetic acid and its 8-methyl regioisomer;
{2-[3-(tert-butoxycarbonyl-cyclopropyl-amino)-propylsulfanyl]-benzoimidazol-1-yl}-acetic acid;
{2-[(2-methyloxycarbonyl-furan-5-yl)-methylsulfanyl]-benzoimidazol-1-yl}-acetic acid;
(2-{3-[diphenylacetyl-(4-piperidin-1-yl-phenyl)-amino]-propylsulfanyl}-benzoimidazol-1-yl)-acetic acid;
{2-[4-(methyl-phenyl-carbamoyl)-butylsulfanyl]-benzoimidazol-1-yl}-acetic acid;
{2-[4-(benzyl-methyl-carbamoyl)-butylsulfanyl]-benzoimidazol-1-yl}-acetic acid;
{2-[3-(4-methoxy-benzoylamino)-propylsulfanyl]-benzoimidazol-1-yl}-acetic acid;
{2-[3-(cyclopropanecarbonyl-amino)-propylsulfanyl]-benzoimidazol-1-yl}-acetic acid;
{5-chloro-2-[2-(4-chloro-phenoxy)-ethylsulfanyl]-benzoimidazol-1-yl}-acetic acid and its 6-chloro regioisomer;
(2-{3-[(biphenyl-4-carbonyl)-amino]-propylsulfanyl}-benzoimidazol-1-yl)-acetic acid;
{2-[3-(3-cyclopentyl-propionylamino)-propylsulfanyl]-benzoimidazol-1-yl}-acetic acid;
[2-(3-octanoylamino-propylsulfanyl)-benzoimidazol-1-yl]-acetic acid;
{2-[2-(1,3-dioxo-1,3-dihydro-isoindol-2-yl)-ethylsulfanyl]-benzoimidazol-1-yl}-acetic acid;
{2-[3-(3-phenyl-acryloylamino)-propylsulfanyl]-benzoimidazol-1-yl}-acetic acid;
{2-[(5-methyloxycarbonyl-pyridin-3-yl)-methylsulfanyl]-benzoimidazol-1-yl}-acetic acid;
[6-iodo-2-(2-phenoxy-ethylsulfanyl)-benzoimidazol-1-yl]-acetic acid;
rac. {2-[3-(2-cyclohexyl-2-phenyl-acetylamino)-propylsulfanyl]-benzoimidazol-1-yl}-acetic acid;
{2-[3-(4-piperidin-1-yl-phenylamino)-propylsulfanyl]-benzoimidazol-1-yl}-acetic acid;
{2-[3-(3-propyl-ureido)-propylsulfanyl]-benzoimidazol-1-yl}-acetic acid;
[2-(3-tert-butoxycarbonylamino-propylsulfanyl)-benzoimidazol-1-yl]-acetic acid;
[2-(2-butoxycarbonylamino-ethylsulfanyl)-benzoimidazol-1-yl]-acetic acid;
(2-{3-[(pyridine-3-carbonyl)-amino]-propylsulfanyl}-benzoimidazol-1-yl)-acetic acid;
{2-[3-(3,3-dimethyl-butyrylamino)-propylsulfanyl]-benzoimidazol-1-yl}-acetic acid;
(2-{3-[1-(4-piperidin-1-yl-phenyl)-3-propyl-ureido]-propylsulfanyl}-benzoimidazol-1-yl)-acetic acid;
(2-cyclopentylsulfanyl-benzoimidazol-1-yl)-acetic acid;
(2-but-3-enylsulfanyl-benzoimidazol-1-yl)-acetic acid;
(2-{3-[(furan-2-carbonyl)-amino]-propylsulfanyl}-benzoimidazol-1-yl)-acetic acid;
{2-[3-(2,2-dimethyl-propionylamino)-propylsulfanyl]-benzoimidazol-1-yl}-acetic acid;
[2-(2-tert-butoxycarbonylamino-ethylsulfanyl)-benzoimidazol-1-yl]-acetic acid;
[2-(2-phenylamino-ethylsulfanyl)-benzoimidazol-1-yl]-acetic acid;
(2-{3-[(1-ethyloxycarbonyl-indazol-3-yl)-oxy]-propylsulfanyl}-benzoimidazol-1-yl)-acetic acid;
[2-(3-pentanoylamino-propylsulfanyl)-benzoimidazol-1-yl]-acetic acid;
[2-(3-ethyloxycarbonyl-propylsulfanyl)-benzoimidazol-1-yl]-acetic acid;
{2-[3-(1-cyclopropyl-3-propyl-ureido)-propylsulfanyl]-benzoimidazol-1-yl}-acetic acid; and [2-(3-benzylamino-propylsulfanyl)-benzoimidazol-1-yl]-acetic acid.

Particularly preferred novel compounds of the present invention include:
rac{2-[1-(3,4-dichloro-benzenesulfonyl)-piperidin-3-ylmethylsulfanyl]-benzoimidazol-1-yl}-acetic acid;
rac{2-[1-(3-phenyl-acryloyl)-piperidin-3-ylmethylsulfanyl]-benzoimidazol-1-yl}-acetic acid;
[2-(1-butyryl-piperidin-3-ylmethylsulfanyl)-5,6-dimethyl-benzoimidazol-1-yl]-acetic acid;
[2-(5-methyloxycarbonyl-benzylsulfanyl)-5,6-dichloro-benzoimidazol-1-yl]-acetic acid;
[2-(5-acetyl-2-methoxy-benzylsulfanyl)-5,6-dichloro-benzoimidazol-1-yl]-acetic acid;
[2-(1-butyryl-piperidin-3-ylmethylsulfanyl)-5,6-dichloro-benzoimidazol-1-yl]-acetic acid;
[2-((R)-1-butyryl-piperidin-3-ylmethylsulfanyl)-benzoimidazol-1-yl]-acetic acid;
[2-(5-acetyl-2-methoxy-benzylsulfanyl)-5,6-difluoro-benzoimidazol-1-yl]-acetic acid;
[2-(5-acetyl-2-methoxy-benzylsulfanyl)-5-fluoro-benzoimidazol-1-yl]-acetic acid;
rac[2-(1-butyryl-piperidin-3-ylmethylsulfanyl)-5-fluoro-benzoimidazol-1-yl]-acetic acid;
rac{5-fluoro-2-[1-(furan-2-carbonyl)-piperidin-3-ylmethylsulfanyl]-benzoimidazol-1-yl}-acetic acid;
rac{2-[1-(4-bromo-benzoyl)-piperidin-3-ylmethylsulfanyl]-5-fluoro-benzoimidazol-1-yl}-acetic acid;

[2-(5-acetyl-2-methoxy-benzylsulfanyl)-5-trifluoromethyl-benzoimidazol-1-yl]-acetic acid;
[2-(5-acetyl-2-methoxy-benzylsulfanyl)-5-methanesulfonyl-benzoimidazol-1-yl]-acetic acid;
[2-(5-acetyl-2-methoxy-benzylsulfanyl)-6-fluoro-benzoimidazol-1-yl]-acetic acid;
[2-(5-acetyl-2-methoxy-benzylsulfanyl)-4-fluoro-benzoimidazol-1-yl]-acetic acid;
[5-acetyl-2-(5-acetyl-2-methoxy-benzylsulfanyl)-benzoimidazol-1-yl]-acetic acid;
[2-(5-acetyl-2-methoxy-benzylsulfanyl)-5-formyl-benzoimidazol-1-yl]-acetic acid;
rac 2-[2-(5-acetyl-2-methoxy-benzylsulfanyl)-5-fluoro-benzoimidazol-1-yl]-propionic acid;
[2-(5-butylcarbamoyl-2-methoxy-benzylsulfanyl)-5-fluoro-benzoimidazol-1-yl]-acetic acid;
[2-(5-benzylcarbamoyl-2-methoxy-benzylsulfanyl)-5-fluoro-benzoimidazol-1-yl]-acetic acid;
{2-[5-(2,3-dihydro-indole-1-carbonyl)-2-methoxy-benzylsulfanyl]-5-fluoro-benzoimidazol-1-yl}-acetic acid;
[2-(5-diethylcarbamoyl-2-methoxy-benzylsulfanyl)-5-fluoro-benzoimidazol-1-yl]-acetic acid;
[2-(5-acetyl-2-methoxy-benzylsulfanyl)-5-nitro-benzoimidazol-1-yl]-acetic acid;
rac{2-[1-(4-bromo-benzoyl)-pyrrolidin-3-ylmethylsulfanyl]-5-fluoro-benzoimidazol-1-yl}-acetic acid;
rac{5-fluoro-2-[1-(furan-2-carbonyl)-pyrrolidin-3-ylmethylsulfanyl]-benzoimidazol-1-yl}-acetic acid;
rac{5-fluoro-2-[1-(2-phenyl-ethenesulfonyl)-pyrrolidin-3-ylmethylsulfanyl]-benzoimidazol-1-yl}-acetic acid;
[2-(5-acetyl-2-butoxy-benzylsulfanyl)-5-fluoro-benzoimidazol-1-yl]-acetic acid;
{2-[5-acetyl-2-(3-hydroxy-propoxy)-benzylsulfanyl]-5-fluoro-benzoimidazol-1-yl}-acetic acid;
[2-(5-benzoyl-2-methoxy-benzylsulfanyl)-5-fluoro-benzoimidazol-1-yl]-acetic acid;
[5-fluoro-2-(6-methoxy-3-oxo-indan-5-ylmethylsulfanyl)-benzoimidazol-1-yl]-acetic acid;
[2-(5-acetyl-2-ethoxy-benzylsulfanyl)-5-fluoro-benzoimidazol-1-yl]-acetic acid;
[2-(5-acetyl-2-propoxy-benzylsulfanyl)-5-fluoro-benzoimidazol-1-yl]-acetic acid; and
rac[2-(5-acetyl-2-methoxy-phenylmethanesulfinyl)-5-fluoro-benzoimidazol-1-yl]-acetic acid.

Further preferred novel compounds of the present invention include:
[2-(1-butyryl-piperidin-4-ylmethylsulfanyl)-benzoimidazol-1-yl]-acetic acid;
[2-(3-isopropyloxycarbonyl-6-methoxy-benzylsulfanyl)-benzoimidazol-1-yl]-acetic acid;
rac{2-[1-(propane-2-sulfonyl)-piperidin-3-ylmethylsulfanyl]-benzoimidazol-1-yl}-acetic acid;
rac[2-(1-methanesulfonyl-piperidin-3-ylmethylsulfanyl)-benzoimidazol-1-yl]-acetic acid;
rac{2-[1-(thiophene-2-sulfonyl)-piperidin-3-ylmethylsulfanyl]-benzoimidazol-1-yl}-acetic acid;
rac{2-[1-(butane-1-sulfonyl)-piperidin-3-ylmethylsulfanyl]-benzoimidazol-1-yl}-acetic acid;
rac[2-(1-phenylmethanesulfonyl-piperidin-3-ylmethylsulfanyl)-benzoimidazol-1-yl]-acetic acid;
rac{2-[1-(naphthalene-2-sulfonyl)-piperidin-3-ylmethylsulfanyl]-benzoimidazol-1-yl}-acetic acid;
rac{2-[1-(toluene-4-sulfonyl)-piperidin-3-ylmethylsulfanyl]-benzoimidazol-1-yl}-acetic acid;
rac{2-[1-(4-methoxy-benzenesulfonyl)-piperidin-3-ylmethylsulfanyl]-benzoimidazol-1-yl}-acetic acid;
[2-(5-methyloxycarbonyl-benzylsulfanyl)-5,6-dimethyl-benzoimidazol-1-yl]-acetic acid;
[2-(5-acetyl-2-methoxy-benzylsulfanyl)-5,6-dimethyl-benzoimidazol-1-yl]-acetic acid;
[2-(5-methyloxycarbonyl-benzylsulfanyl)-4,6-bis-trifluoromethyl-benzoimidazol-1-yl]-acetic acid;
[2-(5-acetyl-2-methoxy-benzylsulfanyl)-4,6-bis-trifluoromethyl-benzoimidazol-1-yl]-acetic acid;
[2-(1-butyryl-piperidin-3-ylmethylsulfanyl)-4,6-bis-trifluoromethyl-benzoimidazol-1-yl]-acetic acid;
[2-(4-methyloxycarbonyl-oxazol-2-ylmethylsulfanyl)-benzoimidazol-1-yl]-acetic acid;
[2-((S)-1-butyryl-piperidin-3-ylmethylsulfanyl)-benzoimidazol-1-yl]-acetic acid;
rac{2-[5-(1-hydroxy-ethyl)-2-methoxy-benzylsulfanyl]-benzoimidazol-1-yl}-acetic acid;
rac{2-[2-methoxy-5-(1-methoxy-ethyl)-benzylsulfanyl]-benzoimidazol-1-yl}-acetic acid;
[2-(3-methyloxycarbonyl-6-phenyl-benzylsulfanyl)-benzoimidazol-1-yl]-acetic acid;
{2-[5-(benzyl-ethyl-carbamoyl)-2-methoxy-benzylsulfanyl]-5-fluoro-benzoimidazol-1-yl}-acetic acid;
{2-[2-methoxy-5-(morpholine-4-carbonyl)-benzylsulfanyl]-5-fluoro-benzoimidazol-1-yl}-acetic acid;
rac[2-(1-butyryl-pyrrolidin-3-ylmethylsulfanyl)-5-fluoro-benzoimidazol-1-yl]-acetic acid;
rac[5-fluoro-2-(1-octanoyl-pyrrolidin-3-ylmethylsulfanyl)-benzoimidazol-1-yl]-acetic acid;
rac{5-fluoro-2-[1-(3-phenyl-propionyl)-pyrrolidin-3-ylmethylsulfanyl]-benzoimidazol-1-yl}-acetic acid;
rac[5-fluoro-2-(1-phenylacetyl-pyrrolidin-3-ylmethylsulfanyl)-benzoimidazol-1-yl]-acetic acid;
rac{2-[1-(butane-1-sulfonyl)-pyrrolidin-3-ylmethylsulfanyl]-5-fluoro-benzoimidazol-1-yl}-acetic acid;
rac{5-fluoro-2-[1-(4-methoxy-benzenesulfonyl)-pyrrolidin-3-ylmethylsulfanyl]-benzoimidazol-1-yl}-acetic acid;
[5-fluoro-2-(3-methoxy-8-oxo-5,6,7,8-tetrahydro-naphthalen-2-ylmethylsulfanyl)-benzoimidazol-1-yl]-acetic acid;
(S)-[5-fluoro-2-(1-benzyloxycarbonyl-azetidin-2-ylmethylsulfanyl)-benzoimidazol-1-yl]-acetic acid; and
[5-fluoro-2-(1-benzyloxycarbonyl-azetidin-3-ylmethylsulfanyl)-benzoimidazol-1-yl]-acetic acid The present invention also relates to precursors of the general Formula II,

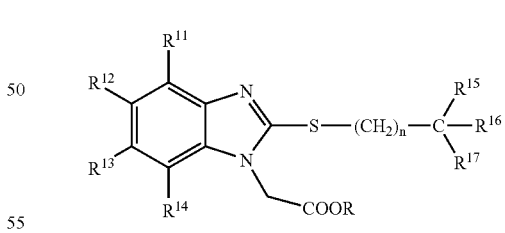

wherein $R^1$-$R^7$ and n are as in Formula I and R represents an alkyl group, preferably ethyl or tert-butyl, are novel with the exception of:
methyl[2-(5-trifluoromethyl-pyridin-2-ylsulfanyl)-benzoimidazol-1-yl]-acetate;
methyl[2-(4-chloro-benzylsulfanyl)-benzoimidazol-1-yl]-acetate;
methyl (2-benzylsulfanyl-benzoimidazol-1-yl)-acetate;
methyl[2-(5-nitro-pyridin-2-ylsulfanyl)-benzoimidazol-1-yl]-acetate;
methyl (2-methylsulfanyl-benzoimidazol-1-yl)-acetate;

ethyl (2-methylsulfanyl-benzoimidazol-1-yl)-acetate;
methyl (2-ethylsulfanyl-benzoimidazol-1-yl)-acetate;
ethyl[2-(1,3,7-trimethyl-2,6-dioxo-2,3,6,7-tetrahydro-1H-purin-8-ylsulfanyl)-benzoimidazol-1-yl]-acetate;
ethyl {2-[3-methyl-4-(2-morpholin-4-yl-ethylsulfanyl)-pyridin-2-ylmethylsulfanyl]-benzoimidazol-1-yl}-acetate (U.S. Pat. No. 5,504,082) and
methyl{2-[3-methyl-4-(2-morpholin-4-yl-ethylsulfanyl)-pyridin-2-ylmethylsulfanyl]-benzoimidazol-1-yl}-acetate (U.S. Pat. No. 5,504,082).

These novel precursors also form part of the present invention. They include, e.g.:

tert-butyl[2-(2-cyclohexyl-ethylsulfanyl)-benzoimidazol-1-yl]-acetic acetate;
tert-butyl (2-hexylsulfanyl-benzoimidazol-1-yl)-acetate;
tert-butyl (2-pentylsulfanyl-benzoimidazol-1-yl)-acetate;
tert-butyl (2-but-3-enylsulfanyl-benzoimidazol-1-yl)-acetate;
tert-butyl (2-butylsulfanyl-benzoimidazol-1-yl)-acetate;
rac tert-butyl[2-(1-phenyl-ethylsulfanyl)-benzoimidazol-1-yl]-acetate;
tert-butyl (2-cyclopentylsulfanyl-benzoimidazol-1-yl)-acetate;
rac tert-butyl[2-(1-methyloxycarbonyl-1-phenyl-methylsulfanyl)-benzoimidazol-1-yl]-acetate;
rac tert-butyl[2-(bicyclo[4.2.0]octa-1,3,5-trien-7-ylsulfanyl)-benzoimidazol-1-yl]-acetate;
rac tert-butyl[2-(1-methyl-2-oxo-2-phenyl-ethylsulfanyl)-benzoimidazol-1-yl]-acetate;
tert-butyl[2-(2-methoxy-benzylsulfanyl)-benzoimidazol-1-yl]-acetate;
tert-butyl (2-benzylsulfanyl-benzoimidazol-1-yl)-acetate;
tert-butyl (2-phenethylsulfanyl-benzoimidazol-1-yl)-acetate;
tert-butyl[2-(3-phenyl-propylsulfanyl)-benzoimidazol-1-yl]-acetate;
tert-butyl[2-(3,3-diphenyl-propylsulfanyl)-berizoimidazol-1-yl]-acetate;
tert-butyl{2-[2-(4-chloro-phenoxy)-ethylsulfanyl]-benzoimidazol-1-yl}-acetate;
tert-butyl[2-(2-phenoxy-ethylsulfanyl)-benzoimidazol-1-yl]-acetate;
tert-butyl{2-[2-(naphthalen-1-yloxy)-ethylsulfanyl]-benzoimidazol-1-yl}-acetate;
tert-butyl{2-[2-(naphthalen-2-yloxy)-ethylsulfanyl]-benzoimidazol-1-yl}-acetate;
tert-butyl[2-(4-phenoxy-butylsulfanyl)-benzoimidazol-1-yl]-acetate;
tert-butyl (2-{3-[(1-ethyloxycarbonyl-indazol-3-yl)-oxy]-propylsulfanyl}-benzoimidazol-1-yl)-acetate;
tert-butyl[2-(4-phenoxy-butylsulfanyl)-benzoimidazol-1-yl]-acetate;
tert-butyl[2-(5-ethyloxycarbonyl-pentylsulfanyl)-benzoimidazol-1-yl]-acetate;
tert-butyl[2-(3-ethyloxycarbonyl-propylsulfanyl)-benzoimidazol-1-yl]-acetate;
tert-butyl[2-(4-ethyloxycarbonyl-butylsulfanyl)-benzoimidazol-1-yl]-acetate;
tert-butyl{2-[4-(benzyl-methyl-carbamoyl)-butylsulfanyl]-benzoimidazol-1-yl}-acetate;
tert-butyl{2-[5-(3,4-dihydro-2H-quinolin-1-yl)-5-oxo-pentylsulfanyl]-benzoimidazol-1-yl}-acetate;
tert-butyl{2-[4-(benzyl-phenyl-carbamoyl)-butylsulfanyl]-benzoimidazol-1-yl}-acetate;
tert-butyl{2-[4-(methyl-phenyl-carbamoyl)-butylsulfanyl]-benzoimidazol-1-yl}-acetate;
tert-butyl{2-[4-(butyl-phenyl-carbamoyl)-butylsulfanyl]-benzoimidazol-1-yl}-acetate;
tert-butyl{2-[3-(2,3-dihydro-1-ethyloxycarbonyl-3-oxo-indazol-2-yl)-propylsulfanyl]-benzoimidazol-1-yl}-acetate;
tert-butyl{2-[3-(1-oxo-1,3-dihydro-isoindol-2-yl)-propylsulfanyl]-benzoimidazol-1-yl}-acetate;
tert-butyl{2-[3-(2-oxo-2,3-dihydro-benzoimidazol-1-yl)-propylsulfanyl]-benzoimidazol-1-yl}-acetate;
tert-butyl{2-[3-(1-oxo-1H-phthalazin-2-yl)-propylsulfanyl]-benzoimidazol-1-yl}-acetate;
tert-butyl{2-[3-(2,4-dioxo-1,4-dihydro-2H-quinazolin-3-yl)-propylsulfanyl]-benzoimidazol-1-yl}-acetate;
tert-butyl{2-[3-(1,3-dioxo-1,3-dihydro-isoindol-2-yl)-propylsulfanyl]-benzoimidazol-1-yl}-acetate;
tert-butyl{2-[3-(1,1,3-trioxo-1,3-dihydro-1$\lambda^6$-benzo[d]isothiazol-2-yl)-propylsulfanyl]-benzoimidazol-1-yl}-acetate;
tert-butyl[2-(3-methoxycarbonyl-benzylsulfanyl)-benzoimidazol-1-yl]-acetate;
tert-butyl{2-[(5-methyloxycarbonyl-pyridin-3-yl)-methylsulfanyl]-benzoimidazol-1-yl}-acetate;
tert-butyl (2-{[(2-chloro-4-methyloxycarbonyl)-pyridin-6-yl]-methyl-sulfanyl}-benzoimidazol-1-yl)-acetate;
tert-butyl{2-[(2-methyloxycarbonyl-furan-5-yl)-methylsulfanyl]-benzoimidazol-1-yl}-acetate;
tert-butyl{2-[(2-bromo-3-methoxycarbonyl)-benzylsulfanyl]-benzoimidazol-1-yl}-aceate;
tert-butyl{2-[(4-bromo-3-methoxycarbonyl)-benzylsulfanyl]-benzoimidazol-1-yl}-acetate;
tert-butyl{2-[(5-bromo-3-methoxycarbonyl)-benzylsulfanyl]-benzoimidazol-1-yl}-acetate;
tert-butyl{2-[(6-bromo-3-methoxycarbonyl)-benzylsulfanyl]-benzoimidazol-1-yl}-acetate;
tert-butyl{2-[(6-methoxy-3-methoxycarbonyl)-benzylsulfanyl]-benzoimidazol-1-yl}-acetate;
tert-butyl[2-(3-acetyl-benzylsulfanyl)-benzoimidazol-1-yl]-acetate;
tert-butyl[2-(5-acetyl-2-methoxy-benzylsulfanyl)-benzoimidazol-1-yl]-acetate;
rac tert-butyl[2-(1-tert-butyloxycarbonyl-piperidin-3-ylmethylsulfanyl)-benzoimidazol-1-yl]-acetate;
rac tert-butyl[2-(1-butyryl-piperidin-3-ylmethylsulfanyl)-benzoimidazol-1-yl]-acetate;
tert-butyl{2-[3-(tert-Butoxycarbonyl-phenethyl-amino)-propylsulfanyl]-benzoimidazol-1-yl}-acetate;
tert-butyl (2-{3-[tert-butoxycarbonyl-(4-piperidin-1-yl-phenyl)-amino]-propylsulfanyl}-benzoimidazol-1-yl)-acetate;
tert-butyl[2-(3-{[(4-ethyloxycarbonyl)-phenyl]-tert-butyloxycarbonyl-amino}-propylsulfanyl)-benzoimidazol-1-yl]-acetate;
tert-butyl{2-[3-(benzyl-tert-butoxycarbonyl-amino)-propylsulfanyl]-benzoimidazol-1-yl}-acetate;
tert-butyl{2-[3-(tert-butoxycarbonyl-cyclopropyl-amino)-propylsulfanyl]-benzoimidazol-1-yl}-acetate;
tert-butyl{2-[3-(tert-butoxycarbonyl-phenyl-amino)-propylsulfanyl]-benzoimidazol-1-yl}-acetate;
tert-butyl (2-{3-[tert-butoxycarbonyl-(2,2-diphenyl-ethyl)-amino]-propylsulfanyl}-benzoimidazol-1-yl)-acetate;
tert-butyl{2-[3-(butoxycarbonyl-phenethyl-amino)-propylsulfanyl]-benzoimidazol-1-yl}-acetate;
tert-butyl{2-[3-(benzyl-butoxycarbonyl-amino)-propylsulfanyl]-benzoimidazol-1-yl}-acetate;
tert-butyl{2-[3-(butoxycarbonyl-cyclohexyl-amino)-propylsulfanyl]-benzoimidazol-1-yl}-acetate;
tert-butyl{2-[3-(butoxycarbonyl-cyclohexylmethyl-amino)-propylsulfanyl]-benzoimidazol-1-yl}-acetate;

tert-butyl{2-[3-(pentanoyl-phenyl-amino)-propylsulfanyl]-benzoimidazol-1-yl}-acetate;
tert-butyl{2-[3-(diphenylacetyl-phenyl-amino)-propylsulfanyl]-benzoimidazol-1-yl}-acetate;
tert-butyl{2-[3-(phenyl-phenylacetyl-amino)-propylsulfanyl]-benzoimidazol-1-yl}-acetate;
tert-butyl (2-{3-[(3,3-diphenyl-propionyl)-phenyl-amino]-propylsulfanyl}-benzoimidazol-1-yl)-acetate;
tert-butyl{2-[3-(benzenesulfonyl-phenyl-amino)-propylsulfanyl]-benzoimidazol-1-yl}-acetate;
rac tert-butyl (2-{3-[(2-cyclohexyl-2-phenyl-acetyl)-phenyl-amino]-propylsulfanyl}-benzoimidazol-1-yl)-acetate;
tert-butyl{2-[3-(1,3-diphenyl-ureido)-propylsulfanyl]-benzoimidazol-1-yl}-acetate;
tert-butyl{2-[3-(3-benzyl-1-phenyl-ureido)-propylsulfanyl]-benzoimidazol-1-yl}-acetate;
tert-butyl (2-{3-[pentanoyl-(4-piperidin-1-yl-phenyl)-amino]-propylsulfanyl}-benzoimidazol-1-yl)-acetate;
tert-butyl (2-{3-[diphenylacetyl-(4-piperidin-1-yl-phenyl)-amino]-propylsulfanyl}-benzoimidazol-1-yl)-acetate;
tert-butyl (2-{3-[phenylmethanesulfonyl-(4-piperidin-1-yl-phenyl)-amino]-propylsulfanyl}-benzoimidazol-1-yl)-acetate;
tert-butyl (2-{3-[phenylacetyl-(4-piperidin-1-yl-phenyl)-amino]-propylsulfanyl}-benzoimidazol-1-yl)-acetate;
tert-butyl (2-{3-[(3,3-diphenyl-propionyl)-(4-piperidin-1-yl-phenyl)-amino]-propylsulfanyl}-benzoimidazol-1-yl)-acetate;
tert-butyl (2-{3-[1-(4-piperidin-1-yl-phenyl)-3-propyl-ureido]-propylsulfanyl}-benzoimidazol-1-yl)-acetate;
tert-butyl (2-{3-[benzenesulfonyl-(4-piperidin-1-yl-phenyl)-amino]-propylsulfanyl}-benzoimidazol-1-yl)-acetate;
tert-butyl[2-(3-{[(4-ethyloxycarbonyl)-phenyl]-pentanoyl-amino}-propylsulfanyl)-benzoimidazol-1-yl]-acetate;
tert-butyl[2-(3-{diphenylacetyl-[(4-ethyloxycarbonyl)-phenyl]-amino}-propylsulfanyl)-benzoimidazol-1-yl]-acetate;
tert-butyl (2-{3-[(4-ethyloxycarbonylphenyl)-(phenylacetyl)-amino]-propylsulfanyl}-benzoimidazol-1-yl)-acetate;
tert-butyl[2-(3-{diphenylpropionyl-[(4-ethyloxycarbonyl)-phenyl]-amino}-propylsulfanyl)-benzoimidazol-1-yl]-acetate;
rac tert-butyl[2-(3-{(2-cyclohexyl-2-phenyl-acetyl)-[(4-ethyloxycarbonyl)-phenyl]-amino}-propylsulfanyl)-benzoimidazol-1-yl]-acetate;
tert-butyl{2-[3-(benzyl-pentanoyl-amino)-propylsulfanyl]-benzoimidazol-1-yl}-acetate;
tert-butyl{2-[3-(benzyl-diphenylacetyl-amino)-propylsulfanyl]-benzoimidazol-1-yl}-acetate;
tert-butyl{2-[3-(benzyl-phenylmethanesulfonyl-amino)-propylsulfanyl]-benzoimidazol-1-yl}-acetate;
tert-butyl{2-[3-(benzyl-phenylacetyl-amino)-propylsulfanyl]-benzoimidazol-1-yl}-acetate;
tert-butyl (2-{3-[benzyl-(3,3-diphenyl-propionyl)-amino]-propylsulfanyl}-benzoimidazol-1-yl)-acetate;
tert-butyl{2-[3-(1-benzyl-3-propyl-ureido)-propylsulfanyl]-benzoimidazol-1-yl}-acetate;
tert-butyl{2-[3-(benzenesulfonyl-benzyl-amino)-propylsulfanyl]-benzoimidazol-1-yl}-acetate;
rac tert-butyl(2-{3-[benzyl-(2-cyclohexyl-2-phenyl-acetyl)-amino]-propylsulfanyl}-benzoimidazol-1-yl)-acetate;
tert-butyl{2-[3-(cyclopropyl-pentanoyl-amino)-propylsulfanyl]-benzoimidazol-1-yl}-acetate;
tert-butyl (2-{3-[(butane-1-sulfonyl)-cyclopropyl-amino]-propylsulfanyl}-benzoimidazol-1-yl)-acetate;
tert-butyl{2-[3-(cyclopropyl-diphenylacetyl-amino)-propylsulfanyl]-benzoimidazol-1-yl}-acetate;
tert-butyl{2-[3-(cyclopropyl-phenylmethanesulfonyl-amino)-propylsulfanyl]-benzoimidazol-1-yl}-acetate;
tert-butyl{2-[3-(cyclopropyl-phenylacetyl-amino)-propylsulfanyl]-benzoimidazol-1-yl}-acetate;
tert-butyl (2-{3-[cyclopropyl-(3,3-diphenyl-propionyl)-amino]-propylsulfanyl}-benzoimidazol-1-yl)-acetate;
tert-butyl{2-[3-(1-cyclopropyl-3-propyl-ureido)-propylsulfanyl]-benzoimidazol-1-yl}-acetate;
tert-butyl{2-[3-(benzenesulfonyl-cyclopropyl-amino)-propylsulfanyl]-benzoimidazol-1-yl}-acetate;
rac tert-butyl (2-{3-[(2-cyclohexyl-2-phenyl-acetyl)-cyclopropyl-amino]-propylsulfanyl}-benzoimidazol-1-yl)-acetate;
tert-butyl{2-[3-(pentanoyl-phenethyl-amino)-propylsulfanyl]-benzoimidazol-1-yl}-acetate;
tert-butyl (2-{3-[(butane-1-sulfonyl)-phenethyl-amino]-propylsulfanyl}-benzoimidazol-1-yl)-acetate;
tert-butyl{2-[3-(diphenylacetyl-phenethyl-amino)-propylsulfanyl]-benzoimidazol-1-yl}-acetate;
tert-butyl{2-[3-(phenethyl-phenylmethanesulfonyl-amino)-propylsulfanyl]-benzoimidazol-1-yl}-acetate;
tert-butyl{2-[3-(phenethyl-phenylacetyl-amino)-propylsulfanyl]-benzoimidazol-1-yl}-acetate;
tert-butyl(2-{3-[(3,3-diphenyl-propionyl)-phenethyl-amino]-propylsulfanyl}-benzoimidazol-1-yl)-acetate;
tert-butyl{2-[3-(1-phenethyl-3-propyl-ureido)-propylsulfanyl]-benzoimidazol-1-yl}-acetate;
tert-butyl{2-[3-(benzenesulfonyl-phenethyl-amino)-propylsulfanyl]-benzoimidazol-1-yl}-acetate;
tert-butyl(2-{3-[(2,2-diphenyl-ethyl)-pentanoyl-amino]-propylsulfanyl}-benzoimidazol-1-yl)-acetate;
tert-butyl (2-{3-[diphenylacetyl-(2,2-diphenyl-ethyl)-amino]-propylsulfanyl}-benzoimidazol-1-yl)-acetate;
tert-butyl (2-{3-[(2,2-diphenyl-ethyl)-phenylmethanesulfonyl-amino]-propylsulfanyl}-benzoimidazol-1-yl)-acetate;
tert-butyl (2-{3-[(2,2-diphenyl-ethyl)-phenylacetyl-amino]-propylsulfanyl}-benzoimidazol-1-yl)-acetate;
tert-butyl (2-{3-[(2,2-diphenyl-ethyl)-(3,3-diphenyl-propionyl)-amino]-propylsulfanyl}-benzoimidazol-1-yl)-acetate;
tert-butyl (2-{3-[1-(2,2-diphenyl-ethyl)-3-propyl-ureido]-propylsulfanyl}-benzoimidazol-1-yl)-acetate;
tert-butyl[2-(3-{butyloxycarbonyl-[(4-ethyloxycarbonyl)-phenyl]-amino}-propylsulfanyl)-benzoimidazol-1-yl]-acetate;
tert-butyl[2-(3-tert-butoxycarbonylamino-propylsulfanyl)-benzoimidazol-1-yl]-acetate;
tert-butyl[2-(3-pentanoylamino-propylsulfanyl)-benzoimidazol-1-yl]-acetate;
tert-butyl{2-[3-(butane-1-sulfonylamino)-propylsulfanyl]-benzoimidazol-1-yl}-acetate;
tert-butyl[2-(3-diphenylacetylamino-propylsulfanyl)-benzoimidazol-1-yl]-acetate;
tert-butyl[2-(3-phenylmethanesulfonylamino-propylsulfanyl)-benzoimidazol-1-yl]-acetate;
tert-butyl[2-(3-phenylacetylamino-propylsulfanyl)-benzoimidazol-1-yl]-acetate;
tert-butyl{2-[3-(3,3-diphenyl-propionylamino)-propylsulfanyl]-benzoimidazol-1-yl}-acetate;
tert-butyl{2-[3-(3-propyl-ureido)-propylsulfanyl]-benzoimidazol-1-yl}-acetate;
tert-butyl[2-(3-benzenesulfonylamino-propylsulfanyl)-benzoimidazol-1-yl]-acetate;
rac tert-butyl{2-[3-(2-cyclohexyl-2-phenyl-acetylamino)-propylsulfanyl]-benzoimidazol-1-yl}-acetate;

tert-butyl{2-[3-(3-phenyl-ureido)-propylsulfanyl]-benzoimidazol-1-yl}-acetate;
tert-butyl[2-(3-benzoylamino-propylsulfanyl)-benzoimidazol-1-yl]-acetate;
tert-butyl{2-[3-(cyclohexanecarbonyl-amino)-propylsulfanyl]-benzoimidazol-1-yl}-acetate;
tert-butyl{2-[3-(4-methoxy-benzoylamino)-propylsulfanyl]-benzoimidazol-1-yl}-acetate;
tert-butyl (2-{3-[(furan-2-carbonyl)-amino]-propylsulfanyl}-benzoimidazol-1-yl)-acetate;
tert-butyl{2-[3-(cyclopropanecarbonyl-amino)-propylsulfanyl]-benzoimidazol-1-yl}-acetate;
tert-butyl (2-{3-[(naphthalene-1-carbonyl)-amino]-propylsulfanyl}-benzoimidazol-1-yl)-acetate;
tert-butyl{2-[3-(3-cyclopentyl-propionylamino)-propylsulfanyl]-benzoimidazol-1-yl}-acetate;
tert-butyl{2-[3-(2,2-dimethyl-propionylamino)-propylsulfanyl]-benzoimidazol-1-yl}-acetate;
tert-butyl{2-[3-(3-phenyl-acryloylamino)-propylsulfanyl]-benzoimidazol-1-yl}-acetate;
tert-butyl{2-[3-(3-phenyl-propionylamino)-propylsulfanyl]-benzoimidazol-1-yl}-aceate;
tert-butyl{2-[3-(1,2-dioxo-2-ethyloxy-ethylamino)-propylsulfanyl]-benzoimidazol-1-yl}-acetate;
tert-butyl (2-{3-[(biphenyl-4-carbonyl)-amino]-propylsulfanyl}-benzoimidazol-1-yl)-acetate;
tert-butyl (2-{3-[(pyridine-3-carbonyl)-amino]-propylsulfanyl}-benzoimidazol-1-yl)-acetate;
tert-butyl{2-[3-(3,3-dimethyl-butyrylamino)-propylsulfanyl]-benzoimidazol-1-yl}-acetate;
tert-butyl[2-(3-octanoylamino-propylsulfanyl)-benzoimidazol-1-yl]-acetate;
tert-butyl{2-[3-(4-bromo-benzoylamino)-propylsulfanyl]-benzoimidazol-1-yl}-acetate;
[3-(1-tert-butoxycarbonylmethyl-1H-benzoimidazol-2-ylsulfanyl)-propyl]-phenethyl-ammonium chloride;
[3-(1-tert-butoxycarbonylmethyl-1H-benzoimidazol-2-ylsulfanyl)-propyl]-(4-piperidin-1-yl-phenyl)-ammonium chloride;
[3-(1-tert-butoxycarbonylmethyl-1H-benzoimidazol-2-ylsulfanyl)-propyl]-(4-ethoxycarbonyl-phenyl)-ammonium chloride;
benzyl-[3-(1-tert-butoxycarbonylmethyl-1H-benzoimidazol-2-ylsulfanyl)-propyl]-ammonium chloride;
[3-(1-tert-butoxycarbonylmethyl-1H-benzoimidazol-2-ylsulfanyl)-propyl]-cyclopropyl-ammonium chloride;
[3-(1-tert-butoxycarbonylmethyl-1H-benzoimidazol-2-ylsulfanyl)-propyl]-phenyl-ammonium chloride;
[3-(1-tert-butoxycarbonylmethyl-1H-benzoimidazol-2-ylsulfanyl)-propyl]-(2,2-diphenyl-ethyl)-ammonium chloride;
3-(1-tert-butoxycarbonylmethyl-1H-benzoimidazol-2-ylsulfanyl)-propyl-ammonium chloride;
tert-butyl{2-[2-(1,3-dioxo-1,3-dihydro-isoindol-2-yl)-ethyl-sulfanyl]-benzoimidazol-1-yl}-acetate;
tert-butyl[2-(2-tert-butoxycarbonylamino-ethylsulfanyl)-benzoimidazol-1-yl]-acetate;
tert-butyl[2-(2-butoxycarbonylamino-ethylsulfanyl)-benzoimidazol-1-yl]-acetate;
tert-butyl[2-(2-diphenylacetylamino-ethylsulfanyl)-benzoimidazol-1-yl]-acetate;
tert-butyl{2-[2-(3-phenyl-ureido)-ethylsulfanyl]-benzoimidazol-1-yl}-acetate;
tert-butyl[6-iodo-2-(2-phenoxy-ethylsulfanyl)-benzoimidazol-1-yl]-acetate;
tert-butyl{5-chloro-2-[2-(4-chloro-phenoxy)-ethylsulfanyl]-benzoimidazol-1-yl}-acetate and its 6-chloro regioisomer;
tert-butyl{2-[2-(4-chloro-phenoxy)-ethylsulfanyl]-4-methyl-benzoimidazol-1-yl}-acetate and its 8-methyl regioisomer;
tert-butyl (2-benzylsulfanyl-5-nitro-benzoimidazol-1-yl)-acetate;
tert-butyl[2-(3,3-diphenyl-propylsulfanyl)-5-nitro-benzoimidazol-1-yl]-acetate;
tert-butyl{5-nitro-2-[2-(4-chlorophenoxy)-ethylsulfanyl]-benzoimidazol-1-yl}-acetate and its 6-nitro regioisomer;
tert-butyl-[5-nitro-2-(2-phenoxy-ethylsulfanyl)-benzoimidazol-1-yl]-acetate;
tert-butyl{2-[3-(1,3-dioxo-1,3-dihydro-isoindol-2-yl)-propylsulfanyl]-5-nitro-benzoimidazol-1-yl}-acetate;
tert-butyl[2-(4-ethyloxycarbonyl-butylsulfanyl)-5-nitro-benzoimidazol-1-yl]-acetate;
tert-butyl[2-(3-methoxycarbonyl-benzylsulfanyl)-5-nitro-benzoimidazol-1-yl]-acetate;
tert-butyl{2-[3-(butoxycarbonyl-phenethyl-amino)-propylsulfanyl]-5-nitro-benzoimidazol-1-yl}-acetate;
tert-butyl{2-[2-(4-chloro-phenoxy)-ethylsulfanyl]-5-methyl-benzoimidazol-1-yl}-acetate and its 6-methyl regioisomer;
tert-butyl[5-cyano-2-(2-phenoxy-ethylsulfanyl)-benzoimidazol-1-yl]-acetate and its 6-cyano regioisomer;
tert-butyl[5-cyano-2-(4-ethyloxycarbonyl-butylsulfanyl)-benzoimidazol-1-yl]-acetate and its 6-cyano regioisomer;
tert-butyl[5-cyano-2-(3-methoxycarbonyl-benzylsulfanyl)-benzoimidazol-1-yl]-acetate and its 6-cyano regioisomer;
tert-butyl[2-(4-ethyloxycarbonyl-butylsulfanyl)-5-trifluoromethyl-benzoimidazol-1-yl]-acetate and its 6-trifluoromethyl regioisomer;
tert-butyl[2-(3-methoxycarbonyl-benzylsulfanyl)-5-trifluoromethyl-benzoimidazol-1-yl]-acetate and its 6-trifluoromethyl regioisomer;
tert-butyl (2-benzylsulfanyl-6-nitro-benzoimidazol-1-yl)-acetate;
tert-butyl[2-(3,3-diphenyl-propylsulfanyl)-6-nitro-benzoimidazol-1-yl]-acetate;
tert-butyl[6-nitro-2-(2-phenoxy-ethylsulfanyl)-benzoimidazol-1-yl]-acetate and its 5-nitro regioisomer;
tert-butyl[2-(4-ethyloxycarbonyl-butylsulfanyl)-6-nitro-benzoimidazol-1-yl]-acetate;
tert-butyl{2-[3-(1,3-dioxo-1,3-dihydro-isoindol-2-yl)-propylsulfanyl]-6-nitro-benzoimidazol-1-yl}-acetate;
tert-butyl[5-fluoro-2-(2-phenoxy-ethylsulfanyl)-benzoimidazol-1-yl]-acetate and its 6-fluoro regioisomer;
tert-butyl[2-(4-ethyloxycarbonyl-butylsulfanyl)-5-fluoro-benzoimidazol-1-yl]-acetate and its 6-fluoro regioisomer; and
tert-butyl[5-fluoro-2-(3-methoxycarbonyl-benzylsulfanyl)-benzoimidazol-1-yl]-acetate and its 6-fluoro regioisomer.

The present invention also relates to novel intermediates of the general Formula

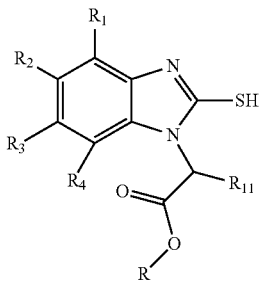

wherein $R^1$-$R^4$ and $R^{11}$ are as defined for Formula I and R represents an alkyl group.

Such novel intermdediates include:
tert-butyl-(2-mercapto-benzoimidazol-1-yl)-acetate;
tert-butyl-(2-mercapto-5-nitro-benzoimidazol-1-yl)-acetate;
tert-butyl-(2-mercapto-6-nitro-benzoimidazol-1-yl)-acetate;
tert-butyl (5-formyl-2-mercapto-benzoimidazol-1-yl)-acetate;
tert-butyl (5,6-difluoro-2-mercapto-benzoimidazol-1-yl)-acetate;
tert-butyl (2-mercapto-5-methanesulfonyl-benzoimidazol-1-yl)-acetate;
tert-butyl (5-acetyl-2-mercapto-benzoimidazol-1-yl)-acetate;
tert-butyl (4-fluoro-2-mercapto-benzoimidazol-1-yl)-acetate;
tert-butyl (2-mercapto-5-trifluoromethyl-benzoimidazol-1-yl)-acetate;
tert-butyl (5-fluoro-2-mercapto-benzoimidazol-1-yl)-acetate;
methyl (6-fluoro-2-mercapto-benzoimidazol-1-yl)-acetate; and
rac ethyl 2-(5-fluoro-2-mercapto-benzoimidazol-1-yl)-propionate.

Unless explicitly stated otherwise, the general terms and names used hereinbefore and hereinafter preferably have within the context of this disclosure the following meanings:

Any reference to a compound of Formula I is to be understood as referring also to optically pure enantiomers, mixtures of enantiomers, racemates, optically pure diastereoisomers, mixtures of diastereoisomers, diastereoisomeric racemates, mixtures of diastereoisomeric racemates, meso forms, geometric isomers, and prodrugs of compounds in which a prodrug forming group is present, as well as salts (especially pharmaceutically acceptable salts) and solvates (including hydrates) of such compounds, and morphological forms, as appropriate and expedient.

The term "alkyl", as used herein, alone or in any combination, refers to a saturated aliphatic group including a straight or branched hydrocarbon chain containing 1-8, preferably 1-4 carbon atoms. Representative examples of alkyl include, but are not limited to, methyl, ethyl, n-propyl, iso-propyl, n-butyl, tert-butyl, iso-butyl (or 2-methylpropyl), cyclopropylmethyl, n-pentyl, iso-pentyl, iso-amyl, n-amyl, n-hexyl, n-heptyl, n-octyl and the like. Less preferred, the alkyl group can be optionally substituted with one or more substituents, each independently selected from alkenyl, alkoxy, alkoxycarbonyl, alkylcarbonyl, alkylcarbonyloxy, alkylendioxy, alkylsulfinyl, alkylsulfonyl, alkylthio, alkynyl, amino, aminocarbonyl, aryl, arylalkenyl, arylalkoxy, aryloxy, aryloxycarbonyl, arylsulfinyl, arylsulfonyl, arylthio, carboxy, cyano, formyl, halogen, haloalkoxy, heterocyclyl, hydroxy, mercapto, nitro, and the like, appended to any carbon atom of the alkyl moiety. In the case $R^9$ is arylalkylcarbonyl, the alkyl group of this radical can for example be substituted by cyclohexyl.

The term "lower alkyl", as used herein, alone or in any combination, refers to alkyl groups with 1-4 carbon atoms. Representative examples of lower alkyl include, but are not limited to, methyl, ethyl, n-propyl, iso-propyl, n-butyl, iso-butyl, tert-butyl and the like.

The term "alkenyl", as used herein, alone or in any combination, refers to a straight or branched hydrocarbon chain containing 2-8, preferably 2-4 carbon atoms with at least one carbon-carbon double bond. Representative examples of alkenyl include, but are not limited to, ethenyl, 2-propenyl, 2-methyl-2-propenyl, 3-butenyl, 4-pentenyl, 5-hexenyl and the like.

The term "alkylenedioxy", as used herein, alone or in any combination, refers to a —O(CH$_2$)$_n$O— group, wherein n is preferably 1 or 2, and wherein the oxygen atoms are appended to two adjacent carbon atoms of the parent molecular moiety. Representative examples of alkylenedioxy include, but are not limited to, methylenedioxy, ethylenedioxy, and the like.

The term "alkynyl", as used herein, alone or in any combination, refers to a straight or branched hydrocarbon chain containing 2-8 carbon atoms with at least one carbon-carbon triple bond. Representative examples of alkynyl include, but are not limited to, 1-propynyl, 2-propynyl, 1-butynyl, 3-butynyl, 2-pentynyl, and the like.

The term "alkoxy", as used herein, alone or in any combination, refers to an alkyl group appended to the parent molecular moiety through an oxygen bridge. Representative examples of alkoxy include, but are not limited to, methoxy, ethoxy, propoxy, 2-propoxy, butoxy, tert-butoxy, pentyloxy, hexyloxy, and the like.

The term "alkoxyalkyl", as used herein, alone or in any combination, refers to an alkoxy group appended to the parent molecular moiety through an alkyl group. Representative examples of alkoxyalkyl include, but are not limited to, tert-butoxymethyl, 2-ethoxyethyl, 2-methoxyethyl, methoxymethyl, and the like.

The term "alkoxycarbonyl", as used herein, alone or in any combination, refers to an alkoxy group appended to the parent molecular moiety through a carbonyl group. Representative examples of alkoxycarbonyl include, but are not limited to, methoxycarbonyl, ethoxycarbonyl, tert-butoxycarbonyl, and the like.

The term "alkoxycarbonylalkyl", as used herein, alone or in any combination, refers to an alkoxycarbonyl group appended to the parent molecular moiety through an alkyl group. Representative examples of alkoxycarbonylalkyl include, but are not limited to, methoxycarbonylpropyl, ethoxycarbonylbutyl, 2-tert-butoxycarbonylethyl, and the like.

The term "alkylcarbonyl" or "acyl", as used herein, alone or in any combination, refers to an alkyl group appended to the parent molecular moiety through a carbonyl group. Representative examples of alkylcarbonyl include, but are not limited to, acetyl, 1-oxopropyl, 2,2-dimethyl-1-oxopropyl, 1-oxobutyl, 1-oxopentyl, and the like.

The term "alkylcarbonylalkyl", as used herein, alone or in any combination, refers to an alkylcarbonyl group appended to the parent molecular moiety through an alkyl group. Representative examples of alkylcarbonylalkyl include, but are not limited to, 2-oxopropyl, 3,3-dimethyl-2-oxopropyl, 3-oxobutyl, 3-oxopentyl and the like.

The term "alkylcarbonyloxy", as used herein, alone or in any combination, refers to an alkylcarbonyl group appended to the parent molecular moiety through an oxygen bridge. Representative examples of alkylcarbonyloxy include, but are not limited to, acetyloxy, ethylcarbonyloxy, tert-butylcarbonyloxy and the like.

The term "alkylsulfinyl", as used herein, alone or in any combination, refers to an alkyl group appended to the parent molecular moiety through a sulfinyl group. Representative examples of alkylsulfinyl include, but are not limited to, methylsulfinyl, ethylsulfinyl and the like.

The term "alkylsulfinylalkyl", as used herein, alone or in any combination, refers to an alkylsulfinyl group appended to the parent molecular moiety through an alkyl group. Representative examples of alkylsulfinylalkyl include, but are not limited to, methylsulfinylmethyl, ethylsulfinylmethyl and the like.

The term "alkylsulfonyl", as used herein, alone or in any combination, refers to an alkyl group appended to the parent molecular moiety through a sulfonyl group. Representative examples of alkylsulfonyl include, but are not limited to, methylsulfonyl, ethylsulfonyl, and the like.

The term "alkylsulfonylalkyl", as used herein, alone or in any combination, refers to an alkylsulfonyl group appended to the parent molecular moiety through an alkyl group. Representative examples of alkylsulfonylalkyl include, but are not limited to, methylsulfonylmethyl, ethylsulfonylmethyl and the like.

The term "alkylthio" (synonym "alkylsulfanyl"), as used herein, alone or in any combination, refers to an alkyl group appended to the parent molecular moiety through an —S— bridge. Representative examples of alkylthio include, but are not limited to, methylthio, ethylthio, tert-butylthio, hexylthio and the like.

The term "alkylthioalkyl" (synonym "alkylsulfanylalkyl"), as used herein, alone or in any combination, refers to an alkylthio group appended to the parent molecular moiety through an alkyl group. Representative examples of alkylthioalkyl include, but are not limited to, methylthiomethyl, 2-(ethylthio)ethyl, and the like.

The term "aminoalkyl", as used herein, alone or in any combination, refers to an amino group appended to the parent molecular moiety through an alkyl group. Representative examples of aminoalkyl include, but are not limited to, aminomethyl, 2-(amino)ethyl, and the like.

The term "aminocarbonyl" or "carbamoyl", as used herein, alone or in any combination, refers to an amino group appended to the parent molecular moiety through a carbonyl group.

The term "aminocarbonylalkyl", as used herein, alone or in any combination, refers to an aminocarbonyl group appended to the parent molecular moiety through an alkyl group.

The term "aryl", as used herein, alone or in any combination, refers to an carbocyclic group having at least one aromatic ring, e.g. phenyl or biphenyl, or multiple condensed ring systems, in which at least one ring is aromatic, e.g. 1,2,3,4-tetrahydronaphthyl, naphthyl, anthryl, phenanthryl, fluorenyl, and the like. The term preferably relates to phenyl or naphthyl, especially to phenyl. The aryl group may be optionally substituted with one or more functional groups individually and independently selected from alkenyl, alkoxy, alkoxyalkyl, alkoxycarbonyl, alkoxycarbonylalkyl, alkyl, cycloalkyl, alkylcarbonyl, alkylcarbonylalkyl, alkylcarbonyloxy, alkylendioxy, alkylsulfinyl, alkylsulfinylalkyl, alkylsulfonyl, alkylsulfonylalkyl, alkylthio, alkylthioalkyl, alkynyl, amino, aminoalkyl, aminocarbonyl, aminocarbonylalkyl, aryl, arylalkenyl, arylalkoxy, arylalkyl, aryloxy, aryloxycarbonyl, aryloxycarbonylalkyl, arylsulfinyl, arylsulfinylalkyl, arylsulfonyl, arylsulfonylalkyl, arylthio, arylthioalkyl, carboxy, carboxyalkyl, cyano, cyanoalkyl, formyl, formylalkyl, halogen, haloalkoxy, haloalkyl, heterocyclyl (preferably piperidinyl), hydroxy, hydroxyalkyl, mercapto, nitro, and the like.

The term "arylalkenyl", as used herein, alone or in any combination, refers to an aryl group appended to the parent molecular moiety through an alkenyl group. The aryl group may be unsubstituted or substituted. Representative examples of arylalkenyl include, but are not limited to, 2-phenylethenyl, 3-phenylpropen-2-yl, 2-naphth-2-ylethenyl, and the like.

The term "arylalkoxy", as used herein, alone or in any combination, refers to an aryl group appended to the parent molecular moiety through an alkoxy group. The aryl group may be unsubstituted or substituted. Representative examples of arylalkoxy include, but are not limited to, 2-phenylethoxy, 5-phenylpentyloxy, 3-naphth-2-ylpropoxy, and the like.

The term "arylalkyl", as used herein, alone or in any combination, refers to an aryl group appended to the parent molecular moiety through an alkyl group. The aryl group may be unsubstituted or substituted. Representative examples of arylalkyl include, but are not limited to, benzyl, 2-phenylethyl, 3-phenylpropyl, 2-naphth-2-ylethyl, and the like.

The term "aryloxy", as used herein, alone or in any combination, refers to an aryl group appended to the parent molecular moiety through an oxygen bridge. The aryl group can be unsubstituted or substituted. Representative examples of aryloxy include, but are not limited to, phenoxy, naphthyloxy, 3-bromophenoxy, 4-chlorophenoxy, 4-methylphenoxy, 3,4-dimethoxyphenoxy, and the like.

The term "carbonyl", as used herein, alone or in any combination, refers to a —C(O)— group.

The term "carboxy", as used herein, alone or in any combination, refers to a —CO$_2$H group.

The term "carboxyalkyl", as used herein, alone or in any combination, refers to a carboxy group appended to the parent molecular moiety through an alkyl group. Representative examples of carboxyalkyl include, but are not limited to, carboxymethyl, 2-carboxyethyl, 3-carboxypropyl, and the like.

The term "cyano", as used herein, alone or in any combination, refers to a —C≡N group.

The term "cyanoalkyl", as used herein, alone or in any combination, refers to a cyano group appended to the parent molecular moiety through an alkyl group. Representative examples of cyanoalkyl include, but are not limited to, cyanomethyl, 2-cyanoethyl, 3-cyanopropyl, and the like.

The term "cycloalkyl", as used herein, alone or in any combination, refers to a saturated cyclic hydrocarbon moiety containing 3-15, preferably 3-6, carbon atoms, optionally (less preferred) substituted with one or more groups, each individually and independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylendioxy, alkylsulfinyl, alkylsulfinylalkyl, alkylsulfonyl, alkylsulfonylalkyl, alkylthio, alkylthioalkyl, alkynyl, amino, aminoalkyl, aminocarbonyl, aminocarbonylalkyl, aryl, arylalkenyl, arylalkoxy, arylalkyl, aryloxy, aryloxycarbonyl, aryloxycarbonylalkyl, arylsulfinyl, arylsulfinylalkyl, arylsulfonyl, arylsulfonylalkyl, arylthio, arylthioalkyl, carboxy, carboxyalkyl, cyano, cyanoalkyl, formyl, formylalkyl, halogen, haloalkoxy, haloalkyl, heterocyclyl, hydroxy, hydroxyalkyl, mercapto, nitro, and the like. Representative examples of cycloalkyl include, but are not limited to, cyclopropyl, cyclobutyl, cyclopentyl, cyclohexyl, cycloheptyl, cyclooctyl and the like.

In polycyclic cycloalkyl groups one of the distal rings may be aromatic, e.g., 1-indanyl, 2-indanyl, tetrahydronaphthyl, bicyclo[4.2.0]octa-1,3,5-trien-7-yl, and the like.

The term "formyl", as used herein, alone or in any combination, refers to a —C(O)H group.

The term "formylalkyl", as used herein, alone or in any combination, refers to a formyl group, appended to the parent molecular moiety through an alkyl group. Representative examples of formylalkyl include, but are not limited to, formylmethyl, 2-formylethyl, and the like.

The term "halo" or "halogen", as used herein, alone or in any combination, refers to fluorine, bromine, chlorine, and iodine.

The term "haloalkyl", as used herein, alone or in any combination, refers to an alkyl group having at least one hydrogen atom replaced with a halogen atom. Representative examples of haloalkyl include, but are not limited to, chloromethyl, 2-fluoroethyl, trifluoromethyl, pentafluoroethyl, 2-chloro-3-fluoropentyl, and the like.

The term "haloalkoxy", as used herein, alone or in any combination, refers to an alkoxy group having at least one hydrogen atom replaced with a halogen atom. Representative examples of haloalkoxy include, but are not limited to, chloromethoxy, 2-fluoroethoxy, trifluoromethoxy, pentafluoroethoxy, and the like.

The term "heterocyclyl", as used herein, alone or in any combination, refers to a monocyclic, bicyclic or polycyclic ring system containing up to 15 ring atoms, at least one of these, preferably 1 or 2, being a hetero atom independently selected from nitrogen, oxygen or sulfinur. The ring system may be saturated, partially unsaturated, unsaturated or aromatic, mono- or bicyclic. Representative examples of heterocyclyl include, but are not limited to, furyl, imidazolyl, imidazolinyl, imidazolidinyl, isothiazolyl, isoxazolyl, morpholinyl, oxadiazolyl, oxazolyl, oxazolinyl, oxazolidinyl, piperazinyl, piperidinyl, pyranyl, pyrazinyl, pyrazolyl, pyridyl, pyrimidinyl, pyridazinyl, pyrrolyl, pyrrolinyl, pyrrolidinyl, tetrahydrofuranyl, tetrahydrofuranyl, tetrahydrothienyl, thiadiazolyl, thiazolyl, thiazolinyl, thiazolidinyl, thienyl, thiomorpholinyl, 1,1-dioxothiomorpholinyl, benzimidazolyl, phthalazinyl, benzothiazolyl, benzothienyl, benzoxazolyl, benzofuranyl, indolyl, indolinyl, indazolyl, isobenzofuranyl, isobenzothienyl, isoindolyl, isoindolinyl, isoquinolinyl, quinolinyl, quinazolinyl and the like. Defined heterocyclyl moieties may be optionally substituted with one or more groups, each individually and independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylendioxy, alkylsulfinyl, alkylsulfinylalkyl, alkylsulfonyl, alkylsulfonylalkyl, alkylthio, alkylthioalkyl, alkynyl, amino, aminoalkyl, aminocarbonyl, aminocarbonylalkyl, aryl, arylalkenyl, arylalkoxy, arylalkyl, aryloxy, arylcarbonyl, arylalkylcarbonyl, (diaryl)alkylcarbonyl, aryloxycarbonyl, aryloxycarbonylalkyl, arylsulfinyl, arylsulfinylalkyl, arylsulfonyl, arylsulfonylalkyl, arylthio, arylthioalkyl, carboxy, carboxyalkyl, cyano, cyanoalkyl, cycloalkyl, cycloalkylcarbonyl, cycloalkylalkylcarbonyl, formyl, formylalkyl, halogen, haloalkoxy, haloalkyl, heterocyclyl, heterocyclylcarbonyl, hydroxy, hydroxyalkyl, mercapto, nitro, and the like. Preferably the substituents are selected from oxo, alkoxycarbonyl, alkylcarbonyl, alkylsulfonyl, arylalkylcarbonyl, alkylakoxycarbonyl, arylalkylsulfonyl, arylcarbonyl, (diaryl)-alkylcarbonyl, arylsulfonyl, arylalkenylsulfonyl, cycloalkylalkylcarbonyl, cycloalkylcarbonyl, heterocyclylcarbonyl, and heterocyclylsulfonyl.

The term "saturated heterocyclyl" is another special case of "heterocyclyl" and refers to saturated rings as defined above for "heterocyclyl", especially to piperidinyl and pyrrolidinyl.

The term "heterocyclylalkenyl", as used herein, alone or in any combination, refers to a heterocyclyl group appended to the parent molecular moiety through an alkenyl group. Representative examples of heterocyclylalkenyl include, but are not limited to, 2-pyrid-3-ylethenyl, 3-quinolin-3-ylpropen-2-yl, 5-pyrid-4-ylpenten-4-yl, and the like.

The term "heterocyclylalkoxy", as used herein, alone or in any combination, refers to a heterocyclyl group appended to the parent molecular moiety through an alkoxy group. Representative examples of heterocyclylalkoxy include, but are not limited to, 2-pyrid-3-ylethoxy, 3-quinolin-3-ylpropoxy, 5-pyrid-4-ylpentyloxy, and the like.

The term "heterocyclylalkyl", as used herein, alone or in any combination, refers to a heterocyclyl group appended to the parent molecular moiety through an alkyl group. Representative examples of heterocyclylalkyl include, but are not limited to, 2-pyrid-3-ylmethyl, 2-pyrimidin-2-ylpropyl, and the like.

The term "heterocyclyloxy", as used herein, alone or in any combination, refers to a heterocyclyl group appended to the parent molecular moiety through an oxy group.

Representative examples of heterocyclyloxy include, but are not limited to, pyrid-3-yloxy, quinolin-3-yloxy, and the like, especially (1-ethyloxycarbonyl-indazol-3-yl)-oxy.

The term "hydroxy" or "hydroxyl" as used herein, alone or in any combination, refers to an —OH group The term "hydroxyalkyl", as used herein, alone or in any combination, refers to an alkyl group having at least one hydrogen atom replaced with a hydroxy group. Representative examples of hydroxyalkyl include, but are not limited to, hydroxymethyl, 2-hydroxyethyl, 3-hydroxypropyl, 2-ethyl-4-hydroxyheptyl, and the like.

The term "nitro", as used herein, alone or in any combination, refers to a —NO$_2$ group.

The term "oxo", as used herein, alone or in any combination, refers to an =O group.

The term "oxy", as used herein, alone or in any combination, refers to an —O— group.

The terms "mercapto" and "thiol", as used herein, alone or in any combination, refer to a —SH group.

The terms "thio" (synonym "sulfanyl"), "sulfinyl" and "sulfonyl", as used herein, alone or in any combination, refer to a —S(O)$_n$ group with n=0, 1 and 2, respectively.

Within the scope of the present invention, unless indicated otherwise, compounds of Formula I or pharmaceutically acceptable salts thereof are included that may exist in, and be isolated in, isomeric forms, including cis- or trans isomers or mixtures thereof, and tautomers. Other compounds of this invention may contain one or more stereogenic or asymmetric centers, such as one or more asymmetric carbon atoms, and thus may give rise to optically pure enantiomers, mixtures of enantiomers, racemates, enantiomer-pure diastereomers, mixtures of diastereomers, epimers, and other stereoisomeric forms that may be defined, in terms of absolute stereochemistry, as (R)-, (S)- or (R,S)-configured, preferably in the (R)- or (S)-configuration. Such isomers can be obtained by methods within the knowledge of one skilled in the art, e.g. by stereochemically controlled synthesis using chiral synthons or chiral reagents, or by means of classical separation techniques, such as chromatographic or crystallization methods, or by other methods known in the art, such as through formation of diastereomeric salts, for example by salt formation with an enantiomerically pure chiral acid, or by means of chromatography, for example by using chromatographic materials modified with chiral ligands. Furthermore, the present invention refers to compounds containing centers of any geometric asymmetry, like, for example, unsymmetrically substituted olefinic double bond, including E or Z geometric isomers and mixtures thereof. Generally, pure isomers of compounds of Formula I are preferred over isomeric mixtures.

In the present invention, the compounds of Formula I may be used in the form of pharmaceutically acceptable salts. The term "pharmaceutically acceptable salts" refers to relatively nontoxic, inorganic or organic acid and base addition salts, which retain the biological effectiveness and properties of the parent compound, and which are not biologically or otherwise undesirable (see, e.g., Berge et al., J. Pharm. Sci. 1977, 66, 1-19).

Certain compounds of the present invention can contain one or more basic functional groups, such as amino, alkylamino, or arylamino, and, thus, be capable of forming pharmaceutically acceptable acid addition salts. These acid addition salts may be prepared by standard procedures in a suitable solvent from the parent compound of Formula I, with an appropriate amount of an inorganic acid, including, but not limited to, for example, hydrochloric acid, hydrobromic acid, sulfuric acid, or phosphoric acid; or of an organic acid, including, but not limited to, acetic acid, propionic acid, octanoic acid, decanoic acid, glycolic acid, pyruvic acid, oxalic acid, maleic acid, malonic acid, succinic acid, fumaric acid, tartaric acid, citric acid, ascorbic acid, amino acids, such as glutamic acid or aspartic acid, benzoic acid, cinnamic acid, salicylic acid, mandelic acid, methanesulfonic acid, ethanesulfonic acid, p-toluenesulfonic acid, or other acidic organic compounds.

Certain compounds of the present invention may, on the other hand, contain one or more acidic functional groups and, thus, be capable of forming pharmaceutically acceptable base addition salts. These salts can be prepared by addition of an appropriate amount, usually in stoichiometric ratio, of an alkaline reagent, such as hydroxide, carbonate or alkoxide, containing the appropriate cation, to the free acid in a suitable solvent. Preferred inorganic salts include, but are not limited to, ammonium, sodium, potassium, calcium or magnesium, also zinc salts and the like. Preferred salts derived from organic bases include, but are not limited to, salts of primary, secondary, and tertiary amines, substituted amines, cyclic amines, and basic ion exchange resins, such as isopropylamine, trimethylamine, diethylamine, triethylamine, tripropylamine, ethanolamine, lysine, arginine, N-ethylpiperidine, piperidine, polyamine resins, and the like.

Compounds of the present invention containing both acidic and basic groups can also form internal salts (zwitter ions).

For isolation or purification purposes, it is also possible to use pharmaceutically unacceptable salts, for example perchlorates, picolinates, picrates, or the like. For therapeutic use, only pharmaceutically acceptable salts or free compounds are employed, where applicable in the form of pharmaceutical preparations, and these are therefore preferred.

Certain compounds of Formula I, including their salts, may exist in solvated as well as unsolvated forms, such as, for example, hydrated forms, or their crystals may, for example, include the solvent used for crystallization. Different crystalline forms may be present. The present invention encompasses all such solvated and unsolvated forms.

The present invention also relates to prodrug derivatives of the parent compounds of Formula I. The term "prodrug" refers to pharmacologically inactive precursors of a drug that may be converted into its therapeutically active form under physiological conditions in vivo, for example, when they undergo solvolysis, or enzymatic degradation in blood, or in cells (Bundgard H., "Design of Prodrugs", pp. 7-9, 21-24, Elsevier, Amsterdam (1985); Silverman R. B., "The Organic Chemistry of Drug Design and Drug Action", pp. 352-401, Academic Press, San Diego, Calif. (1992); Higuchi T. et al., "Pro-drug as Novel Delivery Systems", A.C.S. Symposium Series, Vol. 14). The term "prodrug" also includes any covalently bonded carriers, which release the active parent compound in vivo when administered to a mammal. Prodrug modifications of a compound often offer advantages of solubility, bioavailability, absorption, tissue compatibility, tissue distribution, or delayed release in the mammalian organism. Prodrugs are variations or derivatives of the compounds of Formula I, which have groups cleavable under metabolic conditions, for example, pharmaceutically acceptable esters, or amides. Such groups can be cleaved enzymatically or non-enzymatically, or hydrolytically to the free hydroxy, carboxy, or amino group of the active parent compound. In another embodiment, the prodrug is a reduced form, which is oxidized in vivo to the therapeutic compound, for example, a thiol, which is oxidized to a sulfonate or sulfate, or an alcohol, which is oxidized to a carboxylic acid.

Further included within the scope of the present invention are pharmaceutically acceptable esters of the compounds of Formula I. The term "pharmaceutically acceptable esters" refers to relatively non-toxic, esterified products of the parent compound. These esters can be prepared in situ during the final isolation and purification of the compounds, or by separately reacting the purified compounds in its free acid or hydroxyl form with a suitable esterifying agent. Carboxylic acids can be converted into esters via treatment with an alcohol in the presence of a catalyst. Hydroxyl containing derivatives can be converted into esters via treatment with an esterifying agent such as alkanoyl halides. The term further includes lower hydrocarbon groups capable of being solvated under physiological conditions, for example, alkyl esters, preferred methyl, ethyl, and propyl esters, methoxymethyl esters, methylthiomethyl esters, pivaloyloxymethyl esters and the like (see, e.g., Berge et al., J. Pharm. Sci. 1977, 66, 1-19).

The compounds of the present invention have useful, in particular pharmacologically useful, properties. They are able to specifically antagonize the effect of endogenous $PGD_2$ on the CRTH2 receptor, and may be used for the prevention and/or treatment of chronic and acute allergic immune disorders comprising allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases comprising Churg-Strauss syndrome and sinusitis, basophil-related diseases, comprising basophilic leukemia and basophilic leukocytosis in humans and other mammals.

A compound or a pharmaceutical composition of the invention may thus be used as a drug (medicine) or therapeutic agent for prevention and/or treatment of both chronic and acute allergic/immune disorders such as those mentioned above, especially allergic asthma, rhinitis, COPD, dermatitis, inflammatory bowel disease, and rheumatoid arthritis.

In another aspect, the compounds of Formula I may be used as standard or reference compounds in tests or assays involving the inhibition of the CRTH2 receptor. Such compounds could be made commercially available for use as a reference, quality standard or control, for example in pharmaceutical research when developing new assays or protocols related to CRTH2 activity.

As mentioned earlier, compounds of Formula I, or salts, or prodrugs thereof, antagonize the $PGD_2$ activation of the CRTH2 receptor. The biological effect of such compounds may be tested in a variety of in vitro, ex vivo and in vivo assays.

The ability of the compounds of Formula I to bind to the CRTH2 receptor may be measured by methods similar to those described in Sawyer N. et al., *Br. J. Pharmacol.*, 2002, 137, 1163-1172 and by the method described below in the experimental part.

With this type of assay, $IC_{50}$ values (i.e. the concentrations where half-maximal inhibition of the interaction is found) in the range of 0.001 to 10 µM, preferably values below 1 µM, in particular values below 0.05 µM, are found with test compounds of Formula I. Exemplary $IC_{50}$ values determined in this test are given below in Table 68.

A functional assay with cells expressing the human CRTH2 receptor may be used to detect changes in the levels of intracellular calcium concentration following compound treatment. After addition of the compound the cells are challenged with $PGD_2$. In a Fluorescent Imaging Plate Reader (FLIPR™, Molecular Devices, Sunnyvale, Calif.) fluorescence emission is recorded during both additions, emission peak values above base level after $PGD_2$ addition were exported, normalized to low controls (no $PGD_2$) and high controls (no active compound). The relative values of the remaining activity were used to determine $IC_{50}$ values by curve fitting the data to a single site to a four-parameter logistic sigmoid dose response curve of the equation $(A+((B-A)/(1+((C/x)^{\wedge}D))))$.

The ability of the compounds to inhibit $PGD_2$ induced change of intracellular calcium levels via CRTH2 activation may be measured by methods known of one skilled in the art or by the method described below in the experimental part.

With this assay, $IC_{50}$ values (i.e. the concentration of a compound at which the remaining activity is 50%) in the range of 0.001 and 10 µM, preferably below 0.5 µM, are obtained with test compounds of Formula I. Exemplary $IC_{50}$ values determined in this test are given below in Table 69.

The results of these assays clearly demonstrate, that the present invention provides functional antagonists of the $PGD_2$ receptor.

On the basis of the biological studies discussed hereinabove, a compound of Formula I according to the invention may show therapeutic efficacy against chronic and acute allergic/immune disorders such as allergic asthma, rhinitis, chronic obstructive pulmonary disease (COPD), dermatitis, inflammatory bowel disease, and rheumatoid arthritis.

A compound of Formula I, a pharmaceutically acceptable salt or a prodrug thereof, can be administered alone in pure form or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of Formula I can besides or in addition be administered especially for prevention and/or treatment of both chronic and acute allergic or immune disorders in combination with other inflammatory diseases. Long-term therapy is equally possible as is adjuvant therapy in the context of other treatment strategies, as described above. Other possible treatments are preventive therapies, for example in patients at risk.

The invention relates also to pharmaceutical compositions comprising compounds of Formula I, to their use in therapeutic, in a broader aspect of the invention also prophylactic treatment or a method of treatment of the diseases mentioned above, to the compounds for said use and to the preparation of pharmaceutical formulations (medicines).

The pharmaceutically acceptable compounds of the present invention may be used, for example, for the preparation of pharmaceutical compositions that comprise an effective amount of the active ingredient together or in admixture with a significant amount of one or more inorganic, organic, solid or liquid, pharmaceutically acceptable carriers.

The invention relates also to a pharmaceutical composition that is suitable for administration to a warm-blooded animal, especially a human (or to cells or cell lines derived from a warm-blooded animal, especially a human, for the treatment or, in a broader aspect of the invention, prevention of (i.e. prophylaxis against) a disease that responds to blockade of the interaction of the CRTH2 receptor with $PGD_2$, comprising an amount of a compound of Formula I or a pharmaceutically acceptable salt or a prodrug thereof, which is effective for said inhibition, together with at least one pharmaceutically acceptable carrier.

The pharmaceutical compositions according to the invention are those for enteral administration, such as nasal, buccal, rectal, dermal or, especially oral administration, and for parenteral administration, such as intramuscular, intravenous or subcutaneous, intrasternal, intravitreal, injection or infusion, to warm-blooded animals, especially humans. Such compositions comprise an effective dose of the pharmaceutically active ingredient, alone or together with a significant amount of a pharmaceutically acceptable carrier. The dosage of the active ingredient depends on the species of warm-blooded animal, the body weight, the age and the individual conditions, individual pharmacokinetic data, the disease to be treated and the mode of administration.

The invention relates also to a process or a method for the treatment of a pathological condition mentioned hereinabove, especially a disease, which responds to blockade of the interaction of the CRTH2 receptor with $PGD_2$, especially allergic asthma, rhinitis, chronic obstructive pulmonary disease (COPD), dermatitis, inflammatory bowel disease, and rheumatoid arthritis. The compounds of Formula I or salts or prodrugs thereof can be administered as such or especially in the form of pharmaceutical compositions.

The dose to be administered to warm-blooded animals, for example humans of approximatively 70 kg body weight, is preferably from approximatively 3 mg to approximatively 30 g, more preferably from approximatively 10 mg to approximatively 1000 mg per person per day, divided preferably into 1 to 3 single doses which may, for example, be of the same size. The amount of the compound actually administered will typically be determined by a physician, in the light of the relevant circumstances, including the condition to be treated, the chosen route of administration, the actual compound administered, the age, the weight, and response of the individual patient, the severity of the patient's symptoms, and the like, for example, children usually receive half of the adults dose.

The pharmaceutical compositions comprise from approximately 1% to approximately 95%, preferably from approximately 20% to approximately 90%, active ingredient. Pharmaceutical compositions according to the invention may be, for example, in unit dosage forms such as coated and uncoated tablets, pills, ampoules, vials, suppositories, dragées, or capsules. Further dosage forms are, for example, ointments, creams, pastes, emulsions, foams, chewable gums, tinctures, lip-sticks, drops, sprays or aerosols, syrups or elixirs, dispersions, transdermal patches or pads, or via an intravitreal device that releases the compound in a sustained capacity, and the like. Examples are capsules containing from about 0.05 g to about 1.0 g active ingredient.

The pharmaceutical compositions of the present invention are prepared in a manner known, per se, for example by means of conventional mixing, granulating, coating, dissolving, lyophilizing or confectioning processes.

Solutions of the active ingredient, and also suspensions, and especially isotonic aqueous solutions or suspensions, are preferably used, it being possible, for example in the case of lyophilized compositions, that comprise the active ingredient alone or together with a carrier, for example mannitol, for such solutions or suspensions to be produced prior to use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving or lyophilizing processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chain fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is mono- or poly-hydroxy, for example a mono-, di- or trihydroxy, alcohol, for example methanol, ethanol, propanol, butanol, or pentanol or the isomers thereof, but especially glycol and glycerol. The following examples of fatty acid esters are therefore to be mentioned: ethyl oleate, isopropyl myristate, isopropyl palmitate, "Labrafil M2375" (polyoxyethylene glycol trioleate, Gattefosse, Paris), "Miglyol 812" (triglyceride of saturated fatty acids with chain length of C8 to C12, Hüls AG, Germany), but especially vegetable oils, such as cottonseed oil, almond oil, olive oil, castor oil, sesame oil, soybean oil and more especially groundnut oil.

The injection or infusion compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for them to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice, or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, and/or carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum Arabic, talc, polyvinylpyrrolidone, polyethylene glycol, and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and of soft sealed capsules made of gelatine and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilizers. In soft capsules the active ingredient is preferably dissolved or suspended in suitable oil excipients, such as fatty oils, paraffin oil or liquid polyethylene glycols, it being possible also for stabilizers and/or antibacterial agents to be added. Dyes or pigments may be added to the tablets or dragée coatings or the capsule casings, for example for identification purposes or to indicate different doses of active ingredient.

For parenteral administration, aqueous solutions of an active ingredient in water-soluble form, for example of a water-soluble salt, or aqueous injection suspensions that contain viscosity-increasing substances and stabilizers, are especially suitable. The active ingredient, optionally together with excipients, can also be in the form of a lyophilizate and be made into a solution before parenteral administration by the addition of solvents.

The novel compounds of Formula I can be manufactured in accordance with the invention by a) hydrolyzing a precursor of the general Formula II

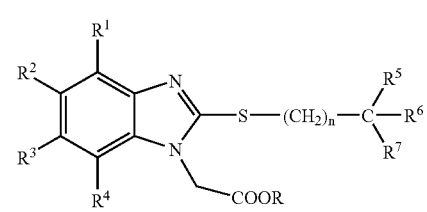

II wherein $R^1$-$R^7$ and n are as in Formula I and R represents an alkyl group, preferably ethyl or tert-butyl, with the exception of:

methyl[2-(5-trifluoromethyl-pyridin-2-ylsulfanyl)-benzoimidazol-1-yl]-acetate;
methyl[2-(4-chloro-benzylsulfanyl)-benzoimidazol-1-yl]-acetate;
methyl (2-benzylsulfanyl-benzoimidazol-1-yl)-acetate;
methyl[2-(5-nitro-pyridin-2-ylsulfanyl)-benzoimidazol-1-yl]-acetate;
methyl (2-methylsulfanyl-benzoimidazol-1-yl)-acetate;
ethyl (2-methylsulfanyl-benzoimidazol-1-yl)-acetate;
methyl (2-ethylsulfanyl-benzoimidazol-1-yl)-acetate;
ethyl[2-(1,3,7-trimethyl-2,6-dioxo-2,3,6,7-tetrahydro-1H-purin-8-ylsulfanyl)-benzoimidazol-1-yl]-acetate;

ethyl{2-[3-methyl-4-(2-morpholin-4-yl-ethylsulfanyl)-pyridin-2-ylmethylsulfanyl]-benzoimidazol-1-yl}-acetate; and methyl{2-[3-methyl-4-(2-morpholin-4-yl-ethylsulfanyl)-pyridin-2-ylmethylsulfanyl]-benzoimidazol-1-yl}-acetate; or b) alkylating a benzoimidazole derivative of the general Formula

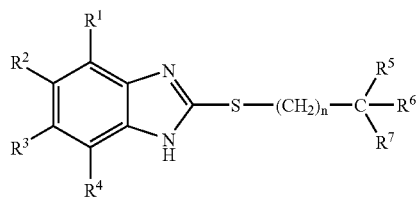

wherein $R^1$-$R^7$ and n are as in Formula I, with a compound of the general Formula

wherein $L^1$ is a leaving group, or c) S-alkylating a mercapto derivative of the general Formula

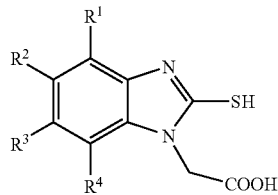

wherein $R^1$-$R^4$ are as in Formula I, with an alkylating agent of the general Formula

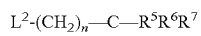

wherein $R^8$-$R^7$ and n are as in Formula I and $L^2$ is a leaving group, and, if desired, converting a compound of Formula I into a pharmaceutically acceptable salt.

Compounds of the invention may be manufactured by the application or adaptation of known methods, by which is meant methods used heretofore or described in the literature, for example those described by Larock R. C. in "Comprehensive organic transformations: a guide to functional group preparations", VCH publishers, 1999.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for example see Greene T. W. and Wuts P. G. M. in "Protective groups in organic synthesis" Wiley-Interscience, 1999.

Generally, a synthesis of 2-sulfanyl-benzoimidazol-1-yl-acetic acid of Formula I starts by alkylating a 2-chlorobenzoimidazole of Formula 1 with a compound of Formula $L^1$-$CH_2CO_2R$, wherein R represents an alkyl group, preferably ethyl or tert-butyl, and $L^1$ is a leaving group, in a suitable polar solvent such as N,N-dimethylformamide, acetone, acetonitrile or the like, in the presence of a base, such as potassium carbonate, cesium carbonate, sodium hydride or the like, to yield an alkyl (2-chloro-benzoimidazol-1-yl)-acetate of Formula 2, as outlined in Scheme 1.

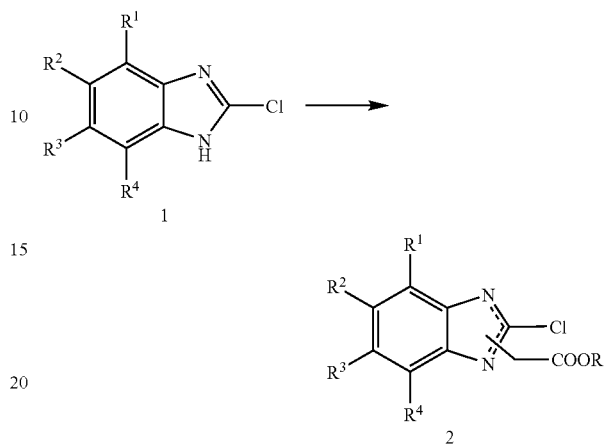

Scheme 1

The dotted lines in Formula 2 indicate that the double bond is in either of the two possible positions; the —$CH_2COOR$ residue is connected to either of the two nitrogen atoms; this is of significance for producing regioisomers, i.e. when $R^1$ and $R^4$, or $R^1$ and $R^3$, are substituents different from each other (cf. below Formulas 2a and 2b).

Suitable is a leaving group $L^1$ such as halo, in particular bromo or chloro. Preferably, a compound of Formula $L^1$-$CH_2CO_2R$ is tert-butyl or ethyl bromoacetate.

Under preferred conditions a solution of a chlorobenzoimidazole of Formula 1 in acetone is stirred with e.g. tert-butyl bromoacetate in presence of potassium carbonate at reflux, or in DMF at room temperature.

It is noteworthy, that under such alkylating conditions an unsymmetrically substituted 2-chlorobenzoimidazole of Formula 1, wherein $R^1$ and $R^4$, or $R^2$ and $R^3$ are different from each other, delivers a mixture of the respective C(4) and C(7), or C(5) and C(6) substituted alkyl (2-chloro-benzoimidazol-1-yl)-acetate regioisomers of Formula 2a and 2b.

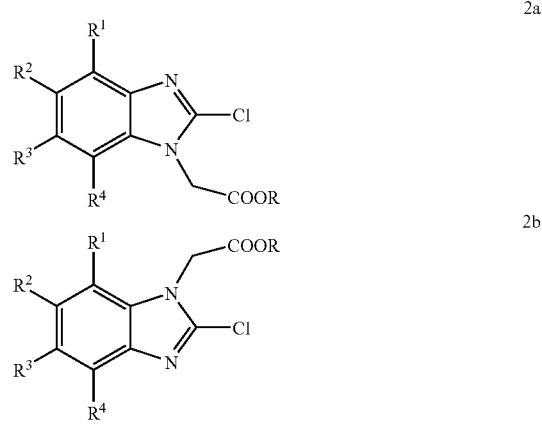

Applying a procedure described by Migawa, M. T. et al., J. Med. Chem. 1998, 41, 1242-1251, an alkyl (2-chloro-benzoimidazol-1-yl)-acetate of Formula 2 is treated with thiourea in a solvent such as methanol or ethanol at reflux, to give an Intermediate of Formula 3.

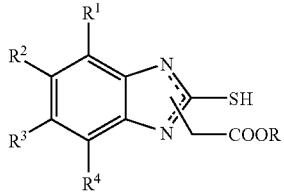

3

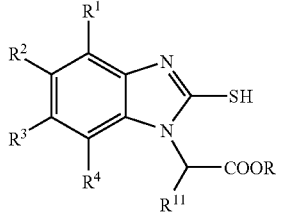

3a

A novel method to regioselectively produce an intermediate of Formula 3a has been developed:

Substituted 1-fluoro-2-nitro-benzene of Formula 12 is converted to a compound of Formula 13.1 by reacting with an amino acid ester in a suitable solvent such as DMSO, EtOH or the like at elevated temperature from 50° C. to 100° C. (McFarlane et al, J. Chem. Soc. Perkin Trans. I 1988, 691-696). Subsequent hydrogenolysis with hydrogen in the presence of a catalyst such as palladium on charcoal in a solvent like tetrahydrofuran leads to a substituted aniline derivative of Formula 13.2, which then is reacted with thiocarbonyle diimidazole to yield Intermediate 3a (Wright, J. L. et al, J. Med. Chem., 2000, 43, 3408-3419; Breslin, H. J. et al, J. Med. Chem. 1995, 38, 771-793).

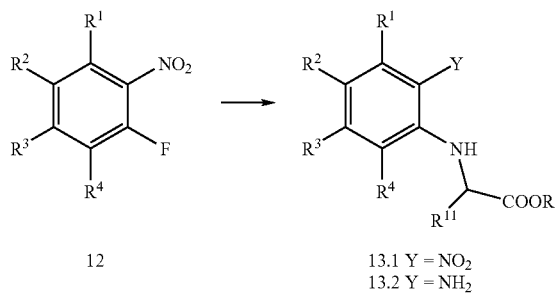

Generally, when a reaction or synthesis involves an Intermediate of Formula 3 and when obtaining the product as only one single regioisomer is wished, then an Intermediate of Formula 3a can be used in place of an Intermediate of Formula 3.

Subsequent S-alkylation of an Intermediate of Formula 3 occurs with a suitable alkylating agent of Formula $L^2$-$(CH_2)_n$—C—$R^5R^6R^7$;

wherein $R^5$, $R^6$, and $R^7$ and n are defined as hereinabove, and $L^2$ is a leaving group such as halo, in particular chloro, bromo, or iodo; alkylsulfonate, or arylsulfonate, such as methylsulfonate, or p-toluenesulfonate;

in a solvent such as N,N-dimethylformamide, acetone, acetonitrile or the like, in the presence of a base such as triethylamine, N,N-diisopropylethylamine, sodium hydroxide, potassium carbonate; affording a Precursor of Formula 4.

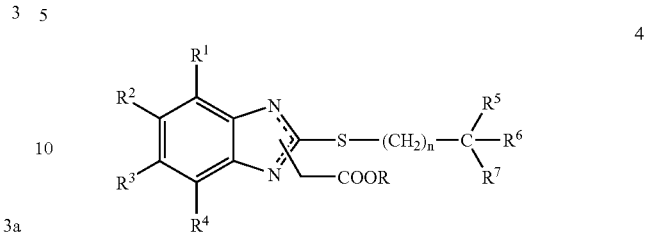

4

Typically, a reagent of Formula $L^2$-$(CH_2)_n$—C—$R^5R^6R^7$ is an optionally substituted alkyl halide, particularly an alkyl chloride, or an alkyl bromide, such as commercially available 2-(2-bromo-ethyl)-isoindole-1,3-dione; (2-bromo-ethyl)-carbamic acid tert-butyl ester; (3-bromo-propyl)-carbamic acid tert-butyl ester; (2-bromo-ethyl)-cyclohexane; 1-bromo-hexane; 1-bromo-pentane; 4-bromo-but-1-ene; 1-bromo-butane; bromo-cyclopentane; (1-bromo-ethyl)-benzene; bromo-phenyl-acetic acid methyl ester; 7-bromo-bicyclo[4.2.0]octa-1(6),2,4-triene; 2-bromo-1-phenyl-propan-1-one; 6-bromo-hexanoic acid ethyl ester; 4-bromo-butyric acid ethyl ester; 5-bromo-pentanoic acid ethyl ester; bromomethyl-benzene; 1-chloromethyl-2-methoxy-benzene; (2-bromo-ethyl)-benzene; (3-bromo-propyl)-benzene; 3,3-diphenyl-propyl bromide; 1-(2-bromo-ethoxy)-4-chloro-benzene; (2-bromo-ethoxy)-benzene; (4-bromo-butoxy)-benzene; (5-bromo-pentyloxy)-benzene; 2-(3-bromo-propyl)-isoindole-1,3-dione; 3-bromomethyl-benzoic acid methyl ester; 5-chloromethyl-furan-2-carboxylic acid ethyl ester; 1-(3-chloromethyl-4-ethoxy-phenyl)-ethanone; or 1-(3-chloromethyl-4-methoxy-phenyl)-ethanone.

More preferred is a reagent of Formula $L^2$-$(CH_2)_n$—C—$R^5R^6R^7$, such as benzyl-(3-chloro propyl)-carbamic acid tert-butyl ester; 5-bromo-pentanoic acid butyl-phenyl-amide; 5-bromo-1-(3,4-dihydro-2H-quinolin-1-yl)-pentan-1-one; 5-bromo-pentanoic acid methyl-phenyl-amide; 1-(2-bromo-ethoxy)-naphthalene; 2-(2-bromo-ethoxy)-naphthalene; 2-(3-chloro-propyl)-2,3-dihydro-isoindol-1-one; 1-(3-chloro-propyl)-1,3-dihydro-benzoimidazol-2-one; 3-(3-chloro-propyl)-1H-quinazoline-2,4-dione; 2-(3-chloro-propyl)-1,1-dioxo-1,2-dihydro-1$\lambda^6$-benzo[d]isothiazol-3-one; 2-bromo-5-bromomethyl-benzoic acid methyl ester; 4-bromo-3-bromomethyl-benzoic acid methyl ester; 3-bromomethyl-4-methoxy-benzoic acid methyl ester; 1-(3-chloromethyl-4-propoxy-phenyl)-ethanone; 1-(3-chloromethyl-4-butoxy-phenyl)-ethanone; (3-chloromethyl-4-methoxy-phenyl)-phenyl-methanone; 2-chloromethyl-oxazole-4-carboxylic acid methyl ester; or 1-(3-bromomethyl-phenyl)-ethanone.

Particularly preferred is a novel alkyl halide of Formula $L^2$-$(CH_2)_n$—C—$R^5R^6R^7$, such as (3-chloro-propyl)-phenethyl-carbamic acid tert-butyl ester; (3-chloro-propyl)-(4-piperidin-1-yl-phenyl)-carbamic acid tert-butyl ester; 4-[tert-butoxycarbonyl-(3-chloro-propyl)-amino]-benzoic acid ethyl ester; (3-chloro-propyl)-cyclopropyl-carbamic acid tert-butyl ester; (3-chloro-propyl)-phenyl-carbamic acid tert-butyl ester; (3-chloro-propyl)-(2,2-diphenyl-ethyl)-carbamic acid tert-butyl ester; (3-chloro-propyl)-phenethyl-carbamic acid butyl ester; benzyl-(3-chloro-propyl)-carbamic acid butyl ester; (3-chloro-propyl)-cyclohexyl-carbamic acid butyl ester; (3-chloro-propyl)-cyclohexylmethyl-carbamic acid butyl ester; 4-[(3-chloro-propyl)-(2-cyclohexyl-2-phenyl-acetyl)-amino]-benzoic acid ethyl ester; pentanoic acid (3-chloro-propyl)-phenethyl-amide; 4-[butoxycarbonyl-(3- chloro-propyl)-amino]-benzoic acid ethyl ester; 5-bromo-pentanoic acid benzyl-phenyl-amide; 5-bromo-pentanoic acid benzyl-methyl-amide; 3-(3-chloro-propoxy)-indazole-1-carboxylic acid ethyl ester; 2-(3-chloro-propyl)-3-oxo-2,3-dihydro-indazole-1-carboxylic acid ethyl ester; 2-(3-chloro-propyl)-2H-phthalazin-1-one; 5-bromomethyl-nicotinic acid methyl ester; 2-bromomethyl-6-chloro-isonicotinic acid methyl ester; 2-bromo-3-bromomethyl-benzoic acid methyl ester; 3-bromo-5-bromomethyl-benzoic acid methyl ester; 3-methoxy-5-chloromethyl-benzoic acid isopropyl ester; 1-[3-chloromethyl-4-(3-hydroxy-propoxy)-phenyl]-etha-none; 7-chloromethyl-6-methoxy-3,4-dihydro-2H-naphtha-len-1-one; and 1-(3-chloromethyl-piperidin-1-yl)-butan-1-one.

Preferred alkyl halides of Formula $L^2$-$(CH_2)_n$—C—$R^5R^6R^7$ are depicted in Formula 5.1 and 5.2. Such compounds can either be prepared and isolated as such, or generated in situ, from a dihaloalkane of Formula $Hal^1$-$(CH_2)_n$-$Hal^2$, wherein $Hal^1$ and $Hal^2$ represent halo, independently selected from chloro, bromo, or iodo; such as 1-chloro-2-iodo-ethane, 1,2-dibromo-ethane, or 1,2-dichloro-ethane; 1-chloro-3-iodo-propane, 1,3-dibromo-propane, or 1,3-dichloropropane; 1-chloro-4-iodo-butane, 1,4-dibromo-butane, or 1,4-dichloro-butane; with a substituted amine of hereinabove defined Formula $HNR^8R^9$, whereby $R^8$ and $R^9$ both are not hydrogen, such as alkylcarbonyl-aryl-amine, alkoxycarbonyl-arylalkyl-amine, alkoxycarbonyl-arylamine, alkoxycarbonyl-cyclylalkyl-amine, alkoxycarbonyl-cycloalkyl-amine, arylalkylcarbonyl-aryl-amine, alkylsulfo-nyl-alkylamine, arylalkylsulfonyl-alkylamine, arylsulfonyl-alkylamine, alkylsulfonyl-cycloalkylamine, arylalkylsulfonyl-cycloalkylamine, arylsulfonyl-cycloalkylamine, alkylsulfonyl-arylalkylamine, arylalkylsulfonyl-arylalkylamine, arylsulfonyl-arylalkylamine, alkylsulfonyl-arylamine, arylalkylsulfonyl-arylamine, arylsulfonyl-arylamine, 1,3-dihydro-benzoimidazol-2-one, 2,3-dihydro-isoindol-1-one, 1,1-dioxo-1,2-dihydro-1$\lambda^6$ benzo[d] isothiazol-3-one, isoindole-1,3-dione, 3-oxo-2,3-dihydro-indazole-1-carboxylic acid ethyl ester, 1H-quinazoline-2,4-dione, 2H-phthalazin-1-one; or with a hydroxy-arene of Formula $HOR^{7'}$, wherein $R^{7'}$ represents a substituted phenyl, naphthyl or heterocyclyl such as indazol-3-yl-1-carboxylic acid ethyl ester; in a polar solvent such as N,N-dimethylfor-mamide, tetrahydrofuran or acetonitrile; in the presence of a base such as sodium hydride, potassium tert-butylate.

A 2-aryloxyethylbromide is obtained by reacting a hydroxyarene with dibromoethane in aqueous sodium hydroxide (Slyn'ko, N. M.; Tormyshev, V. M. Russ. Journal. Org. Chem. 2000, 36(2), 254-257).

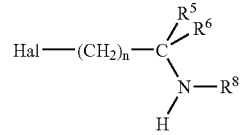

5.3

Alternatively, a primary amine of Formula $H_2NR^8$, wherein $R^8$ represents alkyl, cycloalkyl, cyclylalkyl, or ary-lalkyl, reacts with hereinabove defined dihaloalkane of Formula $Hal^1$-$(CH_2)_n$—$Hal^2$ forming a secondary amine of Formula 5.3, which then is transformed to its respective amide, sulfonamide, carbamate, urethane of Formula 5.1, wherein $R^9$ represents alkenylcarbonyl, alkoxycarbonyl, alkylcar-bamoyl, alkylcarbonyl, alkylsulfonyl, arylalkenylcarbonyl, arylalkylcarbonyl, arylcarbamoyl, arylcarbonyl, arylalkyl-sulfonyl, arylsulfonyl, cycloalkylcarbonyl, or cyclylalkylcar-bonyl (Briner, K. et. al., Bioorg. Med. Chem. 2002, 10, 3649-3661).

Furthermore, an alkylating reagent of Formula $L^2$-$(CH_2)_n$—C—$R^5R^6R^7$ can be obtained through transformation of its respective hydroxy analog of Formula $R^5R^6R^7C$—$(CH_2)_n$—OH, by means of known methods.

Especially preferred alkylating reagents, as depicted in Formula 5.4, 5.5, 5.4bis, are obtained by:

a) halogenation of the methyl group of the benzene and pyridinyl derivatives 6 and 7, respectively, with known methods, e.g. preferably by means of N—X succinim-ide, whereby X represents halogen, such as chloro or bromo, iodo, in a suitable solvent such as tetrachlo-romethane, chloroform or the like (de Meijere, A. et al., Chem. Ber. 1993, 126, 1635-1641).

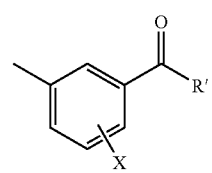

5.4

$L^2$: Hal (Cl, Br, I)
X: Cl, Br, alkoxy, hydroxyalkoxy
R': alkyl, alkoxy

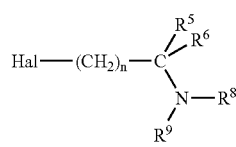

5.1

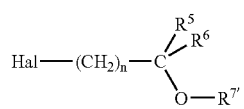

5.2

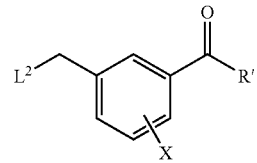

6

X: Cl, Br, alkoxy
R': alkyl, alkoxy

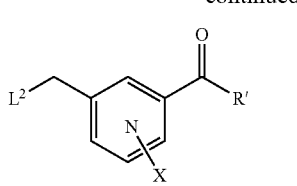

5.5

L²: Hal (Cl, Br, I)
X: Cl, Br
R': alkyl, alkoxy

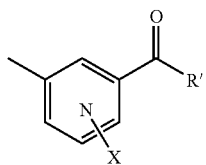

7

X: Cl, Br
R': alkyl, alkoxy b) direct chloromethylation of the benzene derivatives 7bis or of the bicyclic aromatic compounds 7ter with known methods, e.g. preferably by means of methoxyacetyl chloride and aluminium trichloride or a suitable Lewis acid in an polar solvent such as nitromethane, carbon disulfide or the like (McKillop, A.; Madjdabadi, F., A.; Long. D. A. Tetrahedron Lett., 1983, 24, 1933-1936).

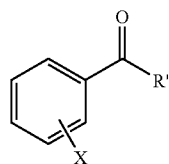

7 bis
X: alkoxy, hydroxyalkyloxy
R': alkyl, aryl, alkoxy

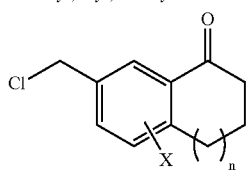

5.4bis
X: alkoxy, hydroxyalkyloxy
n = 0, 1

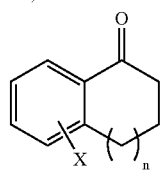

7ter
X: alkoxy, hydroxyalkyloxy
n = 0, 1

In a preferred embodiment, hydroxyalkoxyacetophenone and alkoxyacetophenone 7bis are obtained by alkylation of hydroxyacetophenone with the corresponding hydroxyalkyl or alkyl halide (Mandoli, A. et al Tetrahedron Asymmetry 2003, 14, 3647-3650).

Another preferred alkyl halide of Formula $L^2$-$(CH_2)_n$—C—$R^5R^6R^7$ also comprises a structure of Formula 5.6, wherein $R^{7''}$ represents alkoxy, alkyl-arylamino, arylalkyl-arylamino, or 3,4-dihydro-2H-quinoline. Such compounds are obtained by applying methods known to a skilled person.

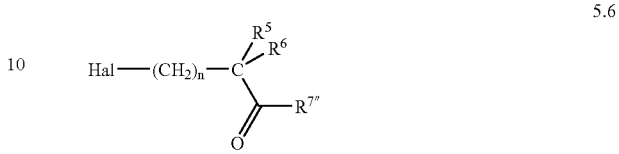

5.6

Under preferred reaction conditions, a solution of an Intermediate of Formula 3 in acetone is heated at reflux with an alkylating agent of Formula $L^2$-$(CH_2)_n$—C—$R^5R^6R^7$ in the presence of a base such as potassium carbonate. In case of $L^2$ representing chloro, or bromo, addition of a catalytic amount of potassium iodide might be beneficial.

Other preferred reaction conditions are those described in:
Yeh, C.-M. and Sun, C.-M. Tetrahedron Lett. 1999, 40, 7247-7250, using alkylbromide in dichloromethane with triethylamine;
Kühler, T. C. et al., J. Med. Chem. 2002, 45, 4282-4299, using benzylchloride in aqueous sodium hydroxide;
Matthews, C. et al., J. Chem. Soc., Dalton Trans., 1996, 1531-1538, using alkylhalides in tetrahydrofuran with N,N-diisopropyl-ethylamine;
Terashima, K. et al., Chem. Pharm. Bull 1995, 43, 1985-1991, using alkylbromides with potassium carbonate in N,N-dimethylformamide;
Ram, S. et al., J. Heterocyclic Chem., 1985, 22, 1269-1274, using alkylbromides with potassium carbonate in ethanol or tetrahydrofuran.

In case $L^2$ in Formula $L^2$-$(CH_2)_n$—C—$R^5R^6R^7$ represents hydroxy, an alternative method can be applied for the alkylation of an Intermediate of Formula 3, following typical Mitsunobu reaction conditions: a compound of Formula 3 reacts with an optionally substituted hydroxyalkyl of Formula $R^5R^6R^7C$—$(CH_2)_n$—OH in the presence of a trialkyl-, or triaryl-phosphane, and a dehydrating agent, such as a dialkyl azodicarboxylate, particularly di-tert-butyl azodicarboxylate, in a suitable solvent, such as toluene, or tetrahydrofurane.

Particularly preferred are hydroxyalkyl of Formula $R^5R^6R^7C$—$(CH_2)_n$—OH, whereby $R^5$ represents hydrogen, $R^6$ and $R^7$ together with the carbon atom to which they are attached form a 4-, 5- or 6-membered heterocyclic ring, containing one nitrogen atom, such as azetidinyl, pyrrolidinyl, or piperidinyl, respectively. Examples are alkylcarbonyl-3-hydroxymethyl-piperidine; alkyloxycarbonyl-3-hydroxymethyl-piperidine, such as tert-butyloxycarbonyl-3-hydroxymethyl-piperidine; arylcarbonyl-3-hydroxymethyl-piperidine; alkylsulfonyl-3-hydroxymethyl-piperidine, arylsulfonyl-3-hydroxymethyl-piperidine, arylalkyloxycarbonyl-3-hydroxymethylazetidine, and arylalkylcarbonyl-2-hydroxymethylazetidine.

An Intermediate of Formula 3 can also be alkylated to yield a compound of Formula 4.1, with a reagent of Formula $L^2$-$(CH_2)_n$—C—$R^5R^6R^7$, wherein either one, e.g. $R^7$, of the substituents $R^5$, $R^6$, or $R^7$, is representing a functional group (FG), opted for further transformations. Such functional groups include carboxy; halo, such as chloro or bromo; hydroxyl; and amino. Preferably, a FG group such as amino is introduced in its protected form using a standard protecting group (PG) such as tert-butoxycarbonyl, benzyloxycarbonyl, or phthaloyl. Prior to further modifications, PG might be removed by means of standard methods.

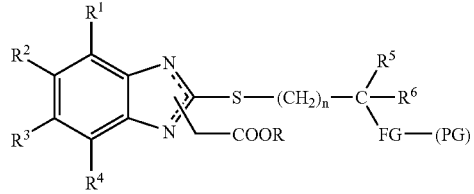

4.1

FG = ——COOH, Cl, Br, I, OH, NH$_2$
PG = protecting group

A compound of Formula 4.1 bearing a FG such as carboxy can be transformed to alkoxycarbonyl, N-alkyl-N-arylalkyl-carbamoyl, N-aryl-N-arylalkyl-carbamoyl, N-alkyl-N-aryl-carbamoyl, by means of methods known to a skilled person.

A FG such as halo can be transformed to aryloxy, heterocyclyloxy; or an amino of hereinabove defined Formula NR$^8$R$^9$, by means of known methods.

A FG such as hydroxy can be converted to aryloxy, heterocyclyloxy; or an amino of hereinabove defined Formula NR$^8$R$^9$, by means of known functional group transformations.

A FG such as amino (NH$_2$) can be converted stepwise to an amino of hereinabove defined Formula NR$^8$R$^9$. Preferred modifications of the nitrogen atom include acylation, alkoxycarbonylation, carbamoylation, or sulfonylation, applying standard conditions.

In a preferred embodiment, R$^5$ in a compound of Formula 4 represents hydrogen, and R$^6$ and R$^7$ are forming a pyrrolidine, or piperidinyl ring, whereby a protecting group (PG) is appended to the pyrrolidinyl, or piperidinyl nitrogen atom, as depicted in Formula 4.2. A standard protecting group (PG), like e.g. tert-butoxycarbonyl, or benzyloxycarbonyl, is removed by means of standard conditions, yielding a compound of Formula 4.3. Subsequently, the nitrogen atom is being further modified with hereinabove defined substituent R$^{10}$, affording a Precursor of Formula 4.4. Preferred modifications of the nitrogen atom include acylation, alkoxycarbonylation, carbamoylation, or sulfonylation, applying standard conditions.

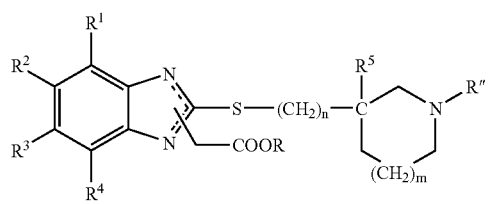

4.2 R″ = PG
4.3 R″ = H
4.4 R″ = R$^{10}$ m = 0, 1

Under the conditions used to remove the protecting group (PG) in a compound of Formula 4.2, the acetic ester group might be hydrolysed, leading to a compound of Formula 4.5. In that case, applying a method described for the conversion of a compound of Formula 4.3 to a compound of Formula 4.4 furnishes directly an example of Formula I-e.

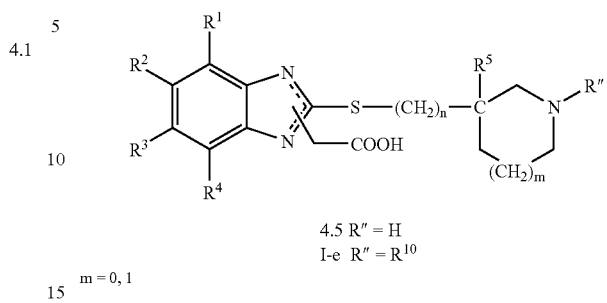

4.5 R″ = H
I-e R″ = R$^{10}$ m = 0, 1

In a preferred embodiment, R$^5$ and R$^6$ in a compound of Formula 4 represent hydrogen and R$^7$ is an aromatic ring bearing two substituents R and X as depicted in Formula 4.6, wherein R′″ corresponds to an alkoxy group and X represents a halogen atom such as bromine; or in Formula 4.8 wherein R′″ represents hydroxy and X represents an alkyloxy group.

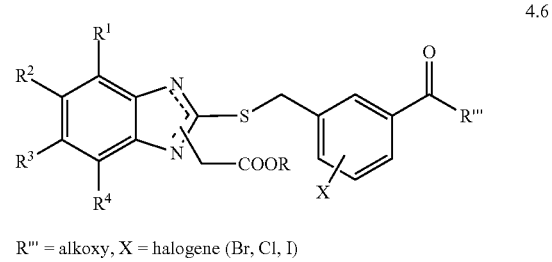

4.6

R′″ = alkoxy, X = halogene (Br, Cl, I)

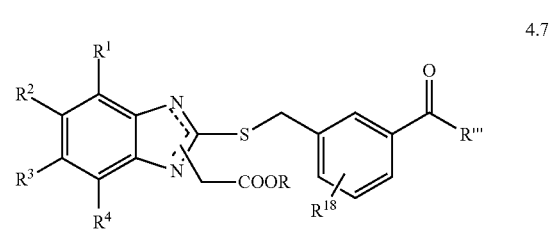

4.7

R′″ = alkoxy, X = R$^{18}$

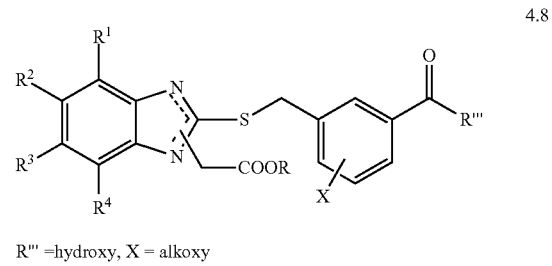

4.8

R′″ = hydroxy, X = alkoxy

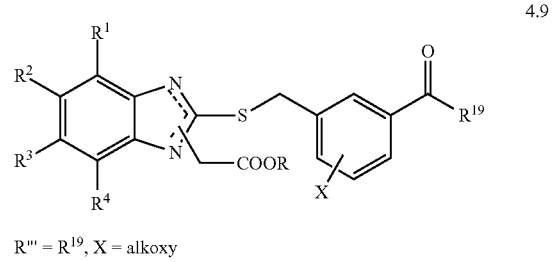

4.9

R′″ = R$^{19}$, X = alkoxy

In the case of a compound of Formula 4.6, the halogen atom can be replaced by a group $R^{18}$ using standard coupling methods known by a person skilled in the art, for example a Suzuki coupling and yielding a compound as depicted in Formula 4.7. Examples are compounds were $R^{18}$ represents an aromatic ring such as a phenyl group.

A compound of Formula 4.8, might be obtained in the typical conditions of a Mitsunobu reaction between an Intermediate of Formula 3 or Formula 3a and a suitable hydroxymethylbenzoic acid. A compound of Formula 4.8 is subsequently modified so that the hydroxy group R''' is replaced by a primary or secondary amine using standard coupling methods such as with HOBt and EDC (N-(3-dimethylaminopropyl)-N'-ethylcarbodiimide) hydrochloride in a DMF/dichloromethane mixture to yield primary or secondary aromatic amides as depicted in Formula 4.9. Examples are compounds wherein $R^{19}$ is an indolino-, butylamino-, morpholino-, benzylamino-, diethylamino- or benzylethylamino-group.

Hydrolysis of the ester group R in a Precursor of Formula 4 can be carried out using routine procedures, as outlined in Scheme 2, for example by means of aqueous lithium hydroxide, or sodium hydroxide in an organic solvent such as tetrahydrofuran, dioxane, methanol, or with trifluoroacetic acid in dichloromethane to give a compound of Formula I-a.

Scheme 2

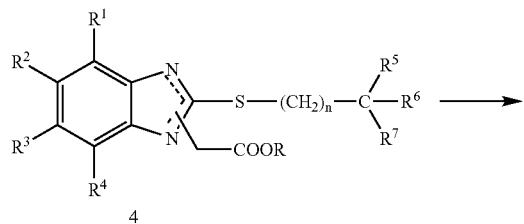

4

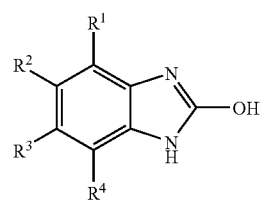

I-a

In a particular case, an example wherein both $R^5$ and $R^6$ represent a hydrogen atom and $R^7$ is an aromatic ring bearing a ketone, as depicted in Formula I-b, can be further modified by a reduction reaction by means of known methods to yield the compound of Formula I-c wherein $R^{20}$ represents hydroxy or alkyloxy. The preferred reaction condition is stirring with sodium borohydride in methanol.

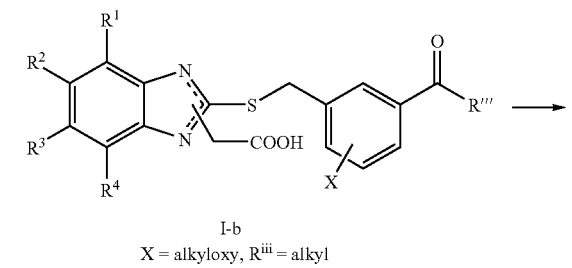

I-b
X = alkyloxy, $R^{iii}$ = alkyl

-continued

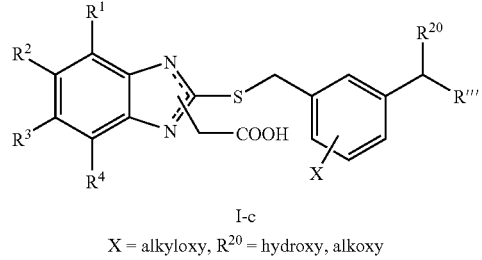

I-c
X = alkyloxy, $R^{20}$ = hydroxy, alkoxy

In a preferred embodiment, a compound of Formula I-a can be further oxidized at the sulphur atom by a method known to a person skilled in the art to yield a sulfoxide as depicted in Formula I-d.

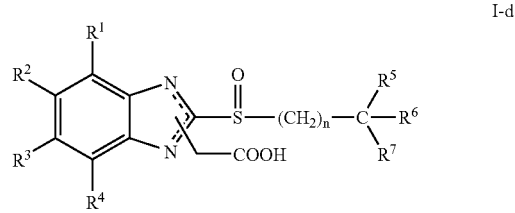

I-d

Starting 2-chlorobenzoimidazole of Formula 1 can be prepared from the corresponding 2-hydroxybenzimidazole of Formula 8 by means of phosphorous oxychloride, either neat or in a suitable solvent (Naef, R.; Balli, H., Helv. Chem. Acta 1978, 61, 2958-2973).

8

2-Chloro-5-nitrobenzimidazole is obtained following a method described in Jung, F.; Delvare, C.; Boucherot, D.; Hamon, A. J. Med. Chem. 1991, 34, 1110-1116.

A Precursor of Formula 4 can also be obtained following a preferred alternative synthetic route, e.g. by changing the sequence of reactions. In a first step, starting 1H-benzoimidazole-2-thiol of Formula 9 can be S-alkylated with hereinabove defined reagent of Formula $L^2\text{-}(CH_2)_n\text{—}C\text{—}R^5R^6R^7$ under aforementioned conditions to yield 2-alkylsulfanyl-1H-benzoimidazole of Formula 10, which then is N-alkylated in a second step with tert-butyl or ethyl bromoacetate to a Precursor of Formula 4. Any further functional group manipulations, as discussed hereinabove for Intermediates 4.1, 4.2, 4.3, and 4.4, are preferably accomplished at this stage, prior to ester hydrolysis to the final compound of Formula I.

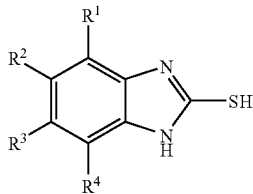
9

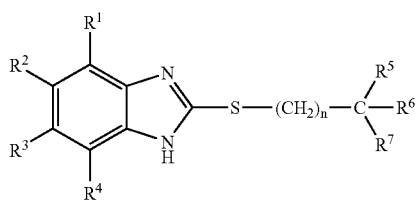
10

Starting 1H-benzoimidazole-2-thiol of Formula 9 is obtained from 1,2-diaminobenzene of Formula 11, with carbon disulfide, thiocarbonyldiimidazole or potassium xanthogenate in a suitable solvent such as dichloromethane; or an alcohol such as methanol, ethanol, propanol; or water; or a mixture of an alcohol and water; in the presence of a base such as potassium hydroxide, sodium hydroxide, at elevated temperature between 50 and 100° C.

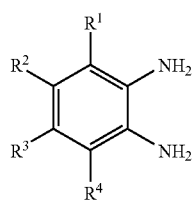
11

Preferred reaction conditions are those described in:

Ikeda, K.; Hata, S.-I.; Tanaka, Y.; Yamamomto, T. OPPI Briefs, 2000, 32, 401-405, using carbondisulfide and potassium hydroxide in a mixture of ethanol and water;

Kühler, T. C.; Fryklund, J.; Bergman, N.-A.; Weilitz, J.; Lee, A.; Larson, H.; J. Med. Chem., 1995, 38, 4906-4916, using potassium ethylxanthogenate in a mixture of ethanol and water;

Ram, S.; Wise, D. S.; Townsend, L. B. J. Heterocyclic Chem., 1985, 22, 1269-1274, using potassium ethylxanthogenate and sodium hydroxide in water;

Wright, J. L.; Gregory, T. F.; Kesten, S. R; Boxer, P. A.; Serpa, K. A.; Meltzer, L. T.; Wise, L. D.; Espitia, S. A.; Konkoy, C. S.; Whittermore, E. R.;

Woodward, R. M.; J. Med. Chem., 2000, 43, 3408-3419 using thiocarbonyldiimidazole in tetrahydrofuran.

EXAMPLES

Temperatures are indicated in degrees Celsius (° C.). Unless otherwise indicated, the reactions are performed at rt.

In mixtures, relations of parts of solvent or eluent or reagent mixtures in liquid form are given as volume relations (v/v), unless indicated otherwise.

Abbreviations and Acronyms Used:

AcOEt: ethyl acetate, AcOH: acetic acid, AIBN: 2,2'-azobisisobutyronitrile, $CDCl_3$: deuterochloroform, $CCl_4$: tetrachlorocarbon, DCE: 1,2-dichloroethane, DBU: 1,8-Diazabicyclo[5.4.0]undec-7-ene, DIPEA: N,N-diisopropylethylamine, DMF: N,N-dimethylformamide, DMSO-$d_6$: deuterated dimethyl sulfoxide, DVB: divinyl benzene, eq.: equivalent, ESI: electon spray inonization, $Et_3N$: triethylamine, $Et_2O$: diethylether, EtOH: ethanol, g: gram, h: hour, HCl: hydrochloric acid, HOBt: 1-hydroxybenzotriazole, HPLC: high-performance liquid chromatography, k: kilo, $KH_2PO_4$: potassium phosphate, $K_2CO_3$: potassium carbonate, l: liter, µ: micro, m: milli, mol: mole, M: molar, MeOH: methanol, Me: methyl, min: minute, $MgSO_4$: magnesium sulfate, MS: mass spectrometry, N: normality of solution, $NaHCO_3$: sodium hydrogencarbonate, $Na_2CO_3$: sodium carbonate, NaOH: sodium hydroxide, $Na_2SO_4$: sodium sulfate, $NH_4Cl$: ammonium chloride, rt: room temperature, $SOCl_2$: thionyl chloride, TFA: trifluoroacetic acid, THF: tetrahydrofuran, $t_R$: retention time.

Instruments and Methods:

HPLC/MS analyses were performed on a Waters 2795 Alliance HPLC instrument, equipped with a Photodiode Array Detector Waters 996 and a Micromass ZQ™ Waters mass spectrometer (electron spray ionization).

Analytical HPLC Conditions:

LC-1: analytical HPLC on an Xterra™ MS $C_{18}$ column (50×2.1 mm, 5 µm, Waters), with a linear gradient of water containing 0.06% formic acid (A) and acetonitrile containing 0.06% formic acid (B), from 5% to 95% B over 6 min; flow rate 0.25 ml/min, column temperature 30° C., detection at 200-400 nm.

LC-2: analytical HPLC on an Xterra™ MS $C_{18}$ column (50×4.6 mm, 5 µm, Waters), with a linear gradient of water containing 0.06% formic acid (A) and acetonitrile containing 0.06% formic acid (B), from 5% to 95% B over 2 min; flow rate 0.75 ml/min, column temperature 30° C., detection at 200-400 nm.

LC-3: analytical HPLC on an Zorbax SB-Aq™ column (50×4.6 mm, 5 µm, Agilent), with a linear gradient of water containing 0.06% formic acid (A) and acetonitrile containing 0.06% formic acid (B), from 5% to 95% B over 1 min; flow rate 3 ml/min, column temperature 30° C., detection at 200-400 nm.

Preparative HPLC Conditions:

Separations and purifications of compounds on a preparative scale are performed on Waters HPLC system, equipped with a Waters 600 controller, a Waters Preparative Xterra™ Prep MS $C_{18}$ column (19×50 mm, 5 µm, a Waters 2767 sample manager, a Waters 996 Photodiode Array Detector, and a Micromass ZQ™ Waters mass spectrometer (electron spray ionization), with a gradient of water containing 0.825% formic acid (A) and acetonitrile containing 0.825% formic acid (B) from 5% to 95% B over 13 min; flow rate 20 ml/min, column temperature 30° C., detection at 200-400 nm.

$^1$H NMR spectra were recorded on a Varian Mercury 300VX FT-NMR spectrometer. Chemical shifts (δ) are reported in parts per million (ppm) downfield by reference to proton resonances resulting from incomplete deuteration of the NMR solvent, e.g. for dimethylsulfoxide δ (H) 2.49 ppm, for chloroform δ (H) 7.24 ppm.

Syntheses of Intermediates of Formula 3:

Intermediate 3-I tert-Butyl-(2-mercapto-benzoimidazol-1-yl)acetate

According to the procedure described in: Migawa, M. T.; Girardet, J.-L.; Walker II, J. A.; Koszalka, G. W.; Chamberlain, S. D.; Drach, J. C.; Townsend, L. B., J. Med. Chem. 1998, 41, 1242-1251, a solution of tert-butyl (2-chloro-benzoimidazol-1-yl)-acetate (Intermediate 2-I, 7 g, 26.3 mmol) and thiourea (7.98 g, 105 mmol) in methanol (100 ml) is refluxed for 2 h. The mixture is cooled down and most of the methanol is removed in vacuo. After addition of saturated aqueous $NH_4Cl$ solution (150 ml), the resulting aqueous phase is extracted three times with $Et_2O$. The combined organic phases are washed with brine and dried over $Na_2SO_4$. The solvent is evaporated in vacuo and the residue dried under high vacuum, yielding the title compound (6.46 g) in 93% as a white powder: $t_R$=6.14 min (LC-1), ESI-MS (neg.): m/z 263.31 [M−H]$^+$; $^1$H-NMR (CDCl$_3$): δ (ppm) 1.50 (s, 9H, tBu), 4.94 (s, 2H, CH$_2$CO$_2$), 6.99-7.05 (m, 1 H$_{arom}$), 7.16-7.24 (m, 1H$_{arom}$), 10.69 (bs, 1H, SH).

Intermediate 3-IIa and Intermediate 3-IIb of the following Table 3 are prepared from a (1:1) mixture of tert-butyl (2-chloro-5-nitro-benzoimidazol-1-yl)-acetate (Intermediate 2-IIa) and its 6-nitro regioisomer (Intermediate 2-IIb) analogous to the procedure described for Intermediate 3-I. They are purified and separated by flash-chromatography on silica-gel (AcOEt/heptane, 1:5).

mixture is filtered through a filter paper and water (100 ml) is added. The resulting aqueous phase is extracted three times with $Et_2O$. The combined organic phases are washed with brine and dried over $MgSO_4$. The solvent is evaporated under reduced pressure yielding the title compound (7.98 g) in 88% as a white powder: $t_R$=2.20 min (LC-2), ESI-MS (pos.): m/z 267.2 [M+H]$^+$; $^1$H-NMR (CDCl$_3$): δ (ppm) 1.48 (s, 9H, tBu), 4.92 (s, 2H, CH$_2$CO$_2$), 7.24-7.40 (m, 3H$_{arom}$), 7.76-7.80 (m, 1H$_{arom}$). Intermediate 2-IIa and 2-IIb tert-Butyl (2-chloro-5-nitro-benzoimidazol-1-yl)-acetate and its 6-nitro regioisomer are prepared according to the same procedure (yield 93%): $t_R$=6.68 min (LC-1), ESI-MS (pos.): m/z 312.08 [M+H]$^+$, 310.28 [M−H]$^+$; $^1$H-NMR (CDCl$_3$): δ (ppm) 1.50 (s, 9H, tBu), 1.52 (s, 9H, tBu), 5.04 and 5.06 (s, 2H, CH$_2$CO$_2$), 7.38 (d, 1H$_{arom}$), 7.86 (d, 1 H$_{arom}$), 8.32-8.40 (m, 3H$_{arom}$), 8.96 (m, 1H$_{arom}$).

Example A-01a

[2-(2-Cyclohexyl-ethylsulfanyl)-benzoimidazol-1-yl]-acetic acid

A solution of tert-butyl[2-(2-cyclohexyl-ethylsulfanyl)-benzoimidazol-1-yl]-acetate (Precursor A-01b, 42 mg, 0.13 mmol) in TFA/dichloromethane (1:1, 0.5 ml) is stirred at rt for 4 h. The solvents are removed in vacuo. The crude residue is sonicated in $Et_2O$/heptane (1:1, 1 ml) until a solid precipitates. It is rinsed with heptane and purified by flash chromatography on silica gel (AcOEt/heptane, 1:1 containing 1% of AcOH), yielding the title compound (12 mg) in 30% as a white solid: $t_R$=6.44 min (LC-1), ESI-MS (pos.): m/z 319.12

TABLE 3

| Intermediate | Name | Formula Mol weight | $t_R$ [min] (Meth.) | MS Data m/z [M + H]$^+$ | MS Data m/z [M − H]$^+$ |
|---|---|---|---|---|---|
| 3-IIa | tert-Butyl (2-mercapto-5-nitro-benzoimidazol-1-yl)-acetate | C13H15N3O4S 309.34 | 2.16 (LC-2) | n/a | 308.32 |
| 3-IIb | tert-Butyl (2-mercapto-6-nitro-benzoimidazol-1-yl)-acetate | C13H15N3O4S 309.34 | 2.16 (LC-2) | n/a | 308.32 |

Syntheses of Intermediates of Formula 2:

Intermediate 2-I tert-Butyl (2-chloro-benzoimidazol-1-yl)-acetate

In a round bottomed flask are added $K_2CO_3$ (9.34 g, 67.7 mmol), 2-chlorobenzimidazole (5.16 g, 33.8 mmol) and tert-butyl bromoacetate (6.6 g, 5 ml, 33.8 mmol) in acetone (100 ml). The resulting suspension is refluxed for 1 h. The crude

[M+H]$^+$, ESI-MS (neg.): m/z 317.37 [M−H]$^+$; $^1$H-NMR (CDCl$_3$): δ (ppm) 0.82-0.94 (m, 2H), 1.09-1.23 (m, 3H), 1.37 (m, 1H), 1.54 (q, 2H, SCH$_2$CH$_2$), 1.68 (m, 5H), 3.34 (t, 2H, SCH$_2$), 4.88 (s, 2H, CH$_2$CO$_2$), 7.22 (s, 3H$_{arom}$), 7.65 (m, 1H$_{arom}$).

Examples A-02a to A-05a of the following Table 1 are prepared analogous to the procedure described for Example A-01a, using Precursors A-02b to A-05b in place of A-01b.

TABLE 1

| Example | Name | Formula Mol weight | $t_R$ [min] (Meth.) | MS Data m/z [M + H]$^+$ | MS Data m/z [M − H]$^{+-}$ |
|---|---|---|---|---|---|
| A-02a | (2-Hexylsulfanyl-benzoimidazol-1-yl)-acetic acid | C15H20N2O2S 292.402 | 6.02 (LC-1) | 293.27 | 291.35 |
| A-03a | (2-Pentylsulfanyl-benzoimidazol-1-yl)-acetic acid | C14H18N2O2S 278.375 | 5.55 (LC-1) | 279.08 | 277.31 |
| A-04a | (2-But-3-enylsulfanyl-benzoimidazol-1-yl)-acetic acid | C13H14N2O2S 262.332 | 4.69 (LC-1) | 263.1 | 261.28 |
| A-05a | (2-Butylsulfanyl-benzoimidazol-1-yl)-acetic acid | C13H16N2O2S 264.348 | 4.9 (LC-1) | 265.28 | 263.23 |

Precursor A-01b tert-Butyl[2-(2-cyclohexyl-ethylsulfanyl)-benzoimidazol-1-yl]-acetate To a suspension of tert-butyl (2-mercapto-benzoimidazol-1-yl)-acetate (Intermediate 3-I, 53 mg, 0.2 mmol) and K$_2$CO$_3$ (41.4 mg, 0.4 mmol) in acetone (0.8 ml) is added 2-cyclohexylethyl bromide (28.8 mg, 22.6 µl). The reaction mixture is kept stirring at reflux for 5 h then filtered on a short plug of silica gel. The solvents are evaporated and the crude is purified by preparative HPLC yielding the title compound in 60% as a colourless oil: $t_R$=7.39 min (LC-1), ESI-MS (pos.): m/z 321.36 [M+H]$^+$; $^1$H NMR (CDCl$_3$): δ (ppm) 0.80-0.91 (m, 2H), 1.04-1.23 (m, 3H), 1.35 (s, 9H, tBu), 1.35 (m, 1H), 1.54-1.72 (m, 6H), 1.83 (br. s, 1H), 3.32 (t, 2H, SCH$_2$), 4.65 (s, 2H, CH$_2$CO$_2$), 7.07-7.17 (m, 3H$_{arom}$), 7.61 (m, 1H$_{arom}$).

Precursors A-02b to A-05b of the following Table 2 are prepared using a procedure analogous to that described for Precursor A-01b, substituting the appropriate alkyl halide for 2-cyclohexylethyl bromide.

TABLE 2

| Precursor | Name | Formula Mol weight | $t_R$ [min] (Meth.) | MS Data m/z [M + H]$^+$ |
|---|---|---|---|---|
| A-02b | tert-Butyl (2-hexylsulfanyl-benzoimidazol-1-yl)-acetate | C19H28N2O2S 348.51 | 7.99 (LC-1) | 349.41 |
| A-03b | tert-Butyl (2-pentylsulfanyl-benzoimidazol-1-yl)-acetate | C18H26N2O2S 334.48 | 7.63 (LC-1) | 335.35 |
| A-04b | tert-Butyl (2-but-3-enylsulfanyl-benzoimidazol-1-yl)-acetate | C17H22N2O2S 318.44 | 7.04 (LC-1) | 319.33 |
| A-05b | tert-Butyl (2-butylsulfanyl-benzoimidazol-1-yl)-acetate | C17H24N2O2S 320.46 | 7.39 (LC-1) | 321.36 |

Example B-01a rac[2-(1-Phenyl-ethylsulfanyl)-benzoimidazol-1-yl]-acetic acid

A solution of rac tert-butyl[2-(1-phenyl-ethylsulfanyl)-benzoimidazol-1-yl]-acetate
(Precursor B-01b, 46.5 mg, 0.13 mmol) is dissolved in TFA/dichloromethane (1:1, 4.0 ml) and stirred at rt for 3 h. The volatiles are removed in vacuo and the residue is dried under high vacuum, affording the title compound (26.7 mg) as a yellow oil in 67% yield: $t_R$=5.50 min (LC-1), MS (pos.): m/z 313.03 [M+H]$^+$, MS (neg.): m/z 311.16 [M−H]$^+$; $^1$H NMR (DMSO-d$_6$): δ (ppm) 1.72 (d, 2H, CHCH$_3$), 4.76 (s, 2H, CH$_2$CO$_2$), 5.03 (m, 2H, SCH$_2$), 7.10 (m, 2H$_{arom}$), 7.23-7.32 (m, 3H$_{arom}$), 7.36 (m, 3H$_{arom}$), 7.54 (m, 1H$_{arom}$).

Examples B-02a to B-05a of the following Table 4 are prepared analogous to the procedure described for Example B-01a, using Precursors B-02b to B-05b in place of B-01b.

TABLE 4

| Example | Name | Formula Mol weight | $t_R$ [min] (Meth.) | MS Data m/z [M + H]$^+$ | MS Data m/z [M − H]$^+$ |
|---|---|---|---|---|---|
| B-02a | (2-Cyclopentylsulfanyl-benzoimidazol-1-yl)-acetic acid | C14H16N2O2S 276.359 | 4.7 (LC-1) | n/a | 275.19 |
| B-03a | rac [2-(1-Methyloxycarbonyl-1-phenyl-methylsulfanyl)-benzoimidazol-1-yl]-acetic acid | C18H16N2O4S 356.401 | 5.79 (LC-1) | 356.99 | 355.13 |
| B-04a | rac [2-(Bicyclo[4.2.0]octa-1,3,5-trien-7-ylsulfanyl)-benzoimidazol-1-yl]-acetic acid | C17H14N2O2S 310.376 | 5.65 (LC-1) | 312.34 | 309.14 |

TABLE 4-continued

| Example | Name | Formula Mol weight | $t_R$ [min] (Meth.) | MS Data m/z [M + H]$^+$ | MS Data m/z [M − H]$^+$ |
|---|---|---|---|---|---|
| B-05a | rac [2-(1-Methyl-2-oxo-2-phenyl-ethylsulfanyl)-benzoimidazol-1-yl]-acetic acid | C18H16N2O3S 340.402 | 5.7 (LC-1) | n/a | 339.15 |

Precursor B-01b tert-Butyl[2-(1-phenyl-ethylsulfanyl)-benzoimidazol-1-yl]-acetate A mixture of tert-butyl (2-mercapto-benzoimidazol-1-yl)-acetate (Intermediate 3-I, 50 mg, 0.19 mmol), 1-bromomethyl-benzene (38.5 mg, 28.5 μl, 0.2 mmol) and K$_2$CO$_3$ (52 mg, 0.38 mmol) in acetone (3 ml) is stirred at reflux overnight. The suspension is cooled to rt and filtered through Celite. Evaporation of the solvent in vacuo and drying under high vacuum yields quantitatively the title compound as a slightly yellow oil. This material is used in the next step without further purification. $t_R$=7.45 min (LC-1), MS (pos.): m/z 369.21 [M+H]$^+$; $^1$H-NMR (DMSO-d$_6$): δ (ppm) 1.36 (s, 9H, tBu), 1.73 (d, 3H, Me), 4.94 (m, 2H, CH$_2$CO$_2$), 5.09 (q, 1H, SCHMePH), 7.16-7.20 (m, 2H$_{arom}$), 7.26-7.36 (m, 3H$_{arom}$), 7.44-7.50 (m, 3H$_{arom}$), 7.61 (m, 1H$_{arom}$).

Precursors B-02b to B-05b of the following Table 5 are prepared using a procedure analogous to that described for Precursor B-01b, substituting the appropriate alkyl halide for 1-bromomethyl-benzene.

Example C-01a

[2-(2-Methoxy-benzylsulfanyl)-benzoimidazol-1-yl]-acetic acid

A solution of tert-butyl[2-(2-methoxy-benzylsulfanyl)-benzoimidazol-1-yl]-acetate (Precursor C-01b, 20 mg, 0.05 mmol) is stirred in TFA/dichloromethane (1:1, 4.0 ml) at rt overnight. The volatiles are removed in vacuo and the residue is dried under high vacuum, yielding the title compound (16.0 mg) in 94% as a white solid: $t_R$=5.27 min (LC-1), MS (pos.): m/z 329.22 [M+H]$^+$, MS (neg.): m/z 327.20 [M−H]$^+$; $^1$H-NMR (DMSO-d$_6$): δ (ppm) 3.82 (s, 3H, OCH$_3$), 4.51 (s, 2H, SCH$_2$), 4.92 (s, 2H, CH$_2$CO$_2$), 6.89 (t, 1H$_{arom}$), 7.04 (d, 1H$_{arom}$), 7.18 (m, 2H$_{arom}$), 7.30 (t, 1H$_{arom}$), 7.40 (d, 1H$_{arom}$), 7.50 (m, 1H$_{arom}$), 7.61 (m, 1H$_{arom}$).

Examples C-02a to C-05a of the following Table 6 are prepared analogous to the procedure described for Example C-01a, using Precursors C-02b to C-05b in place of C-01b.

TABLE 5

| Precursor | Name | Formula Mol weight | $t_R$ [min] (Meth.) | MS Data m/z [M + H]$^+$ | MS Data m/z [M − H]$^-$ |
|---|---|---|---|---|---|
| B-02b | tert-Butyl (2-cyclopentylsulfanyl-benzoimidazol-1-yl)-acetate | C18H24N2O2S 332.46 | 7.24 (LC-1) | 333.18 | n/a |
| B-03b | rac tert-Butyl [2-(1-methyloxycarbonyl-1-phenyl-methylsulfanyl)-benzoimidazol-1-yl]-acetate | C22H24N2O4S 412.5 | 7.25 (LC-1) | 413.16 | 411.19 |
| B-04b | tert-Butyl [2-(bicyclo[4.2.0]octa-1,3,5-trien-7-ylsulfanyl)-benzoimidazol-1-yl]-acetate | C21H22N2O2S 366.48 | 7.51 (LC-1) | 367.14 | n/a |
| B-05b | tert-Butyl [2-(1-methyl-2-oxo-2-phenyl-ethylsulfanyl)-benzoimidazol-1-yl]-acetate | C22H24N2O3S 396.5 | 7.39 (LC-1) | 397.13 | 395.23 |

TABLE 6

| Example | Name | Formula Mol weight | $t_R$ [min] (Meth.) | MS Data m/z [M + H]$^+$ | MS Data m/z [M − H]$^+$ |
|---|---|---|---|---|---|
| C-02a | (2-Benzylsulfanyl-benzoimidazol-1-yl)-acetic acid | C16H14N2O2S 298.365 | 5.37 (LC-1) | 299.21 | 297.22 |
| C-03a | (2-Phenethylsulfanyl-benzoimidazol-1-yl)-acetic acid | C17H16N2O2S 312.392 | 5.51 (LC-1) | 313.09 | 311.22 |
| C-04a | [2-(3-Phenyl-propylsulfanyl)-benzoimidazol-1-yl]-acetic acid | C18H18N2O2S 326.419 | 5.9 (LC-1) | 327.06 | 325.26 |
| C-05a | [2-(3,3-Diphenyl-propylsulfanyl)-benzoimidazol-1-yl]-acetic acid | C24H22N2O2S 402.517 | 6.7 (LC-1) | 403.2 | 401.26 |

Precursor C-01b tert-Butyl[2-(2-methoxy-benzylsulfanyl)-benzoimidazol-1-yl]-acetate A suspension of K$_2$CO$_3$ (31.4 mg, 0.23 mmol) in acetone (3 ml) containing tert-butyl (2-mercapto-benzoimidazol-1-yl)-acetate (Intermediate 3-I, 30 mg, 0.11 mmol) and 2-methoxybenzyl chloride (17.8 mg, 15.8 µl, 0.11 mmol) is stirred at rt overnight. Filtration over Celite and evaporation of the solvent in vacuo affords the pure title compound (27 mg) in 62% yield as a yellow oil: $t_R$=7.47 min (LC-1), MS (pos.): m/z 385.20 [M+H]$^+$; $^1$H NMR (DMSO-d$_6$): δ (ppm) 1.37 (s, 9H, tBu), 3.90 (s, 3H, OCH$_3$), 4.53 (s, 2H, SCH$_2$), 4.92 (s, 2H, CH$_2$CO$_2$), 6.87 (t, 1H$_{arom}$), 7.03 (d, 1H$_{arom}$), 7.21 (m, 2H$_{arom}$), 7.28 (t, 1H$_{arom}$), 7.40 (d, 1H$_{arom}$), 7.50 (m, 1H$_{arom}$), 7.64 (m, 1H$_{arom}$).

Precursors C-02b to C-05b of the following Table 7 are prepared using a procedure analogous to that described for Precursor C-01b, substituting the appropriate benzyl halide for 2-methoxybenzyl chloride.

Example D-01a

{2-[2-(4-Chloro-phenoxy)-ethylsulfanyl]-benzoimidazol-1-yl}-acetic acid

A solution tert-butyl{2-[2-(4-chloro-phenoxy)-ethylsulfanyl]-benzoimidazol-1-yl}-acetate (Precursor D-01b, 33 mg, 0.79 mmol) is stirred in TFA/dichloromethane (1:1, 0.8 ml) at rt for 3 h. The volatiles are removed in vacuo and the residue is purified by flash-chromatography on silica gel (AcOEt/heptane, 1:1; then pure AcOEt), yielding the title compound (27 mg) in 95% as a white solid: $t_R$=5.73 min (LC-1), MS (pos.): m/z 362.8 [M+H]$^+$, MS (neg.): m/z 360.8 [M−H]$^+$; $^1$H-NMR (CDCl$_3$): δ (ppm) 3.88 (m, 2H, SCH$_2$), 4.22 (t, 2H, OCH$_2$), 4.88 (s, 2H, CH$_2$CO$_2$), 6.54 (d, 2H, H$_{arom}$), 7.12 (d, 2 H$_{arom}$), 7.32-7.46 (m, 3H$_{arom}$), 7.82 (m, 1H$_{arom}$).

Examples D-02a to D-07a of the following Table 8 are prepared analogous to the procedure described for Example D-01a, using Precursors D-02b to D-07b in place of D-01b.

TABLE 7

| Precursor | Name | Formula Mol weight | $t_R$ [min] (Meth.) | MS Data m/z [M + H]$^+$ |
|---|---|---|---|---|
| C-02b | tert-Butyl (2-benzylsulfanyl-benzoimidazol-1-yl)-acetate | C20H22N2O2S 354.47 | 7.27 (LC-1) | 355.36 |
| C-03b | tert-Butyl (2-phenethylsulfanyl-benzoimidazol-1-yl)-acetate | C21H24N2O2S 368.5 | 7.46 (LC-1) | 369.35 |
| C-04b | tert-Butyl [2-(3-phenyl-propylsulfanyl)-benzoimidazol-1-yl]-acetate | C22H26N2O2S 382.52 | 2.62 (LC-2) | 383.31 |
| C-05b | tert-Butyl [2-(3,3-diphenyl-propylsulfanyl)-benzoimidazol-1-yl]-acetate | C28H30N2O2S 458.62 | 8.17 (LC-1) | 459.42 |

TABLE 8

| Example | Name | Formula Mol weight | $t_R$ [min] (Meth.) | MS Data m/z [M + H]+ | MS Data m/z [M − H]+ |
|---|---|---|---|---|---|
| D-02a | [2-(2-Phenoxy-ethylsulfanyl)-benzoimidazol-1-yl]-acetic acid | C17H16N2O3S 328.392 | 5.68 (LC-1) | 329.23 | 327.24 |
| D-03a | {2-[2-(Naphthalen-1-yloxy)-ethylsulfanyl]-benzoimidazol-1-yl}-acetic acid | C21H18N2O3S 378.451 | 6.39 (LC-1) | 379.26 | 377.34 |
| D-04a | {2-[2-(Naphthalen-2-yloxy)-ethylsulfanyl]-benzoimidazol-1-yl}-acetic acid | C21H18N2O3S 378.451 | 6.43 (LC-1) | 379.26 | 377.28 |
| D-05a | [2-(3-Phenoxy-propylsulfanyl)-benzoimidazol-1-yl]-acetic acid | C18H18N2O3S 342.418 | 5.81 (LC-1) | 343.27 | 341.22 |
| D-06a | (2-{3-[(1-Ethyloxycarbonyl-indazol-3-yl)-oxy]-propylsulfanyl}-benzoimidazol-1-yl)-acetic acid | C22H22N4O5S 454.506 | 2.44 (LC-2) | 453.26 | 455.11 |
| D-07a | [2-(4-Phenoxy-butylsulfanyl)-benzoimidazol-1-yl]-acetic acid | C19H20N2O3S 356.445 | 6.02 (LC-1) | 357.19 | 355.21 |

Precursor D-02b tert-Butyl[2-(2-phenoxy-ethylsulfanyl)-benzoimidazol-1-yl]-acetate A mixture of tert-butyl (2-mercapto-benzoimidazol-1-yl)-acetate (Intermediate 3-I, 53 mg, 0.2 mmol), 1-(2-bromo-ethoxy)-benzene (48.3 mg, 0.22 mmol) and K$_2$CO$_3$ (41.4 mg, 0.3 mmol) in acetone (0.8 ml) is refluxed for 3 h. The suspension is cooled to rt and filtered through a short pad of silica-gel. The volatiles are removed in vacuo and the residue is dried under high vacuum affording the title compound as a colourless oil. This material was used in the next step without further purification: $t_R$=2.55 min (LC-2), MS (pos.): m/z 385.2 [M+H]+; $^1$H NMR (CDCl$_3$): δ (ppm) 1.48 (s, 9H, tBu), 3.96 (m, 2H, SCH$_2$), 4.48 (t, 2H, OCH$_2$), 4.90 (s, 2H, CH$_2$CO$_2$), 6.90 (d, 2H$_{arom}$), 7.24-7.38 (m, 5H$_{arom}$), 7.86 (m, 1H$_{arom}$).

Precursors D-01b to D-07b of the following Table 9 are prepared using a procedure analogous to that described for Precursor D-02b, substituting the appropriate aryloxyalkylbromide or heterocyclyloxyalkylbromide for (2-bromo-ethoxy)-benzene.

TABLE 9

| Precursor | Name | Formula Mol weight | $t_R$ [min] (Meth.) | MS Data m/z [M + H]+ |
|---|---|---|---|---|
| D-01b | tert-Butyl {2-[2-(4-chloro-phenoxy)-ethylsulfanyl]-benzoimidazol-1-yl}-acetate | C21H24N2O3S 384.49 | 7.25 (LC-1) | 418.66 |
| D-03b | tert-Butyl {2-[2-(naphthalen-1-yloxy)-ethylsulfanyl]-benzoimidazol-1-yl}-acetate | C25H26N2O3S 434.558 | 7.99 (LC-1) | 435.34 |
| D-04b | tert-Butyl {2-[2-(naphthalen-2-yloxy)-ethylsulfanyl]-benzoimidazol-1-yl}-acetate | C25H26N2O3S 434.56 | 7.94 (LC-1) | 435.34 |
| D-05b | tert-Butyl [2-(4-phenoxy-butylsulfanyl)-benzoimidazol-1-yl]-acetate | C23H28N2O3S 412.55 | 2.63 (LC-2) | 413.35 |
| D-06b | tert-Butyl (2-{3-[(1-ethyloxycarbonyl-indazol-3-yl)-oxy]-propylsulfanyl}-benzoimidazol-1-yl)-acetate | C26H30N4O5S 510.61 | 2.94 (LC-2) | 511.24 |
| D-07b | tert-Butyl [2-(4-phenoxy-butylsulfanyl)-benzoimidazol-1-yl]-acetate | C23H28N2O3S 412.55 | 7.68 (LC-1) | 413.37 |

Preparation of 3-(3-chloro-propoxy)-indazole-1-carboxylic acid ethyl ester (alkylating agent D-06-d) is described in the paragraph relating the preparation of 2-(3-chloro-propyl)-3-oxo-2,3-dihydro-indazole-1-carboxylic acid ethyl ester (alkylating agent G-01d).

Example E-01a

[2-(5-Ethyloxycarbonyl-pentylsulfanyl)-benzoimidazol-1-yl]-acetic acid

A solution of tert-butyl[2-(5-ethyloxycarbonyl-pentylsulfanyl)-benzoimidazol-1-yl]-acetate (Precursor E-01b, 44 mg, 0.11 mmol) in TFA/dichloromethane (1:1, 2 ml) is stirred at rt for 3 h. The solvents are removed under a stream of air. The solid residue is suspended in $Et_2O$ (2 ml) and sonicated. Filtration, rinsing with $Et_2O$ and drying under high vacuum yields the title compound (32 mg) as a white solid in 85% yield: $t_R$=5.33 min (LC-1), ESI-MS (pos.): m/z 351.07 $[M+H]^+$, ESI-MS (neg.): m/z 349.22 $[M-H]^+$; $^1$H-NMR ($CDCl_3$): δ (ppm) 1.25 (t, 3H $CH_3$), 1.44 (s, 9H, tBu), 1.32-1.44 (m, 2H), 1.52-1.70 (m, 4H), 2.24 (t, 2H, $CH_2C$=O), 3.24 (t, 2H, $SCH_2$), 4.10 (q, 2H, $OCH_2$), 4.15 (br. s, 1H, $CO_2H$), 4.86 (s, 2H, $CH_2CO_2$), 7.24 (s, $3H_{arom}$), 7.63 (m, $1H_{arom}$).

Examples E-02a to E-03a of the following Table 10 are prepared analogous to the procedure described for Example E-01a, using Precursors E-02b and E-03b in place of E-01b.

Precursors E-02b to E-03b of the following Table 11 are prepared using a procedure analogous to that described for Precursor E-01b, substituting the appropriate alkyl bromide for 6-bromo-hexanoic acid ethyl ester.

TABLE 11

| Precursor | Name | Formula Mol weight | $t_R$ [min] (Meth.) | MS Data m/z $[M + H]^+$ |
|---|---|---|---|---|
| E-02b | tert-Butyl [2-(3-ethyloxycarbonyl-propylsulfanyl)-benzoimidazol-1-yl]-acetate | C19H26N2O4S 378.49 | 2.34 (LC-2) | 379.36 |
| E-03b | tert-Butyl [2-(4-ethyloxycarbonyl-butylsulfanyl)-benzoimidazol-1-yl]-acetate | C20H28N2O4S 392.51 | 7.04 (LC-1) | 393.35 |

TABLE 10

| Example | Name | Formula Mol weight | $t_R$ [min] (Meth.) | MS Data m/z $[M + H]^+$ | MS Data m/z $[M - H]^+$ |
|---|---|---|---|---|---|
| E-02a | [2-(3-Ethyloxycarbonyl-propylsulfanyl)-benzoimidazol-1-yl]-acetic acid | C15H18N2O4S 322.384 | 4.87 (LC-1) | 323.25 | 321.22 |
| E-03a | [2-(4-Ethyloxycarbonyl-butylsulfanyl)-benzoimidazol-1-yl]-acetic acid | C16H20N2O4S 336.411 | 5.09 (LC-1) | 337.12 | 335.31 |

Precursor E-01b tert-Butyl[2-(5-ethyloxycarbonyl-pentylsulfanyl)-benzoimidazol-1-yl]-acetate A mixture of tert-butyl (2-mercapto-benzoimidazol-1-yl)-acetate (Intermediate 3-I, 52 mg, 0.2 mmol), 6-bromo-hexanoic acid ethyl ester (49 mg, 39 µl, 0.22 mmol) and $K_2CO_3$ (55 mg, 0.4 mmol) is refluxed in acetone (2 ml) for 5 h and stirred at rt overnight. Evaporation of the solvent in vacuo affords a residue that is purified by flash-chromatography on silica-gel (AcOEt/heptane, 25:75), yielding the title compound (55 mg) in 68% as a colourless oil: $t_R$=7.24 min (LC-1), ESI-MS (pos.): m/z 407.23 $[M+H]^+$, ESI-MS (neg.) 405.22 $[M-H]^+$; $^1$H-NMR ($CDCl_3$): δ (ppm) 1.25 (t, 3H $CH_3$), 1.44 (s, 9H, tBu), 1.48 (m, 2H), 1.66 (quint., 2H), 1.79 (quint., 2H), 2.30 (t, 2H, $CH_2C$=O), 3.38 (t, 2H, $SCH_2$), 4.10 (q, 2H, $OCH_2$), 4.73 (s, 2H, $CH_2CO_2$), 7.17-7.25 (m, $3H_{arom}$), 7.69 (m, $1H_{arom}$).

Example F-01a

{2-[4-(Methyl-phenyl-carbamoyl)-butylsulfanyl]-benzoimidazol-1-yl}-acetic acid tert-Butyl {2-[4-(methyl-phenyl-carbamoyl)-butylsulfanyl]-benzoimidazol-1-yl}-acetate (Precursor F-01b, 25.6 mg, 0.06 mmol) is dissolved in TFA/dichloromethane (1:1, 3 ml) and stirred for 3 h at rt. Evaporation of the solvent in vacuo and drying under high vacuum yields the title compound (19.4 mg) in 87% as a yellow oil: $t_R$=5.20 min (LC-1), ESI-MS (pos.): m/z 398.20 $[M+H]^+$, ESI-MS (neg.): m/z 396.19 $[M-H]^+$; $^1$H-NMR (DMSO-$d_6$): δ (ppm) 1.56 (m, 4H, $CH_2CH_2$), 2.05 (m, 2H, $CH_2C$=O), 3.14 (s, 3H, NMe), 3.22 (m, 2H, $SCH_2$), 5.00 (s, 2H, $CH_2CO_2$), 7.18-7.32 (m, $5H_{arom}$), 7.38 (m, $2H_{arom}$), 7.53 (m, $2H_{arom}$).

Examples F-02a to F-05a of the following Table 12 are prepared analogous to the procedure described for Example F-01a, using Precursors F-02b to F-05b in place of F-01b.

TABLE 12

| Example | Name | Formula Mol weight | $t_R$ [min] (Meth.) | MS Data m/z [M + H]$^+$ | MS Data m/z [M − H]$^+$ |
|---|---|---|---|---|---|
| F-02a | {2-[5-(3,4-Dihydro-2H-quinolin-1-yl)-5-oxo-pentylsulfanyl]-benzoimidazol-1-yl}-acetic acid | C23H25N3O3S 423.536 | 5.58 (LC-1) | 424.22 | 422.23 |
| F-03a | {2-[4-(Benzyl-phenyl-carbamoyl)-butylsulfanyl]-benzoimidazol-1-yl}-acetic acid | C27H27N3O3S 473.595 | 6.17 (LC-1) | 474.17 | 472.28 |
| F-04a | {2-[4-(benzyl-methyl-carbamoyl)-butylsulfanyl]-benzoimidazol-1-yl}-acetic acid; | C22H25N3O3S 411.525 | 5.31 (LC-1) | 412.2 | 410.16 |
| F-05a | {2-[4-(Butyl-phenyl-carbamoyl)-butylsulfanyl]-benzoimidazol-1-yl}-acetic acid | C24H29N3O3S 439.578 | 6.13 (LC-1) | 440.17 | 438.28 |

Precursor F-01b tert-Butyl {2-[4-(methyl-phenyl-carbamoyl)-butyl-sulfanyl]-benzoimidazol-1-yl}-acetate To a suspension of 5-bromovaleryl chloride (24.8 mg, 16.6 μl, 0.12 mmol) and K$_2$CO$_3$ (31.2 mg, 0.23 mmol) in acetonitrile (3 ml) is added N-methylaniline (14.5 mg, 14.7 μl, 0.14 mmol). After 1 h of stirring, tert-butyl (2-mercapto-benzoimidazol-1-yl)-acetate (Intermediate 3-I, 30 mg, 0.11 mmol) is added and the resulting mixture is refluxed overnight. The crude suspension is filtered over a fritted funnel and the solvent evaporated in vacuo. The crude yellow oil is purified by flash-chromatography on silica gel (AcOEt/heptane, 2:1 containing 3% of Et$_3$N), yielding the title compound (38.4 mg) in 75% as a yellowish oil: $t_R$=6.84 min (LC-1), ESI-MS (pos.): m/z 455.46 [M+H]$^+$, ESI-MS (neg.): m/z 452.19 [M−H]$^+$; $^1$H-NMR (DMSO-d$_6$): δ (ppm) 1.38 (s, 9H, tBu), 1.56 (m, 4H, CH$_2$CH$_2$), 2.03 (m, 2H, CH$_2$C=O), 3.17 (m, 2H, SCH$_2$), 3.31 (s, 3H, NMe), 4.92 (s, 2H, CH$_2$CO$_2$), 7.12-7.16 (m, 2H$_{arom}$), 7.26-7.30 (m, 3H$_{arom}$), 7.36-7.46 (m, 3H$_{arom}$), 7.51 (m, 1H$_{arom}$).

Precursors F-02b to F-05b of the following Table 13 are prepared using a procedure analogous to that described for Precursor F-01b, substituting the corresponding N,N-disubstituted amine for N-methylaniline.

TABLE 13

| Precursor | Name | Formula Mol weight | $t_R$ [min] (Meth.) | MS Data m/z [M + H]$^+$ | MS Data m/z [M − H]+ |
|---|---|---|---|---|---|
| F-02b | tert-Butyl {2-[5-(3,4-dihydro-2H-quinolin-1-yl)-5-oxo-pentylsulfanyl]-benzoimidazol-1-yl}-acetate | C27H33N3O3S 479.63 | 7.23 (LC-1) | 481.31 | n/a |
| F-03b | tert-Butyl {2-[4-(benzyl-phenyl-carbamoyl)-butylsulfanyl]-benzoimidazol-1-yl}-acetate | C31H35N3O3S 529.69 | 7.62 (LC-1) | 531.43 | n/a |
| F-04b | tert-Butyl {2-[4-(benzyl-methyl-carbamoyl)-butylsulfanyl]-benzoimidazol-1-yl}-acetate | C26H33N3O3S 467.62 | 6.91 (LC-1) | 468.08 | 466.34 |
| F-05b | tert-Butyl {2-[4-(butyl-phenyl-carbamoyl)-butylsulfanyl]-benzoimidazol-1-yl}-acetate | C28H37N3O3S 495.68 | 7.7 (LC-1) | 497.44 | n/a |

Example G-01a

{2-[3-(2,3-Dihydro-1-ethyloxycarbonyl-3-oxo-indazol-2-yl)-propylsulfanyl]-benzoimidazol-1-yl}-acetic acid tert-Butyl {2-[3-(2,3-dihydro-1-ethyloxycarbonyl-3-oxo-indazol-2-yl)-propylsulfanyl]-benzoimidazol-1-yl}-acetate (Precursor G-01b, 63.8 mg, 0.1 mmol) is stirred in TFA/dichloromethane (1:1, 2 ml) at rt overnight. The solvents are removed in vacuo. The crude is taken up in chloroform (1 ml) and filtered over cotton wool. The solvent is removed in vacuuo and the residue is dried under high vacuum. This yields the title compound (6 mg) in 11% as a colourless oil: $t_R$=2.24 min (LC-2), ESI-MS (pos.): m/z 455.11 [M+H]$^+$, ESI-MS (neg.): m/z 453.22 [M−H]$^+$; $^1$H-NMR (DMSO-d$_6$): δ (ppm) 1.31 (t, 3H, CH$_3$), 2.03 (quint., 2H, CH$_2$CH$_2$N), 3.18 (m, 2H, SCH$_2$), 4.23 (t, 2H, CH$_2$N), 4.36 (q, 2H, OCH$_2$), 4.94 (s, 2H, CH$_2$CO$_2$), 7.10-7.15 (m, 2H, m), 7.39 (t, 1 H$_{arom}$), 7.46 (m, 2H$_{arom}$), 7.70-7.78 (m, 2H$_{arom}$), 7.87 (d, 1H$_{arom}$)

Examples G-02a to G-07a of the following Table 14 are prepared analogous to the procedure described for Example G-01a, using Precursors G-02b to G-07b in place of G-01b.

TABLE 14

| Example | Name | Formula Mol weight | $t_R$ [min] (Meth.) | MS Data m/z [M + H]$^+$ | MS Data m/z [M − H]$^+$ |
|---|---|---|---|---|---|
| G-02a | {2-[3-(1-Oxo-1,3-dihydro-isoindol-2-yl)-propylsulfanyl]-benzoimidazol-1-yl}-acetic acid | C20H19N3O3S 381.455 | 1.68 (LC-2) | 382.43 | 380.29 |
| G-03a | {2-[3-(2-Oxo-2,3-dihydro-benzoimidazol-1-yl)-propylsulfanyl]-benzoimidazol-1-yl}-acetic acid | C19H18N4O3S 382.443 | 2.00 (LC-2) | 383.19 | 381.21 |
| G-04a | {2-[3-(1-Oxo-1H-phthalazin-2-yl)-propylsulfanyl]-benzoimidazol-1-yl}-acetic acid | C20H18N4O3S 394.454 | 2.13 (LC-2) | 395.1 | 393.19 |
| G-05a | {2-[3-(2,4-Dioxo-1,4-dihydro-2H-quinazolin-3-yl)-propylsulfanyl]-benzoimidazol-1-yl}-acetic acid | C20H18N4O4S 410.453 | 1.99 (LC-2) | 411.15 | 409.18 |
| G-06a | {2-[3-(1,3-Dioxo-1,3-dihydro-isoindol-2-yl)-propylsulfanyl]-benzoimidazol-1-yl}-acetic acid | C20H17N3O4S 395.438 | 5.36 (LC-1) | 396.15 | 394.23 |
| G-07a | {2-[3-(1,1,3-Trioxo-1,3-dihydro-1λ-benzo[d]isothiazol-2-yl)-propylsulfanyl]-benzoimidazol-1-yl}-acetic acid | C19H17N3O5S2 431.492 | 2.21 (LC-2) | 432.05 | 430.14 |

Precursor G-01b tert-Butyl {2-[3-(2,3-dihydro-1-ethyloxycarbonyl-3-oxo-indazol-2-yl)-propylsulfanyl]-benzoimidazol-1-yl}-acetate A mixture of tert-butyl (2-mercapto-benzoimidazol-1-yl)-acetate (Intermediate 3-I, 66 mg, 0.25 mmol), 2-(3-chloropropyl)-3-oxo-2,3-dihydro-indazole-1-carboxylic acid ethyl ester (alkylating agent G-01d, 70 mg, 0.25 mmol), a few crystals of potassium iodide and $K_2CO_3$ (69 mg, 0.5 mmol) in acetone (1 ml) is refluxed overnight. Evaporation of the solvent under a stream of air affords a residue that is purified by flash-chromatography on silica-gel (AcOEt/heptane, 3:2), yielding the title compound as a colourless oil: $t_R$=2.75 min (LC-2), ESI-MS (pos.): m/z 511.15 $[M+H]^+$; $^1$H-NMR ($CDCl_3$): δ (ppm) 1.37 (s, 9H, tBu), 1.37 (t, 3H, $CH_3$), 2.14 (quint., 2H, $CH_2CH_2N$), 3.28 (m, 2H, $SCH_2$), 4.30-4.40 (m, 4H), 4.69 (s, 2H, $CH_2CO_2$), 7.10 (m, $3H_{arom}$), 7.26 (t, $1H_{arom}$), 7.55 (m, $2H_{arom}$), 7.81 (t, $2H_{arom}$).

Precursors G-02b to G-07b of the following Table 15 are prepared using a procedure analogous to that described for Precursor G-01b, substituting the appropriate alkylating agent for G-01d.

TABLE 15

| Precursor | Name | Formula Mol weight | $t_R$ [min] (Meth.) | MS Data m/z $[M + H]^+$ | MS Data m/z $[M − H]^+$ |
|---|---|---|---|---|---|
| G-02b | tert-Butyl {2-[3-(1-oxo-1,3-dihydro-isoindol-2-yl)-propylsulfanyl]-benzoimidazol-1-yl}-acetate | C24H27N3O3S 437.55 | 2.19 (LC-2) | 438.29 | n/a |
| G-03b | tert-Butyl {2-[3-(2-oxo-2,3-dihydro-benzoimidazol-1-yl)-propylsulfanyl]-benzoimidazol-1-yl}-acetate | C23H26N4O3S 438.54 | 2.67 (LC-2) | 439.24 | 437.27 |
| G-04b | tert-Butyl {2-[3-(1-oxo-1H-phthalazin-2-yl)-propylsulfanyl]-benzoimidazol-1-yl}-acetate | C24H26N4O3S 450.55 | 2.67 (LC-2) | 451.22 | n/a |
| G-05b | tert-Butyl {2-[3-(2,4-dioxo-1,4-dihydro-2H-quinazolin-3-yl)-propylsulfanyl]-benzoimidazol-1-yl}-acetate | C24H26N4O4S 466.55 | 2.21 (LC-2) | 467.28 | 465.24 |
| G-06b | tert-Butyl {2-[3-(1,3-dioxo-1,3-dihydro-isoindol-2-yl)-propylsulfanyl]-benzoimidazol-1-yl}-acetate | C24H25N3O4S 451.55 | 6.99 (LC-1) | 452.40 | n/a |
| G-07b | tert-Butyl {2-[3-(1,1,3-trioxo-1,3-dihydro-1$\lambda^6$-benzo[d]isothiazol-2-yl)-propylsulfanyl]-benzoimidazol-1-yl}-acetate | C23H25N3O5S2 487.59 | 2.73 (LC-2) | 488.17 | n/a |

Alkylating Agent G-01d 2-(3-Chloro-propyl)-3-oxo-2,3-dihydro-indazole-1-carboxylic acid ethyl ester To a solution of 3-oxo-2,3-dihydro-indazole-1-carboxylic acid ethyl ester (410 mg, 2 mmol) dissolved in dry DMF (10 ml) is added sodium hydride (60% w/w in oil, 120 mg, 3 mmol). The resulting cloudy solution is allowed to stir for 1 h at rt and is added dropwise under inert atmosphere via a syringe onto a solution of iodochloropropane (268 μl, 2.5 mmol) in dry DMF (2 ml). The resulting solution is allowed to stir at rt overnight. By addition of water and evaporation under reduced pressure most of the DMF is removed from the crude mixture. The residue is dissolved in AcOEt (25 ml) and the resulting organic phase is washed 3 times with water and once with brine. The crude product is purified by chromatography on silica gel (AcOEt/heptane, 2:3), yielding the title compound (78 mg) in 15% as a colourless oil: $t_R$=2.17 min (LC-2), ESI-MS (pos.): m/z 283.05 [M+H]$^+$; $^1$H-NMR (CDCl$_3$): δ (ppm) 1.38 (t, 3H, CH$_3$), 2.08 (quint., 2H, CH$_2$CH$_2$N), 3.42 (t, 2H, CH$_2$Cl), 4.25 (t, 2H, NCH$_2$), 4.39 (q, 2H, OCH$_2$CH$_3$), 7.22 (t, 1H$_{arom}$), 7.53 (t, 1H$_{arom}$), 7.79 (t, 2H$_{arom}$), and 3-(3-chloro-propoxy)-indazole-1-carboxylic acid ethyl ester (125 mg) in 24% as a colourless oil: $t_R$=2.49 min (LC-2), ESI-MS (pos.): m/z 283.05 [M+H]$^+$; $^1$H-NMR (CDCl$_3$): δ (ppm) 1.44 (t, 3H, CH$_3$), 2.26 (quint., 2H, CH$_2$CH$_2$N), 3.71 (t, 2H, CH$_2$Cl), 4.49 (q, 2H, OCH$_2$CH$_3$), 4.59 (t, 2H, OCH$_2$CH$_2$), 7.20 (t, 1H, m), 7.46 (t, 1H$_{arom}$), 7.59 (d, 1H$_{arom}$), 8.02 (d, 1H$_{arom}$). 3-(3-Chloro-propoxy)-indazole-1-carboxylic acid ethyl ester is used as alkylating agent D-06d in the preparation of Precursor D-06b.

Alkylating agents G-03d to G-07d of the following Table 16 are prepared using a procedure analogous to that described for alkylating agent G-01d, substituting the appropriate nitrogen containing heterocycle for 3-oxo-2,3-dihydro-indazole-1-carboxylic acid ethyl ester.

TABLE 16

| Alkylating agent | Name | Formula Mol weight | $t_R$ [min] (Meth.) | MS Data m/z [M + H]$^+$ | MS Data m/z [M − H]$^+$ |
|---|---|---|---|---|---|
| G-03d | 1-(3-Chloro-propyl)-1,3-dihydro-benzoimidazol-2-one | C10H11ClN2O 210.66 | 1.87 (LC-2) | 211.11 | 209.1 |
| G-04d | 2-(3-Chloro-propyl)-2H-phthalazin-1-one | C11H11ClN2O 222.67 | 2.02 (LC-2) | 223.11 | n/a |
| G-05d | 3-(3-Chloro-propyl)-1H-quinazoline-2,4-dione | C11H11ClN2O2 238.67 | 1.9 (LC-2) | 239.06 | 237.05 |
| G-07d | 2-(3-Chloro-propyl)-1,1-dioxo-1,2-dihydro-1λ$^6$-benzo[d]isothiazol-3-one | C10H10ClNO3S 259.71 | 2.15 (LC-2) | 260.01 | n/a |

Example H-01a

[2-(3-Methoxycarbonyl-benzylsulfanyl)-benzoimidazol-1-yl]-acetic acid

A solution of tert-butyl[2-(3-methoxycarbonyl-benzylsulfanyl)-benzoimidazol-1-yl]-acetate (Precursor H-01b, 31 mg, 0.075 mmol) in TFA/dichloromethane (1:1, 2 ml) is stirred at rt for 4 h. The solvents are removed under a stream of air. The solid residue is suspended in Et$_2$O (2 ml) and sonicated. Filtration, rinsing with Et$_2$O and drying under high vacuum, yields the title compound (19.6 mg) in 73% as a white solid: $t_R$=5.52 min (LC-1), ESI-MS (pos.): m/z 357.25 [M+H]$^+$, ESI-MS (neg.): m/z 355.29 [M−H]$^+$; $^1$H-NMR (DMSO-d$_6$): δ (ppm) 3.83 (s, 3H, OMe), 4.65 (s, 2H, SCH$_2$), 4.92 (s, 1H, CH$_2$CO$_2$), 7.15-7.21 (m, 2H$_{arom}$), 7.42-7.48 (m, 2H$_{arom}$), 7.57 (m, 1H$_{arom}$), 7.72 (d, 1H$_{arom}$), 7.81 (d, 1H$_{arom}$), 8.05 (s, 1H$_{arom}$).

Examples H-02a to H-01a of the following Table 17 are prepared analogous to the procedure described for Example H-01a, using Precursors H-02b to H-11b in place of H-01b.

TABLE 17

| Example | Name | Formula Mol weight | $t_R$ [min] (Meth.) | MS Data m/z [M + H]$^+$ | MS Data m/z [M − H]$^+$ |
|---|---|---|---|---|---|
| H-02a | {2-[(5-Methyloxycarbonyl-pyridin-3-yl)-methylsulfanyl]-benzoimidazol-1-yl}-acetic acid | C17H15N3O4S 357.389 | 1.68 (LC-2) | 358.16 | 356.18 |
| H-03a | (2-{[(2-Chloro-4-methyloxycarbonyl)-pyridin-6-yl]-methyl-sulfanyl}-benzoimidazol-1-yl)-acetic acid | C17H14N3O4ClS 391.834 | 5.81 (LC-1) | 392.05 | 390.13 |
| H-04a | {2-[(2-Methyloxycarbonyl-furan-5-yl)-methylsulfanyl]-benzoimidazol-1-yl}-acetic acid | C17H16N2O5S 360.389 | 5.45 (LC-1) | 361.08 | 359.09 |
| H-05a | {2-[(2-Bromo-3-methoxycarbonyl)-benzylsulfanyl]-benzoimidazol-1-yl}-acetic acid | C18H15N2O4BrS 435.297 | 2.04 (LC-2) | 437.02 | 435.1 |
| H-06a | {2-[(4-Bromo-3-methoxycarbonyl)-benzylsulfanyl]-benzoimidazol-1-yl}-acetic acid | C18H15N2O4BrS 435.297 | 2.06 (LC-2) | 436.95 | 435.1 |
| H-07a | {2-[(5-Bromo-3-methoxycarbonyl)-benzylsulfanyl]-benzoimidazol-1-yl}-acetic acid | C18H15N2O4BrS 435.297 | 2.18 (LC-2) | 437.02 | 435.1 |
| H-08a | {2-[(6-Bromo-3-methoxycarbonyl)-benzylsulfanyl]-benzoimidazol-1-yl}-acetic acid | C18H15N2O4BrS 435.297 | 6.02 (LC-1) | 437.05 | 435.03 |
| H-09a | {2-[(6-methoxy-3-methoxycarbonyl)-benzylsulfanyl]-benzoimidazol-1-yl}-acetic acid | C19H18N2O5S 386.427 | 1.80 (LC-2) | 387.2 | 385.16 |
| H-10a | [2-(3-Acetyl-benzylsulfanyl)-benzoimidazol-1-yl]-acetic acid | C18H16N2O3S 340.402 | 6.48 (LC-1) | 341.16 | 339.14 |
| H-11a | [2-(5-Acetyl-2-methoxy-benzylsulfanyl)-benzoimidazol-1-yl]-acetic acid | C19H18N2O4S 370.428 | 5.03 (LC-1) | 371.06 | 369.11 |

Precursor H-01b tert-Butyl[2-(3-methoxycarbonyl-benzylsulfanyl)-benzoimidazol-1-yl]-acetate A mixture of tert-butyl (2-mercapto-benzoimidazol-1-yl)-acetate (Intermediate 3-1,264 mg, 1 mmol), 3-bromomethyl-benzoic acid methyl ester (252 mg, 1.1 mmol) and K$_2$CO$_3$ (276 mg, 2 mmol) in acetone (4 ml) is allowed to stir at rt for 2.5 h. The suspension is cooled down to rt and filtered on a funnel filled with cotton wool. Evaporation of the solvent in vacuo affords a residue that is purified by flash-chromatography on silica-gel (AcOEt/heptane, 1:3), yielding the title compound (310 mg) in 75% as a colourless syrup: $t_R$=7.19 min (LC-1), ESI-MS (pos.): m/z 413.3 [M+H]$^+$; $^1$H-NMR (CDCl$_3$): δ (ppm) 1.42 (s, 9H, tBu), 3.92 (s, 3H, OMe), 4.65 (s, 2H), 4.69 (s, 1H), 7.19-7.26 (m, 3H$_{arom}$), 7.36 (t, 1H$_{arom}$), 7.59 (d, 1H$_{arom}$), 7.73 (m, 1 H$_{arom}$), 7.92 (d, 1H$_{arom}$), 8.06 (s, 1H$_{arom}$).

Precursors H-02b to H-01b of the following Table 18 are prepared using a procedure analogous to that described for Precursor H-01b, substituting the appropriate alkylating agent for 5-bromo-hexanoic acid ethyl ester.

TABLE 18

| Precursor | Name | Formula Mol weight | $t_R$ [min] (meth.) | MS Data m/z [M + H]$^+$ | MS Data m/z [M − H]$^+$ |
|---|---|---|---|---|---|
| H-02b | tert-Butyl {2-[(5-methyloxycarbonyl-pyridin-3-yl)-methylsulfanyl]-benzoimidazol-1-yl}-acetate | C21H23N3O4S 413.49 | 2.21 (LC-2) | 414.21 | n/a |

TABLE 18-continued

| Precursor | Name | Formula Mol weight | $t_R$ [min] (meth.) | MS Data m/z $[M + H]^+$ | MS Data m/z $[M - H]^+$ |
|---|---|---|---|---|---|
| H-03b | tert-Butyl (2-{[(2-chloro-4-methyloxycarbonyl)-pyridin-6-yl]-methyl-sulfanyl}-benzoimidazol-1-yl)-acetate | C21H22ClN3O4S 447.94 | 2.78 (LC-2) | 448.16 | n/a |
| H-04b | tert-Butyl {2-[(2-methyloxycarbonyl-furan-5-yl)-methylsulfanyl]-benzoimidazol-1-yl}-acetate | C21H24N2O5S 416.49 | 2.41 (LC-2) | 417.21 | n/a |
| H-05b | tert-Butyl {2-[(2-bromo-3-methoxycarbonyl)-benzylsulfanyl]-benzoimidazol-1-yl}-aceate | C22H23BrN2O4S 491.4 | 2.58 (LC-2) | 493.08 | n/a |
| H-06b | tert-Butyl {2-[(4-bromo-3-methoxycarbonyl)-benzylsulfanyl]-benzoimidazol-1-yl}-acetate | C22H23BrN2O4S 491.4 | 2.58 (LC-2) | 493.08 | n/a |
| H-07b | tert-Butyl {2-[(5-bromo-3-methoxycarbonyl)-benzylsulfanyl]-benzoimidazol-1-yl}-acetate | C22H23BrN2O4S 491.4 | 2.70 (LC-2) | 493.08 | n/a |
| H-08b | tert-Butyl {2-[(6-bromo-3-methoxycarbonyl)-benzylsulfanyl]-benzoimidazol-1-yl}-acetate | C22H23BrN2O4S 491.4 | 2.69 (LC-2) | 492.77 | n/a |
| H-09b | tert-Butyl {2-[(6-methoxy-3-methoxycarbonyl)-benzylsulfanyl]-benzoimidazol-1-yl}-acetate | C23H26N2O5S 442.53 | 2.82 (LC-2) | 443.26 | n/a |
| H-10b | tert-Butyl [2-(3-acetyl-benzylsulfanyl)-benzoimidazol-1-yl]-acetate | C22H24N2O3S 396.5 | 8.31 (LC-1) | 397.22 | 395.22 |
| H-11b | tert-Butyl [2-(5-acetyl-2-methoxy-benzylsulfanyl)-benzoimidazol-1-yl]-acetate | C25H26N2O4S 426.53 | 6.86 (LC-1) | 427.00 | 425.14 |

Alkylating Agent H-08d

4-Bromo-3-bromomethyl-benzoic acid methyl ester

As described in: Puls, C.; Stolle, A.; de Meijere, A., Chem. Ber. 1992, 1635-1641, and Lew, A.; Chamberlin, A. R., Bioorg. Med. Chem. Lett., 1999, 9, 3267-3272.

A solution of 4-bromo-3-methyl-benzoic acid methyl ester (1 g, 4.37 mmol) and N-bromosuccinimide (855 mg, 4.8 mmol) in $CCl_4$ (5 ml) is refluxed for 2 h. AIBN (20 mg, 0.12 mmol, 3%) is added and the mixture is refluxed for 2 h. This process is repeated twice and the reaction mixture is refluxed overnight. The solvent is evaporated and the yellow residue purified by chromatography on silica-gel (AcOEt/heptane, 1:9), yielding a (2:1) mixture of the title compound and 4-bromo-3,3-dibromomethyl-benzoic acid methyl ester as a colourless solid, which is used without further purification in the next step: $t_R$=2.31 min (LC-2), ESI-MS (pos.): m/z 308.99 $[M+H]^+$; $^1$H-NMR (CDCl$_3$): δ (ppm) 3.92 (s, 3H, OCH$_3$), 4.60 (s, CH$_2$Br), 7.65 (d, 1H$_{arom}$), 7.79 (m, 1H$_{arom}$), 8.10 (d, 1H$_{arom}$).

Alkylating agents H-02d to H-09d of the following Table 19 are prepared using a procedure analogous to that described for alkylating agent H-08d, substituting the corresponding phenyl or pyridyl derivative analogue for 4-bromo-3-methyl-benzoic acid methyl ester.

TABLE 19

| Alkylating agent | Name | Formula Mol weight | $t_R$ [min] (Meth.) | MS Data m/z $[M + H]^+$ |
|---|---|---|---|---|
| H-02d | 5-Bromomethyl-nicotinic acid methyl ester | C8H8BrNO2 230.06 | 1.78 (LC-2) | 232.15 |
| H-03d | 2-Bromomethyl-6-chloro-isonicotinic acid methyl ester | C8H7BrClNO2 264.50 | 2.21 (LC-2) | 266.08 |
| H-05d | 2-Bromo-5-bromomethyl-benzoic acid methyl ester | C9H8Br2O2 307.97 | 2.31 (LC-2) | 308.99 |
| H-06d | 2-Bromo-5-bromomethyl-benzoic acid methyl ester | C9H8Br2O2 307.98 | 2.31 (LC-2) | 308.99 |
| H-07d | 3-Bromo-5-bromomethyl-benzoic acid methyl ester | C9H8Br2O2 307.99 | 2.45 (LC-2) | 308.99 |
| H-09d | 3-Bromomethyl-4-methoxy-benzoic acid methyl ester | C10H11BrO3 259.10 | 2.62 (LC-2) | 259.07 |

Example I-01a rac[2-(1-Butyryl-piperidin-3-ylmethylsulfanyl)-benzoimidazol-1-yl]-acetic acid rac[2-(Piperidin-3-ylmethylsulfanyl)-benzoimidazol-1-yl]-acetic acid hydrochloride (Precursor I-00a, 10 mg, 0.03 mmol) is suspended in dichloromethane (1 ml) and Et$_3$N (12.88 mg, 16.6 μl, 0.10 mmol) as well as butyryl chloride (3.42 mg, 3.35 μl, 0.04 mmol) are added subsequently. The resulting mixture is stirred for 30 min at rt. Water (1 ml) is then added and the crude acid is extracted twice with dichloromethane. The combined organic phases are washed with brine and dried over $Na_2SO_4$. Evaporation of the solvent in vacuo affords 6 mg of a brown oil. It is suspended in $Et_2O$ (1 ml) and sonicated until a solid forms. This solid is rinsed with ether and dried under vacuum, yielding the title compound (5.9 mg) in 55% as a beige solid: $t_R$=1.68 min (LC-2), ESI-MS (pos.): m/z 376.25 $[M+H]^+$, ESI-MS (neg.): m/z 374.21 $[M-H]^+$; $^1$H-NMR (DMSO-$d_6$, 100° C.): δ (ppm) 0.86 (t, 3H, $CH_2CH_3$), 1.27-1.44 (m, 2H), 1.54 (td, 2H, $CH_2CH_3$), 1.68 (m, 1H), 1.79-1.95 (m, 2H), 2.25 (t, 2H, $CH_2C=O$), 2.81 (bm, 2H, $SCH_2$), 3.32 (d, 2H, $CHCH_2N$), 3.65 (bm, 2H, $CH_2CH_2N$), $\overline{4.97}$ (s, 2H, $CH_2CO_2$), $\overline{7.18}$ (m, $2H_{arom}$), 7.44 (m, $1\overline{H}_{arom}$), 7.54 (m, $1H_{arom}$).

Alternatively, Example I-01a is also synthesized starting from tert-butyl[2-(1-butyryl-piperidin-3-ylmethylsulfanyl)-benzoimidazol-1-yl]-acetate (Precursor I-01b): Precursor I-01b (802 mg, 1.86 mmol) is dissolved in TFA/dichloromethane (1:1, 10 ml) and stirred overnight at rt. Evaporation of the solvents in vacuo gives an orange oil which is suspended in $Et_2O$/heptane (1:1, 2 ml) and sonicated. After filtration, thourough rinsing with $Et_2O$ and drying, the title compound (670 mg) is obtained in 96% as a white solid.

Examples I-02a to I-13a of the following Table 20 are prepared analogous to the procedures described for Example I-01a.

TABLE 20

| Example | Name | Formula Mol weight | $t_R$ [min] (Meth.) | MS Data m/z $[M + H]^+$ | MS Data m/z $[M - H]^+$ |
|---|---|---|---|---|---|
| I-02a | rac {2-[1-(2-Methoxy-benzoyl)-piperidin-3-ylmethylsulfanyl]-benzoimidazol-1-yl}-acetic acid | C23H25N3O4S 439.535 | 1.80 (LC-2) | 440.2 | 438.29 |
| I-03a | rac [2-(1-Phenylacetyl-piperidin-3-ylmethylsulfanyl)-benzoimidazol-1-yl]-acetic acid | C23H25N3O3S 423.536 | 1.87 (LC-2) | 424.21 | 422.3 |
| I-04a | rac [2-(1-Cyclohexanecarbonyl-piperidin-3-ylmethylsulfanyl)-benzoimidazol-1-yl]-acetic acid | C22H29N3O3S 415.556 | 1.96 (LC-2) | 416.25 | 414.34 |
| I-05a | rac {2-[1-(3-Cyclopentyl-propionyl)-piperidin-3-ylmethylsulfanyl]-benzoimidazol-1-yl}-acetic acid | C23H31N3O3S 429.583 | 2.11 (LC-2) | 430.26 | 428.35 |
| I-06a | rac [2-(1-Diphenylacetyl-piperidin-3-ylmethylsulfanyl)-benzoimidazol-1-yl]-acetic acid | C29H29N3O3S 499.633 | 2.16 (LC-2) | 500.28 | 498.3 |
| I-07a | rac [2-(1-Acetyl-piperidin 3-ylmethylsulfanyl)-benzoimidazol-1-yl]-acetic acid | C17H21N3O3S 347.438 | 1.51 (LC-2) | 348.16 | 346.25 |
| I-08a | rac [2-(1-Heptanoyl-piperidin-3-ylmethylsulfanyl)-benzoimidazol-1-yl]-acetic acid | C22H31N3O3S 417.572 | 2.1 (LC-2) | 418.29 | 416.31 |
| I-09a | rac {2-[1-(3-Chloro-benzoyl)-piperidin-3-ylmethylsulfanyl]-benzoimidazol-1-yl}-acetic acid | C22H22N3O3ClS 443.954 | 1.97 (LC-2) | 444.15 | 442.24 |
| I-10a | rac {2-[1-(3-Phenyl-propionyl)-piperidin-3-ylmethylsulfanyl]-benzoimidazol-1-yl}-acetic acid | C24H27N3O3S 437.562 | 1.97 (LC-2) | 438.23 | 436.31 |
| I-11a | rac {2-[1-(Furan-2-carbonyl)-piperidin-3-ylmethylsulfanyl]-benzoimidazol-1-yl}-acetic acid | C20H21N3O4S 399.47 | 1.76 (LC-2) | 400.2 | 398.22 |
| I-12a | rac {2-[1-(Naphthalene-1-carbonyl)-piperidin-3-ylmethylsulfanyl]-benzoimidazol-1-yl}-acetic acid | C26H25N3O3S 459.569 | 1.96 (LC-2) | 460.2 | 458.29 |

TABLE 20-continued

| Example | Name | Formula Mol weight | $t_R$ [min] (Meth.) | MS Data m/z $[M + H]^+$ | MS Data m/z $[M - H]^+$ |
|---|---|---|---|---|---|
| I-13a | rac {2-[1-(4-Bromo-benzoyl)-piperidin-3-ylmethylsulfanyl]-benzoimidazol-1-yl}-acetic acid | C22H22N3O3BrS 488.405 | 1.99 (LC-2) | 490.08 | n/a |

Precursor I-00a rac[2-(Piperidin-3-ylmethylsulfanyl)-benzoimidazol-1-yl]-acetic acid hydrochloride To a 2M HCl solution in Et$_2$O (2 ml) is added rac tert-butyl [2-(1-tert-butyloxycarbonyl-piperidin-3-ylmethylsulfanyl)-benzoimidazol-1-yl]-acetate (Precursor I-00b, 36 mg, 0.08 mmol). The mixture is stirred for 4 h at rt. The precipitated solid is filtered and rinsed with Et$_2$O to yield quantitatively the title compound as a slightly yellow solid.

Precursor I-00b rac tert-Butyl[2-(1-tert-butyloxycarbonyl-piperidin-3-ylmethylsulfanyl)-benzoimidazol-1-yl]-acetate tert-butyl (2-mercapto-benzoimidazol-1-yl)-acetate (Intermediate 3-I, 792 mg, 3 mmol), 3-hydroxymethyl-piperidine-1-carboxylic acid tert-butyl ester (838 mg, 3.9 mmol) and triphenylphosphane (1021 mg, 3.9 mmol) are dissolved and stirred under inert atmosphere at 0° C. in dry THF (20 ml). Di-tert-butyl-azodicarboxylate (690 mg, 3 mmol) is added under the same reaction conditions to the solution. The initially deep yellow colour disappears after 10 min. The reaction mixture is slowly allowed to warm up to rt overnight. Evaporation of the solvent in vacuo and purification upon two chromatographies on silica gel (AcOEt/heptane, 1:4), provides the title compound (552 mg) in 38% as a colourless syrup: $t_R$=7.66 min (LC-1), ESI-MS (pos.): m/z 462.32 $[M+H]^+$; $^1$H-NMR (DMSO-d$_6$ at 100° C.): δ (ppm) 1.36 (s, 9H, tBu), 1.40 (m, 2H), 1.42 (s, 9H, tBu), 1.58 (m, 1H), 1.75 (m, 1H), 1.85 (m, 1H), 2.85 (m, 2H, SCH$_2$), 3.24 (m, 2H, NCH$_2$), 3.67 (m, 1H, NCH$_2$), 3.86 (m, 1H, NCH$_2$), 4.96 (m, 2H, CH$_2$CO$_2$), 7.14 (m, 2H$_{arom}$), 7.46 (m, 1H$_{arom}$), 7.53 (m, 1H$_{arom}$).

Precursor I-01b rac tert-Butyl[2-(1-butyryl-piperidin-3-ylmethylsulfanyl)-benzoimidazol-1-yl]-acetate A suspension of tert-butyl (2-mercapto-benzoimidazol-1-yl)-acetate (Precursor 3-I, 1 g, 3.79 mmol), 1-(3-chloromethyl-piperidin-1-yl)-butan-1-one (alkylating agent I-01d, 771 mg, 3.79 mmol) and K$_2$CO$_3$ (1.05 g, 7.58 mmol) in acetone (10 ml) is refluxed for 36 h. The crude mixture is filtered over a fritted-funnel and the solvent evaporated in vacuo. The resulting brown gum is purificated by column chromatography on silica-gel (AcOEt/heptane, 3:7 to 1:1), yielding the title compound (802 mg) in 49% as a colourless oil: $t_R$=2.19 min (LC-1), ESI-MS (pos.): m/z 432.24 $[M+H]^+$.

Alkylating Agent I-01d 1-(3-Chloromethyl-piperidin-1-yl)-butan-1-one

A solution of 1-(3-hydroxymethyl-piperidin-1-yl)-butan-1-one (Starting material 1-01e, 1.33 g, 7.20 mmol) in dry chloroform (10 ml) is cooled down to 0° C. with an ice-water bath. A solution of SOCl$_2$ (1.43 g, 876 µl, 12 mmol) in dry chloroform (10 ml) is added dropwise. The mixture is allowed to stir at reflux for 30 min. The solution is cooled down to rt, SOCl$_2$ (0.48 g, 0.3 ml, 4.1 mmol) is added dropwise and the resulting solution is allowed to stir at reflux for another 30 min. Evaporation of the solvents under reduced pressure gives a brown liquid which is purified by column chromatography on silica-gel (AcOEt/heptane, 35:65), yielding the title compound (1.15 g) in 78% as a colourless liquid: $^1$H-NMR (CDCl$_3$): The product is a (1:1) mixture of rotamers: δ (ppm) 0.95 (t, 3H, CH3), 1.33-1.54 (m, 2H), 1.58-1.95 (m, 3H), 1.68 (quint., 1H, CH$_2$CH$_2$CH$_3$), 2.32 (dd, 2H, CH$_2$C=O), 2.60 (t, 0.5H), 2.83 (t, 0.5H), 2.99 (m, 2H), 3.36-3.55 (m, 2H), 3.77 (d, 0.5H), 3.93 (d, 0.5H), 4.30 (d, 0.5H), 4.54 (d, 0.5H).

Starting Material 1-01e 1-(3-Hydroxymethyl-piperidin-1-yl)-butan-1-one

To a solution of piperidin-3-yl-methanol (2.3 g, 20 mmol) in water (30 ml) is slowly added NaOH (1.2 g, 30 mmol). After total dissolution butyryl chloride (2.15 g, 2.11 ml, 20.2 mmol) is slowly added dropwise. The resulting mixture is allowed to stir overnight at rt. The water phase is extracted three times with dichloromethane. The combined organic phases are washed with brine and dried over Na$_2$SO$_4$. The solvents are evaporated in vacuo yielding the title compound (2.48 g) in 66% as a colourless oil which solidifies on standing: $t_R$=1.52 min (LC-2), ESI-MS (pos.): m/z 208.00 $[M+Na]^+$; $^1$H-NMR (CDCl$_3$): The product is a (1:1) mixture of rotamers: δ (ppm) 0.92 (t, 3H, CH$_3$), 1.21 (m, 0.5H), 1.33-1.52 (m, 2H), 1.57-1.84 (m, 5H), 2.26-2.32 (m, 2H, CH$_2$C=O), 2.74 (dt, 0.5H), 2.87 (dd, 0.5H), 3.10 (dd, 1H), 3.26 (ddd, 1H), 3.39-3.45 (m, 1.5H), 3.51-3.59 (m, 1H), 3.91 (dd, 1H), 4.29 (dt, 0.5H).

Example J-01a

{2-[3-(tert-Butoxycarbonyl-phenethyl-amino)-propylsulfanyl]-benzoimidazol-1-yl}-acetic acid tert-Butyl {2-[3-(tert-butoxycarbonyl-phenethyl-amino)-propylsulfanyl]-benzoimidazol-1-yl}-acetate (Precursor J-01b, 12.7 mg, 0.025 mmol) is suspended in an aqueous 0.2 M NaOH solution (0.67 ml). After addition of THF (1.3 ml) the resulting solution is allowed to stir overnight at rt. It is then treated with 1 M aqueous HCl (3.35 ml), water (2 ml) and dichloromethane (3 ml). The phases are separated and the dichloromethane is removed under reduced pressure. Drying under high vacuum yields the pure title compound: $t_R$=2.12 min (LC-2), ESI-MS (neg.): m/z 470.47 $[M-H]^+$; $^1$H-NMR (DMSO-d$_6$): δ 1.31 (s, 9H, tBu), 1.88 (quint., 2H, SCH$_2$CH$_2$), 2.73 (m, 2H, CH$_2$Ph), 3.24 (t, 2H), 3.28-3.36 (m, 4H), 4.94 (s, 2H, CH$_2$CO$_2$), 7.13 (m, 5H$_{arom}$), 7.23 (t, 2H$_{arom}$), 7.42-7.50 (m, 2H$_{arom}$).

Examples J-02a to J-07a of the following Table 21 are prepared analogous to the procedure described for Example J-01a, using Precursors J-02b to J-07b in place of J-01b.

TABLE 21

| Example | Name | Formula Mol weight | $t_R$ [min] (Meth.) | MS Data m/z [M + H]+ | MS Data m/z [M − H]+ |
|---|---|---|---|---|---|
| J-02a | (2-{3-[tert-Butoxycarbonyl-(4-piperidin-1-yl-phenyl)-amino]-propylsulfanyl}-benzoimidazol-1-yl)-acetic acid | C28H36N4O4S 524.684 | 1.78 (LC-2) | 525.53 | 523.62 |
| J-04a | {2-[3-(Benzyl-tert-butoxycarbonyl-amino)-propylsulfanyl]-benzoimidazol-1-yl}-acetic acid | C24H29N3O4S 455.577 | 2.24 (LC-2) | 456.46 | 454.55 |
| J-05a | {2-[3-(tert-Butoxycarbonyl-cyclopropyl-amino)-propylsulfanyl]-benzoimidazol-1-yl}-acetic acid | C20H27N3O4S 405.517 | 2.05 (LC-2) | 406.38 | 404.47 |
| J-06a | {2-[3-(tert-Butoxycarbonyl-phenyl-amino)-propylsulfanyl]-benzoimidazol-1-yl}-acetic acid | C23H27N3O4S 441.55 | 2.18 (LC-2) | 442.38 | 440.47 |
| J-07a | (2-{3-[tert-Butoxycarbonyl-(2,2-diphenyl-ethyl)-amino]-propylsulfanyl}-benzoimidazol-1-yl)-acetic acid | C31H35N3O4S 545.702 | 2.51 (LC-2) | 546.56 | 544.65 |

Precursor J-01b tert-Butyl {2-[3-(tert-butoxycarbonyl-phenethyl-amino)-propylsulfanyl]-benzoimidazol-1-yl}-acetate 2-[3-(tert-Butoxycarbonyl-phenethyl-amino)-propylsulfanyl]-benzoimidazole (Precursor J-01c, 239 mg, 0.58 mmol), tert-butyl bromoacetate (136 mg, 103 µl, 0.70 mmol) and cesium carbonate (227 mg, 0.70 mmol) are dissolved in dry DMF (6 ml) and allowed to stir for 1 h at rt. N-(2-Mercaptoethyl)aminomethyl polystyrene (1.4 mmol/g, 0.5 g, 0.36 mmol) is added and the crude mixture is stirred at rt for 1 h. After filtration and removal of the solvent in vacuo, the crude product is diluted in dichloromethane, washed with a 10% aqueous citric acid solution and with a saturated aqueous NaHCO3 solution. The organic phase is dried over MgSO4 and the solvent evaporated in vacuo, yielding the title compound: $t_R$=2.79 min (LC-2), ESI-MS (neg.): m/z 526.61 [M−H]+; $^1$H-NMR (CDCl$_3$): δ (ppm) 1.46 (s, 18H, 2×tBu), 2.00 (m, 2H, SCH$_2$CH$_2$), 2.85 (m, 2H, CH$_2$Ph), 3.26-3.85 (m, 6H), 4.77 (s, 2H, CH$_2$CO$_2$), 7.44-7.59 (m, 8H$_{arom}$), 7.94 (m, 1H$_{arom}$).

Precursors J-02b to J-07b from Table 22 are prepared by a procedure analogous to that described for Precursor J-01b, using Intermediates J-02c to J-07c in place of J-01c.

TABLE 22

| Precursor | Name | Formula Mol weight | $t_R$ [min] (Meth.) | MS Data m/z [M + H]+ |
|---|---|---|---|---|
| J-02b | tert-Butyl (2-{3-[tert-butoxycarbonyl-(4-piperidin-1-yl-phenyl)-amino]-propylsulfanyl}-benzoimidazol-1-yl)-acetate | C32H44N4O4S 580.79 | 2.40 (LC-2) | 581.67 |
| J-03b | tert-Butyl [2-(3-{[(4-ethyloxycarbonyl)-phenyl]-tert-butyloxycarbonyl-amino}-propylsulfanyl)-benzoimidazol-1-yl]-acetate | C30H39N3O6S 569.72 | 2.75 (LC-2) | 570.65 |
| J-04b | tert-Butyl {2-[3-(benzyl-tert-butoxycarbonyl-amino)-propylsulfanyl]-benzoimidazol-1-yl}-acetate | C28H37N3O4S 511.69 | 2.73 (LC-2) | 512.59 |
| J-05b | tert-Butyl {2-[3-(tert-butoxycarbonyl-cyclopropyl-amino)-propylsulfanyl]-benzoimidazol-1-yl}-acetate | C24H35N3O4S 461.63 | 2.62 (LC-2) | 462.51 |
| J-06b | tert-Butyl {2-[3-(tert-butoxycarbonyl-phenyl-amino)-propylsulfanyl]-benzoimidazol-1-yl}-acetate | C27H35N3O4S 497.66 | 2.68 (LC-2) | 498.57 |
| J-07b | tert-Butyl (2-{3-[tert-butoxycarbonyl-(2,2-diphenyl-ethyl)-amino]-propylsulfanyl}-benzoimidazol-1-yl)-acetate | C35H43N3O4S 601.81 | 2.89 (LC-2) | 602.70 |

Example K-01a

{2-[3-(Butoxycarbonyl-phenethyl-amino)-propylsulfanyl]-benzoimidazol-1-yl}-acetic acid A solution of tert-butyl{2-[3-(butoxycarbonyl-phenethyl-amino)-propylsulfanyl]-benzoimidazol-1-yl}-acetate (Precursor K-01b, 200 mg, 0.38 mmol) is dissolved in TFA/dichloromethane (1:1, 3 ml). The resulting solution is allowed to stir at rt overnight. The solvent is evaporated under reduced pressure and the crude product is triturated in $Et_2O$ (2 ml) until a solid forms. It is filtered, washed thoroughly with $Et_2O$ and dried under high vacuum, yielding quantitatively the title compound (179 mg) as a white powder: $t_R$=6.82 min (LC-1), ESI-MS (neg.): m/z 470.19 [M−H]$^+$, ESI-MS (neg.): m/z 468.32 [M−H]$^+$; $^1$H-NMR (CDCl$_3$): δ (ppm) 0.82 (t, 3H, CH$_2$CH$_3$), 1.29 (m, 2H, CH$_2$CH$_3$), 1.48 (quint., 2H, OCH$_2$CH$_2$), 1.71 (m; 2H, SCH$_2$CH$_2$), 2.67 (bs, 2H, PhCH$_2$), 3.12 (m, 4H), 3.26 (bs, 2H, PhCH$_2$CH$_2$N), 3.94 (bs, 2H, OCH$_2$), 4.77 (s, 2H, CH$_2$CO$_2$), 7.05 (s, 2H$_{arom}$), 7.08-7.18 (m, 6H$_{arom}$), 7.53 (m, 1H$_{arom}$).

Alternatively, Example K-01a is synthesized analogous to the procedure described for Example J-01a, using Precursor K-01b in place of J-01b.

Examples K-02a to K-04a of the following Table 23 are prepared analogous to the procedures described for Example K-01a, using Precursors K-02b to K-04b in place of K-01b.

Alternatively, Precursor K-01b is Prepared Starting from tert-butyl (2-mercapto-benzoimidazol-1-yl)-acetate (Intermediate 3-I):

To a suspension of tert-butyl (2-mercapto-benzoimidazol-1-yl)-acetate (Intermediate 3-I, 290 mg, 1.1 mmol) and K$_2$CO$_3$ (304 mg, 2.2 mmol, 2 eq.) in acetone (4 ml) are added (3-chloro-propyl)-phenethyl-carbamic acid butyl ester (alkylating agent K-01d, 387 mg, 1.3 mmol) and a few crystals of potassium iodide. The resulting mixture is allowed to stir at reflux overnight. It is cooled down and filtered on a fritted funnel. Evaporation of the solvent in vacuo affords a crude oil that is purified by chromatography on silica gel (AcOEt/heptane, 15:85), yielding the title compound (210 mg) in 36% as a white solid: $t_R$=8.25 min (LC-1), ESI-MS (pos.): m/z 526.28 [M+H]$^+$, ESI-MS (neg.): m/z 524.14 [M−H]$^+$; $^1$H-NMR (CDCl$_3$): δ (ppm) 0.95 (t, 3H, CH$_2$CH$_3$), 1.42 (m, 2H, CH$_2$CH$_3$), 1.46 (s, 9H, tBu), 1.62 (quint., 2H, OCH$_2$CH$_2$), 2.01 (m, 2H, SCH$_2$CH$_2$), 2.85 (bs, 2H, PhCH$_2$),

TABLE 23

| Example | Name | Formula Mol weight | $t_R$ [min] (Meth.) | MS Data m/z [M + H]$^+$ | MS Data m/z [M − H]$^+$ |
|---|---|---|---|---|---|
| K-02a | {2-[3-(Benzyl-butoxycarbonyl-amino)-propylsulfanyl]-benzoimidazol-1-yl}-acetic acid | C24H29N3O4S 455.577 | 2.28 (LC-2) | 456.52 | 454.61 |
| K-03a | {2-[3-(Butoxycarbonyl-cyclohexyl-amino)-propylsulfanyl]-benzoimidazol-1-yl}-acetic acid | C23H33N3O4S 447.598 | 2.39 (LC-2) | 448.49 | 446.58 |
| K-04a | {2-[3-(Butoxycarbonyl-(cyclohexylmethyl)-amino)-propylsulfanyl]-benzoimidazol-1-yl}-acetic acid | C24H35N3O4S 461.625 | 2.50 (LC-2) | 462.57 | 460.60 |

Precursor K-01b tert-Butyl {2-[3-(butoxycarbonyl-phenethyl-amino)-propylsulfanyl]-benzoimidazol-1-yl}-acetate is generally prepared analogous to the procedure described for Precursor J-01b, using K-01c in place of J-01c.

3.34 (m, 2H), 3.45 (m, 2H, SCH$_2$CH$_2$CH$_2$N), 4.08 (bs, 2H, OCH$_2$), 4.74 (s, 2H, CH$_2$CO$_2$), 7.14-7.30 (m, 8H$_{arom}$), 7.64 (m, 1H$_{arom}$).

Precursors K-02b to K-04b in Table 24 are prepared analogous to the procedures described for Precursor K-01b.

TABLE 24

| Precursor | Name | Formula Mol weight | $t_R$ [min] (Meth.) | MS Data m/z $[M+H]^+$ |
|---|---|---|---|---|
| K-02b | tert-Butyl {2-[3-(benzyl-butoxycarbonyl-amino)-propylsulfanyl]-benzoimidazol-1-yl}-acetate | C28H37N3O4S 511.68 | 2.74 (LC-2) | 512.59 |
| K-03b | tert-Butyl {2-[3-(butoxycarbonyl-cyclohexyl-amino)-propylsulfanyl]-benzoimidazol-1-yl}-acetate | C27H41N3O4S 503.71 | 2.86 (LC-2) | 504.56 |
| K-04b | tert-Butyl {2-[3-(butoxycarbonyl-cyclohexylmethyl-amino)-propylsulfanyl]-benzoimidazol-1-yl}-acetate | C28H43N3O4S 517.73 | 2.96 (LC-2) | 518.58 |

Intermediate J-01c

2-[3-(tert-Butoxycarbonyl-phenethyl-amino)-propyl-sulfanyl]-benzoimidazole

Phenethyl-carbamic acid tert-butyl ester (1107 mg, 5.0 mmol) is dissolved in dry DMF (7.75 ml). To this solution, sodium hydride (60% w/w in oil, 302 mg, 7.55 mmol) is added under vigorous stirring and stirring is continued for 30 min. Then 1-chloro-3-iodo-propane (250 mg, 5.0 mmol) is dropped into the solution followed by stirring for 2 h at rt and another hour at 50° C. After switching off the heating and addition of sodium 1H-benzoimidazole-2-thiolate (1722 mg, 10 mmol) the mixture is allowed to stir overnight at rt. All the DMF is evaporated in vacuo and the remaining crude is dissolved in DCE. This organic phase is washed twice with water, dried over $Na_2SO_4$ and evaporated to give the crude product which is purified by flash chromatography on silica gel (AcOEt/heptane, 1:9 to 1:1), yielding the title compound (289 mg) in 14% as a colourless oil: $t_R$=2.24 min (LC-2), ESI-MS (pos.): m/z 412.43 $[M+H]^+$, MS (neg.): m/z 410.46 $[M-H]^+$; $^1$H-NMR (CDCl$_3$): δ (ppm) 1.48 (s, 9H, tBu), 1.89 (br. s, 2H, SCH$_2$CH$_2$), 2.83 (t, 2H, PhCH$_2$CH$_2$N), 3.09 (br. s, 2H), 3.26 (br. s, 1H), 3.42 (t, 2H, PhCH$_2$CH$_2$N), 3.47 (br. s, 2H), 7.13-7.30 (m, 7H$_{arom}$), 7.52 (m, 2H).

Intermediates J-02c to J-07c and K-01c to K-04c of the following Table 25 are prepared using a procedure analogous to that described for Intermediate J-01c, substituting the appropriate carbamate or amide for phenethyl-carbamic acid tert-butyl ester.

TABLE 25

| Intermediate | Name | Formula Mol weight | $t_R$ [min] (Meth.) | MS Data m/z $[M+H]^+$ | MS Data m/z $[M-H]+$ |
|---|---|---|---|---|---|
| J-02c | 2-{3-[tert-Butoxycarbonyl-(4-piperidin-1-yl-phenyl)-amino]-propylsulfanyl}-benzoimidazole | C26H34N4O2S 466.648 | 1.84 (LC-2) | 467.48 | 465.50 |
| J-03c | 2-(3-{[(4-Ethyloxycarbonyl)-phenyl]-tert-butyloxycarbonyl-amino}-propylsulfanyl)-benzoimidazole | C24H29N3O4S 455.577 | 2.20 (LC-2) | 456.46 | 454.48 |
| J-04c | 2-[3-(Benzyl-tert-butoxycarbonyl-amino)-propylsulfanyl]-benzoimidazole | C22H27N3O2S 397.541 | 2.18 (LC-2) | 398.38 | 396.46 |
| J-05c | 2-[3-(tert-Butoxycarbonyl-cyclopropyl-amino)-propylsulfanyl]-benzoimidazole | C18H25N3O2S 347.482 | 1.96 (LC-2) | 348.42 | 346.38 |
| J-06c | 2-[3-(tert-Butoxycarbonyl-phenyl-amino)-propylsulfanyl]-benzoimidazole | C21H25N3O2S 383.514 | 2.13 (LC-2) | 384.40 | 382.41 |
| J-07c | 2-{3-[tert-Butoxycarbonyl-(2,2-diphenyl-ethyl)-amino]-propylsulfanyl}-benzoimidazole | C29H33N3O2S 487.666 | 2.44 (LC-2) | 488.44 | 486.53 |

TABLE 25-continued

| Intermediate | Name | Formula Mol weight | $t_R$ [min] (Meth.) | MS Data m/z [M + H]+ | MS Data m/z [M − H]+ |
|---|---|---|---|---|---|
| K-01c | 2-[3-(Butoxycarbonyl-phenethyl-amino)-propylsulfanyl]-benzoimidazole | C23H29N3O2S 411.56 | 2.23 (LC-2) | 412.37 | 410.52 |
| K-02c | 2-[3-(Benzyl-butoxycarbonyl-amino)-propylsulfanyl]-benzoimidazole | C22H27N3O2S 397.53 | 2.15 (LC-2) | 398.43 | 396.44 |
| K-03c | 2-[3-(Butoxycarbonyl-cyclohexyl-amino)-propylsulfanyl]-benzoimidazole | C21H31N3O2S 389.55 | 2.26 (LC-2) | 390.39 | 388.48 |
| K-04c | 2-{3-[Butoxycarbonyl-(cyclohexylmethyl)-amino]-propylsulfanyl}-benzoimidazole | C22H33N3O2S 403.58 | 2.41 (LC-2) | 404.47 | 402.56 |

Alkylating Agent K-01d (3-Chloro-propyl)-phenethyl-carbamic acid butyl ester

To a solution of phenethyl-carbamic acid butyl ester (3.9 g, 17.64 mmol) in dry DMF (20 ml) cooled to 0° C. with an ice-water bath is added sodium hydride (60% w/w in oil, 705 mg, 17.64 mmol). After addition is complete the resulting slurry is allowed to stir at rt for 30 min. It is then cooled down to 0° C. again and iodochloropropane (9.0 g, 4.73 ml, 44.1 mmol) is added over 5 min. The slurry is allowed to stir at rt overnight. Water is added until pH=7 and the water phase is extracted twice with AcOEt. The combined organic phases are washed with water/brine (1:1) and dried over MgSO$_4$. The solvent is evaporated in vacuo to afford 5 g of a yellow oil containing some DMF. It is purified by flash chromatography on silica-gel (AcOEt/heptane, 1:1), yielding the title compound (1.45 g) in 30% as a colourless oil: $t_R$=7.77 min (LC-1), ESI-MS (pos.): m/z 298.18 [M+H]+; $^1$H-NMR (CDCl$_3$): δ (ppm) 0.96 (t, 3H, CH$_3$), 1.40 (m, 2H, CH$_2$CH$_2$), 1.64 (m, 2H, CH$_2$CH$_2$), 1.99 (m, 2H, CH$_2$CH$_2$N), 2.87 (m, 2H, CH$_2$Ph), 3.32 (m, 2H, CH$_2$N), 3.46-3.53 (m, 4H), 7.16-7.22 (m, 3H$_{arom}$), 7.24-7.32 (m, 3H$_{arom}$).

Example Q-01a

{2-[3-(Pentanoyl-phenethyl-amino)-propylsulfanyl]-benzoimidazol-1-yl}-acetic

A solution of tert-butyl{2-[3-(pentanoyl-phenethyl-amino)-propylsulfanyl]-benzoimidazol-1-yl}-acetate (Precursor Q-01b, 5.5 mg, 0.01 mmol) in TFA/dichloromethane (1:1, 1.5 ml) is stirred for 3 h at rt. Toluene (2 ml) is added in the reaction mixture and the solvents are evaporated in vacuo yielding the title compound: $t_R$=2.17 min (LC-2), ESI-MS (pos.): m/z 454; 55 [M+H]+, ESI-MS (neg.): m/z 452.57 [M−H]+; $^1$H-NMR (DMSO-d$_6$ at 100° C.): δ (ppm) 0.80 (t, 3H, CH$_2$CH$_3$), 1.19 (m, 2H, CH$_2$CH$_3$), 1.31-1.46 (m, 2H, CH$_2$CH$_2$CH$_3$), 1.93 (m, 2H, CH$_2$CH$_2$N), 2.09 (m, 1H, COCH$_a$), 2.27 (m, 1H, COCH$_b$), 2.71-2.81 (m, 2H, CH$_2$Ph), 3.24-3.34 (m, 2H), 3.37-3.51 (m, 4H), 5.01 (m, 2H, CH$_2$CO$_2$), 7.15-7.28 (m, 7H$_{arom}$), 7.53 (m, 2H$_{arom}$).

All the Examples of the following Table 26 are prepared analogous to the procedure described for Example Q-01a, using the appropriate Precursor in place of Q-01b.

TABLE 26

| Example | Name | Formula Mol weight | $t_R$ [min] (Meth.) | MS Data m/z [M + H]+ | MS Data m/z [M − H]+ |
|---|---|---|---|---|---|
| L-01a | {2-[3-(Pentanoyl-phenyl-amino)-propylsulfanyl]-benzoimidazol-1-yl}-acetic acid | C23H27N3O3S 425.551 | 2.15 (LC-2) | 426.45 | 424.54 |
| L-02a | {2-[3-(Diphenylacetyl-phenyl-amino)-propylsulfanyl]-benzoimidazol-1-yl}-acetic acid | C32H29N3O3S 535.666 | 2.40 (LC-2) | 536.49 | 535.64 |
| L-03a | {2-[3-(Phenyl-phenylacetyl-amino)-propylsulfanyl]-benzoimidazol-1-yl}-acetic acid | C26H25N3O3S 459.569 | 2.13 (LC-2) | 460.41 | 458.56 |
| L-04a | (2-{3-[(3,3-diphenyl-propionyl)-phenyl-amino]-propylsulfanyl}- | C33H31N3O3S 549.693 | 2.39 (LC-2) | 550.57 | 548.66 |

TABLE 26-continued

| Example | Name | Formula Mol weight | $t_R$ [min] (Meth.) | MS Data m/z $[M + H]^+$ | MS Data m/z $[M - H]^+$ |
|---|---|---|---|---|---|
| | benzoimidazol-1-yl)-acetic acid; | | | | |
| L-05a | {2-[3-(Benzenesulfonyl-phenyl-amino)-propylsulfanyl]-benzoimidazol-1-yl}-acetic acid | C24H23N3O4S2 481.596 | 2.12 (LC-2) | 482.45 | 480.48 |
| L-06a | rac (2-{3-[(2-Cyclohexyl-2-phenyl-acetyl)-phenyl-amino]-propylsulfanyl}-benzoimidazol-1-yl)-acetic acid | C32H35N3O3S 541.714 | 2.65 (LC-2) | 542.54 | 540.7 |
| L-07a | {2-[3-(1,3-Diphenyl-ureido)-propylsulfanyl]-benzoimidazol-1-yl}-acetic acid | C25H24N4O3S 460.557 | 2.04 (LC-2) | 461.43 | 459.58 |
| L-08a | {2-[3-(3-Benzyl-1-phenyl-ureido)-propylsulfanyl]-benzoimidazol-1-yl}-acetic acid | C26H26N4O3S 474.583 | 2.02 (LC-2) | 475.51 | 473.53 |
| M-01a | (2-{3-[Pentanoyl-(4-piperidin-1-yl-phenyl)-amino]-propylsulfanyl}-benzoimidazol-1-yl)-acetic acid | C28H36N4O3S 508.685 | 1.99 (LC-2) | 509.53 | 507.62 |
| M-02a | (2-{3-[Diphenylacetyl-(4-piperidin-1-yl-phenyl)-amino]-propylsulfanyl}-benzoimidazol-1-yl)-acetic acid | C37H38N4O3S 618.8 | 2.41 (LC-2) | 619.66 | 617.74 |
| M-03a | (2-{3-[Phenylmethanesulfonyl-(4-piperidin-1-yl-phenyl)-amino]-propylsulfanyl}-benzoimidazol-1-yl)-acetic acid | C30H34N4O4S2 578.756 | 1.99 (LC-2) | 579.57 | 577.66 |
| M-04a | (2-{3-[Phenylacetyl-(4-piperidin-1-yl-phenyl)-amino]-propylsulfanyl}-benzoimidazol-1-yl)-acetic acid | C31H34N4O3S 542.702 | 2.03 (LC-2) | 543.56 | n/a |
| M-05a | (2-{3-[(3,3-Diphenyl-propionyl)-(4-piperidin-1-yl-phenyl)-amino]-propylsulfanyl}-benzoimidazol-1-yl)-acetic acid | C38H40N4O3S 632.827 | 2.41 (LC-2) | 633.68 | 631.76 |
| M-06a | (2-{3-[1-(4-Piperidin-1-yl-phenyl)-3-propyl-ureido]-propylsulfanyl}-benzoimidazol-1-yl)-acetic acid | C27H35N5O3S 509.673 | 1.68 (LC-2) | 510.55 | 508.64 |
| M-07a | (2-{3-[Benzenesulfonyl-(4-piperidin-1-yl-phenyl)-amino]-propylsulfanyl}-benzoimidazol-1-yl)-acetic acid | C29H32N4O4S2 564.729 | 2.01 (LC-2) | 565.55 | 563.57 |
| N-01a | [2-(3-{[(4-Ethyloxycarbonyl)-phenyl]-pentanoyl-amino}-propylsulfanyl)-benzoimidazol-1-yl]-acetic acid | C26H31N3O5S 497.614 | 2.21 (LC-2) | 498.51 | 496.6 |
| N-02a | [2-(3-{Diphenylacetyl-[(4-ethyloxycarbonyl)-phenyl]-amino}-propylsulfanyl)-benzoimidazol-1-yl]-acetic acid | C35H33N3O5S 607.729 | 2.47 (LC-2) | 608.63 | 606.72 |
| N-03a | (2-{3-[(4-Ethyloxycarbonylphenyl)-(phenylacetyl)-amino]-propylsulfanyl}-benzoimidazol-1-yl)-acetic acid | C29H29N3O5S 531.631 | 2.22 (LC-2) | 532.48 | 530.56 |
| N-04a | [2-(3-{Diphenylpropionyl-[(4-ethyloxycarbonyl)-phenyl]-amino}-propylsulfanyl)-benzoimidazol-1-yl]-acetic acid | C36H35N3O5S 621.756 | 2.45 (LC-2) | 622.65 | 620.67 |

TABLE 26-continued

| Example | Name | Formula Mol weight | $t_R$ [min] (Meth.) | MS Data m/z [M + H]+ | MS Data m/z [M − H]+ |
|---|---|---|---|---|---|
| N-05a | rac [2-(3-{(2-Cyclohexyl-2-phenyl-acetyl)-[(4-ethyloxycarbonyl)-phenyl]-amino}-propylsulfanyl)-benzoimidazol-1-yl]-acetic acid | C35H39N3O5S 613.777 | 2.71 (LC-2) | 614.62 | 612.71 |
| O-01a | {2-[3-(Benzyl-pentanoyl-amino)-propylsulfanyl]-benzoimidazol-1-yl}-acetic acid | C24H29N3O3S 439.578 | 2.10 (LC-2) | 440.47 | 438.55 |
| O-02a | {2-[3-(Benzyl-diphenylacetyl-amino)-propylsulfanyl]-benzoimidazol-1-yl}-acetic acid | C33H31N3O3S 549.693 | 2.38 (LC-2) | 550.51 | 548.66 |
| O-03a | {2-[3-(Benzyl-(phenylmethanesulfonyl)-amino)-propylsulfanyl]-benzoimidazol-1-yl}-acetic acid | C26H27N3O4S2 509.649 | 2.20 (LC-2) | 510.43 | 508.58 |
| O-04a | {2-[3-(Benzyl-(phenylacetyl)-amino)-propylsulfanyl]-benzoimidazol-1-yl}-acetic acid | C27H27N3O3S 473.595 | 2.11 (LC-2) | 474.49 | 472.58 |
| O-05a | (2-{3-[Benzyl-(3,3-diphenyl-propionyl)-amino]-propylsulfanyl}-benzoimidazol-1-yl)-acetic acid | C34H33N3O3S 563.72 | 2.37 (LC-2) | 564.59 | 562.62 |
| O-06a | {2-[3-(1-Benzyl-3-propyl-ureido)-propylsulfanyl]-benzoimidazol-1-yl}-acetic acid | C23H28N4O3S 440.566 | 1.93 (LC-2) | 441.48 | 439.57 |
| O-07a | {2-[3-(Benzenesulfonyl-benzyl-amino)-propylsulfanyl]-benzoimidazol-1-yl}-acetic acid | C25H25N3O4S2 495.622 | 2.20 (LC-2) | 496.41 | 494.5 |
| O-08a | rac (2-{3-[Benzyl-(2-cyclohexyl-2-phenyl-acetyl)-amino]-propylsulfanyl}-benzoimidazol-1-yl)-acetic acid | C33H37N3O3S 555.741 | 2.58 (LC-2) | 556.56 | 554.72 |
| P-01a | {2-[3-(Cyclopropyl-pentanoyl-amino)-propylsulfanyl]-benzoimidazol-1-yl}-acetic acid | C20H27N3O3S 389.518 | 1.93 (LC-2) | 390.46 | 388.48 |
| P-02a | (2-{3-[(Butane-1-sulfonyl)-cyclopropyl-amino]-propylsulfanyl}-benzoimidazol-1-yl)-acetic acid | C19H27N3O4S2 425.572 | 1.96 (LC-2) | 426.39 | 424.47 |
| P-03a | {2-[3-(Cyclopropyl-diphenylacetyl-amino)-propylsulfanyl]-benzoimidazol-1-yl}-acetic acid | C29H29N3O3S 499.633 | 2.25 (LC-2) | 500.49 | 498.57 |
| P-04a | {2-[3-(Cyclopropyl-(phenylmethanesulfonyl)-amino)-propylsulfanyl]-benzoimidazol-1-yl}-acetic acid | C22H25N3O4S2 459.589 | 1.99 (LC-2) | 460.41 | 458.5 |
| P-05a | {2-[3-(Cyclopropyl-(phenylacetyl)-amino)-propylsulfanyl]-benzoimidazol-1-yl}-acetic acid | C23H25N3O3S 423.536 | 1.94 (LC-2) | 424.41 | 422.5 |
| P-06a | (2-{3-[Cyclopropyl-(3,3-diphenyl-propionyl)-amino]-propylsulfanyl}-benzoimidazol-1-yl)-acetic acid | C30H31N3O3S 513.66 | 2.23 (LC-2) | 514.51 | 512.66 |
| P-07a | {2-[3-(1-Cyclopropyl-3-propyl-ureido)-propylsulfanyl]-benzoimidazol-1-yl}-acetic acid | C19H26N4O3S 390.506 | 1.71 (LC-2) | 391.41 | 389.5 |
| P-08a | {2-[3-(Benzenesulfonyl-cyclopropyl-amino)-propylsulfanyl]-benzoimidazol-1-yl}-acetic acid | C21H23N3O4S2 445.563 | 2.06 (LC-2) | 446.45 | 444.48 |

TABLE 26-continued

| Example | Name | Formula Mol weight | $t_R$ [min] (Meth.) | MS Data m/z [M + H]+ | MS Data m/z [M − H]+ |
|---|---|---|---|---|---|
| P-09a | rac (2-{3-[(2-Cyclohexyl-2-phenyl-acetyl)-cyclopropyl-amino]-propylsulfanyl}-benzoimidazol-1-yl)-acetic acid | C29H35N3O3S 505.681 | 2.48 (LC-2) | 506.60 | 504.63 |
| Q-02a | (2-{3-[(Butane-1-sulfonyl)-phenethyl-amino]-propylsulfanyl}-benzoimidazol-1-yl)-acetic acid | C24H31N3O4S2 489.659 | 2.25 (LC-2) | 490.55 | 488.51 |
| Q-03a | {2-[3-(Diphenylacetyl-phenethyl-amino)-propylsulfanyl]-benzoimidazol-1-yl}-acetic acid | C34H33N3O3S 563.72 | 2.42 (LC-2) | 564.66 | 562.62 |
| Q-04a | {2-[3-(phenethyl-(phenylmethanesulfonyl)-amino)-propylsulfanyl]-benzoimidazol-1-yl}-acetic acid; | C27H29N3O4S2 523.676 | 2.26 (LC-2) | 524.57 | 522.53 |
| Q-05a | {2-[3-(Phenethyl-(phenylacetyl)amino)-propylsulfanyl]-benzoimidazol-1-yl}-acetic acid | C28H29N3O3S 487.622 | 2.17 (LC-2) | 488.57 | 486.53 |
| Q-06a | (2-{3-[(3,3-Diphenyl-propionyl)-phenethyl-amino]-propylsulfanyl}-benzoimidazol-1-yl)-acetic acid | C35H35N3O3S 577.747 | 2.42 (LC-2) | 578.68 | 576.64 |
| Q-07a | {2-[3-(1-Phenethyl-3-propyl-ureido)-propylsulfanyl]-benzoimidazol-1-yl}-acetic acid | C24H30N4O3S 454.593 | 2.00 (LC-2) | 455.57 | 453.53 |
| Q-08a | {2-[3-(Benzenesulfonyl-phenethyl-amino)-propylsulfanyl]-benzoimidazol-1-yl}-acetic acid | C26H27N3O4S2 509.649 | 2.27 (LC-2) | 510.55 | 508.52 |
| R-01a | (2-{3-[(2,2-Diphenyl-ethyl)-pentanoyl-amino]-propylsulfanyl}-benzoimidazol-1-yl)-acetic acid | C31H35N3O3S 529.703 | 2.37 (LC-2) | 530.69 | 528.65 |
| R-02a | (2-{3-[Diphenylacetyl-(2,2-diphenyl-ethyl)-amino]-propylsulfanyl}-benzoimidazol-1-yl)-acetic acid | C40H37N3O3S 639.818 | 2.59 (LC-2) | 640.75 | 638.71 |
| R-03a | (2-{3-[(2,2-Diphenyl-ethyl)-(phenylmethanesulfonyl)-amino]-propylsulfanyl}-benzoimidazol-1-yl)-acetic acid | C33H33N3O4S2 599.774 | 2.43 (LC-2) | 600.66 | 598.62 |
| R-04a | (2-{3-[(2,2-Diphenyl-ethyl)-(phenylacetyl)-amino]-propylsulfanyl}-benzoimidazol-1-yl)-acetic acid | C34H33N3O3S 563.72 | 2.38 (LC-2) | 564.66 | 562.62 |
| R-05a | (2-{3-[(2,2-Diphenyl-ethyl)-(3,3-diphenyl-propionyl)-amino]-propylsulfanyl}-benzoimidazol-1-yl)-acetic acid | C41H39N3O3S 653.845 | 2.58 (LC-2) | 654.83 | 652.73 |
| R-06a | (2-{3-[1-(2,2-Diphenyl-ethyl)-3-propyl-ureido]-propylsulfanyl}-benzoimidazol-1-yl)-acetic acid | C30H34N4O3S 530.691 | 2.22 (LC-2) | 531.65 | 529.61 |
| T-02a | [2-(3-Pentanoylamino-propylsulfanyl)-benzoimidazol-1-yl]-acetic acid | C17H23N3O3S 349.454 | 1.62 (LC-2) | 350.45 | 348.42 |
| T-03a | {2-[3-(Butane-1-sulfonylamino)-propylsulfanyl]-benzoimidazol-1-yl}-acetic acid | C16H23N3O4S2 385.508 | 1.73 (LC-2) | 386.44 | 384.4 |
| T-04a | [2-(3-Diphenylacetylamino-propylsulfanyl)- | C26H25N3O3S 459.569 | 2.05 (LC-2) | 460.53 | 458.56 |

TABLE 26-continued

| Example | Name | Formula Mol weight | $t_R$ [min] (Meth.) | MS Data m/z [M + H]+ | MS Data m/z [M − H]+ |
|---|---|---|---|---|---|
| | benzoimidazol-1-yl]-acetic acid | | | | |
| T-05a | [2-(3-Phenylmethanesulfonylamino-propylsulfanyl)-benzoimidazol-1-yl]-acetic acid | C19H21N3O4S2 419.525 | 1.78 (LC-2) | 420.46 | 418.42 |
| T-06a | [2-(3-Phenylacetylamino-propylsulfanyl)-benzoimidazol-1-yl]-acetic acid | C20H21N3O3S 383.471 | 1.67 (LC-2) | 384.47 | 382.43 |
| T-07a | {2-[3-(3,3-Diphenyl-propionylamino)-propylsulfanyl]-benzoimidazol-1-yl}-acetic acid | C27H27N3O3S 473.595 | 2.02 (LC-2) | 474.55 | 472.58 |
| T-08a | {2-[3-(3-Propyl-ureido)-propylsulfanyl]-benzoimidazol-1-yl}-acetic acid | C16H22N4O3S 350.442 | 1.47 (LC-2) | 351.47 | 349.43 |
| T-09a | [2-(3-Benzenesulfonylamino-propylsulfanyl)-benzoimidazol-1-yl]-acetic acid | C18H19N3O4S2 405.498 | 1.76 (LC-2) | 406.44 | 404.41 |
| T-10a | rac {2-[3-(2-Cyclohexyl-2-phenyl-acetylamino)-propylsulfanyl]-benzoimidazol-1-yl}-acetic acid | C26H31N3O3S 465.616 | 2.23 (LC-2) | 466.65 | 464.55 |
| T-11a | {2-[3-(3-Phenyl-ureido)-propylsulfanyl]-benzoimidazol-1-yl}-acetic acid | C19H20N4O3S 384.459 | 1.67 (LC-2) | 385.49 | 383.38 |
| T-12a | [2-(3-Benzoylamino-propylsulfanyl)-benzoimidazol-1-yl]-acetic acid | C19H19N3O3S 369.444 | 2.27 (LC-2) | 370.28 | 368.36 |
| T-13a | {2-[3-(Cyclohexanecarbonyl-amino)-propylsulfanyl]-benzoimidazol-1-yl}-acetic acid | C19H25N3O3S 375.492 | 1.75 (LC-2) | 376.38 | 374.39 |
| T-14a | {2-[3-(4-Methoxy-benzoylamino)-propylsulfanyl]-benzoimidazol-1-yl}-acetic acid | C20H21N3O4S 399.47 | 1.68 (LC-2) | 400.31 | 399.47 |
| T-15a | (2-{3-[(Furan-2-carbonyl)-amino]-propylsulfanyl}-benzoimidazol-1-yl)-acetic acid | C17H17N3O4S 359.405 | 1.51 (LC-2) | 360.27 | 358.29 |
| T-16a | {2-[3-(Cyclopropanecarbonyl-amino)-propylsulfanyl]-benzoimidazol-1-yl}-acetic acid | C16H19N3O3S 333.411 | 1.42 (LC-2) | 334.29 | 332.37 |
| T-17a | (2-{3-[(Naphthalene-1-carbonyl)-amino]-propylsulfanyl}-benzoimidazol-1-yl)-acetic acid | C23H21N3O3S 419.504 | 1.88 (LC-2) | 420.33 | 418.40 |
| T-18a | {2-[3-(3-Cyclopentyl-propionylamino)-propylsulfanyl]-benzoimidazol-1-yl}-acetic acid | C20H27N3O3S 389.518 | 2.08 (LC-2) | 390.36 | n/a |
| T-19a | {2-[3-(2,2-Dimethyl-propionylamino)-propylsulfanyl]-benzoimidazol-1-yl}-acetic acid | C17H23N3O3S 349.454 | 1.61 (LC-2) | 350.33 | 348.41 |
| T-20a | {2-[3-(3-Phenyl-acryloylamino)-propylsulfanyl]-benzoimidazol-1-yl}-acetic acid | C21H21N3O3S 395.482 | 1.80 (LC-2) | 396.27 | 394.41 |
| T-21a | {2-[3-(3-Phenyl-propionylamino)-propylsulfanyl]-benzoimidazol-1-yl}-acetic acid | C21H23N3O3S 397.498 | 1.74 (LC-2) | 398.32 | 396.39 |
| T-22a | {2-[3-(1,2-Dioxo-2-ethyloxy-ethylamino)-propylsulfanyl]-benzoimidazol-1-yl}-acetic acid | C16H19N3O5S 365.409 | 1.50 (LC-2) | 366.24 | 364.32 |
| T-23a | (2-{3-[(Biphenyl-4-carbonyl)-amino]-propylsulfanyl}- | C25H23N3O3S 445.542 | 2.09 (LC-2) | 446.32 | 444.46 |

TABLE 26-continued

| Example | Name | Formula Mol weight | $t_R$ [min] (Meth.) | MS Data m/z $[M + H]^+$ | MS Data m/z $[M - H]^+$ |
|---|---|---|---|---|---|
| | benzoimidazol-1-yl)-acetic acid | | | | |
| T-24a | (2-{3-[(Pyridine-3-carbonyl)-amino]-propylsulfanyl}-benzoimidazol-1-yl)-acetic acid | C18H18N4O3S 370.432 | 1.34 (LC-2) | 371.31 | 369.38 |
| T-25a | {2-[3-(3,3-Dimethyl-butyrylamino)-propylsulfanyl]-benzoimidazol-1-yl}-acetic acid | C18H25N3O3S 363.481 | 1.70 (LC-2) | 364.38 | 362.39 |
| T-26a | [2-(3-Octanoylamino-propylsulfanyl)-benzoimidazol-1-yl]-acetic acid | C20H29N3O3S 391.534 | 2.03 (LC-2) | 392.42 | 390.43 |
| T-27a | {2-[3-(4-Bromo-benzoylamino)-propylsulfanyl]-benzoimidazol-1-yl}-acetic acid | C19H18BrN3O3S 448.34 | 1.90 (LC-2) | 450.23 | 448.31 |

Precursor Q-01b tert-Butyl{2-[3-(pentanoyl-phenethyl-amino)-propyl-sulfanyl]-benzoimidazol-1-yl}-acetate

[3-(1-tert-Butoxycarbonylmethyl-1H-benzoimidazol-2-ylsulfanyl)-propyl]-phenethyl-ammonium chloride (Precursor U-01b, 11.6 mg, 0.025 mmol) and Et$_3$N (12.2 mg, 17.2 μl, 0.1 mmol) are dissolved in 1,2-dichloroethane (0.2 ml). To this solution is added valerylchloride (9 mg, 8.95 μl, 0.075 mmol) and the stirring is continued for 2 h. Then 1,2-dichloroethane (0.4 ml) and tris-(2-aminoethyl)amine polystyrene (3.4 mmol/g, 22 mg, 0.075 mmol) are added. After 30 min of shaking the resin is filtered off. Then methylisocyanate polystyrene (2.5 mmol/g, 30 mg, 0.075 mmol) is added as well as 1,2-dichloroethane (0.5 ml) and the resulting suspension is stirred for 2 h. It is filtered and the organic filtrate is washed with an aqueous KH$_2$PO$_4$ solution (pH=4) and water. Finally the organic phase is dried over Na$_2$SO$_4$ and evaporated to dryness yielding the title compound: $t_R$=2.62 min (LC-2), ESI-MS (pos.): m/z 510.49 [M+H]$^+$; $^1$H-NMR (DMSO-d$_6$ at 100° C.): δ (ppm) 0.80 (t, 3H, CH$_2$CH$_3$), 1.19 (m, 2H, CH$_2$CH$_3$), 1.37 (m, 2H, CH$_2$CH$_2$CH$_3$), 1.40 (s, 9H, tBu), 1.91 (m, 2H, CH$_2$CH$_2$N), 2.08 (m, 1H, COCH$_a$), 2.24 (m, 1H, COCH$_b$), 2.71-2.83 (m, 2H, CH$_2$Ph), 3.30 (m, 2H), 3.32-3.43 (m, 4H), 4.98 (m, 2H, CH$_2$CO$_2$), 7.12-7.26 (m, 7 Harm), 7.50 (m, 2H$_{arom}$).

Alternatively, Precursor Q-01b is synthesized analogous to the procedure described for Precursor K-01b, using alkylating agent Q-01d in place of K-01d.

All the Precursors of the following Table 27 are prepared analogous to the procedures described for Precursor Q-01b.

TABLE 27

| Precursor | Name | Formula Mol weight | $t_R$ [min] (Meth.) | MS Data m/z $[M + H]^+$ |
|---|---|---|---|---|
| L-01b | tert-Butyl {2-[3-(pentanoyl-phenyl-amino)-propylsulfanyl]-benzoimidazol-1-yl}-acetate | C27H35N3O3S 481.66 | 2.63 (LC-2) | 482.45 |
| L-02b | tert-Butyl {2-[3-(diphenylacetyl-phenyl-amino)-propylsulfanyl]-benzoimidazol-1-yl}-acetate | C36H37N3O3S 591.77 | 2.79 (LC-2) | 592.57 |
| L-03b | tert-Butyl {2-[3-(phenyl-phenylacetyl-amino)-propylsulfanyl]-benzoimidazol-1-yl}-acetate | C30H33N3O3S 515.67 | 2.59 (LC-2) | 516.48 |
| L-04b | tert-Butyl (2-{3-[(3,3-diphenyl-propionyl)-phenyl-amino]-propylsulfanyl}-benzoimidazol-1-yl)-acetate | C37H39N3O3S 605.80 | 2.78 (LC-2) | 506.59 |
| L-05b | tert-Butyl {2-[3-(benzenesulfonyl-phenyl-amino)-propylsulfanyl]-benzoimidazol-1-yl}-acetate | C28H31N3O4S2 537.70 | 2.57 (LC-2) | 538.40 |
| L-06b | rac tert-Butyl (2-{3-[(2-cyclohexyl-2-phenyl-acetyl)-phenyl-amino]-propylsulfanyl}-benzoimidazol-1-yl)-acetate | C36H43N3O3S 597.82 | 3.02 (LC-2) | 598.62 |
| L-07b | tert-Butyl {2-[3-(1,3-diphenyl-ureido)-propylsulfanyl]-benzoimidazol-1-yl}-acetate | C29H32N4O3S 516.66 | 2.51 (LC-2) | 517.44 |
| L-08b | tert-Butyl {2-[3-(3-benzyl-1-phenyl-ureido)-propylsulfanyl]-benzoimidazol-1-yl}-acetate | C30H34N4O3S 530.69 | 2.48 (LC-2) | 531.46 |

TABLE 27-continued

| Precursor | Name | Formula Mol weight | $t_R$ [min] (Meth.) | MS Data m/z $[M + H]^+$ |
|---|---|---|---|---|
| M-01b | tert-Butyl (2-{3-[pentanoyl-(4-piperidin-1-yl-phenyl)-amino]-propylsulfanyl}-benzoimidazol-1-yl)-acetate | C32H44N4O3S 564.79 | 2.66 (LC-2) | 565.61 |
| M-02b | tert-Butyl (2-{3-[diphenylacetyl-(4-piperidin-1-yl-phenyl)-amino]-propylsulfanyl}-benzoimidazol-1-yl)-acetate | C41H46N4O3S 674.91 | 2.90 (LC-2) | 675.67 |
| M-03b | tert-Butyl (2-{3-[phenylmethanesulfonyl-(4-piperidin-1-yl-phenyl)-amino]-propylsulfanyl}-benzoimidazol-1-yl)-acetate | C34H42N4O4S2 634.86 | 2.54 (LC-2) | 635.59 |
| M-04b | tert-Butyl (2-{3-[phenylacetyl-(4-piperidin-1-yl-phenyl)-amino]-propylsulfanyl}-benzoimidazol-1-yl)-acetate | C35H42N4O3S 598.81 | 2.64 (LC-2) | 599.64 |
| M-05b | tert-Butyl (2-{3-[(3,3-diphenyl-propionyl)-(4-piperidin-1-yl-phenyl)-amino]-propylsulfanyl}-benzoimidazol-1-yl)-acetate | C42H48N4O3S 688.93 | 2.90 (LC-2) | 689.70 |
| M-06b | tert-Butyl (2-{3-[1-(4-piperidin-1-yl-phenyl)-3-propyl-ureido]-propylsulfanyl}-benzoimidazol-1-yl)-acetate | C31H43N5O3S 565.78 | 2.30 (LC-2) | 566.63 |
| M-07b | tert-Butyl (2-{3-[benzenesulfonyl-(4-piperidin-1-yl-phenyl)-amino]-propylsulfanyl}-benzoimidazol-1-yl)-acetate | C33H40N4O4S2 620.84 | 2.60 (LC-2) | 621.57 |
| N-01b | tert-Butyl [2-(3-{[(4-ethyloxycarbonyl)-phenyl]-pentanoyl-amino}-propylsulfanyl)-benzoimidazol-1-yl]-acetate | C30H39N3O5S 553.72 | 2.67 (LC-2) | 554.52 |
| N-02b | tert-Butyl [2-(3-{diphenylacetyl-[(4-ethyloxycarbonyl)-phenyl]-amino}-propylsulfanyl)-benzoimidazol-1-yl]-acetate | C39H41N3O5S 663.84 | 2.83 (LC-2) | 664.65 |
| N-03b | tert-Butyl (2-{3-[(4-ethyloxycarbonylphenyl)-(phenylacetyl)-amino]-propylsulfanyl}-benzoimidazol-1-yl)-acetate | C33H37N3O5S 587.74 | 2.64 (LC-2) | 588.56 |
| N-04b | tert-Butyl [2-(3-{diphenylpropionyl-[(4-ethyloxycarbonyl)-phenyl]-amino}-propylsulfanyl)-benzoimidazol-1-yl]-acetate | C40H43N3O5S 677.86 | 2.83 (LC-2) | 678.67 |
| N-05b | rac tert-Butyl [2-(3-{(2-cyclohexyl-2-phenyl-acetyl)-[(4-ethyloxycarbonyl)-phenyl]-amino}-propylsulfanyl)-benzoimidazol-1-yl]-acetate | C39H47N3O5S 669.88 | 3.07 (LC-2) | 670.70 |
| O-01b | tert-Butyl {2-[3-(benzyl-pentanoyl-amino)-propylsulfanyl]-benzoimidazol-1-yl}-acetate | C28H37N3O3S 495.69 | 2.59 (LC-2) | 496.47 |
| O-02b | tert-Butyl {2-[3-(benzyl-diphenylacetyl-amino)-propylsulfanyl]-benzoimidazol-1-yl}-acetate | C37H39N3O3S 605.80 | 2.78 (LC-2) | 606.59 |
| O-03b | tert-Butyl {2-[3-(benzyl-phenylmethanesulfonyl-amino)-propylsulfanyl]-benzoimidazol-1-yl}-acetate | C30H35N3O4S2 565.76 | 2.61 (LC-2) | 566.51 |
| O-04b | tert-Butyl {2-[3-(benzyl-phenylacetyl-amino)-propylsulfanyl]-benzoimidazol-1-yl}-acetate | C31H35N3O3S 529.70 | 2.57 (LC-2) | 530.50 |
| O-05b | tert-Butyl (2-{3-[benzyl-(3,3-diphenyl-propionyl)-amino]-propylsulfanyl}-benzoimidazol-1-yl)-acetate | C38H41N3O3S 619.83 | 2.76 (LC-2) | 620.61 |

TABLE 27-continued

| Precursor | Name | Formula Mol weight | $t_R$ [min] (Meth.) | MS Data m/z $[M + H]^+$ |
|---|---|---|---|---|
| O-06b | tert-Butyl {2-[3-(1-benzyl-3-propyl-ureido)-propylsulfanyl]-benzoimidazol-1-yl}-acetate | C27H36N4O3S 496.67 | 2.42 (LC-2) | 497.49 |
| O-07b | tert-Butyl {2-[3-(benzenesulfonyl-benzyl-amino)-propylsulfanyl]-benzoimidazol-1-yl}-acetate | C29H33N3O4S2 551.73 | 2.63 (LC-2) | 552.49 |
| O-08b | rac tert-Butyl(2-{3-[benzyl-(2-cyclohexyl-2-phenyl-acetyl)-amino]-propylsulfanyl}-benzoimidazol-1-yl)-acetate | C37H45N3O3S 611.85 | 2.96 (LC-2) | 612.64 |
| P-01b | tert-Butyl {2-[3-(cyclopropyl-pentanoyl-amino)-propylsulfanyl]-benzoimidazol-1-yl}-acetate | C24H35N3O3S 445.63 | 2.48 (LC-2) | 440.34 |
| P-02b | tert-Butyl (2-{3-[(butane-1-sulfonyl)-cyclopropyl-amino]-propylsulfanyl}-benzoimidazol-1-yl)-acetate | C23H35N3O4S2 481.68 | 2.48 (LC-2) | 482.45 |
| P-03b | tert-Butyl {2-[3-(cyclopropyl-diphenylacetyl-amino)-propylsulfanyl]-benzoimidazol-1-yl}-acetate | C33H37N3O3S 555.74 | 2.68 (LC-2) | 556.56 |
| P-04b | tert-Butyl {2-[3-(cyclopropyl-phenylmethanesulfonyl-amino)-propylsulfanyl]-benzoimidazol-1-yl}-acetate | C26H33N3O4S2 515.70 | 2.50 (LC-2) | 516.42 |
| P-05b | tert-Butyl {2-[3-(cyclopropyl-phenylacetyl-amino)-propylsulfanyl]-benzoimidazol-1-yl}-acetate | C27H33N3O3S 479.64 | 2.45 (LC-2) | 480.41 |
| P-06b | tert-Butyl (2-{3-[cyclopropyl-(3,3-diphenyl-propionyl)-amino]-propylsulfanyl}-benzoimidazol-1-yl)-acetate | C34H39N3O3S 569.77 | 2.67 (LC-2) | 570.58 |
| P-07b | tert-Butyl {2-[3-(1-cyclopropyl-3-propyl-ureido)-propylsulfanyl]-benzoimidazol-1-yl}-acetate | C23H34N4O3S 446.61 | 2.30 (LC-2) | 447.47 |
| P-08b | tert-Butyl {2-[3-(benzenesulfonyl-cyclopropyl-amino)-propylsulfanyl]-benzoimidazol-1-yl}-acetate | C25H31N3O4S2 501.67 | 2.50 (LC-2) | 502.40 |
| P-09b | rac tert-Butyl (2-{3-[(2-cyclohexyl-2-phenyl-acetyl)-cyclopropyl-amino]-propylsulfanyl}-benzoimidazol-1-yl)-acetate | C33H43N3O3S 561.79 | 2.90 (LC-2) | 562.62 |
| Q-02b | tert-Butyl (2-{3-[(butane-1-sulfonyl)-phenethyl-amino]-propylsulfanyl}-benzoimidazol-1-yl)-acetate | C28H39N3O4S2 545.77 | 2.68 (LC-2) | 546.49 |
| Q-03b | tert-Butyl {2-[3-(diphenylacetyl-phenethyl-amino)-propylsulfanyl]-benzoimidazol-1-yl}-acetate | C38H41N3O3S 619.83 | 2.79 (LC-2) | 620.61 |
| Q-04b | tert-Butyl {2-[3-(phenethyl-phenylmethanesulfonyl-amino)-propylsulfanyl]-benzoimidazol-1-yl}-acetate | C31H37N3O4S2 579.78 | 2.66 (LC-2) | 580.53 |
| Q-05b | tert-Butyl {2-[3-(phenethyl-phenylacetyl-amino)-propylsulfanyl]-benzoimidazol-1-yl}-acetate | C32H37N3O3S 543.73 | 2.62 (LC-2) | 544.52 |
| Q-06b | tert-Butyl (2-{3-[(3,3-diphenyl-propionyl)-phenethyl-amino]-propylsulfanyl}-benzoimidazol-1-yl)-acetate | C39H43N3O3S 633.85 | 2.80 (LC-2) | 634.63 |
| Q-07b | tert-Butyl {2-[3-(1-phenethyl-3-propyl-ureido)-propylsulfanyl]-benzoimidazol-1-yl}-acetate | C28H38N4O3S 510.70 | 2.48 (LC-2) | 511.51 |
| Q-08b | tert-Butyl {2-[3-(benzenesulfonyl-phenethyl-amino)-propylsulfanyl]-benzoimidazol-1-yl}-acetate | C30H35N3O4S2 565.76 | 2.68 (LC-2) | 566.51 |

TABLE 27-continued

| Precursor | Name | Formula Mol weight | $t_R$ [min] (Meth.) | MS Data m/z $[M + H]^+$ |
|---|---|---|---|---|
| R-01b | tert-Butyl (2-{3-[(2,2-diphenyl-ethyl)-pentanoyl-amino]-propylsulfanyl}-benzoimidazol-1-yl)-acetate | C35H43N3O3S 585.81 | 2.78 (LC-2) | 586.58 |
| R-02b | tert-Butyl (2-{3-[diphenylacetyl-(2,2-diphenyl-ethyl)-amino]-propylsulfanyl}-benzoimidazol-1-yl)-acetate | C44H45N3O3S 695.93 | 2.90 (LC-2) | 696.71 |
| R-03b | tert-Butyl (2-{3-[(2,2-diphenyl-ethyl)-phenylmethanesulfonyl-amino]-propylsulfanyl}-benzoimidazol-1-yl)-acetate | C37H41N3O4S2 655.88 | 2.78 (LC-2) | 656.62 |
| R-04b | tert-Butyl (2-{3-[(2,2-diphenyl-ethyl)-phenylacetyl-amino]-propylsulfanyl}-benzoimidazol-1-yl)-acetate | C38H41N3O3S 619.83 | 2.75 (LC-2) | 620.61 |
| R-05b | tert-Butyl (2-{3-[(2,2-diphenyl-ethyl)-(3,3-diphenyl-propionyl)-amino]-propylsulfanyl}-benzoimidazol-1-yl)-aceate | C45H47N3O3S 709.95 | 2.90 (LC-2) | 710.73 |
| R-06b | tert-Butyl (2-{3-[1-(2,2-diphenyl-ethyl)-3-propyl-ureido]-propylsulfanyl}-benzoimidazol-1-yl)-acetate | C34H42N4O3S 586.80 | 2.62 (LC-2) | 587.60 |
| T-02b | tert-Butyl [2-(3-pentanoylamino-propylsulfanyl)-benzoimidazol-1-yl]-acetate | C21H31N3O3S 405.56 | 2.23 (LC-2) | 406.44 |
| T-03b | tert-Butyl {2-[3-(butane-1-sulfonylamino)-propylsulfanyl]-benzoimidazol-1-yl}-acetate | C20H31N3O4S2 441.61 | 2.32 (LC-2) | 442.38 |
| T-04b | tert-Butyl [2-(3-diphenylacetylamino-propylsulfanyl)-benzoimidazol-1-yl]-acetate | C30H33N3O3S 515.67 | 2.50 (LC-2) | 516.48 |
| T-05b | tert-Butyl [2-(3-phenylmethanesulfonylamino-propylsulfanyl)-benzoimidazol-1-yl]-acetate | C23H29N3O4S2 475.63 | 2.35 (LC-2) | 476.40 |
| T-06b | tert-Butyl [2-(3-phenylacetylamino-propylsulfanyl)-benzoimidazol-1-yl]-acetate | C24H29N3O3S 439.57 | 2.24 (LC-2) | 440.40 |
| T-07b | tert-Butyl {2-[3-(3,3-diphenyl-propionylamino)-propylsulfanyl]-benzoimidazol-1-yl}-acetate | C31H35N3O3S 529.70 | 2.47 (LC-2) | 530.50 |
| T-08b | tert-Butyl {2-[3-(3-propyl-ureido)-propylsulfanyl]-benzoimidazol-1-yl}-acetate | C20H30N4O3S 406.55 | 2.08 (LC-2) | 407.40 |
| T-09b | tert-Butyl [2-(3-benzenesulfonylamino-propylsulfanyl)-benzoimidazol-1-yl]-acetate | C22H27N3O4S2 461.60 | 2.33 (LC-2) | 462.38 |
| T-10b | rac tert-Butyl {2-[3-(2-cyclohexyl-2-phenyl-acetylamino)-propylsulfanyl]-benzoimidazol-1-yl}-acetate | C30H39N3O3S 521.72 | 2.67 (LC-2) | 522.53 |
| T-11b | tert-Butyl {2-[3-(3-phenyl-ureido)-propylsulfanyl]-benzoimidazol-1-yl}-acetate | C23H28N4O3S 440.56 | 2.23 (LC-2) | 441.42 |

Alkylating Agent N-05d rac 4-[(3-Chloro-propyl)-(2-cyclohexyl-2-phenyl-acetyl)-amino]-benzoic acid ethyl ester To a solution of 4-(2-cyclohexyl-2-phenyl-acetylamino)-benzoic acid ethyl ester (Starting material N-05e, 1 g, 2.74 mmol) and 1,3-iodochloropropane (559 mg, 294 µl, 2.74 mmol, 1 eq.) in dry DMF (10 ml) is added sodium hydride (60% w/w in oil, 72 mg, 3 mmol). After addition is complete, the resulting slurry is allowed to stir for 1 h. Then the same quantity of 1,3-iodochloropropane and of sodium hydride are added again and the resulting slurry is heated up to 50° C. overnight. After cooling to rt, water is added until pH=7 and the water phase is extracted twice with AcOEt. The organic phase is washed with water/brine (1:1). The organic phase is dried over MgSO$_4$ and the solvent evaporated to afford a yellow oil containing some DMF. It is purified by flash chromatography on silica-gel (AcOEt/heptane/AcOH, 1:9:0.5), yielding the title compound (365 mg) in 30% as a colourless oil: $t_R$=8.74 min (LC-1), ESI-MS (pos.): m/z 442.20 [M+H]$^+$.

Starting Material N-05e rac 4-(2-Cyclohexyl-2-phenyl-acetylamino)-benzoic acid ethyl ester

To a flask containing thionyl chloride (1.52 g, 929 µl, 12.8 mmol) and 1 drop of DMF is added cyclohexylphenylacetic acid (1.87 g, 8.54 mmol). The resulting solution is stirred for 1 h. The thionyl chloride is evaporated under reduced pressure and the resulting crude acid chloride is diluted in dichloromethane (15 ml). To this solution is added dropwise a solution of 4-amino-benzoic acid ethyl ester (1.41 g, 8.54 mmol) and triethylamine (1.49 ml, 1.08 g, 10.67 mmol) in dichloromethane (15 ml). The resulting mixture is stirred for 30 min at rt. It is diluted with dichloromethane and the resulting organic phase is washed with a 10% aqueous citric acid solution, with a saturated aqueous $Na_2CO_3$ solution and with water. It is dried over $Na_2SO_4$ and the solvent is evaporated in vacuo. The crude residue is purified on silica gel (AcOEt/heptane, 1.4), yielding the title compound (3.04 g) in 97% as a white solid: $t_R$=8.00 min (LC-1), ESI-MS (pos.): m/z 366.18 [M+H]$^+$, ESI-MS (neg.): m/z 364.25 [M−H]$^+$.

Alkylating Agent Q-01d

Pentanoic Acid (3-chloro-propyl)-phenethyl-amide

To a solution of valeryl chloride (342 mg, 338 µl, 2.83 mmol) in dichloromethane (6 ml) and cooled to 0° C. is added a solution of (3-chloro-propyl)-phenethyl-amine (Starting material Q-01e, 560 mg, 2.83 mmol). The colourless solution turns yellow and after 2 min, a solid crystallizes out. Upon dropwise addition of $Et_3N$ (315 mg, 409 µl, 2.83 mmol) the solution turns colourless again and the solid dissolves instantaneously. The mixture is allowed to stir for 4 h at which time yet again a solid had crystallized out. Saturated aqueous $NH_4Cl$ solution is added and the organic phase is washed once with some saturated aqueous $NaHCO_3$ solution and dried over $Na_2SO_4$. The solvent is removed in vacuo and the residue is dried under high vacuum, yielding the title compound as an orange oil: $t_R$=2.48 min (LC-2), ESI-MS (pos.): m/z 282.07 [M+H]$^+$; $^1$H-NMR ($CDCl_3$): δ (ppm) 0.86-0.97 (m, 3H, $CH_3$), 1.23-1.44 (m, 4H, $CH_2CH_3$), 1.55 (quint., 1H, $CH_2CH_2CH_3$), 1.65 (quint., 1H, $\overline{CH_2}CH_2CH_3$), 1.95 (quint., 2$\overline{H}$, $CH_2CH_2N$), 2.03-2.19 (m, 2$\overline{H}$, $CH_2C$=O), 2.90 (t, 2H, $CH_2P\overline{h}$), 3.35-3.59 (m, 6H), 7.15-7.34 (m, 2H$_{arom}$).

Starting Material Q-01e

(3-Chloro-propyl)-phenethyl-amine

This compound is synthesized according to the procedure described in Brinner, K. M.; Kim, J. M.; Habashita, H.; Gluzman, I. Y.; Goldberg, D. E.; Ellman, J. A., Bioorg. Med. Chem. 2002,10, 3649, 3661.

A mixture of phenethylamine (7.1 g, 7.38 ml, 58.5 mmol) and bromochloropropane (3.07 g, 1.93 ml, 19.5 mmol) in acetonitrile (15 ml) is stirred for 16 h. In the course of the reaction a white crystalline solid forms. Saturated aqueous $NaHCO_3$ solution is added to adjust the pH to 9-10. The free amine is extracted three times with AcOEt. The combined organic phases are dried over $Na_2SO_4$. Evaporation of the solvent in vacuo yields a yellow oil. It is purified by chromatography on silica-gel (dichloromethane/MeOH, 95:5), yielding the title compound (1.02 g) in 26% as a slightly yellow oil which crystallizes on standing: $^1$H-NMR ($CDCl_3$): δ (ppm) 1.91 (quint., 2H, $CH_2CH_2N$), 2.75 (m, 4H), 2.81-2.89 (m, 2H), 3.59 (t, 2H, $C\overline{H_2}Cl$), 7.20 (m, 3H$_{arom}$), 7.24-7.32 (m, 2H$_{arom}$).

Example S-01a

[2-(3-{Butyloxycarbonyl-[(4-ethyloxycarbonyl)-phenyl]-amino}-propylsulfanyl)-benzoimidazol-1-yl]-acetic acid tert-Butyl[2-(3-{butyloxycarbonyl-[(4-ethyloxycarbonyl)-phenyl]-amino}-propylsulfanyl)-benzoimidazol-1-yl]-acetate (Precursor S-01b, 233 mg, 0.41 mmol) is dissolved in TFA/dichloromethane (1:1, 5 ml). The solution is allowed to stir at rt overnight. Evaporation of the solvents in vacuo and drying under high vacuum yields the title compound (206 mg) in 97% as an off-white solid: $t_R$=6.71 min (LC-1), ESI-MS (pos.): m/z 514.23 [M+H]$^+$, ESI-MS (neg.): m/z 512.31 [M−H]$^+$; $^1$H-NMR ($CDCl_3$): δ (ppm) 0.86 (t, 3H, $CH_2CH_3$), 1.25 (m, 2H, $CH_2CH_3$), 1.39 (t, 3H, $OCH_2CH_3$), 1.50 (quint., 2H, $OCH_2CH_2$), 1.89 (br. t, 2H, $SCH_2CH_2$), 3.38 (br. t, 2H, $SCH_2$), 3.81 (m, 2H, $CH_2N$), 4.04 (t, 2H, $OCH_2CH_2$), 4.39 (q, 2H, $OCH_2CH_3$) 4.88 (s, 2H, $CH_2CO_2$), 7.20 (d, 2H$_{arom}$), 7.40 (m, 2H$_{arom}$), 7.59 (br. s, 1H, ac. H), 7.71 (d, 2 H$_{arom}$), 8.14 (d, 2H$_{arom}$).

Precursor S-01b tert-Butyl[2-(3-{butyloxycarbonyl-[(4-ethyloxycarbonyl)-phenyl]-amino}-propylsulfanyl)-benzoimidazol-1-yl]-acetate To a suspension of tert-butyl (2-mercapto-benzoimidazol-1-yl)-acetate (Intermediate 3-I, 264 mg, 1 mmol) and $K_2CO_3$ (276 mg, 2 mmol, 2 eq.) in acetone (3 ml) are added 4-[butoxycarbonyl-(3-chloro-propyl)-amino]-benzoic acid ethyl ester (341 mg, 1 mmol) and a few crystals of sodium iodide. The resulting mixture is allowed to stir at reflux for 36 h. It is then cooled down and filtered on a fritted funnel to remove all solid impurities. Evaporation of the solvent in vacuo affords a crude oil that is purified by chromatography on silica gel (AcOEt/heptane, 1:4) yielding the title compound (280 mg) in 49% as a white solid: $t_R$=8.07 min (LC-1), ESI-MS (pos.): m/z 570.31 [M+H]$^+$; $^1$H-NMR ($CDCl_3$): δ (ppm) 0.88 (t, 3H, $CH_2CH_3$), 1.25-1.32 (m, 2H, $CH_2CH_3$), 1.34 (t, 3H, $OCH_2CH_3$), 1.40 (s, 9H, tBu), 1.50 (m, 2H, $OCH_2CH_2$), 2.05 (quint., 2H, $SCH_2CH_2$), 3.38 (hr. t, 2H, $SCH_2$), 3.87 (m, 2H, $CH_2N$), 4.06 (t, 2H, $OCH_2CH_2$), 4.35 (q, 2H, $OCH_2CH_3$), 4.66 (s, 2H, $CH_2CO_2$), 7.14-7.24 (m, 3H$_{arom}$), 7.28 (d, 2H$_{arom}$), 7.68 (m, 2H$_{arom}$), 8.00 (d, 2H$_{arom}$).

Alkylating Agent S-01d

4-[Butoxycarbonyl-(3-chloro-propyl)-amino]-benzoic acid ethyl ester is prepared analogous to the procedure described for alkylating agent K-01d, substituting the appropriate carbamate for phenethyl-carbamic acid tert-butyl ester. It is obtained as a colourless oil: $t_R$=2.60 min (LC-2), MS (pos.): m/z 342.17 [M+H]$^+$.

Example T-01a

[2-(3-tert-Butoxycarbonylamino-propylsulfanyl)-benzoimidazol-1-yl]-acetic acid is prepared analogous to the procedure described for Example J-01a, using Precursor T-Olb in place of J-01b: $t_R$=1.78 min (LC-2), ESI-MS (pos.): m/z 366.31 [M+H]$^+$, ESI-MS (neg.): m/z 364.40 [M−H]$^+$.

Precursor T-01b tert-Butyl[2-(3-tert-butoxycarbonylamino-propylsulfanyl)-benzoimidazol-1-yl]-acetate A solution of tert-butyl (2-mercapto-benzoimidazol-1-yl)-acetate (Intermediate 3-I, 502 mg, 1.9 mmol) and DBU (289 mg, 284 µl, 1.9 mmol) in THF (1 ml) is added onto a solution of (3-bromo-propyl)-carbamic acid tert-butyl ester (407 mg, 1.71 mmol) in THF (1 ml). The resulting solution is stirred at rt for 2 h. It becomes slowly turbid and the undesired solid is filtered on a fritted funnel. The solution is diluted with THF (2 ml) and DIPEA (491 mg, 650 µl, 3.8 mmol) is added. The mixture is poured onto a suspension of 2-chlorotrityl chloride resin (200-400 mesh), 1% DVB (1.0-1.6 mmol/g, 475 mg, 0.76 mmol) in THF (1 ml) and allowed to stir for 3 h. The resin is filtered and rinsed with THF. The solvent is removed in vacuo and the residue diluted with dichloromethane (5 ml). This organic phase is washed with an aqueous citric acid solution (pH=4) and with water. The solvent is evaporated under reduced pressure. The same purification process is repeated using dichloromethane instead of THF as the solvent. The obtained organic phase is washed with a saturated aqueous $KH_2PO_4$ solution and water. Evaporation of the solvent in vacuo affords a residue that is purified by flash chromatography on silica-gel (AcOEt/heptane, 1:2), yielding the title compound (587 mg) in 73% as a colourless oil: $t_R$=2.41 min (LC-2), ESI-MS (pos.): m/z 422.50 [M+H]$^+$; $^1$H-NMR ($CDCl_3$): δ (ppm) 1.37 (s, 9H, tBu), 1.39 (s, 9H, tBu), 1.74 (quint. 2H, $CH_2CH_2N$), 3.20 (dd, 2H), 3.38 (t, 2H), 4.67 (s, 2H, $CH_2CO_2$), 5.82 (br. s, 1H, NH), 7.10-7.29 (m, 3H$_{arom}$), 7.65 (m, 1H$_{arom}$).

Precursor T-12b tert-Butyl[2-(3-benzoylamino-propylsulfanyl)-benzoimidazol-1-yl]-acetate To a suspension of 3-(1-tert-butoxycarbonylmethyl-1H-benzoimidazol-2-ylsulfanyl)-propyl-ammonium chloride (Precursor U-08b, 6 mg, 0.02 mmol) in dichloromethane (0.4 ml) are added subsequently DIPEA (10 mg, 15 µl, 0.085 mmol) and benzoyl chloride (3.9 mg, 3.24 1l, 0.03 mmol) and the resulting solution is allowed to stir for 1 h at rt. Tris-(2-aminoethyl)amine polystyrene (3.4 mmol/g, 33 mg, 0.11 mmol) is added and the mixture is allowed to stir for another 3 h at rt. The solvent is evaporated and the residue dried under high vacuum, yielding the title compound as a colourless oil: $t_R$=2.62 min (LC-2), ESI-MS (pos.): m/z 510.49 [M+H]$^+$.

Precursors T-13b to T-27b of the following Table 28 are prepared using a procedure analogous to that described for Precursor T-2b, substituting the appropriate acyl chloride for benzoyl chloride.

TABLE 28

| Ex. | Name | Formula Mol weight | $t_R$ [min] (Meth.) | MS Data m/z [M + H]$^+$ | MS Data m/z [M − H]$^-$ |
|---|---|---|---|---|---|
| T-13b | {2-[3-(Cyclohexanecarbonyl-amino)-propylsulfanyl]-benzoimidazol-1-yl}-acetic acid tert-butyl ester | C23H33N3O3S 431.59 | 2.34 (LC-2) | 432.29 | n/a |
| T-14b | {2-[3-(4-Methoxy-benzoylamino)-propylsulfanyl]-benzoimidazol-1-yl}-acetic acid tert-butyl ester | C24H29N3O4S 455.57 | na (LC-2) | n/a | n/a |
| T-15b | (2-{3-[(Furan-2-carbonyl)-amino]-propylsulfanyl}-benzoimidazol-1-yl)-acetic acid tert-butyl ester | C21H25N3O4S 415.51 | 2.15 (LC-2) | 416.41 | n/a |
| T-16b | {2-[3-(Cyclopropanecarbonyl-amino)-propylsulfanyl]-benzoimidazol-1-yl}-acetic acid tert-butyl ester | C20H27N3O3S 389.51 | 2.10 (LC-2) | 390.43 | 388.47 |
| T-17b | (2-{3-[(Naphthalene-1-carbonyl)-amino]-propylsulfanyl}-benzoimidazol-1-yl)-acetic acid tert-butyl ester | C27H29N3O3S 475.61 | 2.41 (LC-2) | 476.48 | 474.62 |
| T-18b | {2-[3-(3-Cyclopentyl-propionylamino)-propylsulfanyl-benzoimidazol-1-yl}-acetic acid tert-butyl ester | C24H35N3O3S 445.63 | 2.45 (LC-2) | 446.44 | 444.58 |
| T-19b | {2-[3-(2,2-Dimethyl-propionylamino)-propylsulfanyl]-benzoimidazol-1-yl}-acetic acid tert-butyl ester | C21H31N3O3S 405.56 | 2.26 (LC-2) | 406.47 | n/a |
| T-20b | {2-[3-(3-Phenyl-acryloylamino)-propylsulfanyl]-benzoimidazol-1-yl}-acetic acid tert-butyl ester | C25H29N3O3S 451.59 | 2.33 (LC-2) | 452.48 | 450.49 |
| T-21b | {2-[3-(3-Phenyl-propionylamino)-propylsulfanyl]-benzoimidazol-1-yl}-acetic acid tert-butyl ester | C25H31N3O3S 453.60 | 2.29 (LC-2) | 454.47 | 452.60 |
| T-22b | N-[3-(1-tert-Butoxycarbonylmethyl-1H-benzoimidazol-2-ylsulfanyl)- | C20H27N3O5S 421.52 | 2.39 (LC-2) | 422.45 | 420.52 |

TABLE 28-continued

| Ex. | Name | Formula Mol weight | $t_R$ [min] (Meth.) | MS Data m/z [M + H]$^+$ | MS Data m/z [M − H]$^-$ |
|---|---|---|---|---|---|
| | propyl]-oxalamic acid ethyl ester | | | | |
| T-23b | (2-{3-[(Biphenyl-4-carbonyl)-amino]-propylsulfanyl}-benzoimidazol-1-yl)-acetic acid tert-butyl ester | C29H31N3O3S 501.65 | 2.55 (LC-2) | 502.47 | 500.48 |
| T-24b | (2-{3-[(Pyridine-3-carbonyl)-amino]-propylsulfanyl}-benzoimidazol-1-yl)-acetic acid tert-butyl ester | C22H26N4O3S 426.54 | 1.97 (LC-2) | 427.39 | 425.53 |
| T-25b | {2-[3-(3,3-Dimethyl-butyrylamino)-propylsulfanyl]-benzoimidazol-1-yl}-acetic acid tert-butyl ester | C22H33N3O3S 419.59 | 2.30 (LC-2) | 420.46 | n/a |
| T-26b | [2-(3-Octanoylamino-propylsulfanyl)-benzoimidazol-1-yl]-acetic acid tert-butyl ester | C24H37N3O3S 447.64 | 2.54 (LC-2) | 448.50 | 446.57 |
| T-27b | {2-[3-(4-Bromo-benzoylamino)-propylsulfanyl]-benzoimidazol-1-yl}-acetic acid tert-butyl ester | C23H26BrN3O3S 504.45 | 2.45 (LC-2) | 506.38 | 504.46 |

Example U-01a

[2-(3-Phenethylamino-propylsulfanyl)-benzoimidazol-1-yl]-acetic acid tert-Butyl {2-[3-(tert-butoxycarbonyl-phenethyl-amino)-propylsulfanyl]-benzoimidazol-1-yl}-acetate (Precursor J-01b, 5.5 mg, 0.015 mmol) is dissolved in TFA/dichloromethane (1:1, 1.5 ml) and stirred at rt for 1.5 h. The solvents are evaporated under reduced pressure and the residue is dried under high vacuum, yielding the pure title compound: $t_R$=1.51 min (LC-2), ESI-MS (pos.): m/z 370.39 [M+H]$^+$; ESI-MS (neg.): m/z 368.42 [M−H]$^+$.

Examples U-02a to U-07a of the following Table 29 are prepared analogous to the procedure described for Example U-01a, using Precursors J-02b to J-07b in place of J-01b.

TABLE 29

| Example | Name | Formula Mol weight | $t_R$ [min] (Meth.) | MS Data m/z [M + H]$^+$ | MS Data m/z [M − H]$^+$ |
|---|---|---|---|---|---|
| U-02a | {2-[3-(4-Piperidin-1-yl-phenylamino)-propylsulfanyl]-benzoimidazol-1-yl}-acetic acid | C23H28N4O2S 424.567 | 1.41 (LC-2) | 425.43 | n/a |
| U-04a | [2-(3-Benzylamino-propylsulfanyl)-benzoimidazol-1-yl]-acetic acid | C19H21N3O2S 355.461 | 1.45 (LC-2) | 356.38 | 354.47 |
| U-06a | [2-(3-Phenylamino-propylsulfanyl)-benzoimidazol-1-yl]-acetic acid | C18H19N3O2S 341.434 | 1.65 (LC-2) | 342.30 | 340.39 |
| U-07a | {2-[3-(2,2-Diphenyl-ethylamino)-propylsulfanyl]-benzoimidazol-1-yl}-acetic acid | C26H27N3O2S 445.585 | 1.73 (LC-2) | 446.39 | n/a |

Precursor U-01b

[3-(1-tert-Butoxycarbonylmethyl-1H-benzoimidazol-2-ylsulfanyl)-propyl]-phenethyl-ammonium chloride tert-Butyl {2-[3-(tert-butoxycarbonyl-phenethyl-amino)-propylsulfanyl]-benzoimidazol-1-yl}-acetate (Precursor J-01b, 199 mg, 0.38 mmol) is dissolved in a 1M HCl solution in ethyl acetate (1.89 ml). The resulting solution is stirred at rt for 1 h. The solvent is evaporated and the crude solid is dissolved in dichloromethane, the resulting organic phase is washed with a saturated aqueous $NaHCO_3$ solution and with water. Evaporation of the solvent in vacuo and chromatography of the residue on silica-gel (dichloromethane/MeOH, 92:8) yields the title compound (107 mg) in 61% as a white solid: $t_R$=2.62 min (LC-2), ESI-MS (pos.): m/z 510.49 $[M+H]^+$.

Precursors U-02b to U-08b of the following Table 30 are prepared analogous to the procedure described for Precursor U-01b, using Precursors J-02b to J-08b in place of J-01b.

TABLE 30

| Precursor | Name | Formula Mol weight | $t_R$ [min] (Meth.) | MS Data m/z $[M + H]^+$ |
|---|---|---|---|---|
| U-02b | [3-(1-tert-Butoxycarbonylmethyl-1H-benzoimidazol-2-ylsulfanyl)-propyl]-(4-piperidin-1-yl-phenyl)-ammonium chloride | C27H37ClN4O2S 517.12 | 1.82 (LC-2) | 481.43 |
| U-03b | [3-(1-tert-Butoxycarbonylmethyl-1H-benzoimidazol-2-ylsulfanyl)-propyl]-(4-ethoxycarbonyl-phenyl)-ammonium chloride | C25H32ClN3O4S 506.05 | 2.55 (LC-2) | 470.41 |
| U-04b | Benzyl-[3-(1-tert butoxycarbonylmethyl-1H-benzoimidazol-2-ylsulfanyl)-propyl]-ammonium chloride | C23H30ClN3O2S 448.02 | 1.81 (LC-2) | 411.55 |
| U-05b | [3-(1-tert-Butoxycarbonylmethyl-1H-benzoimidazol-2-ylsulfanyl)-propyl]-cyclopropyl-ammonium chloride | C19H28ClN3O2S 397.96 | 1.70 (LC-2) | 362.36 |
| U-06b | [3-(1-tert-Butoxycarbonylmethyl-1H-benzoimidazol-2-ylsulfanyl)-propyl]-phenyl-ammonium chloride | C22H28ClN3O2S 433.99 | 2.39 (LC-2) | 398.4 |
| U-07b | [3-(1-tert-Butoxycarbonylmethyl-1H-benzoimidazol-2-ylsulfanyl)-propyl]-(2,2-diphenyl-ethyl)-ammonium chloride | C30H36ClN3O2S 538.14 | 1.97 (LC-2) | 502.46 |
| U-08b | 3-(1-tert-Butoxycarbonylmethyl-1H-benzoimidazol-2-ylsulfanyl)-propyl-ammonium chloride | C16H24ClN3O2S 357.90 | 1.60 (LC-2) | 322.37 |

Example V-01a

{2-[2-(1,3-Dioxo-1,3-dihydro-isoindol-2-yl)-ethyl-sulfanyl]-benzoimidazol-1-yl}-acetic acid

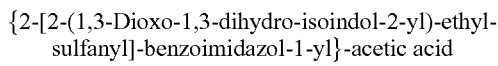

is prepared analogous to the procedure described for Example G-01a, using Precursor V-01b in place of G-01b: $t_R$=5.21 min (LC-1), ESI-MS (pos.): m/z 382.15 [M+H]$^+$, ESI-MS (neg.): m/z 380.20 [M−H]$^+$.

Example V-02a

[2-(2-tert-Butoxycarbonylamino-ethylsulfanyl)-benzoimidazol-1-yl]-acetic acid

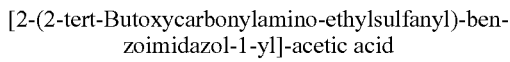

tert-Butyl[2-(2-tert-butoxycarbonylamino-ethylsulfanyl)-benzoimidazol-1-yl]-acetate (Precursor V-02b, 28.5 mg, 0.07 mmol) is suspended in 0.2 M aqueous NaOH (2.1 ml), THF (3.95 ml) is then added and the initially turbid suspension becomes a clear solution. After 7 h, 1M aqueous HCl solution (420 µl) is added. The solution is diluted with water (10 ml) and extracted with dichloromethane (15 ml). The organic phase is dried over MgSO$_4$ filtered over a fritted funnel and the solvents are evaporated in vacuo. Drying of the residue under high vacuum yields the title compound (19 mg) in 77% as a colourless solid: $t_R$=1.74 min (LC-2), ESI-MS (pos.): m/z 352.17 [M+H]$^+$, ESI-MS (neg.): m/z 350.20 [M−H]$^+$.

Examples V-03a to V-05a of the following Table 31 are prepared analogous to the procedure described for Example V-02a, using Precursors V-03b to V-05b in place of V-02b.

ethyl)-carbamic acid tert-butyl ester (1.17 g, 5.22 mmol) in dry THF (2.6 ml) is then added and the resulting mixture is allowed to stir for 2 h. The solvent is removed under reduced pressure and saturated aqueous KH$_2$PO$_4$ solution (50 ml) is added. The product is extracted with AcOEt (150 ml), the organic phase is washed once with water and once with brine and dried over Na$_2$SO$_4$. The solvent is removed in vacuo and the crude mixture is purified by flash chromatography on silica-gel (AcOEt/heptane, 1:12), yielding the title compound (1.41 g) in 69% as a colourless oil: $t_R$=2.35 min (LC-2), ESI-MS (pos.): m/z 408.27 [M+H]$^+$.

Precursor V-03b tert-Butyl[2-(2-butoxycarbonylamino-ethylsulfanyl)-benzoimidazol-1-yl]-acetate

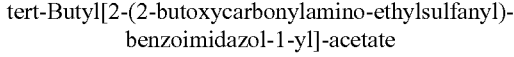

tert-butyl[2-(2-tert-butoxycarbonylamino-ethylsulfanyl)-benzoimidazol-1-yl]-acetate (Precursor V-02b) is dissolved in 3M HCl in AcOEt and stirred for 1 h at rt. Evaporation of the solvent in vacuo yields 2-(1-tert-butoxycarbonylmethyl-1H-benzoimidazol-2-ylsulfanyl)-ethyl-ammonium chloride as a colourless solid. To a solution of n-butylchloroformate (14.9 mg, 14 µl, 0.11 mmol) in dry THF (0.5 ml) cooled to 0° C. is added a solution of HOBt (17.3 mg, 0.11 mmol) and DIPEA (18 mg, 23.8 µl, 0.14 mmol) in dry THF (0.5 ml). The resulting mixture is stirred for 10 min. It is then added dropwise at 0° C. onto a solution of 2-(1-tert-butoxycarbonylm-

TABLE 31

| Example | Name | Formula Mol weight | $t_R$ [min] (Meth.) | MS Data m/z [M + H]$^+$ | MS Data m/z [M − H]$^+$ |
|---|---|---|---|---|---|
| V-03a | [2-(2-Butoxycarbonylamino-ethylsulfanyl)-benzoimidazol-1-yl]-acetic acid | C16H21N3O4S 351.42 | 1.74 (LC-2) | 352.2 | 350.2 |
| V-04a | [2-(2-Diphenylacetylamino-ethylsulfanyl)-benzoimidazol-1-yl]-acetic acid | C25H23N3O3S 445.53 | 2.00 (LC-2) | 446.26 | 444.29 |
| V-05a | {2-[2-(3-Phenyl-ureido)-ethylsulfanyl]-benzoimidazol-1-yl}-acetic acid | C18H18N4O3S 370.43 | 1.58 (LC-2) | 371.22 | 369.12 |

Precursor V-01b tert-Butyl {2-[2-(1,3-dioxo-1,3-dihydro-isoindol-2-yl)-ethylsulfanyl]-benzoimidazol-1-yl}-acetate

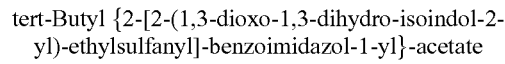

is prepared using a procedure analogous to that described for Precursor G-01b, substituting 2-(2-bromo-ethyl)-isoindole-1,3-dione for G-01d: $t_R$=6.84 min (LC-1), ESI-MS (pos.): m/z 438.35 [M+H]$^+$.

Precursor V-02b tert-Butyl[2-(2-tert-butoxycarbonylamino-ethylsulfanyl)-benzoimidazol-1-yl]-acetate

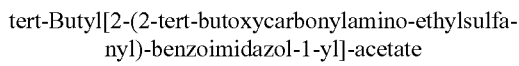

To a solution of tert-butyl (2-mercapto-benzoimidazol-1-yl)-acetate (Intermediate 3-I, 1.31 g, 4.97 mmol) in dry THF (2.6 ml) cooled to 0° C. is added a solution of DBU (756.6 mg, 742.5 µl, 0.47 mmol) in dry THF (1 ml). This yields a paste that is diluted with dry THF (2.5 ml). A solution of (2-bromoethyl-1H-benzoimidazol-2-ylsulfanyl)-ethyl-ammonium chloride (30 mg, 0.09 mmol) and DIPEA (11.2 mg, 14.9 µl, 0.09 mmol) in dry THF (0.7 ml). The resulting mixture is stirred for 1 h at rt. Then tris-(2-aminoethyl)amine polystyrene (3.4 mmol/g, 25.6 mg) is added and the resulting slurry is allowed to stir for 2 h at rt and then filtered. The solvent is removed in vacuo and the residue is diluted with dichloromethane (5 ml). This organic phase is washed once with a saturated aqueous NaHCO$_3$ solution and a saturated aqueous KH$_2$PO$_4$ solution. Evaporation of the solvent in vacuo yields the title compound (17.1 mg) in 48% as a colourless oil: $t_R$=2.35 min (LC-2), ESI-MS (pos.): m/z 408.29 [M+H]$^+$.

Precursors V-04b and V-05b of the following Table 32 are prepared using a procedure analogous to that described for Precursor V-03b, substituting the appropriate acid chloride or isocyanate for n-butylchloroformate. In the case of the isocyanate, no HOBt is used.

TABLE 32

| Precursor | Name | Formula Mol weight | $t_R$ [min] (Meth.) | MS Data m/z $[M + H]^+$ | MS Data m/z $[M - H]^+$ |
|---|---|---|---|---|---|
| V-04b | tert-Butyl [2-(2-diphenylacetylamino-ethylsulfanyl)-benzoimidazol-1-yl]-acetate | C29H31N3O3S 501.64 | 2.46 (LC-2) | 502.33 | 500.3 |
| V-05b | tert-Butyl {2-[2-(3-phenyl-ureido)-ethylsulfanyl]-benzoimidazol-1-yl}-acetate | C22H26N4O3S 426.53 | 2.17 (LC-2) | 427.28 | 425.3 |

Intermediate 4-I tert-Butyl[2-(2-bromo-ethylsulfanyl)-benzoimidazol-1-yl]-acetate To a solution of tert-butyl (2-mercapto-benzoimidazol-1-yl)-acetate (Intermediate 3-I, 0.5 g, 1.9 mmol) in THF (1 ml) is added DBU (304 mg, 300 µl, 2 mmol) and the resulting mixture is allowed to stir 2 min at rt. This solution is added slowly dropwise onto dibromoethane (7.5 ml, 88 mmol). The resulting solution is allowed to stir at rt for 1 h. After addition of dichloromethane (20 ml) the organic phase is washed with aqueous citric acid solution (pH=4), with water and with brine. Evaporation of the solvents in vacuo yields the title compound as a colourless oil: $t_R$=1.43 min (LC-2), ESI-MS (pos.): m/z 373.23 $[M+H]^+$.

Example W-01a

[2-(2-Phenylamino-ethylsulfanyl)-benzoimidazol-1-yl]-acetic acid

To tert-butyl[2-(2-bromo-ethylsulfanyl)-benzoimidazol-1-yl]-acetate (Intermediate 4-I, 25 mg, 0.065 mmol) in EtOH (0.7 ml) is added aniline (31.3 mg, 0.34 mmol). The resulting mixture is heated up to 70° C. for 1 h. After cooling the solvent is evaporated in vacuo and the crude ester is dissolved in TFA/dichloromethane (3:2, 2 ml) and stirred at rt for 2 h. Evaporation of the solvents in vacuo affords a crude product that is purified by chromatography on silica-gel (dichloromethane/MeOH, 100:7.5), yielding the pure title compound: $t_R$=2.11 min (LC-2), ESI-MS (pos.): m/z 328.33 $[M+H]^+$, ESI-MS (neg.): m/z 326.34 $[M-H]^+$.

Example (5/6)-Me-D-01a

{2-[2-(4-Chloro-phenoxy)-ethylsulfanyl]-5-methyl-benzoimidazol-1-yl}-acetic acid and its 6-methyl regioisomer A solution of tert-butyl-{2-[2-(4-chloro-phenoxy)-ethylsulfanyl]-5-methyl-benzoimidazol-1-yl}-acetate and its 6-methyl regioisomer (Precursor (5/6)-Me-D-01b, 80.5 mg, 0.15 mmol) in TFA/dichloromethane (1:1, 0.5 ml) is stirred overnight at rt. The solvents are evaporated in vacuo. The product solidifies by addition of AcOEt/heptane (1:1, 1 ml) and sonication. It is filtered and rinsed with the same solvent twice then dried under high vacuum. The title compound and its 6-methyl regioisomer (42 mg) are obtained as a (3:2) mixture in 74% total yield as a white solid: $t_R$=6.32 min (LC-1), ESI-MS (pos.): m/z 377.18 $[M+H]^+$, ESI-MS (neg.): m/z 375.24 $[M-H]^+$; $^1$H-NMR (DMSO-d$_6$): δ (ppm) 2.41 (s, 3H, Me), 3.67 (t, 2H, SCH$_2$), 4.30 (t, 2H, CH$_2$O), 4.96 and 4.97 (s, 2H, CH$_2$CO$_2$), 6.97-7.01 (m, 3H$_{arom}$), 7.27-7.36 (m, 3H, m), 7.44 (d, 1H$_{arom}$).

Example (5/6)-CN—H-01a

[5-Cyano-2-(3-methoxycarbonyl-benzylsulfanyl)-benzoimidazol-1-yl]-acetic acid and its 6-cyano regioisomer A solution tert-butyl[(5-cyano-2-(3-methoxycarbonyl-benzylsulfanyl)-benzoimidazol-1-yl]-acetate and its 6-cyano regioisomer (Precursor (5/6)-CN—H-01b, 20 mg, 0.045 mmol) in TFA/dichloromethane (1:1, 1 ml) is stirred at rt overnight. The solvents are evaporated in vacuo. The residue is precipitated in AcOEt/heptane (1:1, containing 1% of AcOH), filtered and dried under high vacuum. The title compound and its 6-cyano regioisomer are obtained (5 mg) as a (1:1) mixture in 28% total yield as a white solid: $t_R$=5.97 min (LC-1), ESI-MS (pos.): m/z 382.13 $[M+H]^+$, ESI-MS (neg.): m/z 380.14 $[M-H]^+$; $^1$H-NMR (DMSO-d$_6$): δ (ppm) 3.82 (s, 3H, Me), 4.72 and 4.73 (s, 2H, SCH$_2$), 5.03 and 5.04 (s, 2H, CH$_2$CO$_2$), 7.44 (t, 1H$_{arom}$), 7.58 (dt, 1H, m), 7.69-7.76 (m, 2H$_{arom}$), 7.83 (d, 1H$_{arom}$), 8.08 and 8.17 (s, 1H$_{arom}$), 8.08 (m, 1H$_{arom}$).

Example (5/6)-F-E-03a

[2-(4-Ethyloxycarbonyl-butylsulfanyl)-5-fluoro-benzoimidazol-1-yl]-acetic acid and its 6-fluoro regioisomer A solution of tert-butyl[2-(4-ethyloxycarbonyl-butylsulfanyl)-5-fluoro-benzoimidazol-1-yl]-acetate and its 6-fluoro regioisomer (Precursor (5/6)-F-E-03b, 24 mg, 0.075 mmol) in TFA/dichloromethane (1:1, 2 ml) is stirred overnight at rt. The solvents are evaporated in vacuo and the crude mixture is taken up in Et$_2$O (1 ml) and sonicated. The solid is filtered, rinsed twice with Et$_2$O and dried under high vacuum. The title compound and its 6-fluoro regioisomer are obtained (8 mg) as a (1:1) mixture in 30% total yield as a white solid: $t_R$=1.96 min (LC-2), ESI-MS (pos.): m/z 355.04 $[M+H]^+$, ESI-MS (neg.): m/z 353.13 $[M-H]^+$; $^1$H-NMR (CDCl$_3$): δ (ppm) 1.19 (t, 3H, CH$_3$), 1.72 (m, 4H), 2.36 (t, 2H, CH$_2$CO), 3.32 (t, 2H, SCH$_2$), 4.06 (q, 2H, CH$_2$O), 5.00 and 5.02 (s, 1H, CH2CO2), 7.01 (dt, 1H$_{arom}$), 7.39 and 7.47 (dd, 1H$_{arom}$), 7.52 (m, 1H$_{arom}$).

Examples 6-I-D-02a to (5/6)-F-H-01a of the following Table 33 are prepared using a procedure analogous to one of those described for Examples (5/6)-Me-D-01a, (5/6)-CN—H-01a, or (5/6)-F-E-03a, using Precursors 6-I-D-02b to (5/6)-F-H-01b in place of (5/6)-Me-D-01b, (5/6)-CN-H-01b, or (5/6)-F-E-03b, respectively.

TABLE 33

| Example | Name | Formula Mol weight | $t_R$ [min] (Meth.) | MS Data m/z $[M + H]^+$ | MS Data m/z $[M - H]^+$ |
|---|---|---|---|---|---|
| 6-I-D-02a | [6-Iodo-2-(2-phenoxy-ethylsulfanyl)-benzoimidazol-1-yl]-acetic acid | C17H15IN2O3S 454.283 | 6.75 (LC-1) | 455.18 | 453.29 |
| (5/6)-Cl-D-01a | {5-Chloro-2-[2-(4-chloro-phenoxy)-ethylsulfanyl]-benzoimidazol-1-yl}-acetic acid and its 6-chloro regioisomer | C17H14Cl2N2O3S 397.281 | 6.98 (LC-1) | 397.13 | 395.18 |
| (4/7)-Me-D-01a | {2-[2-(4-Chloro-phenoxy)-ethylsulfanyl]-4-methyl-benzoimidazol-1-yl}-acetic acid and its 7-methyl regioisomer | C18H17ClN2O3S 376.863 | 6.49 (LC-1) | 377.19 | 375.24 |
| (5/6)-CN-D-02a | [5-Cyano-2-(2-phenoxy-ethylsulfanyl)-benzoimidazol-1-yl]-acetic acid and its 6-cyano regioisomer | C18H15N3O3S 353.401 | 6.18 (LC-1) | 354.14 | 352.14 |
| (5/6)-CN-E-03a | [5-Cyano-2-(4-ethyloxycarbonyl-butylsulfanyl)-benzoimidazol-1-yl]-acetic acid and its 6-cyano regioisomer | C16H17N3O4S 347.394 | 5.77 (LC-1) | 362.16 | 360.18 |
| (5/6)-CF3-E-03a | [2-(4-Ethyloxycarbonyl-butylsulfanyl)-5-trifluoromethyl-benzoimidazol-1-yl]-acetic acid and its 6-trifluoromethyl regioisomer | C17H19F3N2O4S 404.408 | 6.46 (LC-1) | 405.27 | 403.36 |
| (5/6)-CF3-H-01a | [2-(3-Methoxycarbonyl-benzylsulfanyl)-5-trifluoromethyl-benzoimidazol-1-yl]-acetic acid and its 6-trifluoromethyl regioisomer | C19H15N2O4F3S 424.398 | 6.58 (LC-1) | 425.16 | 423.08 |
| (5/6)-F-D-02a | [5-Fluoro-2-(2-phenoxy-ethylsulfanyl)-benzoimidazol-1-yl]-acetic acid and its 6-fluoro regioisomer | C17H15N2O3FS 346.381 | 2.1 (LC-2) | 345.1 | 347.08 |
| (5/6)-F-H-01a | [5-Fluoro-2-(3-methoxycarbonyl-benzylsulfanyl)-benzoimidazol-1-yl]-acetic acid and its 6-fluoro regioisomer | C18H15N2O4FS 374.391 | 2.02 (LC-2) | 373.13 | 375.1 |

Precursor (5/6)-Me-D-01b tert-Butyl-{2-[2-(4-chloro-phenoxy)-ethylsulfanyl]-5-methyl-benzoimidazol-1-yl}-acetate and its 6-methyl regioisomer A suspension of 2-[2-(4-chloro-phenoxy)-ethylsulfanyl]-5-methyl-benzoimidazole (Intermediate 5-Me-D-01c, 106 mg, 0.3 mmol), tert-butyl bromoacetate (59 mg, 44.3 µl, 0.3 mmol) and $K_2CO_3$ (83 mg, 0.6 mmol) in DMF (2 ml) is stirred at rt for 3 h. After addition of water, the aqueous phase is extracted twice with AcOEt. The combined organic phases are washed with water/brine (1:1) and dried over $Na_2SO_4$. Evaporation of the solvent in vacuo and drying of the residue under high vacuum affords the title compound and its 6-methyl regioisomer (131 mg) as a (3:2) mixture in a quantitative total yield as a colourless oil. It is used without purification in the next step: $t_R$=2.73 min (LC-2), ESI-MS (pos.): m/z 433.29 $[M+H]^+$.

Precursor (5/6)-CN—H-01b tert-Butyl[5-cyano-2-(3-methoxycarbonyl-benzylsulfanyl)-benzoimidazol-1-yl]-acetate and its 6-cyano regioisomer A suspension of 5-cyano-2-(3-methoxycarbonyl-benzylsulfanyl)-benzoimidazole (Intermediate 5-CN—H-01c, 25 mg, 0.075 mmol), tert-butyl bromoacetate (12 mg, 9 µl, 0.06 mmol) and $K_2CO_3$ (30 mg, 0.155 mmol) in acetone (0.3 ml) is stirred at reflux for 2 h. The crude suspension is cooled down and filtered on a short pad of silica gel using AcOEt as eluent. The solvent is evaporated in vacuo and the residue dried under high vacuum. The title compound and its 6-cyano regioisomer are obtained as a (1:1) mixture as a brownish oil which is used without purification in the next step: $t_R$=2.47 min (LC-2), ESI-MS (pos.): m/z 438.14.29 $[M+H]^+$.

Precursor (5/6)-F-E-03b tert-Butyl[2-(4-ethyloxycarbonyl-butylsulfanyl)-5-fluoro-benzoimidazol-1-yl]-acetate and its 6-fluoro regioisomer A suspension of 2-(4-ethyloxycarbonyl-butylsulfanyl)-5-fluoro-benzoimidazole (Intermediate 5-F-E-03c, 44 mg, 0.15 mmol), tert-butyl bromoacetate (31 mg, 24 µl, 0.155 mmol) and $K_2CO_3$ (41 mg, 0.3 mmol) in acetone (0.5 ml) is stirred at reflux for 3 h. The crude suspension is cooled down and filtered on a short pad of silica gel using AcOEt as eluent. The solvent is removed under vacuum and the residue purified by flash chromatography on silica-gel (AcOEt/heptane, 3:7). The title compound and its 6-fluoro regioisomer are obtained as a (1:1) mixture as a colourless solid: $t_R$=7.25 min (LC-1), ESI-MS (pos.): m/z 411.26 $[M+H]^+$, ESI-MS (neg.): m/z 408.93 $[M-H]^+$; $^1$H-NMR (CDCl$_3$): δ (ppm) 1.25 (t, 3H, CH$_3$), 1.42 and 1.44 (s, 9H, tBu), 1.79 (m, 4H), 2.34 (t, 2H, CH$_2$CO), 3.36 (dd, 2H, SCH$_2$), 4.12 (q, 2H, CH$_2$O), 4.70 and 4.72 (s, 1H, CH$_2$CO$_2$), 6.86 and 7.01 (dd, 1H$_{arom}$), 6.94 (t, 1H$_{arom}$), 7.39 and 7.56 (dd, 1H$_{arom}$).

Precursors 5-Cl-D-01b to 5-F-H-01b of the following Table 34 as well as Precursor D-01b are prepared using a procedure analogous to one of those described for Precursors (5/6)-Me-D-01b, (5/6)-CN—H-01b or (5/6)-F-E-03b, using Intermediates 5-Cl-D-01c to 5-F-H-01b and D-01c in place of 5-Me-D-01c, 5-CN—H-01c or 5-F-E-03c.

TABLE 34

| Precursor | Name | Formula Mol weight | $t_R$ [min] (Meth.) | MS Data m/z $[M + H]^+$ |
|---|---|---|---|---|
| (5/6)-Cl-D-01b | tert-Butyl {5-chloro-2-[2-(4-chloro-phenoxy)-ethylsulfanyl]-benzoimidazol-1-yl}-acetate and its 6-chloro regioisomer | C21H22Cl2N2O3S 453.38 | 2.81 (LC-2) | 453.18 |
| (4/7)-Me-D-01b | tert-Butyl {2-[2-(4-chloro-phenoxy)-ethylsulfanyl]-4-methyl-benzoimidazol-1-yl} acetate and its 7-methyl regioisomer | C22H25ClN2O3S 432.96 | 2.8 (LC-2) | 433.23 |
| (5/6)-CN-D-02b | tert-Butyl [5-cyano-2-(2-phenoxy-ethylsulfanyl)-benzoimidazol-1-yl]-acetate and its 6-cyano regioisomer | C22H23N3O3S 409.5 | 2.58 (LC-2) | 410.14 |
| (5/6)-CN-E-03b | tert-Butyl [5-cyano-2-(4-ethyloxycarbonyl-butylsulfanyl)-benzoimidazol-1-yl]-acetate and its 6-cyano regioisomer | C21H27N3O4S 417.52 | 2.45 (LC-2) | 418.23 |
| (5/6)-CF3-E-03b | tert-Butyl [2-(4-ethyloxycarbonyl-butylsulfanyl)-5-trifluoromethyl-benzoimidazol-1-yl]-acetate and its 6-trifluoromethyl regioisomer | C21H27F3N2O4S 460.51 | 2.64 (LC-2) | 461.40 |
| (5/6)-CF3-H-01b | tert-Butyl [2-(3-methoxycarbonyl-benzylsulfanyl)-5-trifluoromethyl-benzoimidazol-1-yl]-acetate its 6-trifluoromethyl regioisomer | C23H23F3N2O4S 480.5 | 7.85 (LC-1) | 481.24 |
| (5/6)-F-D-02b | tert-Butyl [2-(2-phenoxy-ethylsulfanyl)-5-fluoro-benzoimidazol-1-yl]-acetate and its 6-fluoro regioisomer | C21H23N2O3FS 402.49 | 2.6 (LC-2) | 403.20 |
| (5/6)-F-H-01b | tert-Butyl [5-fluoro-2-(3-methoxycarbonyl-benzylsulfanyl)-benzoimidazol-1-yl]-acetate its 6-fluoro regioisomer | C22H23N2O4FS 430.50 | 2.49 (LC-2) | 431.16 |

Intermediate D-01c

2-[2-(4-Chloro-phenoxy)-ethylsulfanyl]-benzoimidazole

According to a procedure described by Matthews, C. J.; Clegg, W.; Elsegood, M. R. J.; Leese, T. A.; Thorp, D.; Thornton, P.; Lockart, J. C., J. Chem. Soc. Dalton Trans., 1996, 1531-1538.

A solution of 2-sulfanylbenzimidazole (159 mg, 1.06 mmol) and DIPEA (150 mg, 200 µl, 1.16 mmol) in dry THF (3 ml) is refluxed for half an hour. After cooling to rt, 1-(2-bromo-ethoxy)-4-chloro-benzene (250 mg, 1.06 mmol) is added. After a further 4 h of reflux, the solvents are removed in vacuo and the residue purified by flash chromatography on silica gel (AcOEt/heptane, 1:9 to 3:7), yielding the title compound (285 mg) in 88% as a white solid: $t_R$=5.40 min (LC-1), ESI-MS (neg.): m/z 303.0 [M−H]$^+$; $^1$H-NMR (CDCl$_3$): δ 3.76 (t, 2H, SCH$_2$), 4.31 (t, 2H, OCH$_2$), 6.76 (d, 2H$_{arom}$), 7.18 (d, 2H$_{arom}$), 7.22-7.32 (m, 3H$_{arom}$), 7.57 (m, 1H$_{arom}$).
Intermediate 5-Me-D-01c

2-[2-(4-Chloro-phenoxy)-ethylsulfanyl]-5-methyl-benzoimidazole

A suspension of 5-methyl-1H-benzoimidazole-2-thiol (492 mg, 3 mmol), 1-(2-bromo-ethoxy)-4-chloro-benzene (777 mg, 3.3 mmol) and K$_2$CO$_3$ (828 mg, 6 mmol) in acetone (1.0 ml) is refluxed for 3 h. It is cooled down and filtered on filter paper. The solvent is removed in vacuo and the crude purified by flash chromatography on silica-gel (AcOEt/heptane, 3:7), yielding the title compound (530 mg) in 55% as an off-white solid: $t_R$=2.02 min (LC-2), ESI-MS (pos.): m/z 319.21 [M+H]$^+$, ESI-MS (neg.): m/z 317.23 [M−H]$^+$; $^1$H-NMR (CDCl$_3$): δ (ppm) 2.36 (s, 3H, Me), 3.59 (t, 2H, SCH$_2$), 4.23 (t, 2H, CH$_2$O), 6.75 (d, 2H$_{arom}$), 6.97 (d, 1H$_{arom}$), 7.13 (d, 2H$_{arom}$), 7.18 (s, 1H$_{arom}$), 7.34 (d, 1H$_{arom}$).
Intermediate 5-CN—H-01c

5-Cyano-2-(3-methoxycarbonyl-benzylsulfanyl)-benzoimidazole

A suspension of 5-cyano-1H-benzoimidazole-2-thiol (35 mg, 0.2 mmol), 3-bromomethyl-benzoic acid methyl ester (46 mg, 0.2 mmol) and K$_2$CO$_3$ (55 mg, 0.4 mmol) in acetone (0.6 ml) and 3 drops of DMF is refluxed for 2 h. It is cooled down and filtered over a short plug of silica gel and rinsed with AcOEt. The solvent is removed under a stream of air. The crude residue is purified by flash chromatography on silica-gel (AcOEt/heptane, 1:2), yielding the title compound (38 mg) in 59% as a yellowish gum: $t_R$=6.14 min (LC-1), ESI-MS (pos.): m/z 324.14 [M+H]$^+$, ESI-MS (neg.): m/z 322.22 [M−H]$^+$; $^1$H-NMR (CDCl$_3$): δ (ppm) 3.92 (s, 3H, Me), 4.67 (s, 2H, SCH$_2$), 5.29 (s, 1H, NH), 7.36-7.56 (m, 4H$_{arom}$), 7.65 (d, 1H$_{arom}$), 7.94 (d, 1H$_{arom}$), 8.10 (s, 1H$_{arom}$)
Intermediate 5-F-E-03c

2-(4-Ethyloxycarbonyl-butylsulfanyl)-5-fluoro-benzoimidazole

A suspension of 5-fluoro-1H-benzoimidazole-2-thiol (168 mg, 1 mmol), 5-bromo-pentanoic acid ethyl ester (188 mg, 0.9 mmol, 145 µl) and K$_2$CO$_3$ (276 mg, 2 mmol) in acetone (2 ml) is refluxed for 3 h. It is cooled down and filtered over a short plug of silica gel and rinsed with AcOEt. The solvent is removed in vacuo. The crude is purified by flash chromatography on silica-gel (AcOEt/heptane, 1:2), yielding the title compound (190 mg) in 64% as a brown oil: $t_R$=1.87 min (LC-2), ESI-MS (pos.): m/z 297.28 [M+H]$^+$, ESI-MS (neg.): m/z 295.30 [M−H]$^+$; $^1$H-NMR (CDCl$_3$): δ (ppm) 1.25 (t, 3H, CH$_3$), 1.79 (br. t, 4H), 2.36 (br. t, 2H, CH$_2$CO), 3.28 (br. t, 2H, SCH$_2$), 4.14 (q, 2H, CH$_2$O), 6.93 (dt, 1H$_{arom}$), 7.20 (dd, 1H$_{arom}$), 7.41 (dd, 1H$_{arom}$).

Intermediates 5-Cl-D-01c to 5-F-H-01c of the following Table 35 are prepared using a procedure analogous to one of those described for Intermediates 5-Me-D-01c, 5-CN—H-01c or 5-F-E-03c, using the appropriate 5-substituted benzimidazole-2-thiol in place of 5-methyl-1H-benzoimidazole-2-thiol, 5-cyano-1H-benzoimidazole-2-thiol or 5-fluoro-1H-benzoimidazole-2-thiol.

TABLE 35

| Intermediate | Name | Formula Mol weight | $t_R$ [min] (Meth.) | MS Data m/z [M + H]$^+$ | MS Data m/z [M − H]$^+$ |
|---|---|---|---|---|---|
| 5-Cl-D-01c | 5-Chloro-2-[2-(4-chloro-phenoxy)-ethylsulfanyl]-benzoimidazole | C15H12Cl2N2OS 339.24 | 7.23 (LC-1) | 353.12 | 355.15 |
| 4-Me-D-01c | 2-[2-(4-Chloro-phenoxy)-ethylsulfanyl]-4-methyl-benzoimidazole | C16H15ClN2OS 318.82 | 6.18 (LC-1) | 317.13 | 319.19 |
| 5-CN-D-02c | 5-Cyano-2-(2-phenoxy-ethylsulfanyl)-benzoimidazole | C16H13N3OS 295.36 | 6.37 (LC-1) | 296.02 | 294.21 |
| 5-CN-E-03c | 5-Cyano-2-(4-ethyloxycarbonyl-butylsulfanyl)-benzoimidazole | C15H17N3O2S 303.38 | 5.96 (LC-1) | 304.17 | 302.22 |
| 5-CF3-E-03c | 2-(4-Ethyloxycarbonyl-butylsulfanyl)-5-trifluoromethyl-benzoimidazole | C15H17F3N2O2S 346.37 | 6.66 (LC-1) | 347.3 | 345.4 |
| 5-CF3-H-01c | 2-(3-Methoxycarbonyl-benzylsulfanyl)-5-trifluoromethyl-benzoimidazole | C17H13F3N2O2S 366.36 | 4.14 (LC-1) | 300.19 | 298.17 |
| 5-F-D-02c | 5-Fluoro-2-(2-phenoxy-ethylsulfanyl)-benzoimidazole | C15H13N2OFS 288.345 | 2.11 (LC-2) | 289.19 | 287.22 |
| 5-F-H-01c | 5-Fluoro-2-(3-methoxycarbonyl-benzylsulfanyl)-benzoimidazole | C16H13N2O2FS 316.355 | 6.05 (LC-1) | 317.11 | 315.26 |

Example 5-NO2-C-02a

(2-Benzylsulfanyl-5-nitro-benzoimidazol-1-yl)-acetic acid tert-Butyl (2-benzylsulfanyl-5-nitro-benzoimidazol-1-yl)-acetate (Precursor 5-NO2-C-02b, 20 mg, 0.05 mmol) is dissolved in TFA/dichloromethane (1:1, 0.5 ml) and stirred for 2 h at rt. The solvents are evaporated under a stream of air and $Et_2O$ (1 ml) is added to the crude mixture. The solid obtained is filtered, rinsed twice with $Et_2O$ and dried under high vacuum yielding the title compound (10.4 mg) in 60% as a slightly yellow solid: $t_R$=6.30 min (LC-1), ESI-MS (pos.): m/z 344.23 $[M+H]^+$, ESI-MS (neg.): m/z 342.34 $[M-H]^+$; $^1$H-NMR (DMSO-$d_6$): δ (ppm) 4.66 (s, 2H, $SCH_2$), 5.07 (s, 2H, $CH_2CO_2$), 7.23-7.33 (m, $3H_{arom}$), 7.46 (dd, $2H_{arom}$), 7.74 (d, $1H_{arom}$), 8.13 (dd, 1 $H_{arom}$), 8.44 (d, $1H_{arom}$).

Examples 5-NO2-D-01a to 6-NO2-G-06a of the following Table 36 are prepared analogous to the procedure described for Example 5-NO2-C-02a, using Precursors 5-NO12-D-01b to 6-NO2-G-06b in place of 5-NO2-C-02b.

TABLE 36

| Example | Name | Formula Mol weight | $t_R$ [min] (Meth.) | MS Data m/z $[M + H]^+$ | MS Data m/z $[M - H]^+$ |
|---|---|---|---|---|---|
| 5-NO2-D-01a | {5-Nitro-2-[2-(4-chloro)-phenoxy-ethylsulfanyl]-benzoimidazol-1-yl}-acetic acid | C17H14ClN3O5S 407.833 | 6.84 (LC-1) | 408.12 | 406.21 |
| (5/6)-NO2-D-02a | 5-Nitro-2-(2-phenoxy-ethylsulfanyl)-benzoimidazol-1-yl]-acetic acid and its 6-Nitro regioisomer | C17H15N3O5S 373.388 | 6.46 (LC-1) | 374.25 | 372.36 |
| 5-NO2-C-02a | (2-Benzylsulfanyl-5-nitro-benzoimidazol-1-yl)-acetic acid | C16H13N3O4S 343.362 | 6.3 (LC-1) | 344.23 | 342.34 |
| 5-NO2-C-05a | [2-(3,3-Diphenyl-propylsulfanyl)-5-nitro-benzoimidazol-1-yl]-acetic acid | C24H21N3O4S 447.514 | 7.24 (LC-1) | 448.36 | 446.4 |
| 5-NO2-E-03a | [2-(4-Ethyloxycarbonyl-butylsulfanyl)-5-nitro-benzoimidazol-1-yl]-acetic acid | C16H19N3O6S 381.408 | 6.11 (LC-1) | 382.3 | 380.34 |
| 5-NO2-G-06a | {2-[3-(1,3-Dioxo-1,3-dihydro-isoindol-2-yl)-propylsulfanyl]-5-nitro-benzoimidazol-1-yl}-acetic acid | C20H16N4O6S 440.435 | 6.14 (LC-1) | 441.29 | 439.33 |
| 5-NO2-H-01a | [2-(3-Methoxycarbonyl-benzylsulfanyl)-5-nitro-benzoimidazol-1-yl]-acetic acid | C18H15N3O6S 401.398 | 6.24 (LC-1) | 402.24 | 400.28 |
| 5-NO2-K-01a | {2-[3-(Butoxycarbonyl-phenethyl-amino)-propylsulfanyl]-5-nitro-benzoimidazol-1-yl}-acetic acid | C25H30N4O6S 514.601 | 7.37 (LC-1) | 513.3 | 515.2 |
| 5-NO2-T-04a | [2-(3-Diphenylacetylamino-propylsulfanyl)-5-nitro-benzoimidazol-1-yl]-acetic acid | C26H24N4O5S 504.56 | 2.24 (c) | 505.58 | 503.54 |
| 6-NO2-C-02a | (2-Benzylsulfanyl-6-nitro-benzoimidazol-1-yl)-acetic acid | C16H13N3O4S 343.362 | 6.27 (LC-1) | 344.3 | 342.34 |
| 6-NO2-C-05a | [2-(3,3-Diphenyl-propylsulfanyl)-6-nitro-benzoimidazol-1-yl]-acetic acid | C24H21N3O4S 447.514 | 7.26 (LC-1) | 448.36 | 446.4 |
| 6-NO2-E-03a | [2-(4-Ethyloxycarbonyl-butylsulfanyl)-6-nitro-benzoimidazol-1-yl]-acetic acid | C16H19N3O6S 381.408 | 6.07 (LC-1) | 382.3 | 380.34 |
| 6-NO2-G-06a | {2-[3-(1,3-Dioxo-1,3-dihydro-isoindol-2-yl)-propylsulfanyl]-6-nitro-benzoimidazol-1-yl}-acetic acid | C20H16N4O6S 440.435 | 6.11 (LC-1) | 441.29 | 439.4 |

Precursor 5-NO2-C-02b tert-Butyl (2-benzylsulfanyl-5-nitro-benzoimidazol-1-yl

A suspension of tert-butyl-(2-mercapto-5-nitro-benzoimidazol-1-yl)-acetate (Intermediate 3-IIa, 31 mg, 0.1 mmol), benzyle bromide (18.8 mg, 13 µl, 0.11 mmol) and $K_2CO_3$ (28 mg, 0.2 mmol) in acetone (1 ml) is refluxed for 2 h 30 min. The crude mixture is filtered on a short pad of silica-gel and rinsed with acetone. Evaporation of the solvent in vacuo and drying under high vacuum yields the title compound as a yellow oil which is used in the next step without further purification: $t_R$=7.69 min (LC-1), ESI-MS (pos.): m/z 400.28 $[M+H]^+$; $^1$H-NMR (CDCl$_3$): δ (ppm) (CDCl$_3$): 1.33 (s, 9H, tBu), 4.60 (s, 2H), 4.65 (s, 2H), 7.13 (d, $2H_{arom}$), 7.17-7.26 (m, $3H_{arom}$), 7.34 (m, $2H_{arom}$), 8.12 (dd, $1H_{arom}$), 8.55 (d, $1H_{arom}$).

Precursors 5-NO2-C-05b to 6-NO2-G-06b of the following Table 37 are prepared analogously to the procedure described for Precursor 5-NO2-C-02b, using the appropriate alkyl or aryl halogenide for benzyl bromide and the appropriate Intermediate 3-IIa or Intermediate 3-IIb, or a (1:1) mixture of both, respectively.

TABLE 37

| Precursor | Name | Formula Mol weight | $t_R$ [min] (Meth.) | MS Data m/z $[M + H]^+$ | MS Data m/z $[M - H]^+$ |
|---|---|---|---|---|---|
| 5-NO2-C-02b | tert-Butyl (2-Benzylsulfanyl-5-nitro-benzoimidazol-1-yl)-acetate | C20H21N3O4S 399.46 | 7.69 (LC-1) | 400.28 | n/a |
| 5-NO2-C-05b | tert-Butyl [2-(3,3-diphenyl-propylsulfanyl)-5-nitro-benzoimidazol-1-yl]-acetate | C28H29N3O4S 503.61 | 8.42 (LC-1) | 504.43 | 502.47 |
| 5-NO2-D-01b | tert-Butyl {5-nitro-2-[2-(4-chloro)-phenoxy-ethylsulfanyl]-benzoimidazol-1-yl}-acetate | C21H22ClN3O5S 463.93 | 8.03 (LC-1) | 464.14 | 462.27 |
| (5/6)-NO2-D-02b | tert-Butyl [5-nitro-2-(2-phenoxy-ethylsulfanyl)-benzoimidazol-1-yl]-acetate and its 6-nitro regioisomer | C21H23N3O5S 429.49 | 7.76 (LC-2) | 430.31 | 428.24 |
| 5-NO2-E-03b | tert-Butyl [2-(4-ethyloxycarbonyl-butylsulfanyl)-5-nitro-benzoimidazol-1-yl]-acetate | C20H27N3O6S 437.51 | 7.45 (LC-1) | 438.35 | 436.39 |
| 5-NO2-G-06b | tert-Butyl {2-[3-(1,3-dioxo-1,3-dihydro-isoindol-2-yl)-propylsulfanyl]-5-nitro-benzoimidazol-1-yl}-acetate | C24H24N4O6S 496.54 | 7.38 (LC-1) | 497.36 | 495.4 |
| 5-NO2-H-01b | tert-Butyl [2-(3-methoxycarbonyl-benzylsulfanyl)-5-nitro-benzoimidazol-1-yl]-acetate | C22H23N3O6S 457.5 | 2.54 (LC-2) | 458.38 | 456.58 |
| 5-NO2-K-01b | tert-Butyl {2-[3-(butoxycarbonyl-phenethyl-amino)-propylsulfanyl]-5-nitro-benzoimidazol-1-yl}-acetate | C29H38N4O6S 570.7 | 8.43 (LC-1) | 571.30 | 569.4 |
| 6-NO2-C-02b | tert-Butyl (2-benzylsulfanyl-6-nitro-benzoimidazol-1-yl)-acetate | C20H21N3O4S 399.46 | 7.67 (LC-1) | 400.35 | n/a |
| 6-NO2-C-05b | tert-Butyl [2-(3,3-diphenyl-propylsulfanyl)-6-nitro-benzoimidazol-1-yl]-acetate | C28H29N3O4S 503.61 | 8.44 (LC-1) | 504.33 | 502.54 |
| 6-NO2-D-02b | tert-Butyl [6-nitro-2-(2-phenoxy-ethylsulfanyl)-benzoimidazol-1-yl]-acetate | C21H23N3O5S 429.49 | 7.76 (LC-1) | 430.31 | 428.24 |
| 6-NO2-E-03b | tert-Butyl [2-(4-ethyloxycarbonyl-butylsulfanyl)-6-nitro-benzoimidazol-1-yl]-acetate | C20H27N3O6S 437.51 | 7.43 (LC-1) | 438.35 | 436.39 |
| 6-NO2-G-06b | tert-Butyl {2-[3-(1,3-dioxo-1,3-dihydro-isoindol-2-yl)-propylsulfanyl]-6-nitro-benzoimidazol-1-yl}-acetate | C24H24N4O6S 496.54 | 7.38 (LC-1) | 497.36 | 495.4 |

Examples H-12a to H-14a of the following Table 38 are prepared analogous to the procedure described for Example H-01a, using Precursors H-12b to H-14b in place of H-01b.

TABLE 38

| Example | Name | Formula Mol weight | $t_R$ [min] (Meth.) | MS Data m/z $[M + H]^+$ | MS Data m/z $[M - H]^+$ |
|---|---|---|---|---|---|
| H-12a | [2-(3-Isopropyloxycarbonyl-6-methoxy-benzylsulfanyl)-benzoimidazol-1-yl]-acetic acid | C21H22N2O5S 414.47 | 0.86 (LC-3) | 415.23 | n/a |
| H-13a | [2-(3-Methyloxycarbonyl-6-phenyl-benzylsulfanyl)-benzoimidazol-1-yl]-acetic acid | C24H20N2O4S 432.49 | 1.05 (LC-3) | 432.92 | 431.04 |
| H-14a | [2-(4-Methyloxycarbonyl-oxazol-2-ylmethylsulfanyl)-benzoimidazol-1-yl]-acetic acid | C15H13N3O5S 347.35 | 1.70 (LC-2) | 347.88 | 346 |

Precursors H-12b and H-14b of the following Table 39 are prepared using a procedure analogous to that described for Precursor H-01b, using Alkylating agents H-12d and H-14d in place of 5-bromo-hexanoic acid ethyl ester.

TABLE 39

| Precursor | Name | Formula Mol weight | $t_R$ [min] (Meth.) | MS Data m/z $[M + H]^+$ |
|---|---|---|---|---|
| H-12b | tert-Butyl [2-(3-isopropyloxycarbonyl-6-methoxy-benzylsulfanyl)-benzoimidazol-1-yl]-acetate | C25H30N2O5S 470.58 | 2.70 (LC-2) | 471.99 |
| H-14b | tert-Butyl [2-(4-methyloxycarbonyl-oxazol-2-ylmethylsulfanyl)-benzoimidazol-1-yl]-acetate | C19H21N3O5S 403.45 | 2.24 (LC-2) | 403.92 |

Alkylating Agent H-12d

3-Chloromethyl-4-methoxy-benzoic acid isopropyl ester

As described in: McKillop, A.; Madjdabadi, F., A.; Long. D. A. Tetrahedron Lett., 1983, 24, 1933-1936.

To a solution of 4-methoxybenzoic acid isopropyl ester (370 mg, 1.89 mmol) in dry nitromethane (10 ml) is added AlCl$_3$ (301 mg, 2.26 mmol, 1.2 eq.) and methoxyacetylchloride (181 µl, 215 mg, 1.98 mmol, 1.05 eq.) and the mixture is stirred overnight at rt. Water (10 ml) is added and the aqueous phase is extracted twice with dichloromethane. The organic phase is dried over Na$_2$SO$_4$ and the solvent removed in vacuo. The yellowish residue is purified by chromatography on silica-gel (AcOEt/heptane, 1:4), yielding the title compound (87 mg) in 29%: $t_R$=2.47 min (LC-2), ESI-MS (pos.): m/z 242.95 [M+H]$^+$; $^1$H-NMR (CDCl$_3$): δ (ppm) 1.33 (d, 6H, CH(CH$_3$)$_2$), 3.91 (s, 3H, OCH$_3$), 4.61 (s, CH$_2$Cl), 5.19 (sept., 1H, C$\underline{H}$(CH$_3$)$_2$), 6.87 (d, 1$\overline{H_{arom}}$), 7.98 (m, $\overline{2H_{arom}}$).

Alkylating agent H14-d is prepared accordingly to the described 4 steps procedure: Hermitage, S. A.; Cardwell, K. S.; Chapman, T.; Cooke, J. W. B.; Newton, R. Org. Proc. Res. Development, 2001, 5, 37-44.

Precursor H-13b tert-Butyl[2-(3-methyloxycarbonyl-6-phenyl-benzylsulfanyl)-benzoimidazol-1-yl]-acetate To tert-butyl{2-[(6-bromo-3-methoxycarbonyl)-benzylsulfanyl]-benzoimidazol-1-yl}-acetate (Precursor H-08b, 49.1 mg, 0.1 mmol) in 1,2-dimethoxyethane (1.5 ml) are added phenylboronic acid (12.2 mg, 0.1 mmol, 1 eq.), bis(triphenylphosphine)palladium dichloride (0.7 mg, 1 µmol, 1% mol) and some saturated Na$_2$CO$_3$ solution in water (0.3 ml). The resulting biphasic mixture is allowed to stir 25 h at 80° C. then 2 h at reflux. Then another load of catalyst is added and the reaction is refluxed overnight. The mixture is allowed to cool down to rt and the solvents are removed in vacuo. The yellowish residue is purified twice by chromatography on silica-gel (AcOEt/heptane, 1:4), yielding the title compound (9 mg) in 19% as a colourless oil: $t_R$=1.22 min (LC-3), ESI-MS (pos.): m/z 488.98 [M+H]$^+$.

Examples H-15a and H-16a rac{2-[2-Methoxy-5-(1-methoxy-ethyl)-benzylsulfanyl]-benzoimidazol-1-yl}-acetic acid and rac{2-[5-(1-Hydroxy-ethyl)-2-methoxy-benzylsulfanyl]-benzoimidazol-1-yl}-acetic acid To a solution of [2-(5-acetyl-2-methoxy-benzylsulfanyl)-benzoimidazol-1-yl]-acetic acid (Example H-11a, 75 mg, 0.2 mmol) in dry methanol (1 ml) is added sodium borohydride (36 mg, 0.92 mmol, 0.46 eq.) and the mixture is stirred at rt for a few minutes. Some 1 N aqueous HCl solution (5 ml) is added and the mixture is extracted three times with AcOEt. The combined organic phase is washed with brine and dried over MgSO$_4$. The solvents are removed under a stream of air to afford a yellowish solid residue which is purified by preparative HPLC yielding: rac{2-[2-methoxy-5-(1-methoxy-ethyl)-benzylsulfanyl]-benzoimidazol-1-yl}-acetic acid (4.6 mg) in 6% as a white solid: $t_R$=1.70 min (LC-2), ESI-MS (pos.): m/z 385.16 [M+H]$^+$ and rac{2-[5-(1-hydroxy-ethyl)-2-methoxy-benzylsulfanyl]-benzoimidazol-1-yl}-acetic acid (2.9 mg) in 4% as a white solid: $t_R$=1.73 min (LC-2), ESI-MS (pos.): m/z 372.24 [M+H]$^+$.

Examples (R)-I-01a and (S)-I-01a of the following Table 40 are prepared over two steps analogous to the procedures described for Example I-01a, using Precursors (R)-I-00b and (S)-I-00b in place of I-00b. They both were purified by preparative thin-layer chromatography on silica-gel: Eluent (Chloroform/MeOH/AcOH, 90:10:1).

TABLE 40

| Example | Name | Formula Mol weight | $t_R$ [min] (Meth.) | MS Data m/z [M + H]$^+$ |
|---|---|---|---|---|
| (R)-I-01a | [2-((R)-1-Butyryl-piperidin-3-ylmethylsulfanyl)-benzoimidazol-1-yl]-acetic acid | C19H25N3O3S 375.493 | 0.72 (LC-3) | 376.33 |
| (S)-I-01a | [2-((S)-1-Butyryl-piperidin-3-ylmethylsulfanyl)-benzoimidazol-1-yl]-acetic acid | C19H25N3O3S 375.494 | 0.72 (LC-3) | 376.33 |

Examples (R)-I-00b and (S)-I-00b of the following Table 41 are prepared analogous to the procedures described for Example I-01b, using (R)-3-hydroxymethyl-piperidine-1-carboxylic acid tert-butyl ester or (S)-3-hydroxymethyl-piperidine-1-carboxylic acid tert-butyl ester instead of rac 3-hydroxymethyl-piperidine-1-carboxylic acid tert-butyl ester.

TABLE 41

| Precursor | Name | Formula Mol weight | $t_R$ [min] (Meth.) | MS Data m/z [M + H]$^+$ |
|---|---|---|---|---|
| (R)-I-00b | tert-Butyl [2-((R)-1-tert-butyloxycarbonyl-piperidin-3-ylmethylsulfanyl)-benzoimidazol-1-yl]-acetate | C24H35N3O4S 461.63 | 1.02 (LC-3) | 462.36 |
| (S)-I-00b | tert-Butyl [2-((S)-1-tert-butyloxycarbonyl-piperidin-3-ylmethylsulfanyl)-benzoimidazol-1-yl]-acetate | C24H35N3O4S 461.64 | 1.02 (LC-3) | 462.36 |

Example I-14a rac{2-[1-(3-Phenyl-acryloyl)-piperidin-3-ylmethylsulfanyl]-benzoimidazol-1-yl}-acetic acid rac tert-Butyl {2-[1-(2-phenyl-ethenesulfonyl)-piperidin-3-ylmethylsulfanyl]-benzoimidazol-1-yl}-acetate (Precursor I-14b, 6 mg, 0.011 mmol) in TFA/dichloromethane (1:1, 1 ml) is allowed to stir overnight at rt. The solvents are removed under a stream of air and the resulting product is dried under high vacuum. This yields the title compound (5.6 mg) in 100% as a colourless oil which crystallizes on standing: $t_R$=1.06 min (LC-3), ESI-MS (pos.): m/z 471.88 [M+H]$^+$.

Examples I-15a to I-23a of the following Table 42 are prepared analogous to the procedures described for Example I-14a, using Precursors I-15b to I-23b in place of I-14b.

TABLE 42

| Example | Name | Formula Mol weight | $t_R$ [min] (Meth.) | MS Data m/z [M + H]$^+$ |
|---|---|---|---|---|
| I-15a | rac {2-[1-(3,4-Dichloro-benzenesulfonyl)-piperidin-3-ylmethylsulfanyl]-benzoimidazol-1-yl}-acetic acid | C21H21Cl2N3O4S2 514.45 | 1.16 (LC-3) | 513.84 |
| I-16a | rac [2-(1-Phenylmethanesulfonyl-piperidin-3-ylmethylsulfanyl)-benzoimidazol-1-yl]-acetic acid | C22H25N3O4S2 459.58 | 1.01 (LC-3) | 459.91 |
| I-17a | rac {2-[1-(Toluene-4-sulfonyl)-piperidin-3-ylmethylsulfanyl]-benzoimidazol-1-yl}-acetic acid | C22H25N3O4S2 459.58 | 1.06 (LC-3) | 459.91 |
| I-18a | rac {2-[1-(Naphthalene-2-sulfonyl)-piperidin-3-ylmethylsulfanyl]- | C25H25N3O4S2 495.61 | 1.12 (LC-3) | 495.91 |

TABLE 42-continued

| Example | Name | Formula Mol weight | $t_R$ [min] (Meth.) | MS Data m/z [M + H]$^+$ |
|---|---|---|---|---|
| | benzoimidazol-1-yl}-acetic acid | | | |
| I-19a | rac {2-[1-(Butane-1-sulfonyl)-piperidin-3-ylmethylsulfanyl]-benzoimidazol-1-yl}-acetic acid | C19H27N3O4S2 425.57 | 0.98 (LC-3) | 425.92 |
| I-20a | rac {2-[1-(4-Methoxy-benzenesulfonyl)-piperidin-3-ylmethylsulfanyl]-benzoimidazol-1-yl}-acetic acid | C22H25N3O5S2 475.58 | 1.02 (LC-3) | 475.9 |
| I-21a | rac {2-[1-(Propane-2-sulfonyl)-piperidin-3-ylmethylsulfanyl]-benzoimidazol-1-yl}-acetic acid | C18H25N3O4S2 411.54 | 0.89 (LC-3) | 411.87 |
| I-22a | rac {2-[1-(Thiophene-2-sulfonyl)-piperidin-3-ylmethylsulfanyl]-benzoimidazol-1-yl}-acetic acid | C19H21N3O4S3 451.58 | 1.00 (LC-3) | 451.81 |
| I-23a | rac [2-(1-Methanesulfonyl-piperidin-3-ylmethylsulfanyl)-benzoimidazol-1-yl]-acetic acid | C16H21N3O4S2 383.49 | 0.80 (LC-3) | 383.91 |

Precursor I-14b rac tert-Butyl{2-[1-(2-phenyl-ethenesulfonyl)-piperidin-3-ylmethylsulfanyl]-benzoimidazol-1-yl}-acetate To a solution of DIPEA (63.9 µl, 48.3 mg, 0.37 mmol, 4.5 eq.) and 2-phenyl-ethenesulfonyl chloride (25.2 mg, 0.125 mmol, 1.5 eq.) in 1,2-dichloroethane (0.5 ml) was added 3-(1-tert-butoxycarbonylmethyl-1H-benzoimidazol-2-ylsulfanylmethyl)-piperidinium chloride (Intermediate I-00b-bis, 30 mg, 0.083 mmol) in 1,2-dichloroethane (1 ml). The reaction mixture is stirred at rt overnight. The solvents are evaporated under reduced pressure and the crude is purified by preparative HPLC yielding the title compound in 18% as a colourless oil: $t_R$=1.20 min (LC-3), ESI-MS (pos.): m/z 528.35 [M+H]$^+$.

Precursors I-15b to I-23b of the following Table 43 are prepared using a procedure analogous to that described for Precursor I-14b, substituting the appropriate sulfonyl chloride for 2-phenyl-ethenesulfonyl chloride

TABLE 43

| Precursor | Name | Formula Mol weight | $t_R$ [min] (Meth.) | MS Data m/z [M + H]$^+$ | MS Data m/z [M − H]$^+$ |
|---|---|---|---|---|---|
| I-15b | rac tert-Butyl {2-[1-(3,4-dichloro-benzenesulfonyl)-piperidin-3-ylmethylsulfanyl]-benzoimidazol-1-yl}-acetate | C25H29Cl2N3O4S2 570.55 | n/a (LC-3) | n/a | n/a |
| I-16b | rac tert-Butyl [2-(1-phenylmethanesulfonyl-piperidin-3-ylmethylsulfanyl)-benzoimidazol-1-yl]-acetate | C26H33N3O4S2 515.69 | 1.18 (LC-3) | 516.3 | n/a |
| I-17b | rac tert-Butyl {2-[1-(toluene-4-sulfonyl)-piperidin-3-ylmethylsulfanyl]-benzoimidazol-1-yl}-acetate | C26H33N3O4S2 515.69 | 1.21 (LC-3) | 516.3 | n/a |
| I-18b | rac tert-Butyl {2-[1-(naphthalene-2-sulfonyl)-piperidin-3-ylmethylsulfanyl]-benzoimidazol-1-yl}-acetate | C29H33N3O4S2 551.72 | 1.24 (LC-3) | 552.39 | 550.45 |
| I-19b | rac tert-Butyl {2-[1-(butane-1-sulfonyl)-piperidin-3-ylmethylsulfanyl]-benzoimidazol-1-yl}-acetate | C23H35N3O4S2 481.67 | 1.17 (LC-3) | 482.3 | n/a |
| I-20b | rac tert-Butyl {2-[1-(4-methoxy-benzenesulfonyl)-piperidin-3- | C26H33N3O5S2 531.69 | 1.19 (LC-3) | n/a | n/a |

TABLE 43-continued

| Precursor | Name | Formula Mol weight | $t_R$ [min] (Meth.) | MS Data m/z $[M + H]^+$ | MS Data m/z $[M - H]^+$ |
|---|---|---|---|---|---|
| I-21b | ylmethylsulfanyl]-benzoimidazol-1-yl}-acetate rac tert-Butyl {2-[1-(9ropane-2-sulfonyl)-piperidin-3-ylmethylsulfanyl]-benzoimidazol-1-yl}-acetate | C22H33N3O4S2 467.65 | 1.13 (LC-3) | 468.31 | n/a |
| I-22b | rac tert-Butyl {2-[1-(thiophene-2-sulfonyl)-piperidin-3-ylmethylsulfanyl]-benzoimidazol-1-yl}-acetate | C23H29N3O4S3 507.69 | 1.17 (LC-3) | 508.27 | n/a |
| I-23b | rac tert-Butyl [2-(1-methanesulfonyl-piperidin-3-ylmethylsulfanyl)-benzoimidazol-1-yl]-acetate | C20H29N3O4S2 439.59 | 1.08 (LC-3) | 440.26 | n/a |

Intermediate I-00b-bis 3-(1-tert-Butoxycarbonylmethyl-1H-benzoimidazol-2-ylsulfanylmethyl)-piperidinium chloride rac tert-Butyl[2-(1-tert-butyloxycarbonyl-piperidin-3-yl-methylsulfanyl)-benzoimidazol-1-yl]-acetate (Intermediate I-00b, 409 mg, 0.89 mmol) is dissolved in AcOEt/Et$_2$O (1:1, 4 ml), and 2.2 ml of a 2M HCl solution in Et$_2$O are added. After 45 min the solvent is removed in vacuo and the crude solid formed is dried under high vacuum, yielding the title compound (360 mg) in 100% as a white solid: $t_R$=0.74 min (LC-3), ESI-MS (pos.): m/z 362.31 [M+H]$^+$.

Example I-24a of the following Table 44 is prepared analogous to the procedures described for Example 1-01a, using Precursors I-24b in place of 1-01b. It is purified by flash-chromatography on silica-gel using (AcOEt/Acetone/Water/Acetic acid) (16:2:1:1) as the eluent.

TABLE 44

| Example | Name | Formula Mol weight | $t_R$ [min] (Meth.) | MS Data m/z $[M + H]^+$ | MS Data m/z $[M - H]^+$ |
|---|---|---|---|---|---|
| I-24a | [2-(1-Butyryl-piperidin-4-ylmethylsulfanyl)-benzoimidazol-1-yl]-acetic acid | C19H25N3O3S 375.49 | 2.00 (LC-2) | 376.25 | 374.21 |

Precursor I-24b of the following Table 45 is prepared analogous to the procedures described for Example I-00b, using 4-hydroxymethyl-piperidine-1-carboxylic acid tert-butyl ester in place of 3-hydroxymethyl-piperidine-1-carboxylic acid tert-butyl ester

TABLE 45

| Precursor | Name | Formula Mol weight | $t_R$ [min] (Meth.) | MS Data m/z $[M + H]^+$ |
|---|---|---|---|---|
| I-24b | rac tert-Butyl [2-(1-tert-butyloxycarbonyl-piperidin-4-ylmethylsulfanyl)-benzoimidazol-1-yl]-acetate | C24H35N3O4S 461.62 | 8.95 (LC-1) | 462.26 |

Example 5-NO2-H-11a of the following Table 46 is prepared analogous to the procedure described for Example 5-NO2-C-02a, using Precursor 5-NO2-H-11b in place of 5-NO2-C-02b.

TABLE 46

| Example | Name | Formula Mol weight | $t_R$ [min] (Meth.) | MS Data m/z $[M + H]^+$ | MS Data m/z $[M - H]^+$ |
|---|---|---|---|---|---|
| 5-NO2-H-11a | [2-(5-Acetyl-2-methoxy-benzylsulfanyl)-5-nitro-benzoimidazol-1-yl]-acetic acid | C19H17N3O6S 415.42 | 1.02 (LC-3) | 416.06 | 414.12 |

Precursor 5-NO2-H-11b of the following Table 47 is prepared analogous to the procedure described for Precursor 5-NO2-C-02b, using 1-(3-chloromethyl-4-methoxy-phenyl)-ethanone in place of benzyl bromide.

TABLE 47

| Precursor | Name | Formula Mol weight | $t_R$ [min] (Meth.) | MS Data m/z $[M + H]^+$ | MS Data m/z $[M - H]^+$ |
|---|---|---|---|---|---|
| 5-NO2-H-11b | tert-Butyl [2-(5-acetyl-2-methoxy-benzylsulfanyl)-5-nitro-benzoimidazol-1-yl]-acetate | C23H25N3O6S 471.53 | 1.17 (LC-3) | 472.10 | 470.16 |

Examples 4,6-CF32-H-01a to 5,6-Cl2-I-01a of the following Table 48 are prepared using a procedure analogous to one of those described for Examples (5/6)-Me-D-01a, (5/6)-CN—H-01a, or (5/6)-F-E-03a, using Precursors 4,6-CF32-H-01b to 5,6-Cl2-1-01b in place of (5/6)-Me-D-01b, (5/6)-CN—H-01b, or (5/6)-F-E-03b, respectively.

TABLE 48

| Example | Name | Formula Mol weight | $t_R$ [min] (Meth.) | MS Data m/z $[M + H]^+$ |
|---|---|---|---|---|
| 4,6-CF32-H-01a | [2-(5-Methyloxycarbonyl-benzylsulfanyl)-4,6-bis-trifluoromethyl-benzoimidazol-1-yl]-acetic acid | C20H14F6N2O4S 492.39 | 2.60 (LC-2) | 492.91 |
| 4,6-CF32-H-11a | [2-(5-Acetyl-2-methoxy-benzylsulfanyl)-4,6-bis-trifluoromethyl-benzoimidazol-1-yl]-acetic acid | C21H16F6N2O4S 506.42 | 2.55 (LC-2) | 506.95 |
| 4,6-CF32-I-01a | [2-(1-Butyryl-piperidin-3-ylmethylsulfanyl)-4,6-bis-trifluoromethyl-benzoimidazol-1-yl]-acetic acid | C21H23F6N3O3S 511.48 | 1.19 (LC-3) | 512.04 |
| 5,6-Me2-H-01a | [2-(5-Methyloxycarbonyl-benzylsulfanyl)-5,6-dimethyl-benzoimidazol-1-yl]-acetic acid | C20H20N2O4S 384.45 | 0.98 (LC-3) | 384.95 |
| 5,6-Me2-H-11a | [2-(5-Acetyl-2-methoxy-benzylsulfanyl)-5,6-dimethyl-benzoimidazol-1-yl]-acetic acid | C21H22N2O4S 398.48 | 0.96 (LC-3) | 399.24 |
| 5,6-Me2-I-01a | [2-(1-Butyryl-piperidin-3-ylmethylsulfanyl)-5,6-dimethyl-benzoimidazol-1-yl]-acetic acid | C21H29N3O3S 403.54 | 0.90 (LC-3) | 404.12 |
| 5,6-Cl2-H-01a | [2-(5-Methyloxycarbonyl-benzylsulfanyl)-5,6-dichloro-benzoimidazol-1-yl]-acetic acid | C18H14Cl2N2O4S 425.29 | 1.14 (LC-3) | 425.02 |

TABLE 48-continued

| Example | Name | Formula Mol weight | $t_R$ [min] (Meth.) | MS Data m/z [M + H]$^+$ |
|---|---|---|---|---|
| 5,6-Cl2-H-11a | [2-(5-Acetyl-2-methoxy-benzylsulfanyl)-5,6-dichloro-benzoimidazol-1-yl]-acetic acid | C19H16Cl2N2O4S 439.31 | 0.97 (LC-3) | 439.1 |
| 5,6-Cl2-I-01a | [2-(1-Butyryl-piperidin-3-ylmethylsulfanyl)-5,6-dichloro-benzoimidazol-1-yl]-acetic acid | C19H23Cl2N3O3S 444.38 | 1.09 (LC-3) | 443.99 |

Precursors 4,6-CF32-H-01b to 5,6-Cl2-H-11b of the following Table 49 are prepared using a procedure analogous to one of those described for Precursors (5/6)-Me-D-01b, (5/6)-CN—H-01b or (5/6)-F-E-03b, using Intermediates 4,6-CF32-H-01b to 5,6-Cl2-H-11b in place of 5-Me-D-01c, 5-CN—H-01c or 5-F-E-03c.

TABLE 49

| Precursor | Name | Formula Mol weight | $t_R$ [min] (Meth.) | MS Data m/z [M + H]$^+$ |
|---|---|---|---|---|
| 4,6-CF32-H-01b | tert-Butyl [2-(5-methyloxycarbonyl-benzylsulfanyl)-4,6-bis-trifluoromethyl-benzoimidazol-1-yl]-acetate | C24H22F6N2O4S 548.50 | 1.33 (LC-3) | 548.95 |
| 4,6-CF32-H-11b | tert-Butyl [2-(5-Acetyl-2-methoxy-benzylsulfanyl)-4,6-bis-trifluoromethyl-benzoimidazol-1-yl]-acetate | C25H24F6N2O4S 562.52 | 1.32 (LC-3) | 562.94 |
| 4,6-CF32-I-01b | tert-Butyl [2-(1-butyryl-piperidin-3-ylmethylsulfanyl)-4,6-bis-trifluoromethyl-benzoimidazol-1-yl]-acetate | C25H31F6N3O3S 567.59 | 1.33 (LC-3) | 568.06 |
| 5,6-Me2-H-01b | tert-Butyl [2-(5-Methyloxycarbonyl-benzylsulfanyl)-5,6-dimethyl-benzoimidazol-1-yl]-acetate | C24H28N2O4S 440.56 | 1.21 (LC-3) | 441.01 |
| 5,6-Me2-H-11b | tert-Butyl [2-(5-acetyl-2-methoxy-benzylsulfanyl)-5,6-dimethyl-benzoimidazol-1-yl]-acetate | C25H30N2O4S 454.58 | 1.17 (LC-3) | 454.99 |
| 5,6-Me2-I-01b | tert-Butyl [2-(1-butyryl-piperidin-3-ylmethylsulfanyl)-5,6-dimethyl-benzoimidazol-1-yl]-acetate | C25H37N3O3S 459.64 | 1.16 (LC-3) | 460.05 |
| 5,6-Cl2-H-01b | tert-Butyl [2-(5-methyloxycarbonyl-benzylsulfanyl)-5,6-dichloro-benzoimidazol-1-yl]-acetate | C22H22Cl2N2O4S 481.39 | 1.27 (LC-3) | 480.88 |
| 5,6-Cl2-H-11b | tert-Butyl [2-(5-acetyl-2-methoxy-benzylsulfanyl)-5,6-dichloro-benzoimidazol-1-yl]-acetate | C23H24Cl2N2O4S 495.42 | 1.26 (LC-3) | 494.87 |
| 5,6-Cl2-I-01b | rac tert-Butyl [2-(1-butyryl-piperidin-3-ylmethylsulfanyl)-5,6-dichloro-benzoimidazol-1-yl]-acetate | C23H31Cl2N3O3S 500.48 | 1.26 (LC-3) | 499.92 |

Intermediates 4,6-CF$_{32}$—H-01c to 5,6-C12-1-01c of the following Table 50 are prepared using a procedure analogous to one of those described for Intermediates 5-Me-D-01c, 5-CN—H-01c or 5-F-E-03c, using the appropriate 5-substituted benzimidazole-2-thiol in place of 5-methyl-1H-benzoimidazole-2-thiol, 5-cyano-1H-benzoimidazole-2-thiol or 5-fluoro-1H-benzoimidazole-2-thiol, respectively.

TABLE 50

| Intermediate | Name | Formula Mol weight | $t_R$ [min] (Meth.) | MS Data m/z [M + H]$^+$ | MS Data m/z [M − H]$^+$ |
|---|---|---|---|---|---|
| 4,6-CF32-H-01c | 4,6-bis-Trifluoromethyl-2-(3-methyloxycarbonyl-benzylsulfanyl)-benzoimidazole | C18H12F6N2O2S 434.36 | 1.22 (LC-3) | 434.85 | 433.26 |
| 4,6-CF32-H-11c | 4,6-bis-Trifluoromethyl-2-(3-acetyl-6-methoxybenzylsulfanyl)-benzoimidazole | C19H14F6N2O2S 448.38 | 1.21 (LC-3) | 448.83 | 447.17 |
| 4,6-CF32-I-01c | rac 4,6-Bis-trifluoromethyl-2-(1-butanoyl-piperidin-3-ylmethylsulfanyl)-benzoimidazole | C19H21F6N3OS 453.44 | 1.19 (LC-3) | 453.89 | 453.26 |
| 5,6-Me2-H-01c | 5,6-Dimethyl-2-(3-methyloxycarbonyl-benzylsulfanyl)-benzoimidazole | C18H18N2O2S 326.41 | 0.93 (LC-3) | 326.91 | 325.11 |
| 5,6-Me2-H-11c | 5,6-Dimethyl-2-(3-acetyl-6-methoxybenzylsulfanyl)-benzoimidazole | C19H20N2O2S 340.44 | 0.88 (LC-3) | 340.95 | 339.22 |
| 5,6-Me2-I-01c | rac 5,6-Dimethyl-2-(1-butanoyl-piperidin-3-ylmethylsulfanyl)-benzoimidazole | C19H27N3OS 345.50 | 0.85 (LC-3) | 346 | 344.27 |
| 5,6-Cl2-H-01c | 5,6-dichloro-2-(3-methyloxycarbonyl-benzylsulfanyl)-benzoimidazole | C16H12Cl2N2O2S 367.25 | 0.93 (LC-3) | 326.91 | 325.11 |
| 5,6-Cl2-H-11c | 5,6-dichloro-2-(3-acetyl-6-methoxybenzylsulfanyl)-benzoimidazole | C17H14Cl2N2O2S 381.28 | 1.14 (LC-3) | 380.87 | n/a |
| 5,6-Cl2-I-01c | rac 5,6-Dichloro-2-(1-butanoyl-piperidin-3-ylmethylsulfanyl)-benzoimidazole | C17H21Cl2N3OS 386.34 | 1.1 (LC-3) | 385.92 | n/a |

Example 5-HCO—H-11a

[2-(5-Acetyl-2-methoxy-benzylsulfanyl)-5-formyl-benzoimidazol-1-yl]-acetic acid

A solution of tert-butyl[2-(5-acetyl-2-methoxy-benzylsulfanyl)-5-formyl-benzoimidazol-1-yl]-acetate (Precursor 5-HCO—H-11b, 16 mg, 0.035 mmol) in TFA/dichloromethane (1:1, 4 ml) is allowed to stir overnight at rt. The solvents are removed under a stream of air and the resulting products are dried under high vacuum. This yields the title compound (14 mg) in 100% as a yellow solid: $t_R$=0.94 min (LC-3), ESI-MS (pos.): m/z 398.86 [M+H]$^+$, ESI-MS (neg.): m/z 397.06 [M−H]$^+$; $^1$H-NMR (DMSO-d$_6$): δ (ppm) 2.46 (s, 3H, COCH$_3$), 3.88 (s, 3H, OCH$_3$), 4.59 (s, 2H, SCH$_2$), 4.96 (s, 2H, CH$_2$CO$_2$), 7.11 (d, 1H$_{arom}$), 7.65 (d, 1H$_{arom}$), 7.74 (d, 1H$_{arom}$), 7.90 (dd, 1H$_{arom}$), 8.06 (d, 1H$_{arom}$), 8.12 (d, 1H$_{arom}$), 10.01 (s, 1H, CHO).

Examples 5,6-F2-H-11a to 5-F-H-11a of the following Table 51 are prepared analogous to the procedure described for Example 5-HCO—H-11a, using Precursors 5,6-F2-H-11b to 5-F-H-11b in place of 5-HCO—H-11b.

TABLE 51

| Example | Name | Formula Mol weight | $t_R$ [min] (Meth.) | MS Data m/z [M + H]$^+$ | MS Data m/z [M − H]$^+$ |
|---|---|---|---|---|---|
| 5,6-F2-H-11a | [2-(5-Acetyl-2-methoxy-benzylsulfanyl)-5,6-difluoro-benzoimidazol-1-yl]-acetic acid | C19H16F2N2O4S 406.40 | 1.01 (LC-2) | 406.96 | 405.09 |
| 5-MeSO2-H-11a | [2-(5-Acetyl-2-methoxy-benzylsulfanyl)-5-methanesulfonyl-benzoimidazol-1-yl]-acetic acid | C20H20N2O6S2 448.51 | 0.91 (LC-3) | 448.83 | 447.03 |

TABLE 51-continued

| Example | Name | Formula Mol weight | $t_R$ [min] (Meth.) | MS Data m/z $[M + H]^+$ | MS Data m/z $[M - H]^+$ |
|---|---|---|---|---|---|
| 5-MeCO-H-11a | [5-Acetyl-2-(5-acetyl-2-methoxy-benzylsulfanyl)-benzoimidazol-1-yl]-acetic acid | C21H20N2O5S 412.46 | 0.94 (LC-3) | 412.84 | 411.04 |
| 4-F-H-11a | [2-(5-Acetyl-2-methoxy-benzylsulfanyl)-4-fluoro-benzoimidazol-1-yl]-acetic acid | C19H17FN2O4S 388.41 | 0.99 (LC-3) | 388.83 | 387.03 |
| 5-CF3-H-11a | [2-(5-Acetyl-2-methoxy-benzylsulfanyl)-5-trifluoromethyl-benzoimidazol-1-yl]-acetic acid | C20H17F3N2O4S 438.42 | 1.07 (LC-3) | 438.86 | 437.06 |
| 5-F-H-11a | [2-(5-Acetyl-2-methoxy-benzylsulfanyl)-5-fluoro-benzoimidazol-1-yl]-acetic acid | C19H17FN2O4S 388.41 | 0.96 (LC-3) | 388.94 | 387.08 |

Example 6-F-H-11a

[2-(5-Acetyl-2-methoxy-benzylsulfanyl)-6-fluoro-benzoimidazol-1-yl]-acetic acid

To a solution of methyl[2-(5-acetyl-2-methoxy-benzylsulfanyl)-6-fluoro-benzoimidazol-1-yl]-acetate (Precursor 6-F-H-11b, 11.3 mg, 0.029 mmol) in dry THF (0.3 ml) is added some 1 N aqueous lithium hydroxide solution (0.140 ml, 5 eq.). The resulting biphasic solution is allowed to stir 1 h at rt. The solvents are removed in vacuo, water is added as well as 1N HCl in water so as to set the pH of the aqueous solution to pH=1. The resulting acidic aqueous phase is extracted three times with AcOEt. The organic phase is dried over $Na_2SO_4$ and the solvent removed in vacuo and the product was dried under high vacuum. This yields the title compound (6 mg) in 55% as a greyish solid: $t_R$=0.95 min (LC-3), ESI-MS (pos.): m/z 388.89 $[M+H]^+$, ESI-MS (neg.): m/z 387.10 $[M-H]^+$; $^1$H-NMR (DMSO-$d_6$): δ (ppm) 2.40 (s, 3H, COCH$_3$), 3.87 (s, 3H, OCH$_3$), 4.49 (s, 2H, SCH$_2$), 4.82 (s, 2H, CH$_2$CO$_2$), 7.01 (t, 1H$_{arom}$), 7.09 (d, 1H$_{arom}$), 7.42 (d, 1H$_{arom}$), 7.53 (dd, 1H$_{arom}$), 7.86 (d, 1H$_{arom}$), 7.98 (s, 1H$_{arom}$).

Example 5-F-H-11a (1'-Me) of the following Table 52 is prepared analogous to the procedure described for Example 6-F-H-11a, using Precursor 5-F-H-11b (1'-Me) in place of 6-F-H-11b.

TABLE 52

| Example | Name | Formula Mol weight | $t_R$ [min] (Meth.) | MS Data m/z $[M + H]^+$ | MS Data m/z $[M - H]^+$ |
|---|---|---|---|---|---|
| 5-F-H-11a (1'-Me) | rac 2-[2-(5-Acetyl-2-methoxy-benzylsulfanyl)-5-fluoro-benzoimidazol-1-yl]-propionic acid | C20H19FN2O4S 402.44 | 1.00 (LC-3) | 402.87 | 401.07 |

Precursors 5-HCO-H11b to 5-F-H-11b (1'-Me) of the following Table 53 are prepared using a procedure analogous to that described for Precursor H-01b, substituting 1-(3-chloromethyl-4-methoxy-phenyl)-ethanone for 5-bromo-hexanoic acid ethyl ester and using Intermediates 3-III to 3-IXbis for Intermediate 3-I.

H$_2$ atmosphere. The crude mixture is then filtered over celite to remove any solid particle. The celite is rinsed once with dry THF. To the resulting light yellow solution is added, under argon, 1,1'-thiocarbonyldiimidazole (89 mg, 0.5 mmol, 2 eq.). The resulting orange solution is allowed to stir at rt for 5 h. Water is then added. The yellow solid formed is filtered

TABLE 53

| Precursor | Name | Formula Mol weight | $t_R$ [min] (Meth.) | MS Data m/z [M + H]$^+$ | MS Data m/z [M − H]$^+$ |
|---|---|---|---|---|---|
| 5-HCO-H-11b | tert-Butyl [2-(5-acetyl-2-methoxy-benzylsulfanyl)-5-formyl-benzoimidazol-1-yl]-acetate | C24H26N2O5S 454.54 | 1.13 (LC-3) | 454.92 | n/a |
| 5,6-F2-H-11b | tert-Butyl [2-(5-acetyl-2-methoxy-benzylsulfanyl)-5,6-difluoro-benzoimidazol-1-yl]-acetate | C23H24F2N2O4S 462.51 | 1.06 (LC-3) | 463.32 | n/a |
| 5-MeSO2-H-11b | tert-Butyl [2-(5-acetyl-2-methoxy-benzylsulfanyl)-5-methanesulfonyl-benzoimidazol-1-yl]-acetate | C24H28N2O6S2 504.62 | 1.08 (LC-3) | 504.91 | 503.25 |
| 5-MeCO-H-11a | tert-Butyl [5-acetyl-2-(5-acetyl-2-methoxy-benzylsulfanyl)-benzoimidazol-1-yl]-acetate | C25H28N2O5S 468.57 | 1.13 (LC-3) | 468.98 | n/a |
| 4-F-H-11b | tert-Butyl [2-(5-acetyl-2-methoxy-benzylsulfanyl)-4-fluoro-benzoimidazol-1-yl]-acetate | C23H25FN2O4S 444.52 | 1.16 (LC-3) | 444.89 | n/a |
| 5-CF3-H-11b | tert-Butyl [2-(5-acetyl-2-methoxy-benzylsulfanyl)-5-trifluoromethyl-benzoimidazol-1-yl]-acetate | C24H25F3N2O4S 494.53 | 1.21 (LC-3) | 494.94 | n/a |
| 5-F-H-11b | tert-Butyl [2-(5-acetyl-2-methoxy-benzylsulfanyl)-5-fluoro-benzoimidazol-1-yl]-acetate | C23H25FN2O4S 444.52 | 1.16 (LC-3) | 445.03 | n/a |
| 6-F-H-11b | Methyl [2-(5-acetyl-2-methoxy-benzylsulfanyl)-6-fluoro-benzoimidazol-1-yl]-acetate | C20H19FN2O4S 402.44 | 1.06 (LC-3) | 402.87 | n/a |
| 5-F-H-11a (1'-Me) | Ethyl 2-[2-(5-acetyl-2-methoxy-benzylsulfanyl)-5-fluoro-benzoimidazol-1-yl]-propionate | C22H23FN2O4S 430.49 | 1.12 (LC-3) | 430.97 | n/a |

Intermediate 3-VIII tert-Butyl (2-mercapto-5-trifluoromethyl-benzoimidazol-1-yl)-acetate In a test tube equipped with a septum, tert-butyl (2-nitro-4-trifluoromethyl-phenylamino)-acetate (Starting material 5-VIII, 80 mg, 0.25 mmol) is dissolved in dry THF (0.5 ml). Argon is allowed to bubble through this solution for 10 min. Then dry palladium on carbon (10% w/w, 26 mg, 10% mol) is added and the flask is set under H$_2$ atmosphere. The resulting mixture is shaken vigorously at rt overnight. If necessary, another 8% mol of palladium on charcoal 10% w/w is added and the resulting suspension is stirred for another hour under over a fritted funnel, rinsed thoroughly with water and dried under high vacuum. This yields the title compound (60 mg) in 73% as a yellow solid: $t_R$=1.10 min (LC-3), ESI-MS (pos.): m/z 332.99 [M+H]$^+$, 331.13 [M−H]$^+$; $^1$H-NMR (DMSO-d$_6$): δ (ppm) 1.41 (s, 9H, tBu), 5.06 (s, 2H, NHCH$_2$CO$_2$), 7.44 (s, 1H, H$_{arom}$), 7.57 (s, 2H, H$_{arom}$), 13.25 (br. s, 1H, SH).

Intermediates 3-III to 3-IXbis of the following Table 54 are prepared using a procedure analogous to that described for Intermediate 3-VIII, using Starting materials 5-III to 5-IXbis in place of Starting material 5-VIII.

In some cases the product was purified by flash-chromatography on silica-gel using a suitable (AcOEt/heptane) mixture [(3:7), (4:6) or (5:5)] as the eluent.

TABLE 54

| Intermediate | Name | Formula Mol weight | $t_R$ [min] (Meth.) | MS Data m/z [M + H]$^+$ | MS Data m/z [M − H]$^+$ |
| --- | --- | --- | --- | --- | --- |
| 3-III | tert-Butyl (5-formyl-2-mercapto-benzoimidazol-1-yl)-acetate | C14H16N2O3S 292.35 | 1 (LC-3) | n/a | 291.15 |
| 3-IV | tert-Butyl (5,6-difluoro-2-mercapto-benzoimidazol-1-yl)-acetate | C13H14F2N2O2S 300.32 | 1.21 (LC-3) | n/a | 299.17 |
| 3-V | tert-Butyl (2-mercapto-5-methanesulfonyl-benzoimidazol-1-yl)-acetate | C14H18N2O4S2 342.43 | 0.97 (LC-3) | 342.82 | 341.16 |
| 3-VI | tert-Butyl (5-acetyl-2-mercapto-benzoimidazol-1-yl)-acetate | C15H18N2O3S 306.38 | 1 (LC-3) | n/a | 305.12 |
| 3-VII | tert-Butyl (4-fuoro-2-mercapto-benzoimidazol-1-yl)-acetate | C13H15FN2O2S 282.33 | 1.03 (LC-3) | n/a | 281.13 |
| 3-IX | tert-Butyl (5-fluoro-2-mercapto-benzoimidazol-1-yl)-acetate | C13H15FN2O2S 282.33 | 1.05 (LC-2) | n/a | 281.13 |
| 3-X | Methyl (6-fluoro-2-mercapto-benzoimidazol-1-yl)-acetate | C10H9FN2O2S 240.25 | 0.9 (LC-3) | 240.89 | 239.17 |
| 3-IXbis | rac Ethyl 2-(5-fluoro-2-mercapto-benzoimidazol-1-yl)-propionate | C12H13FN2O2S 268.31 | 0.99 (LC-3) | 268.99 | 267.09 |

Starting Material 5-VIII tert-Butyl (2-nitro-4-trifluoromethyl-phenylamino)-acetate A mixture of 4-fluoro-3-nitrobenzotrifluoride (209 mg, 1 mmol), glycine tert-butyl ester hydrochloride (201 mg, 1.2 mmol) and NaHCO$_3$ (128 mg, 2 mmol) in dry DMSO (1 ml) is stirred overnight at 50 or 65° C. In case the reaction is not complete a further heating at 85° C. to 100° C. for 3 h is necessary. The reaction is then cooled to rt and water is added. The yellow to orange solid formed is filtered over a fritted funnel, rinsed thoroughly with water and dried under high vacuum. This yields the title compound (254 mg) in 79% as a yellow solid: $t_R$=1.08 min (LC-3), ESI-MS (pos.): m/z 403.2 [M+2AcCN]$^+$, m/z 321.56 [M+H]$^+$, $^1$H-NMR (DMSO-d$_6$): δ (ppm) 1.44 (s, 9H, tBu), 4.23 (d, 2H, NHCH$_2$CO$_2$), 7.08 (d, 1H, H$_{arom}$), 7.80 (dd, 1H, H, m), 8.34 (br. s, 1H, H$_{arom}$), 8.65 (t, 1H, NH).

Starting materials 5-III to 5-IXbis of the following Table 55 are prepared using a procedure analogous to that described for Starting material 5-V, substituting the appropriate o-nitrofluorobenzene for 4-fluoro-3-nitrobenzotrifluoride and the appropriate amino-acid ester hydrochloride for glycine tert-butyl ester hydrochloride. In some cases the product is purified by recrystallization out of a heptane/toluene (1:1) mixture or by flash-chromatography on silica gel using a heptane/AcOEt (4:1) mixture as eluent.

TABLE 55

| Starting material | Name | Formula Mol weight | $t_R$ [min] (Meth.) | MS Data m/z [M + H]$^+$ | MS Data m/z [M − H]$^+$ |
| --- | --- | --- | --- | --- | --- |
| 5-III | tert-Butyl (4-formyl-2-nitro-phenylamino)-acetate | C13H16N2O5 280.28 | 1.09 (LC-3) | n/a | 279.33 |
| 5-IV | tert-Butyl (4,5-difluoro-2-nitro-phenylamino)-acetate | C12H14F2N2O4 288.25 | 1.09 (LC-3) | n/a | 287.14 |
| 5-V | tert-Butyl (4-methanesulfonyl-2-nitro-phenylamino)-acetate | C13H18N2O6S 330.36 | 1.04 (LC-3) | n/a | 329.19 |
| 5-VI | tert-Butyl (4-acetyl-2-nitro-phenylamino)-acetate | C14H18N2O5 294.30 | 1.1 (LC-3) | 294.89 | n/a |
| 5-VII | tert-Butyl (3-fluoro-2-nitro-phenylamino)-acetate | C12H15FN2O4 270.26 | 1.01 (LC-3) | n/a | n/a |
| 5-IX | tert-Butyl (4-fluoro-2-nitro-phenylamino)-acetate | C12H15FN2O4 270.26 | 1.03 (LC-3) | 271.21 | n/a |
| 5-X | Methyl (5-fluoro-2-nitro-phenylamino)-acetate | C9H9FN2O4 228.18 | 1.94 (LC-2) | 228.8 | 227.2 |
| 5-IXbis | rac Ethyl 2-(4-Fluoro-2-nitro-phenylamino)-propionate | C11H13FN2O4 256.23 | 1.14 (LC-3) | 271.03 | n/a |

Example 5-F-H-17a

{2-[5-(2,3-Dihydro-indole-1-carbonyl)-2-methoxy-benzylsulfanyl]-5-fluoro-benzoimidazol-1-yl}-acetic acid tert-Butyl {2-[5-(2,3-dihydro-indole-1-carbonyl)-2-methoxy-benzylsulfanyl]-5-fluoro-benzoimidazol-1-yl}-acetate (Precursor 5-F-H-17b, 26 mg, 0.047 mmol) in a TFA/dichloromethane mixture (1:1, 0.5 ml) is allowed to stir at rt for 4 h. The solvents are removed under a stream of air. The product is precipitated in Et$_2$O, filtered, rinsed with Et$_2$O and dried under high vacuum. This yields the title compound (22 mg) in 99% as a light pink solid: t$_R$=1.04 min (LC-3), ESI-MS (pos.): m/z 492.11 [M+H]$^+$, ESI-MS (neg.): m/z 490.18 [M–H]$^+$; $^1$H-NMR (DMSO-d$_6$): δ (ppm) 2.88 (t, 2H, NCH$_2$C$\underline{H_2}$Ar), 3.85 (t, 2H, NC$\underline{H_2}$CH$_2$Ar), 3.89 (s, 3H, OCH$_3$), 4.54 (s, 2H, SCH$_2$), 4.95 (s, 2H, CH$_2$CO$_2$), 6.97 (t, 1H$_{arom}$), 7.02-7.09 (m, 4H$_{arom}$), 7.11 (d, 1H$_{arom}$), 7.21 (d, 1H$_{arom}$), 7.38-7.57 (m, 3H$_{arom}$).

Examples 5-F-H-18a to 5-F-H-29a of the following Table 56 are prepared analogous to the procedure described for Example 5-F-H-17a, using Precursors 5-F-H-18b to 5-F-H-29b in place of 5-F-H-17b. In some cases purification must be carried out by preparative HPLC.

TABLE 56

| Example | Name | Formula Mol weight | t$_R$ [min] (Meth.) | MS Data m/z [M + H]$^+$ | MS Data m/z [M – H]$^+$ |
|---|---|---|---|---|---|
| 5-F-H-18a | [2-(5-Butylcarbamoyl-2-methoxy-benzylsulfanyl)-5-fluoro-benzoimidazol-1-yl]-acetic acid | C22H24FN3O4S 445.51 | 1.00 (LC-3) | 446.12 | 444.18 |
| 5-F-H-19a | {2-[2-Methoxy-5-(morpholine-4-carbonyl)-benzylsulfanyl]-5-fluoro-benzoimidazol-1-yl}-acetic acid | C22H22FN3O5S 459.49 | 0.88 (LC-3) | 460.18 | 458.17 |
| 5-F-H-20a | [2-(5-Benzylcarbamoyl-2-methoxy-benzylsulfanyl)-5-fluoro-benzoimidazol-1-yl]-acetic acid | C25H22FN3O4S 479.52 | 1.01 (LC-3) | 480.13 | 478.19 |
| 5-F-H21a | [2-(5-Diethylcarbamoyl-2-methoxy-benzylsulfanyl)-5-fluoro-benzoimidazol-1-yl]-acetic acid | C22H24FN3O4S 445.51 | 0.96 (LC-3) | 446.19 | 444.18 |
| 5-F-H22a | {2-[5-(Benzyl-ethyl-carbamoyl)-2-methoxy-benzylsulfanyl]-5-fluoro-benzoimidazol-1-yl}-acetic acid | C27H26FN3O4S 507.58 | 1.04 (LC-3) | 508.19 | 506.25 |
| 5-F-H23a | [2-(5-Acetyl-2-ethoxy-benzylsulfanyl)-5-fluoro-benzoimidazol-1-yl]-acetic acid | C20H19FN2O4S 402.44 | 1.01 (LC-3) | 403.04 | 401.1 |
| 5-F-H-24a | {2-[5-Acetyl-2-(3-hydroxy-propoxy)-benzylsulfanyl]-5-fluoro-benzoimidazol-1-yl}-acetic acid | C21H21FN2O5S 432.47 | 1.48 (LC-3) | 433.3 | 431.16 |
| 5-F-H-25a | [2-(5-Acetyl-2-propoxy-benzylsulfanyl)-5-fluoro-benzoimidazol-1-yl]-acetic acid | C21H21FN2O4S 416.47 | 1.05 (LC-3) | 417.1 | 415.16 |
| 5-F-H26a | [2-(5-Acetyl-2-butoxy-benzylsulfanyl)-5-fluoro-benzoimidazol-1-yl]-acetic acid | C22H23FN2O4S 430.49 | 1.09 (LC-3) | 431.06 | 429.15 |
| 5-F-H27a | [2-(5-Benzoyl-2-methoxy-benzylsulfanyl)-5-fluoro-benzoimidazol-1-yl]-acetic acid | C24H19FN2O4S 450.48 | 1.07 (LC-3) | 451.04 | 448.96 |
| 5-F-H28a | [5-Fluoro-2-(6-methoxy-3-oxo-indan-5-ylmethylsulfanyl)-benzoimidazol-1-yl]-acetic acid | C20H17FN2O4S 400.42 | 0.96 (LC-3) | 401.04 | 399.1 |
| 5-F-H29a | [5-Fluoro-2-(3-methoxy-8-oxo-5,6,7,8-tetrahydro-naphthalen-2-ylmethylsulfanyl)-benzoimidazol-1-yl]-acetic acid | C21H19FN2O4S 414.45 | 1.00 (LC-3) | 415.03 | 413.09 |

5-F-H-17b tert-Butyl {2-[5-(2,3-dihydro-indole-1-carbonyl)-2-methoxy-benzylsulfanyl]-5-fluoro-benzoimidazol-1-yl}-acetate To a solution of tert-butyl[2-(3-hydroxycarbonyl-benzylsulfanyl)-5-fluoro-benzoimidazol-1-yl]-acetate (Precursor 5-F-H-00b, 44.6 mg, 0.1 mmol) in dry DMF (0.8 ml) are added successively Et$_3$N (21.1 µl, 15.2 mg, 0.15 mmol, 1.5 eq.), HOBt (23.0 mg, 0.15 mmol, 1.5 eq.), N-(3-dimethylaminopropyl)-N'-ethylcarbodiimide hydrochloride (28.8 mg, 0.15 mmol, 1.5 eq.) and indoline (16.8 µl, 17.9 mg, 0.15 mmol, 1.5 eq.). The reaction mixture is stirred at rt overnight. The solvents are evaporated under reduced pressure, dichloromethane (4 ml) is added and the resulting organic phase is washed once with 2 ml of a 1 M NaHCO$_3$ solution in water and once with 2 ml of a 1 M solution of sodium hydrogen sulfate in water. The acidic aqueous phase was extracted once with dichloromethane (2 ml). The combined organic phase is washed with brine. The solvent is removed under a stream of air and the resulting crude product is dried under high vacuum overnight yielding the title compound (40 mg) in 83% as a light brown oil: $t_R$=1.20 min (LC-3), ESI-MS (pos.): m/z 548.23 [M+H]$^+$, $^1$H-NMR (CDCl$_3$): δ (ppm) 1.400 (s, 9H, tBu), 2.95 (t, 2H, NCH$_2$CH$_2$Ar), 3.91 (s, 3H, OCH$_3$), 3.95 (t, 2H, NCH$_2$CH$_2$Ar), 4.65 (s, 2H, SCH$_2$), 4.72 (s, 2H, CH$_2$CO$_2$), 6.91-7.19 (m, 7H$_{arom}$), 7.45 (m, 1H$_{arom}$), 7.52 (m, 1H$_{arom}$), 7.64 (m, 1H$_{arom}$).

Precursors 5-F-H-18b to 5-F—H22b of the following Table 57 are prepared using a procedure analogous to that described for Precursor 5-F-H-17b, substituting the appropriate sulfonyl chloride for 2-phenyl-ethenesulfonyl chloride.

TABLE 57

| Precursor | Name | Formula Mol weight | $t_R$ [min] (Meth.) | MS Data m/z [M + H]$^+$ | MS Data m/z [M − H]$^+$ |
|---|---|---|---|---|---|
| 5-F-H-18b | tert-Butyl [2-(5-butylcarbamoyl-2-methoxy-benzylsulfanyl)-5-fluoro-benzoimidazol-1-yl]-acetate | C26H32FN3O4S 501.61 | 1.16 (LC-3) | 502.23 | 500.23 |
| 5-F-H-19b | tert-Butyl {5-fluoro-2-[2-methoxy-5-(morpholine-4-carbonyl)-benzylsulfanyl]-benzoimidazol-1-yl}-acetate | C26H30FN3O5S 515.60 | 1.09 (LC-3) | 516.29 | 514.56 |
| 5-F-H-20b | tert-Butyl [2-(5-benzylcarbamoyl-2-methoxy-benzylsulfanyl)-5-fluoro-benzoimidazol-1-yl]-acetate | C29H30FN3O4S 535.63 | 1.17 (LC-3) | 536.24 | 534.23 |
| 5-F-H21b | tert-Butyl [2-(5-diethylcarbamoyl-2-methoxy-benzylsulfanyl)-5-fluoro-benzoimidazol-1-yl]-acetate | C26H32FN3O4S 501.61 | 1.14 (LC-3) | 502.3 | n/a |
| 5-F-H22b | tert-Butyl {2-[5-(benzyl-ethyl-carbamoyl)-2-methoxy-benzylsulfanyl]-5-fluoro-benzoimidazol-1-yl}-acetate | C31H34FN3O4S 563.68 | 1.21 (LC-3) | 564.30 | n/a |

Precursor 5-F-H-00b tert-Butyl[2-(3-hydroxycarbonyl-benzylsulfanyl)-5-fluoro-benzoimidazol-1-yl]-acetate To a solution of 3-hydroxymethyl-4-methoxy-benzoic acid (Starting material H-00e, 910 mg, 5 mmol) in dry THF (50 ml) cooled to 0° C. under inert atmosphere are added successively triphenylphosphine (1782 mg, 6 mmol, 1.2 eq.) and di-tert-butyl-azodicarboxylate (1381 mg, 6 mmol, 1.2 eq). The initially deep yellow colour disappears after 10 min. Then tert-butyl (5-fluoro-2-mercapto-benzoimidazol-1-yl)-acetate (Intermediate 3-III, 1270 mg, 0.9 mmol, 0.9 eq.) is added. The reaction mixture is allowed to warm up to rt and stirred at this temperature for 1 h. Evaporation of the solvent in vacuo and purification by flash-chromatography on silica gel (AcOEt/heptane/AcOH, 10:90:1), provides the title compound (680 mg) in 30% as beige solid:

$t_R$=1.08 min (LC-3), ESI-MS (pos.): m/z 447.09 [M+H]$^+$, ESI-MS (neg.): m/z 426.18 [M−H]$^+$.

Starting material H-00e

3-Hydroxymethyl-4-methoxy-benzoic acid

Onto a warm solution of Ca(OCl)$_2$ (7.14 g, 49.95 mmol, 3.3 eq.) in water (25 ml) is added a warm solution of K$_2$CO$_3$ (5.14 g, 37.35 mmol, 2.49 eq.) and KOH (1.46 g, 26.1 mmol, 1.74 eq.) in water (25 ml). After 30 min of vigourous stirring, the undesired solid formed is filtered and rinsed with little water. The solution obtained is poured onto a suspension of 1-(3-chloromethyl-4-methoxy-phenyl)-ethanone (2.98 g, 15 mmol) in 1,4-dioxane (10 ml). The resulting suspension is stirred 2 h at rt and 2 h at 70° C. Under cooling of the suspension in an ice bath, are subsequently added solid NaHSO$_3$ (100 mg), then 96% sulfuric acid until pH=3. The aqueous phase thus obtained is extracted four times with AcOEt. The combined organic phase is washed with brine and dried over Na$_2$SO$_4$. Evaporation of the solvent in vacuo yields the title compound (1.8 g) in 66% as a white solid. $t_R$=0.72 min (LC-3), ESI-MS (pos.): m/z 182.99 [M+H]$^+$.

Precursors 5-F-H-23b to 5-F-H-29b of the following Table 58 are prepared using a procedure analogous to that described for Precursor H-01b, using Alkylating agents H-23d to H-29d in place of 5-bromo-hexanoic acid ethyl ester.

TABLE 58

| Precursor | Name | Formula Mol weight | $t_R$ [min] (Meth.) | MS Data m/z [M + H]$^+$ |
|---|---|---|---|---|
| 5-F-H23b | tert-Butyl [2-(5-acetyl-2-ethoxy-benzylsulfanyl)-5-fluoro-benzoimidazol-1-yl]-acetate | C24H27FN2O4S 458.55 | 1.18 (LC-3) | 459.14 |
| 5-F-H-24b | tert-Butyl {2-[5-acetyl-2-(3-hydroxy-propoxy)-benzylsulfanyl]-5-fluoro-benzoimidazol-1-yl}-acetate | C25H29FN2O5S 488.57 | 1.08 (LC-3) | 489.07 |
| 5-F-H-25b | tert-Butyl [2-(5-acetyl-2-propoxy-benzylsulfanyl)-5-fluoro-benzoimidazol-1-yl]-acetate | C25H29FN2O4S 472.57 | 1.22 (LC-3) | 473.20 |
| 5-F-H26b | tert-Butyl [2-(5-acetyl-2-butoxy-benzylsulfanyl)-5-fluoro-benzoimidazol-1-yl]-acetate | C26H31FN2O4S 486.60 | 1.24 (LC-3) | 487.13 |
| 5-F-H27b | tert-Butyl [2-(5-benzoyl-2-methoxy-benzylsulfanyl)-5-fluoro-benzoimidazol-1-yl]-acetate | C28H27FN2O4S 506.59 | 1.22 (LC-3) | 507.22 |
| 5-F-H28b | tert-Butyl [5-fluoro-2-(6-methoxy-3-oxo-indan-5-ylmethylsulfanyl)-benzoimidazol-1-yl]-acetate | C24H25FN2O4S 456.53 | 1.16 (LC-3) | 457.14 |
| 5-F-H29b | tert-Butyl [5-fluoro-2-(3-methoxy-8-oxo-5,6,7,8-tetrahydro-naphthalen-2-ylmethylsulfanyl)-benzoimidazol-1-yl]-acetate | C25H27FN2O4S 470.56 | 1.17 (LC-3) | 471.20 |

Alkylating agents H-23d to H-29d of the following Table 59 are prepared using a procedure analogous to that described for Alkylating agent H-12d, substituting the corresponding reagent or H-24 g for 4-methoxybenzoic acid isopropyl ester.

TABLE 59

| Alkylating agent | Name | Formula Mol weight | $t_R$ [min] (Meth.) | MS Data m/z [M + H]+ |
|---|---|---|---|---|
| H-23d | 1-(3-Chloromethyl-4-ethoxy-phenyl)-ethanone | C11H13ClO2 212.67 | 1.07 (LC-3) | 213.09 |
| H-24d | 1-[3-Chloromethyl-4-(3-hydroxy-propoxy)-phenyl]-ethanone | C12H15ClO3 242.70 | 0.92 (LC-3) | 243.05 |
| H-25d | 1-(3-Chloromethyl-4-propoxy-phenyl)-ethanone | C12H15ClO2 226.70 | 1.11 (LC-3) | 227.13 |
| H-26d | 1-(3-Chloromethyl-4-butoxy-phenyl)-ethanone | C13H17ClO2 240.73 | 1.15 (LC-3) | 241.11 |
| H-27d | (3-Chloromethyl-4-methoxy-phenyl)-phenyl-methanone | C15H13ClO2 260.72 | 1.01 (LC-3) | 261.11 |
| H-28d | 6-Chloromethyl-5-methoxy-indan-1-one | C11H11ClO2 210.66 | 0.99 (LC-3) | 211.08 |
| H-29d | 7-Chloromethyl-6-methoxy-3,4-dihydro-2H-naphthalen-1-one | C12H13ClO2 224.68 | 1.04 (LC-3) | 225.06 |

Starting Material H-24g

1-[4-(3-Hydroxy-propoxy)-phenyl]-ethanone is prepared according to the procedure described in: Mandoli, A.; Calamante, M.; Fering a, B. L.; Salvadori, P. Tetrahedron Asymmetry 2003, 14, 3647-3650.

Examples 5-F-I-01a to 5-F-1-35a of the following Table 60 are prepared analogous to the second procedure described for the synthesis of Example 1-01a, using Precursors 5-F-1-01b to 5-F-1-35b in place of 5-F-H-17b. The products which did not crystallize were pure enough to be used as such in the next step.

TABLE 60

| Example | Name | Formula Mol weight | $t_R$ [min] (Meth.) | MS Data m/z [M + H]+ | MS Data m/z [M − H]+ |
|---|---|---|---|---|---|
| 5-F-I-01a | rac [2-(1-Butyryl-piperidin-3-ylmethylsulfanyl)-5-fluoro-benzoimidazol-1-yl]-acetic acid | C19H24FN3O3S 393.48 | 0.92 (LC-3) | 394.02 | 392.22 |
| 5-F-I-11a | rac {5-Fluoro-2-[1-(furan-2-carbonyl)-piperidin-3-ylmethylsulfanyl]-benzoimidazol-1-yl}-acetic acid | C20H20FN3O4S 417.45 | 0.94 (LC-3) | 417.89 | 416.16 |
| 5-F-I-13a | rac {2-[1-(4-Bromo-benzoyl)-piperidin-3-ylmethylsulfanyl]-5-fluoro-benzoimidazol-1-yl}-acetic acid | C22H21BrFN3O3S 506.39 | 1.01 (LC-3) | 507.89 | 506.09 |
| 5-F-I-34a | (S)-[5-Fluoro-2-(1-benzyloxycarbonyl-azetidin-2-ylmethylsulfanyl)-benzoimidazol-1-yl]-acetic acid | C21H20FN3O4S 429.46 | 1.02 (LC-3) | 430.12 | 428.18 |
| 5-F-I-35a | [5-Fluoro-2-(1-benzyloxycarbonyl-azetidin-3-ylmethylsulfanyl)-benzoimidazol-1-yl]-acetic acid | C21H20FN3O4S 429.46 | 1.01 (LC-3) | 429.98 | 428.11 |

Precursor 5-F-1-01b rac tert-Butyl[2-(1-butyryl-piperidin-3-ylmethylsulfanyl)-5-fluoro-benzoimidazol-1-yl]-acetate To a solution of 1-(3-hydroxymethyl-piperidin-1-yl)-butan-1-one (Starting material 1-01e, 278 mg, 1.5 mmol, 1.5 eq.) in dry THF (10 ml) cooled to 0° C. under inert atmosphere are added successively triphenylphosphine (458 mg, 1.75 mmol, 1.75 eq.) and di-tert-butyl-azodicarboxylate (402 mg, 1.75 mmol, 1.75 eq). The initially deep yellow colour disappears after 10 min. Then tert-butyl (5-fluoro-2-mercapto-benzoimidazol-1-yl)-acetate (Intermediate 3-III, 280 mg, 1 mmol) is added. The reaction mixture is slowly allowed to warm up to rt overnight. Evaporation of the solvent in vacuuo and purification by flash-chromatography on silica gel (AcOEt/heptane, 2:3), provides the title compound (217 mg) in 95% as a slightly yellow resin:

$t_R$=1.14 min (LC-3), ESI-MS (pos.): m/z 450.08 [M+H]$^+$.

Precursors 5-F-I-11b to 5-I-35b of the following Table 61 are prepared using a procedure analogous to that described for Precursor 5-F-1-01b, using Starting material I-11e to I-35e in place of Starting material 1-01e.

TABLE 61

| Precursor | Name | Formula Mol weight | $t_R$ [min] (Meth.) | MS Data m/z [M + H]$^+$ |
|---|---|---|---|---|
| 5-F-I-11b | rac tert-Butyl {5-fluoro-2-[1-(furan-2-carbonyl)-piperidin-3-ylmethylsulfanyl]-benzoimidazol-1-yl}-acetate | C24H28FN3O4S 473.56 | 1.19 (LC-3) | 474.03 |
| 5-F-I-13b | rac tert-Butyl {2-[1-(4-bromo-benzoyl)-piperidin-3-ylmethylsulfanyl]-5-fluoro-benzoimidazol-1-yl}-acetate | C26H29BrFN3O3S 562.49 | 1.18 (LC-3) | 563.98 |
| 5-F-I-34b | (S)-tert-Butyl [5-Fluoro-2-(1-benzyloxycarbonyl-azetidin-2-ylmethylsulfanyl)-benzoimidazol-1-yl]-acetate | C25H28FN3O4S 485.57 | 1.19 (LC-3) | 485.98 |
| 5-F-I-35b | tert-Butyl [5-fluoro-2-(1-benzyloxycarbonyl-azetidin-3-ylmethylsulfanyl)-benzoimidazol-1-yl]-acetate | C25H28FN3O4S 485.57 | 1.16 (LC-3) | 486.02 |

Starting materials I-11e and I-13e of the following Table 62 are prepared using a procedure analogous to that described for Starting material I-01e, substituting the corresponding acid chloride to butyryl chloride.

TABLE 62

| Starting material | Name | Formula Mol weight | $t_R$ [min] (Meth.) | MS Data m/z [M + H]$^+$ |
|---|---|---|---|---|
| I-11e | Furan-2-yl-(3-hydroxymethyl-piperidin-1-yl)-methanone | C11H15NO3 209.24 | 0.62 (LC-3) | 210.15 |
| I-13e | (4-Bromo-phenyl)-(3-hydroxymethyl-piperidin-1-yl)-methanone | C13H16BrNO2 298.18 | 0.77 (LC-3) | 298.1 |

Starting Material I-34e

(S)-2-Hydroxymethyl-azetidine-1-carboxylic acid benzyl ester

To a solution of (S)-Azetidine-1,2-dicarboxylic acid 1-benzyl ester (Starting material I-34f, 94 mg, 0.4 mmol) in 0.3 ml dry THF cooled to 0° C. is added dropwise 450 μl of a 1 M solution of borane in THF. The resulting solution is allowed to stir for 1 h at 0° C. and warm up to rt overnight. AcOH (1 ml) and water (1 ml) are then added as well as some saturated NaHCO$_3$ solution in water until pH=9 and no more gas evolution occurs. The resulting aqueous phase is extracted three times with AcOEt. The combined organic phase is washed once with some saturated NaHCO$_3$ solution in water and once with water. The solvents are evaporated in vacuo and the crude oil dried under high vacuum overnight, yielding the title compound (79 mg) in 89% as a colourless oil: $t_R$=0.84 min (LC-3), ESI-MS (pos.): m/z 222.08 [M+H]$^+$; $^1$H-NMR (CDCl$_3$): δ (ppm) 2.00 (m, 1H, CH$_2$CH$_2$N), 2.22 (m, 1H, CH$_2$CH$_2$N), 3.78-4.01 (m, 5H, CH$_2$N and CH$_2$OH), 4.52 (s, 2H, OCH$_2$Ph), 7.35 (s, 5H, H$_{arom.}$). Starting material I-35e of the following Table 63 is prepared using a procedure analogous to that described for Starting material I-34e, substituting Starting material I-35f for I-34f.

TABLE 63

| Starting material | Name | Formula Mol weight | $t_R$ [min] (Meth.) | MS Data m/z [M + H]$^+$ |
|---|---|---|---|---|
| I-35e | 3-Hydroxymethyl-azetidine-1-carboxylic acid benzyl ester | C12H15NO3 221.26 | 0.87 (LC-3) | 222.22 |

Starting Material I-34f

(S)-Azetidine-1,2-dicarboxylic acid 1-benzyl ester

To a solution of L-azetidine-2-carboxylic acid (101.1 mg, 1 mmol) in 2N aqueous NaOH (0.675 ml) is added benzylchloroformiate (169 μl, 204.7 mg, 1.2 eq.) and the resulting mixture is stirred at rt for 2 h. The aqueous phase is washed once with Et$_2$O. The aqueous solution is set to pH=2 with a concentrated aqueous HCl solution and then saturated with solid Na$_2$SO$_4$. It is extracted three times with AcOEt. The combined organic phase is dried over Na$_2$SO$_4$. The solvents are evaporated under a stream of air and the crude oil dried under high vacuum overnight, yielding the title compound (126 mg)

in 53% as a colourless oil: $t_R$=0.76 min (LC-3), ESI-MS (pos.): m/z 277.16 [M+Na]$^+$; $^1$H-NMR (CDCl$_3$): δ (ppm) 2.53 (bs, 2H, CH$_2$CH$_2$N), 4.01 (t, 2H, CH$_2$N), 4.82 (t, 1H, CHCO$_2$H), 5.15 (s, 2H, OCH$_2$Ph), 7.35 (s, 5H, H$_{arom.}$).

Starting material I-35f of the following Table 64 is prepared using a procedure analogous to that described for Starting material I-34f, substituting 3-azetidine carboxylic acid for L-azetidine-2-carboxylic acid.

TABLE 64

| Intermediate | Name | Formula Mol weight | $t_R$ [min] (Meth.) | MS Data m/z [M + H]$^+$ |
|---|---|---|---|---|
| I-35f | Azetidine-1,3-dicarboxylic acid monobenzyl ester | C12H13NO4 235.25 | 0.75 (LC-3) | 236.14 |

Example 5-F-I-29a rac[5-Fluoro-2-(1-phenylacetyl-pyrrolidin-3-ylmethylsulfanyl)-benzoimidazol-1-yl]-acetic acid rac[2-(Pyrrolidin-3-ylmethylsulfanyl)-benzoimidazol-1-yl]-acetic acid (Precursor 5-F-I-36a, 17.3 mg, 0.05 mmol) is suspended in dichloromethane (1 ml) and Et$_3$N (10.2 mg, 14.3 μl, 0.1 mmol, 2 eq.) as well as phenylacetyl chloride (9.28 mg, 8.00 μl, 0.06 mmol, 1.2 eq.) are added subsequently. The resulting mixture is stirred for 1 h at rt. Some 1N aqueous NaOH solution (1 ml) was added and the mixture is allowed to stir at rt for 1 h. Then dichloromethane (1 ml) and water (1 ml) are added and the aqueous solution is washed twice with dichloromethane to remove non-acidic impurities. The combined organic phase is washed with brine. Both aqueous phases (basic+brine) are then made acidic with 1 ml AcOH and the crude acid is extracted twice with dichloromethane (2 ml). The combined organic phases are washed with brine and dried over Na$_2$SO$_4$. Evaporation of the solvent in vacuo and drying under high vacuum, yields the title compound (15 mg) in 68% as a white solid: $t_R$=0.94 min (LC-2), ESI-MS (pos.): m/z 428.11 [M+H]$^+$, ESI-MS (neg.): m/z 426.18 [M−H]$^+$.

Examples 5-F-I-25a to 5-F-I-33a of the following Table 65 are prepared analogous to the procedures described for 5-F-I-29a, substituting the corresponding acid chloride or sulfonyl chloride for phenylacetyl chloride.

TABLE 65

| Example | Name | Formula Mol weight | $t_R$ [min] (Meth.) | MS Data m/z [M + H]$^+$ | MS Data m/z [M − H]$^+$ |
|---|---|---|---|---|---|
| 5-F-I-25a | rac {2-[1-(4-Bromo-benzoyl)-pyrrolidin-3-ylmethylsulfanyl]-5-fluoro-benzoimidazol-1-yl}-acetic acid | C21H19BrFN3O3S 492.36 | 0.99 (LC-3) | 493.92 | 491.98 |
| 5-F-I-26a | rac {5-Fluoro-2-[1-(furan-2-carbonyl)-pyrrolidin-3-ylmethylsulfanyl]-benzoimidazol-1-yl}-acetic acid | C19H18FN3O4S 403.43 | 0.90 (LC-3) | 404.08 | 402.14 |
| 5-F-I-27a | rac [2-(1-Butyryl-pyrrolidin-3-ylmethylsulfanyl)-5-fluoro-benzoimidazol-1-yl]-acetic acid | C18H22FN3O3S 379.45 | 0.89 (LC-3) | 380.12 | 378.11 |
| 5-F-I-28a | rac {5-Fluoro-2-[1-(3-phenyl-propionyl)-pyrrolidin-3-ylmethylsulfanyl]-benzoimidazol-1-yl}-acetic acid | C23H24FN3O3S 441.52 | 0.99 (LC-3) | 442.11 | 440.17 |
| 5-F-I-30a | rac [5-Fluoro-2-(1-octanoyl-pyrrolidin-3-ylmethylsulfanyl)-benzoimidazol-1-yl]-acetic acid | C22H30FN3O3S 435.56 | 1.08 (LC-3) | 436.15 | 434.21 |
| 5-F-I-31a | rac {5-Fluoro-2-[1-(2-phenyl-ethenesulfonyl)-pyrrolidin-3-ylmethylsulfanyl]-benzoimidazol-1-yl}-acetic acid | C22H22FN3O4S2 475.56 | 1.04 (LC-3) | 476.04 | 474.1 |
| 5-F-I-32a | rac {2-[1-(Butane-1-sulfonyl)-pyrrolidin-3-ylmethylsulfanyl]-5-fluoro-benzoimidazol-1-yl}-acetic acid | C18H24FN3O4S2 429.53 | 0.99 (LC-3) | 430.05 | 428.18 |

TABLE 65-continued

| Example | Name | Formula Mol weight | $t_R$ [min] (Meth.) | MS Data m/z $[M + H]^+$ | MS Data m/z $[M - H]^+$ |
|---|---|---|---|---|---|
| 5-F-I-33a | rac {5-Fluoro-2-[1-(4-methoxy-benzenesulfonyl)-pyrrolidin-3-ylmethylsulfanyl]-benzoimidazol-1-yl}-acetic acid | C21H22FN3O5S2 479.54 | 1.01 (LC-3) | 480.06 | 478.12 |

Precursor 5-F-1-36a of the following Table 66 is prepared using a procedure analogous to that described for Precursor I-00a, substituting the corresponding Precursor 5-F-1-25b for Precursor I-00b.

TABLE 66

| Example | Name | Formula Mol weight | $t_R$ [min] (Meth.) | MS Data m/z $[M + H]^+$ |
|---|---|---|---|---|
| 5-F-I-36a | [5-Fluoro-2-(pyrrolidin-3-ylmethylsulfanyl)-benzoimidazol-1-yl]-acetic acid | C14H16FN3O2S 309.36 | 0.62 (LC-3) | 310.12 |

Precursor 5-F-1-25b of the following Table 67 is prepared using a procedure analogous to that described for Precursor I-00b, substituting the corresponding Intermediate 3-III for Intermediate 3-1 and 3-hydroxymethyl-pyrrolidin-1-carboxylic acid tert-butyl ester for 3-hydroxymethyl-piperidine-1-carboxylic acid tert-butyl ester.

TABLE 67

| Precursor | Name | Formula Mol weight | $t_R$ [min] (Meth.) | MS Data m/z $[M + H]^+$ |
|---|---|---|---|---|
| 5-F-I-25b | rac tert-Butyl [2-(1-tert-butyloxycabonyl-pyrrolidin-3-ylmethylsulfanyl)-5-fluoro-benzoimidazol-1-yl]-acetate | C23H32FN3O4S 465.58 | 1.18 (LC-3) | 466.28 |

Example Oxy-F-H-11a rac[2-(5-Acetyl-2-methoxy-phenylmethanesulfinyl)-5-fluoro-benzoimidazol-1-yl]-acetic acid To a suspension of [2-(5-acetyl-2-methoxy-benzylsulfanyl)-5-fluoro-benzoimidazol-1-yl]-acetic acid (Example 5-F-H-11a, 194 mg, 0.5 mmol) in dichloromethane (3 ml) cooled to 0° C. is added m-chloroperbenzoic acid (103 mg, 0.6 mmol, 1.2 eq.) and the mixture is stirred at rt for 3 h. The solid is filtered over a fritted funnel and rinsed thoroughly with dichloromethane. The white solid obtained is dried under high vacuum yielding the title compound (120 mg) in 59% as a white solid: $t_R$=0.89 min (LC-3), ESI-MS (pos.): m/z 404.91 $[M+H]^+$; $^1$H-NMR (DMSO-$d_6$): δ (ppm) 2.39 (s, 3H, C=OCH$_3$), 3.65 (s, 3H, OCH$_3$), 4.66 (dd, 2H, S=OCH$_2$), 5.20 (d, 2H, CHCO$_2$H), 7.11 (d, 1H, H$_{arom.}$), 7.29 (dt, 1H, H$_{arom.}$), 7.59 (dd, 1H, H$_{arom.}$), 7.75 (m, 1H, H$_{arom.}$), 7.98 (dd, 1H, H$_{arom.}$).

Biological Assays:

Preparation of CRTH2 Membranes and Radioligand Binding Assay:

Preparation of the Membranes and Radioligand Binding Assays are Performed According to known procedures, e.g. Sawyer N. et al. (*Br. J. Pharmacol.*, 2002, 137, 1163-1172). A clonal HEK 293 cell line, expressing high level of recombinant hCRTH2 receptor, is selected for the preparation of membranes. Cells are detached from culture plates in 5 ml buffer A per plate (5 mM Tris, 1 mM MgCl$_2$x6H$_2$O, 0.1 mM PMSF, 0.1 mM phenanthroline) using a police rubber and transferred into centrifugation tubes and frozen at −80° C. After thawing, the cells are centrifuged at 500 g for 5 min and then resuspended in buffer A. Cells are then fragmented by homogenization with a Polytron homogenizer for 30 s. The membrane fragments are centrifuged at 3000 g for 40 min and resuspended in membranes in buffer B (50 mM Tris, 25 mM MgCl$_2$, 250 mM saccharose, pH 7.4) and aliquots are stored frozen.

Binding assay is performed in a total volume of 250 µl. In each well, 75 µl buffer C [50 mM Tris, 100 mM NaCl, 1 mM EDTA, 0.1% BSA (protease free), 0.01% NaN$_3$, pH 7.4] is mixed with 50 µl {$^3$H}-PGD$_2$ [at 2.5 nM (220.000 dpm per well) from Amersham, TRK734], 100 µl CRTH2 membranes to give 80 µg per well and 25 µl of test compound in buffer C containing 1% DMSO. For unspecific binding, PGD2 is added to the reaction mixture at 1 µM final concentration. This binding assay mix is incubated at rt for 90 min and then filtered through a GF/C filter plate. The filter is washed three times with ice cold binding buffer. Then, 40 µl per well Microscint-40 (Packard) are added and the bound radioactivity is quantified by means of Topcount (Packard).

Test for Antagonist Binding to the CRTH2 Receptor:

Compounds of Formula I display $IC_{50}$ values of less than 10 μM, as exemplified in the following Table 68.

TABLE 68

| Compound Name | hCRTH2 BDG $IC_{50}$ (μM) |
|---|---|
| {2-[3-(Butoxycarbonyl-phenethyl-amino)-propylsulfanyl]-5-nitro-benzoimidazol-1-yl}-acetic acid | 0.001 |
| {2-[5-Acetyl-2-(3-hydroxy-propoxy)-benzylsulfanyl]-5-fluoro-benzoimidazol-1-yl}-acetic acid | 0.002 |
| [2-(1-Butyryl-piperidin-3-ylmethylsulfanyl)-5,6-dichloro-benzoimidazol-1-yl]-acetic acid | 0.004 |
| [2-(5-Acetyl-2-methoxy-benzylsulfanyl)-5-formyl-benzoimidazol-1-yl]-acetic acid | 0.006 |
| rac. [2-(3-{(2-Cyclohexyl-2-phenyl-acetyl)-[(4-ethyloxycarbonyl)-phenyl]-amino}-propylsulfanyl)-benzoimidazol-1-yl]-acetic acid | 0.007 |
| [2-(5-Acetyl-2-methoxy-benzylsulfanyl)-benzoimidazol-1-yl]-acetic acid | 0.009 |
| {2-[3-(Butoxycarbonyl-phenethyl-amino)-propylsulfanyl]-benzoimidazol-1-yl}-acetic acid and its sodium salt | 0.010 |
| {2-[3-(Pentanoyl-phenethyl-amino)-propylsulfanyl]-benzoimidazol-1-yl}-acetic acid | 0.012 |
| rac 2-[2-(5-Acetyl-2-methoxy-benzylsulfanyl)-5-fluoro-benzoimidazol-1-yl]-propionic acid | 0.013 |
| (2-{3-[(2,2-Diphenyl-ethyl)-pentanoyl-amino]-propylsulfanyl}-benzoimidazol-1-yl)-acetic acid | 0.015 |
| [2-(3-Methoxycarbonyl-benzylsulfanyl)-5-nitro-benzoimidazol-1-yl]-acetic acid | 0.015 |
| rac. {2-[1-(4-Bromo-benzoyl)-piperidin-3-ylmethylsulfanyl]-benzoimidazol-1-yl}-acetic acid | 0.018 |
| rac. [2-(1-Butyryl-piperidin-3-ylmethylsulfanyl)-benzoimidazol-1-yl]-acetic acid | 0.022 |
| rac {2-[1-(4-Bromo-benzoyl)-pyrrolidin-3-ylmethylsulfanyl]-5-fluoro-benzoimidazol-1-yl}-acetic acid | 0.023 |

Intracellular Calcium Mobilization Assay (FLIPR):

Cells (HEK-293), stably expressing the $hCRTH_2$ receptor under the control of the cytomegalovirus promotor from a single insertion of the expression vector pcDNA5 (Invitrogen), are grown to confluency in DMEM (low glucose, Gibco) medium supplemented with 10% fetal calf serum (both Bioconcept, Switzerland) under standard mammalian cell culture conditions (37° C. in a humidified atmosphere of 5% $CO_2$). Cells are detached from culture dishes using a dissociation buffer (0.02% EDTA in PBS, Gibco) for 1 min, and collected by centrifugation at 200 g at rt for 5 min in assay buffer [equal parts of Hank's BSS (HBSS, Bioconcept) and DMEM (low glucose, without phenol red, Gibco)]. After incubation for 45 min (37° C. and 5% $CO_2$) in the presence of 1 μM Fluo-4 and 0.04% Pluronic F-127 (both Molecular Probes), 20 mM HEPES (Gibco) in assay buffer, the cells are washed with and resuspended in assay buffer, then seeded onto 384-well FLIPR assay plates (Greiner) at 50,000 cells in 66 μl per well, and sedimented by centrifugation.

Stock solutions of test compounds are made up at a concentration of 10 mM in DMSO, and serially diluted in assay buffer to concentrations required for inhibition dose response curves. Prostaglandin $D_2$ (Biomol, Plymouth Meeting, Pa.) is used as an agonist.

A FLIPR384 instrument (Molecular Devices) is operated according to the manufacturer's standard instructions, adding 4 μl of test compound dissolved at 10 mM in DMSO and diluted prior to the experiment in assay buffer to obtain the desired final concentration. An assay buffer containing 10 μl of 80 nM prostaglandin $D_2$ (Biomol, Plymouth Meeting, Pa.), supplemented with 0.8% bovine serum albumin (fatty acid content <0.02%, Sigma), is then added to obtain a final concentration of 10 nM and 0.1%, respectively. Changes in fluorescence are monitored before and after the addition of test compounds at $\lambda_{ex}$=488 nm and $\lambda_{em}$=540 nm. Emission peak values above base level after prostaglandin $D_2$ addition are exported after base line subtraction. Values are normalized to high-level control (no test compound added) after subtraction of base line value (no prostaglandin $D_2$ added). The program XL1fit 3.0 (IDBS) is used to fit the data to a single site dose response curve of the equation $(A+((B-A)/(1+((C/x)^D))))$ and to calculate the $IC_{50}$ values.

Antagonist Analysis:

Compounds of Formula I antagonize prostaglandin D2 mediated hCRTH2 receptor activity with an $IC_{50}$ of less than 10 μM as exemplified in the following Table 69.

TABLE 69

| Compound Name | hCRTH2 FLIPR $IC_{50}$ (μM) |
|---|---|
| {2-[5-(2,3-Dihydro-indole-1-carbonyl)-2-methoxy-benzylsulfanyl]-5-fluoro-benzoimidazol-1-yl}-acetic acid | 0.004 |
| [2-(3-Methoxycarbonyl-benzylsulfanyl)-5-nitro-benzoimidazol-1-yl]-acetic acid | 0.015 |
| [2-(5-Butylcarbamoyl-2-methoxy-benzylsulfanyl)-5-fluoro-benzoimidazol-1-yl]-acetic acid | 0.021 |
| rac {2-[1-(4-Bromo-benzoyl)-pyrrolidin-3-ylmethylsulfanyl]-5-fluoro-benzoimidazol-1-yl}-acetic acid | 0.088 |
| [2-(3-Methoxycarbonyl-benzylsulfanyl)-5-trifluoromethyl-benzoimidazol-1-yl]-acetic acid and its 6 trifluoromethyl regioisomer | 0.098 |
| [2-(3-{Diphenylpropionyl-[(4-ethyloxycarbonyl)-phenyl]-amino}-propylsulfanyl)-benzoimidazol-1-yl]-acetic acid | 0.128 |
| [2-(1-Butyryl-piperidin-3-ylmethylsulfanyl)-5,6-dichloro-benzoimidazol-1-yl]-acetic acid | 0.148 |
| rac {2-[1-(3-Chloro-benzoyl)-piperidin-3-ylmethylsulfanyl]-benzoimidazol-1-yl}-acetic acid | 0.156 |
| {2-[(6-Methoxy-3-methoxycarbonyl)-benzylsulfanyl]-benzoimidazol-1-yl}-acetic acid | 0.201 |
| [2-(3,3-Diphenyl-propylsulfanyl)-6-nitro-benzoimidazol-1-yl]-acetic acid | 0.212 |

Formulations:

The compounds of the invention can be formulated as the active ingredient according to methods known per se to give e.g. pharmaceutical preparations of the following composition:

1. 500 mg tablets

| | |
|---|---|
| Active ingredient | 500 mg |
| Powdered lactose | 149 mg |
| Polyvinylpyrrolidone | 15 mg |
| Dioctyl sodium sulfosuccinate | 1 mg |
| Sodium carboxymethyl starch | 30 mg |
| Magnesium stearate | 5 mg |
| Total | 700 mg |

2. 50 mg tablets

| | |
|---|---|
| Active ingredient | 50 mg |
| Powdered lactose | 50 mg |
| Microcrystalline cellulose | 82 mg |
| Sodium carboxymethyl starch | 15 mg |
| Total | 200 mg |

3. 100 mg capsules

| | |
|---|---|
| Active ingredient | 100.0 mg |
| Powdered lactose | 104.7 mg |
| Corn starch | 70.0 mg |
| Hydroxypropylmethyl cellulose | 10.0 mg |
| Dioctyl sodium sulfosuccinate | 0.3 mg |
| Talc | 12.0 mg |
| Magnesium stearate | 3.0 mg |
| Total | 300.0 mg |

4. 500 mg suppositories

| | |
|---|---|
| Active ingredient | 500 mg |
| Suppository mass | ad 2000 mg |

5. 100 mg soft gelatine capsules

| | |
|---|---|
| Active ingredient | 100 mg |
| Medium chain triglyceride | 300 mg |
| Total | 400 mg |

The invention claimed is:
1. A compound of the formula I:

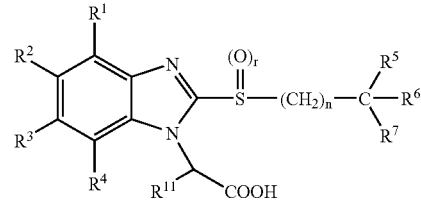

wherein
$R^1$, $R^2$, $R^3$ and $R^4$ each independently represent hydrogen; alkyl; haloalkyl; halogen; nitro; cyano; formyl; methylsulfonyl; or methylcarbonyl;
n is 0 or an integer from 1 to 10;
r is 0 or 1;
$R^5$, $R^6$ and $R^7$ each independently represent hydrogen; alkyl; alkenyl; cycloalkyl; aryl; aryloxy; alkylcarbonyl; cycloalkylcarbonyl; arylcarbonyl; arylalkylcarbonyl; N-alkyl-N-aryl-carbamoyl; N-alkyl-N-arylalkyl-carbamoyl; N-arylalkyl-N-aryl-carbamoyl; heterocyclyl; heterocyclyloxy; heterocyclylcarbonyl; or an amino of Formula $NR^8R^9$; or two of $R^5$-$R^7$ together with the carbon atom to which they are attached form cycloalkyl or saturated heterocyclyl;
$R^8$ represents hydrogen or $R^9$;
$R^9$ independently from $R^8$ represents cycloalkyl; cycloalkylalkyl; aryl; cycloalkylarylalkyl; arylalkyl; (diaryl)-alkyl; alkylcarbonyl; alkenylcarbonyl; cycloalkylcarbonyl; cycloalkylalkylcarbonyl; alkoxycarbonyl; alkoxydicarbonyl; arylcarbonyl; arylalkylcarbonyl; arylalkenylcarbonyl; (diaryl)-alkylcarbonyl; cycloalkylarylalkylcarbonyl; heterocyclylcarbonyl; alkylcarbamoyl; arylcarbamoyl; arylalkylcarbamoyl; alkylsulfonyl; arylsulfonyl; arylalkylsulfonyl; or
$R^8$ and $R^9$, together with the nitrogen atom to which they are attached, form a heterocyclyl group; and
$R^{11}$ is hydrogen or methyl;
wherein aryl groups present as $R^5$-$R^9$, alone or in combination, are unsubstituted or mono- or di-substituted with substituents independently selected from lower alkyl; hydroxy-lower alkyl; lower alkoxy; lower alkoxy-lower alkyl; halogen; cyano; lower alkylcarbonyl; aryl; aryl-lower alkyl; cycloalkyl; 2,3-dihydro-indole-1-carbonyl; lower alkylcarbamoyl; morpholine-4-carbonyl; aryl-lower alkylcarbamoyl; N,N-di-lower alkylcarbamoyl; N-lower alkyl-N-aryl-lower alkyl-carbamoyl; hydroxy-lower alkoxy; arylcarbonyl; or heterocyclyl;
or a pharmaceutically acceptable salt of the compound;
or an optically pure enantiomer, a mixture of enantiomers, a racemate, an optically pure diastereoisomer, a mixture of diastereoisomers, a diastereoisomeric racemate, a mixture of diastereoisomeric racemates, a meso form, a geometric isomer, or pharmaceutically acceptable salts thereof,
wherein the following compounds are excluded:
(2-octylsulfanyl-benzoimidazol-1-yl)-acetic acid;
(2-butylsulfanyl-benzoimidazol-1-yl)-acetic acid;
(2-propylsulfanyl-benzoimidazol-1-yl)-acetic acid;
(2-ethylsulfanyl-benzoimidazol-1-yl)-acetic acid;
(2-methylsulfanyl-benzoimidazol-1-yl)-acetic acid;
(2-isopropylsulfanyl-benzoimidazol-1-A-acetic acid;
(2-sec-butylsulfanyl-benzoimidazol-1-yl)-acetic acid;

(2-isobutylsulfanyl-benzoimidazol-1-yl)-acetic acid;
(2-allylsulfanyl-benzoimidazol-1-yl)-acetic acid;
(2-cyclohexylsulfanyl-benzoimidazol-1-yl)-acetic acid;
(2-benzylsulfanyl-benzoimidazol-1-yl)-acetic acid;
(2-phenethylsulfanyl-benzoimidazol-1-yl(-acetic acid;
[2-(naphthalen-1-ylmethylsulfanyl)-benzoimidazol-1-yl]-acetic acid;
{2-[2-(4-tert-butyl-phenoxy)-ethylsulfanyl]-benzoimidazol-1-yl}-acetic acid;
{2-[2-(4-propoxy-phenoxy)-ethylsulfanyl]-benzoimidazol-1-yl}-acetic acid;
{2-[2-(4-ethoxy-phenoxy)-ethylsulfanyl]-benzoimidazol-1-yl}-acetic acid;
{2-[2-(3,4-dimethyl-phenoxy)-ethylsulfanyl]-benzoimidazol-1-yl}-acetic acid;
{2-[2-(3-methylphenoxy)-ethylsulfanyl]-benzoimidazol-1-yl}-acetic acid;
{2-[2-(naphthalen-2-yloxy)-ethylsulfanyl]-benzoimidazol-1-yl}-acetic acid;
{2-[2-(4-methoxy-phenoxy)-ethylsulfanyl]-benzoimidazol-1-yl}-acetic acid;
{2-[2-(4-butoxy-phenoxy)-ethylsulfanyl]-benzoimidazol-1-yl}-acetic acid;
{2-[2-(4-methylphenoxy)-ethylsulfanyl]-benzoimidazol-1-yl}-acetic acid;
[2-(2-phenoxy-ethylsulfanyl)-benzoimidazol-1-yl]-acetic acid;
{2-[2-(4-ethyl-phenoxy)-ethylsulfanyl]-benzoimidazol-1-yl}-acetic acid;
{2-[2-(2-methylphenoxy)-ethylsulfanyl]-benzoimidazol-1-yl}-acetic acid;
{2-[2-(4-chloro-phenoxy)-ethylsulfanyl]-benzoimidazol-1-yl}-acetic acid;
{2-[2-(2-isopropyl-4-methyl-phenoxy)-ethylsulfanyl]-benzoimidazol-1-yl}-acetic acid;
{2-[2-(naphthalen-1-yloxy)-ethylsulfanyl]-benzoimidazol-1-yl}-acetic acid;
{2-[2-(2,6-Dimethyl-phenoxy)-ethylsulfanyl]-benzoimidazol-1-yl}-acetic acid;
{2-[2-(4-isopropoxy-phenoxy)-ethylsulfanyl]-benzoimidazol-1-yl}-acetic acid;
{2-[2-(2-fluoro-phenoxy)-ethylsulfanyl]-benzoimidazol-1-yl}-acetic acid;
{2-[2-(2-methoxy-phenoxy)-ethylsulfanyl]-benzoimidazol-1-yl}-acetic acid; and
{2-[3-methyl-4-(2-morpholin-4-yl-ethylsulfanyl)-pyridin-2-ylmethylsulfanyl]benzoimidazol-1-yl}-acetic acid.

2. The compound according to claim 1, wherein:
$R^5$ represents hydrogen;
$R^6$ represents hydrogen; or alkyl; and
$R^7$ represents N-alkyl-N-arylalkyl-carbamoyl; N-alkyl-N-aryl-carbamoyl;
alkylcarbonyl; N-arylalkyl-N-aryl-carbamoyl; arylalkylcarbonyl; arylcarbonyl;
cycloalkylcarbonyl; heterocyclylcarbonyl; heterocyclyloxy; an amino of Formula $NR^8R^9$; aryl substituted with one or two of lower alkoxy, and lower alkylcarbonyl, and optionally an additional halogen; or heterocyclyl substituted with alkylcarbonyl, cycloalkylcarbonyl, alkoxycarbonyl, arylcarbonyl, arylalkylcarbonyl, (diaryl)alkyl carbonyl or heterocyclylcarbonyl and optionally an additional halogen; or
$R^6$ represents alkyl or alkoxycarbonyl and $R^7$ represents aryl; or $R^6$ and $R^7$ together with the carbon atom to which they are attached form cycloalkyl or saturated heterocyclyl;
or a pharmaceutically acceptable salt thereof.

3. The compound according to claim 1, wherein:
$R^1$, $R^2$, $R^3$ and $R^4$ each independently represent hydrogen; alkyl; haloalkyl; halogen; nitro; cyano; formyl; methylsulfonyl; or methylcarbonyl;
n is 0 or an integer from 1 to 5;
r is 0 or 1;
$R^5$, $R^6$ and $R^7$ each independently represent hydrogen; alkyl; alkenyl; cycloalkyl; aryl; aryloxy; arylcarbonyl; N-alkyl-N-aryl-carbamoyl; N-alkyl-N-arylalkyl-carbamoyl; N-arylalkyl-N-aryl-carbamoyl; heterocyclyl; heterocyclyloxy; heterocyclylcarbonyl; or an amino of Formula $NR^8R^9$; or two of $R^5$-$R^7$ together with the carbon atom to which they are attached form cycloalkyl or saturated heterocyclyl;
$R^8$ represents hydrogen or $R^9$;
$R^9$ independently from $R^8$ represents cycloalkyl; cycloalkylalkyl; aryl; arylalkyl; (diaryl)-alkyl; alkylcarbonyl; cycloalkylcarbonyl; cycloalkylalkylcarbonyl; alkoxycarbonyl; alkoxydicarbonyl; arylcarbonyl; arylalkylcarbonyl; arylalkenylcarbonyl; (diaryl)-alkylcarbonyl; heterocyclylcarbonyl; alkylcarbamoyl; arylcarbamoyl; arylalkylcarbamoyl; alkylsulfonyl; arylsulfonyl; arylalkylsulfonyl; or
$R^8$ and $R^9$, together with the nitrogen atom to which they are attached, form a heterocyclyl group; and
$R^{11}$ is hydrogen or methyl;
or a pharmaceutically acceptable salt thereof.

4. The compound according to claim 1, wherein $R^6$ and $R^7$ together with the carbon atom, to which they are attached, form a saturated heterocyclyl ring containing one nitrogen atom which is substituted with $R^{10}$, wherein $R^{10}$ represents alkylcarbamoyl; alkylcarbonyl; alkoxycarbonyl; alkyl sulfonyl; arylalkylcarbamoyl; arylalkylcarbonyl; arylalkoxycarbonyl; arylalkylsulfonyl; arylcarbamoyl; arylcarbonyl; (diaryl)-alkylcarbonyl; aryloxycarbonyl; arylsulfonyl; arylalkenylsulfonyl; cycloalkylcarbamoyl; cycloalkylalkylcarbonyl; cycloalkylcarbonyl; cycloalkyloxycarbonyl; cycloalkylsulfonyl; heterocyclylcarbamoyl; heterocyclylcarbonyl; heterocyclyloxycarbonyl; or heterocyclylsulfonyl; or a pharmaceutically acceptable salt thereof.

5. The compound according to claim 1, wherein $R^1$, $R^2$, $R^3$ and $R^4$ each independently represent hydrogen; methyl; trifluoromethyl; fluoro; chloro; bromo; nitro; cyano; or formyl; or a pharmaceutically acceptable salt thereof.

6. The compound according to claim 1, wherein n is 1 or 2; $R^5$ and $R^6$ each represents hydrogen; $R^7$ represents an amino of Formula $NR^8R^9$;
$R^8$ represents hydrogen; and
$R^9$ represents cycloalkyl; aryl; arylalkyl; (diaryl)-alkyl; alkylcarbonyl; cycloalkyl-alkylcarbonyl; cycloalkylcarbonyl; alkenylcarbonyl; alkoxycarbonyl; alkoxydicarbonyl; arylcarbonyl; arylalkylcarbonyl; (diaryl)-alkylcarbonyl; heterocyclylcarbonyl; alkylcarbamoyl; arylcarbamoyl; arylalkylcarbamoyl; alkylsulfonyl; arylsulfonyl; arylalkylsulfonyl; or
$R^8$ represents cycloalkyl; arylalkyl; aryl; alkoxycarbonyl; and
$R^9$ represents cycloalkyl; cyclylalkyl-alkyl; aryl; arylalkyl; (diaryl)-alkyl; cycloalkyl-alkylcarbonyl; alkylcarbonyl; arylalkylcarbonyl; (diaryl)-alkylcarbonyl; alkylcarbamoyl; arylcarbamoyl; arylalkylcarbamoyl; alkylsulfonyl; arylsulfonyl; arylalkylsulfonyl; or R⁸ and R⁹, together with the nitrogen atom to which they are attached, form a phthalazinyl; isoindolyl; benzoimidazolyl; indazolyl; quinazolinyl; or benzoisothiazolyl ring system;

or a pharmaceutically acceptable salt thereof.

7. The compound according to claim 6, wherein R⁸ represents hydrogen; and

R⁹ represents 3-phenyl-acryloyl; butoxycarbonyl; tert-butoxycarbonyl; ethoxydicarbonyl; propylcarbamoyl; 2,2-dimethyl-propionyl; 3,3-dimethyl-butyryl; 3-octanoyl; pentanoyl; butane-1-sulfonyl; 4-piperidin-1-yl-phenyl; phenyl; 2,2-diphenyl-ethyl; 3-benzyl; 2-cyclohexyl-2-phenyl-acetyl; 3,3-diphenyl-propionyl; 3-phenyl-propionyl; diphenylacetyl; phenylacetyl; phenylmethanesulfonyl; phenylcarbamoyl; 4-bromo-benzoyl; 4-methoxy-benzoyl; benzoyl; biphenyl-4-carbonyl; naphthalene-1-carbonyl; benzenesulfonyl; cyclohexanecarbonyl; cyclopropanecarbonyl; 3-cyclopentyl-propionyl; furan-2-carbonyl; or pyridine-3-carbonyl; or R⁸ represents butoxycarbonyl; tert-butoxycarbonyl; 4-piperidin-1-yl-phenyl; phenyl; benzyl; 2,2-diphenyl-ethyl; phenethyl; cyclopropyl; and R⁹ represents propylcarbamoyl; pentanoyl; butane-1-sulfonyl; 4-piperidin-1-yl-phenyl; phenyl; benzyl; phenethyl; 2,2-diphenyl-ethyl; benzylcarbamoyl; 2-cyclohexyl-2-phenyl-acetyl; 2-phenylacetyl; 3,3-diphenyl-propionyl; diphenylacetyl; phenylmethanesulfonyl; phenylcarbamoyl; benzenesulfonyl; cyclohexyl; cyclopropyl; or cyclohexylmethyl; or R⁸ and R⁹, together with the nitrogen atom to which they are attached, represent 1-oxo-1H-phthalazin-2-yl; 1-oxo-1,3-dihydro-isoindol-2-yl; 2-oxo-2,3-dihydro-benzoimidazol-1-yl; 1-ethoxycarbonyl-3-oxo-2,3-dihydro-indazole-2-yl; 2,4-dioxo-1,4-dihydro-2H-quinazolin-3-yl; 1,3-dioxo-1,3-dihydro-isoindol-2-yl; or 1,1,3-trioxo-1,3-dihydro-1,6-benzo[d]isothiazol-2-yl;

or a pharmaceutically acceptable salt thereof.

8. The compound according to claim 1, wherein n is 0; R⁵ and R⁶ each represents hydrogen; and R⁷ represents phenyl; furanyl; oxazolyl; pyridinyl; or thiazolyl, all substituted with one or two of lower alkoxy and lower alkylcarbonyl and optionally an additional halogen;

or a pharmaceutically acceptable salt thereof.

9. The compound according to claim 1, wherein n is 0; R⁵ and R⁶ each represents hydrogen; and R⁷ represents phenyl, optionally mono- or di-substituted wherein the substituents are independently hydroxy-lower alkyl, lower alkoxy, lower alkoxy-lower alkyl, halo, lower alkylcarbonyl, phenyl, 2,3-dihydro-indole-1-carbonyl, lower alkylcarbamoyl, morpholine-4-carbonyl, benzylcarbamoyl, N,N-di-lower alkylcarbamoyl, N-lower alkyl-N-benzyl-carbamoyl, hydroxy-lower alkoxy or benzoyl; or R⁷ represents 3-oxo-indan-5-yl or 8-oxo-5,6,7,8-tetrahydro-naphthalen-2-yl, both substituted by alkoxy;

or a pharmaceutically acceptable salt thereof.

10. The compound according to claim 1,
wherein n is 1;
R⁵ represents hydrogen; and R⁶ and R⁷ together with the carbon atom to which they are attached form a 5- or 6-membered saturated heterocyclyl containing one nitrogen ring atom, wherein this nitrogen ring atom contains a substituent R¹⁰, wherein R¹⁰ represents alkylcarbamoyl; alkylcarbonyl; alkoxycarbonyl; alkylsulfonyl; arylalkylcarbamoyl; arylalkylcarbonyl; arylalkoxycarbonyl; arylalkylsulfonyl; arylcarbamoyl; arylcarbonyl; (diaryl)-alkylcarbonyl; aryloxycarbonyl; arylsulfonyl; arylalkenylsulfonyl; cycloalkylcarbamoyl; cycloalkylalkylcarbonyl; cycloalkylcarbonyl; cycloalkyloxycarbonyl; cycloalkylsulfonyl; heterocyclylcarbamoyl; heterocyclylcarbonyl; heterocyclyloxycarbonyl; or heterocyclylsulfonyl;

or a pharmaceutically acceptable salt thereof.

11. The compound according to claim 1 which is:
{2-[3-(butoxycarbonyl-phenethyl-amino)-propylsulfanyl]-5-nitro-benzoimidazol-1-yl}-acetic acid;
(2-{3-[(2,2-diphenyl-ethyl)-pentanoyl-amino]-propylsulfanyl}-benzoimidazol-1-yl)-acetic acid;
{2-[1-(4-bromo-benzoyl)-piperidin-3-ylmethylsulfanyl]-benzoimidazol-1-yl}-acetic acid;
[2-(4-ethyloxycarbonyl-butylsulfanyl)-5-nitro-benzoimidazol-1-yl]-acetic acid;
{2-[1-(furan-2-carbonyl)-piperidin-3-ylmethylsulfanyl]-benzoimidazol-1-yl}-acetic acid;
{2-[3-(benzyl-butoxycarbonyl-amino)-propylsulfanyl]-benzoimidazol-1-yl}-acetic acid;
{2-[1-(3-phenyl-propionyl)-piperidin-3-ylmethylsulfanyl]-benzoimidazol-1-yl}-acetic acid;
{2-[3-(benzyl-pentanoyl-amino)-propylsulfanyl]-benzoimidazol-1-yl}-acetic acid;
{2-[3-(cyclopropyl-diphenylacetyl-amino)-propylsulfanyl]-benzoimidazol-1-yl}-acetic acid;
[2-(1-methyl-2-oxo-2-phenyl-ethylsulfanyl)-benzoimidazol-1-yl]-acetic acid;
[2-(3,3-diphenyl-propylsulfanyl)-6-nitro-benzoimidazol-1-yl]-acetic acid;
(2-benzylsulfanyl-5-nitro-benzoimidazol-1-yl)-acetic acid and its 6-nitro isomer;
{2-[3-(1-phenethyl-3-propyl-ureido)-propylsulfanyl]-benzoimidazol-1-yl}-acetic acid;
{2-[1-(3-chloro-benzoyl)-piperidin-3-ylmethylsulfanyl]-benzoimidazol-1-yl}-acetic acid;
{2-[3-(1,3-dioxo-1,3-dihydro-isoindol-2-yl)-propylsulfanyl]-5-nitro-benzoimidazol-1-yl}-acetic acid;
{2-[3-(1,3-trioxo-1,3-dihydro-1λ⁶-benzo[d]isothiazol-2-yl)-propylsulfanyl]-benzoimidazol-1-yl}-acetic acid;
(2-{3-[(2,2-diphenyl-ethyl)-(3,3-diphenyl-propionyl)-amino]-propylsulfanyl}-benzoimidazol-1-yl)-acetic acid;
(2-{3-[cyclopropyl-(3,3-diphenyl-propionyl)-amino]-propylsulfanyl}-benzoimidazol-1-yl)-acetic acid;
(2-{3-[(2-cyclohexyl-2-phenyl-acetyl)-cyclopropyl-amino]-propylsulfanyl}-benzoimidazol-1-yl)-acetic acid;
(2-{3-[diphenylacetyl-(2,2-diphenyl-ethyl)-amino]-propylsulfanyl}-benzoimidazol-1-yl)-acetic acid;
[2-(1-heptanoyl-piperidin-3-ylmethyl sulfanyl)-benzoimidazol-1-yl]-acetic acid;
(2-[3-(3,3-diphenyl-propionylamino)-propylsulfanyl] benzoimidazol-1-yl)-acetic acid;
(2-{3-[(butane-1-sulfonyl)-phenethyl-amino]-propylsulfanyl}-benzoimidazol-1-yl)-acetic acid;
{2-[3-(benzyl-(phenylmethanesulfonyl)-amino)-propylsulfanyl]-benzoimidazol-1-yl}-acetic acid;
(2-{3-[2,2-diphenyl-ethyl)-(phenylacetyl)-amino]-propylsulfanyl}-benzoimidazol-1-yl)-acetic acid;
{2-[3-(benzenesulfonyl-cyclopropyl-amino)-propylsulfanyl]-benzoimidazol-1-yl}-acetic acid;
{2-[3-(phenethyl-(phenylmethanesulfonyl)-amino)-propylsulfanyl]-benzoimidazol-1-yl}-acetic acid;
[2-(3,3-diphenyl-propylsulfanyl)-benzoimidazol-1-yl]-acetic acid;
{2-[3-(phenethyl-(phenylacetyl)amino)-propylsulfanyl]-benzoimidazol-1-yl}-acetic acid;

{2-[3-(diphenylacetyl-phenethyl-amino)-propylsulfanyl]-benzoimidazol-1-yl}-acetic acid;
{2-[(2-chloro-4-methyloxycarbonyl)-pyridin-6-yl]-methyl-sulfanyl}-benzoimidazol-1-yl)-acetic acid;
[2-(bicyclo[4.2.0]octa-1,3,5-trien-7-ylsulfanyl)-benzoimidazol-1-yl]-acetic acid;
[2-(3-acetyl-benzylsulfanyl)-benzoimidazol-1-yl]-acetic acid;
[5-fluoro-2-(2-phenoxy-ethylsulfanyl)-benzoimidazol-1-yl]-acetic acid and its 6-fluoro regioisomer;
[2-(3-phenylmethanesulfonylamino-propylsulfanyl)-benzoimidazol-1-yl]-acetic acid;
[2-(4-ethyloxycarbonyl-butylsulfanyl)-6-nitro-benzoimidazol-1-yl]-acetic acid;
{2-[3-(1,3-dioxo-1,3-dihydro-isoindol-2-yl)-propylsulfanyl]-benzoimidazol-1-yl}-acetic acid;
{2-[3-(1,3-dioxo-1,3-dihydro-isoindol-2-yl)-propylsulfanyl]-6-nitro-benzoimidazol-1-yl}-acetic acid;
(2-{3-[phenylmethanesulfonyl-(4-piperidin-1-yl-phenyl)-amino]-propylsulfanyl}-benzoimidazol-1-yl)-acetic acid;
[2-(4-ethyloxycarbonyl-butylsulfanyl)-5-fluoro-benzoimidazol-1-yl]-acetic acid and its 6-fluoro regioisomer;
[2-(3-diphenylacetylamino-propylsulfanyl)-5-nitro-benzoimidazol-1-yl]-acetic acid;
{2-[3-(cyclopropyl-(phenylmethanesulfonyl)-amino)-propylsulfanyl]-benzoimidazol-1-yl}-acetic acid;
{5-nitro-2-[2-(4-chloro-phenoxy)-ethylsulfanyl]-benzoimidazol-1-yl}-acetic acid;
[2-(3,3-diphenyl-propylsulfanyl)-5-nitro-benzoimidazol-1-yl]-acetic acid;
{2-[3-(2,4-dioxo-1,4-dihydro-2H-quinazolin-3-yl)-propylsulfanyl]-benzoimidazol-1-yl}-acetic acid;
{2-[3-(benzyl-(phenylacetyl)-amino)-propylsulfanyl]-benzoimidazol-1-yl}-acetic acid;
(2-{3-[(2,2-diphenyl-ethyl)-(phenylmethanesulfonyl)-amino]-propylsulfanyl}-benzoimidazol-1-yl)-acetic acid;
[2-(1-acetyl-piperidin-3-ylmethylsulfanyl)-benzoimidazol-1-yl]-acetic acid;
(2-{3-[benzyl-(3,3-diphenyl-propionyl)-amino]-propylsulfanyl}-benzoimidazol-1-yl)-acetic acid;
{2-[3-(cyclopropyl-(phenylacetyl)-amino)-propylsulfanyl]-benzoimidazol-1-yl}-acetic acid;
{2-[3-(butoxycarbonyl-cyclohexyl-amino)-propylsulfanyl]-benzoimidazol-1-yl}-acetic acid;
[2-(3-diphenylacetylamino-propylsulfanyl)-benzoimidazol-1-yl]-acetic acid;
{2-[3-(1,3-diphenyl-ureido)-propylsulfanyl]-benzoimidazol-1-yl}-acetic acid;
(2-benzylsulfanyl-6-nitro-benzoimidazol-1-yl)-acetic acid;
[2-(1-diphenylacetyl-piperidin-3-ylmethylsulfanyl)-benzoimidazol-1-yl]-acetic acid;
{2-[3-(cyclopropyl-pentanoyl-amino)-propylsulfanyl]-benzoimidazol-1-yl}-acetic acid;
(2-{3-[benzenesulfonyl-(4-piperidin-1-yl-phenyl)-amino]-propylsulfanyl}-benzoimidazol-1-yl)-acetic acid;
{2-[3-(benzyl-diphenylacetyl-amino)-propylsulfanyl]-benzoimidazol-1-yl}-acetic acid;
{2-[3-(tert-butoxycarbonyl-phenyl-amino)-propylsulfanyl]-benzoimidazol-1-yl}-acetic acid;
[2-(3-phenyl-propylsulfanyl)-benzoimidazol-1-yl]-acetic acid;
[2-(3-benzenesulfonylamino-propylsulfanyl)-benzoimidazol-1-yl]-acetic acid;
{2-[3-(1-benzyl-3-propyl-ureido)-propylsulfanyl]-benzoimidazol-1-yl}-acetic acid;
(2-{3-[1-(2,2-diphenyl-ethyl)-3-propyl-ureido]-propylsulfanyl}-benzoimidazol-1-yl)-acetic acid;
[2-(4-ethyloxycarbonyl-butylsulfanyl)-5-trifluoromethyl-benzoimidazol-1-yl]-acetic acid and its 6-trifluoromethyl regioisomer;
[5-cyano-2-(4-ethyloxycarbonyl-butylsulfanyl)-benzoimidazol-1-yl]-acetic acid and its 6-cyano regioisomer;
[2-(5-ethyloxycarbonyl-pentylsulfanyl)-benzoimidazol-1-yl]-acetic acid;
(2-{3-[(3,3-diphenyl-propionyl)-phenyl-amino]-propylsulfanyl}-benzoimidazol-1-yl)-acetic acid;
{2-[3-(butoxycarbonyl-(cyclohexylmethyl)-amino)-propyl sulfanyl]-benzoimidazol-1-yl}-acetic acid;
(2-{3-[tert-butoxycarbonyl-(4-piperidin-1-yl-phenyl)-amino]-propylsulfanyl}-benzoimidazol-1-yl)-acetic acid;
(2-{3-[phenylacetyl-(4-piperidin-1-yl-phenyl)-amino]-propylsulfanyl}-benzoimidazol-1-yl)-acetic acid;
{2-[3-(2,3-dihydro-1-ethyloxycarbonyl-3-oxo-indazol-2-yl)-propylsulfanyl]-benzoimidazol-1-yl}-acetic acid;
{2-[1-(3-cyclopentyl-propionyl)-piperidin-3-ylmethylsulfanyl]-benzoimidazol-1-yl}-acetic acid;
(2-{3-[tert-butoxycarbonyl-(2,2-diphenyl-ethyl)-amino]-propylsulfanyl}-benzoimidazol-1-yl)-acetic acid;
{2-[3-(benzenesulfonyl-phenethyl-amino)-propylsulfanyl]-benzoimidazol-1-yl}-acetic acid; or
{2-[5-(3,4-dihydro-2H-quinolin-1-yl)-5-oxo-pentylsulfanyl]-benzoimidazol-1-yl}-acetic acid;
or a pharmaceutically acceptable salt thereof.

12. The compound according to claim 1 which is:
{2-[1-(3,4-dichloro-benzenesulfonyl)-piperidin-3-ylmethyl sulfanyl]-benzoimidazol-1-yl}-acetic acid;
{2-[1-(3-phenyl-acryloyl)-piperidin-3-ylmethylsulfanyl]-benzoimidazol-1-yl}-acetic acid;
[2-(1-butyryl-piperidin-3-ylmethylsulfanyl)-5,6-dimethyl-benzoimidazol-1-yl]-acetic acid;
[2-(5-acetyl-2-methoxy-benzylsulfanyl)-5,6-dichloro-benzoimidazol-1-yl]-acetic acid;
[2-(1-butyryl-piperidin-3-ylmethylsulfanyl)-5,6-dichloro-benzoimidazol-1-yl]-acetic acid;
[2-((R)-1-butyryl-piperidin-3-ylmethylsulfanyl)-benzoimidazol-1-yl]-acetic acid;
[2-(5-acetyl-2-methoxy-benzylsulfanyl)-5,6-difluoro-benzoimidazol-1-yl]-acetic acid;
[2-(5-acetyl-2-methoxy-benzylsulfanyl)-5-fluoro-benzoimidazol-1-yl]-acetic acid;
[2-(1-butyryl-piperidin-3-ylmethylsulfanyl)-5-fluoro-benzoimidazol-1-yl]-acetic acid;
{5-fluoro-2-[1-(furan-2-carbonyl)-piperidin-3-ylmethylsulfanyl]-benzoimidazol-1-yl}-acetic acid;
{2-[1-(4-bromo-benzoyl)-piperidin-3-ylmethylsulfanyl]-5-fluoro-benzoimidazol-1-yl}-acetic acid;
[2-(5-acetyl-2-methoxy-benzylsulfanyl)-5-trifluoromethyl-benzoimidazol-1-yl]-acetic acid;
[2-(5-acetyl-2-methoxy-benzylsulfanyl)-5-methanesulfonyl-benzoimidazol-1-yl]-acetic acid;
[2-(5-acetyl-2-methoxy-benzylsulfanyl)-6-fluoro-benzoimidazol-1-yl]-acetic acid;
[2-(5-acetyl-2-methoxy-benzylsulfanyl)-4-fluoro-benzoimidazol-1-yl]-acetic acid;
[5-acetyl-2-(5-acetyl-2-methoxy-benzylsulfanyl)-benzoimidazol-1-yl]-acetic acid;

[2-(5-acetyl-2-methoxy-benzylsulfanyl)-5-formyl-benzoimidazol-1-yl]-acetic acid;
2-[2-(5-acetyl-2-methoxy-benzylsulfanyl)-5-fluoro-benzoimidazol-1-yl]-propionic acid;
[2-(5-butylcarbamoyl-2-methoxy-benzylsulfanyl)-5-fluoro-benzoimidazol-1-yl]-acetic acid;
[2-(5-benzylcarbamoyl-2-methoxy-benzylsulfanyl)-5-fluoro-benzoimidazol-1-yl]-acetic acid;
{2-[5-(2,3-dihydro-indole-1-carbonyl)-2-methoxy-benzylsulfanyl]-5-fluoro-benzoimidazol-1-yl}-acetic acid;
[2-(5-diethylcarbamoyl-2-methoxy-benzylsulfanyl)-5-fluoro-benzoimidazol-1-yl]-acetic acid;
[2-(5-acetyl-2-methoxy-benzylsulfanyl)-5-nitro-benzoimidazol-1-yl]-acetic acid;
{2-[1-(4-bromo-benzoyl)-pyrrolidin-3-ylmethylsulfanyl]-5-fluoro-benzoimidazol-1-yl}-acetic acid;
{5-fluoro-2-[1-(furan-2-carbonyl)-pyrrolidin-3-ylmethylsulfanyl]-benzoimidazol-1-yl}-acetic acid;
{5-fluoro-2-[1-(2-phenyl-ethenesulfonyl)-pyrrolidin-3-ylmethylsulfanyl]-benzoimidazol-1-yl}-acetic acid;
[2-(5-acetyl-2-butoxy-benzylsulfanyl)-5-fluoro-benzoimidazol-1-yl]-acetic acid;
{2-[5-acetyl-2-(3-hydroxy-propoxy)-benzylsulfanyl]-5-fluoro-benzoimidazol-1-yl}-acetic acid;
[2-(5-benzoyl-2-methoxy-benzylsulfanyl)-5-fluoro-benzoimidazol-1-yl]-acetic acid;
[5-fluoro-2-(6-methoxy-3-oxo-indan-5-ylmethylsulfanye-benzoimidazol-1-yl]-acetic acid;
[2-(5-acetyl-2-ethoxy-benzylsulfanyl)-5-fluoro-benzoimidazol-1-yl]-acetic acid;
[2-(5-acetyl-2-propoxy-benzylsulfanyl)-5-fluoro-benzoimidazol-1-yl]-acetic acid; or
[2-(5-acetyl-2-methoxy-phenylmethanesulfinyl)-5-fluoro-benzoimidazol-1-yl]-acetic acid;
or a pharmaceutically acceptable salt thereof.

13. A pharmaceutical composition comprising a therapeutically effective amount of one or more compounds according to claim 1 and a pharmaceutically acceptable carrier.

14. The compound according to claim 1, wherein aryl groups present as $R^5$-$R^9$, alone or in combination, are unsubstituted or mono- or di-substituted with substituents independently selected from hydroxy-lower alkyl; lower alkoxy; lower alkoxy-lower alkyl; halogen; lower alkylcarbonyl; phenyl; 2,3-dihydro-indole-1-carbonyl; lower alkylcarbamoyl; morpholine-4-carbonyl; benzylcarbamoyl; N,N-di-lower alkylcarbamoyl; N-lower alkyl-N-benzyl-carbamoyl; hydroxy-lower alkoxy; benzoyl; or piperidinyl.

* * * * *